United States Patent
Luo et al.

(10) Patent No.: US 10,689,434 B2
(45) Date of Patent: Jun. 23, 2020

(54) ANTIBODY AGAINST HEPATITIS B SURFACE ANTIGEN AND USE THEREOF

(71) Applicants: XIAMEN UNIVERSITY, Xiamen (CN); YANG SHENG TANG COMPANY, LTD., Haikou (CN)

(72) Inventors: Wenxin Luo, Xiamen (CN); Bing Zhou, Xiamen (CN); Juan Zhang, Xiamen (CN); Quan Yuan, Xiamen (CN); Tianying Zhang, Xiamen (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Haikou (CN)

(*) Notice: Subject to any disclaimer, the term of this patent is extended or adjusted under 35 U.S.C. 154(b) by 155 days.

(21) Appl. No.: 15/766,593

(22) PCT Filed: Oct. 9, 2016

(86) PCT No.: PCT/CN2016/101560
§ 371 (c)(1),
(2) Date: Apr. 6, 2018

(87) PCT Pub. No.: WO2017/059813
PCT Pub. Date: Apr. 13, 2017

(65) Prior Publication Data
US 2019/0389939 A1  Dec. 26, 2019

(30) Foreign Application Priority Data
Oct. 9, 2015  (CN) .......................... 2015 1 0647977

(51) Int. Cl.
*C07K 16/08* (2006.01)
*A61K 39/00* (2006.01)

(52) U.S. Cl.
CPC ...... *C07K 16/082* (2013.01); *A61K 2039/505* (2013.01); *C07K 2317/24* (2013.01); *C07K 2317/56* (2013.01); *C07K 2317/565* (2013.01); *C07K 2317/622* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 8,840,895 | B2 | 9/2014 | Kim et al. |
| 9,200,062 | B2 | 12/2015 | Kim et al. |
| 9,683,029 | B2 * | 6/2017 | Kim .................. A61K 38/21 |
| 2012/0264921 | A1 | 10/2012 | Kim et al. |
| 2014/0302598 | A1 | 10/2014 | Kim et al. |
| 2015/0246948 | A1 | 9/2015 | Yuan et al. |
| 2016/0326233 | A1 | 11/2016 | Mondelli |
| 2018/0002382 | A1 | 1/2018 | Yuan et al. |
| 2019/0389939 | A1 * | 12/2019 | Luo ..................... C12N 15/63 |

FOREIGN PATENT DOCUMENTS

| CN | 102786592 A | 11/2012 |
| CN | 102906111 A | 1/2013 |
| CN | 103483421 A | 1/2014 |
| JP | 2004-517636 A | 6/2004 |
| WO | WO 02/059318 A1 | 8/2002 |
| WO | WO 2009/093263 A1 | 7/2009 |
| WO | WO 2015/107126 A1 | 7/2015 |

OTHER PUBLICATIONS

International Search Report dated Jan. 23, 2017 in PCT/CN2016/101560 filed Oct. 9, 2016.
Higuchi, K. et al., "Cell display library for gene cloning of variable regions of human antibodies to hepatitis B surface antigen", Journal of Immunological Methods, 1997, pp. 193-204.
Ihara, S. et al., "Production of Recombinant Human Antibody against Hepatitis B Virus Surface Antigen", Artificial Blood, vol. 10, No. 4, 2002, pp. 116-119.
Kim, S. H. et al., "Neutralization of hepatitis B virus (HBV) by human monoclonal antibody against HBV surface antigen (HBsAg) in chimpanzees", Antiviral Research, vol. 79, 2008, pp. 188-191.
Shin, Y. W. et al., Human monoclonal antibody against Hepatitis B virus surface antigen (HBsAg), Antiviral Research, vol. 75, 2007, pp. 113-120.
Zhu, Y. et al., "Toward the development of monoclonal antibody-based assays to probe virion-like epitopes in hepatitis B vaccine antigen", Human Vaccines & Immunotherapeutics, vol. 10, No. 4, Apr. 2014, 12 pages.
Qiu, X. et al., "Identification and Characterization of a C(K/R)TC Motif as a Common Epitope Present in All Subtypes of Hepatitis B Surface Antigen", The Journal of Immunology, XP2041204, vol. 156, 1996, pp. 3350-3356.

* cited by examiner

*Primary Examiner* — Shanon A. Foley
(74) *Attorney, Agent, or Firm* — Oblon, McClelland, Maier & Neustadt, L.L.P.

(57) ABSTRACT

The invention provides an antibody (in particular, a humanized antibody) against hepatitis B surface antigen (HBsAg), a nucleic acid molecule encoding the same, a method for preparing the same, and a pharmaceutical composition comprising the same. The invention also provides use of the antibody and pharmaceutical composition. The antibody and pharmaceutical composition according to the invention can be used for preventing and/or treating HBV infection or a disease associated with HBV infection (such as Hepatitis B), for neutralizing HBV virulence in a subject (such as human), or for reducing the serum level of HBV DNA and/or HBsAg in a subject.

17 Claims, 32 Drawing Sheets
Specification includes a Sequence Listing.

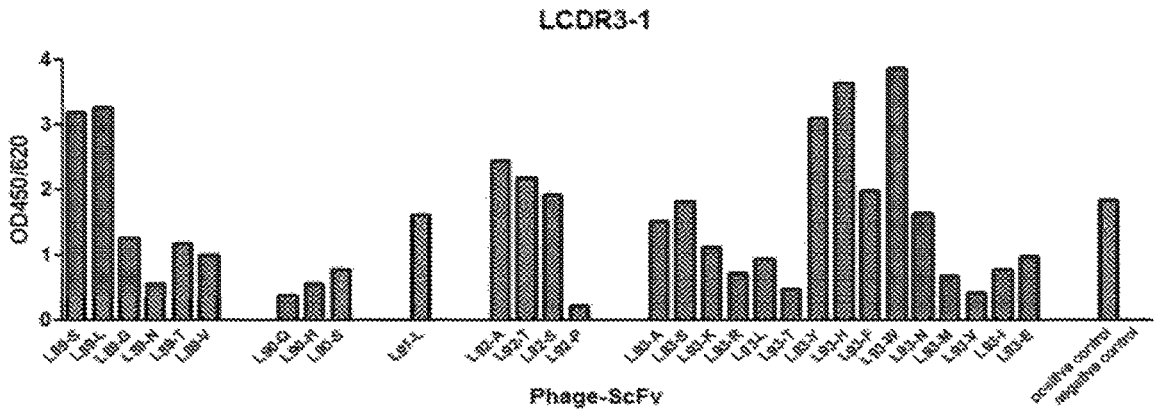
FIG. 5H
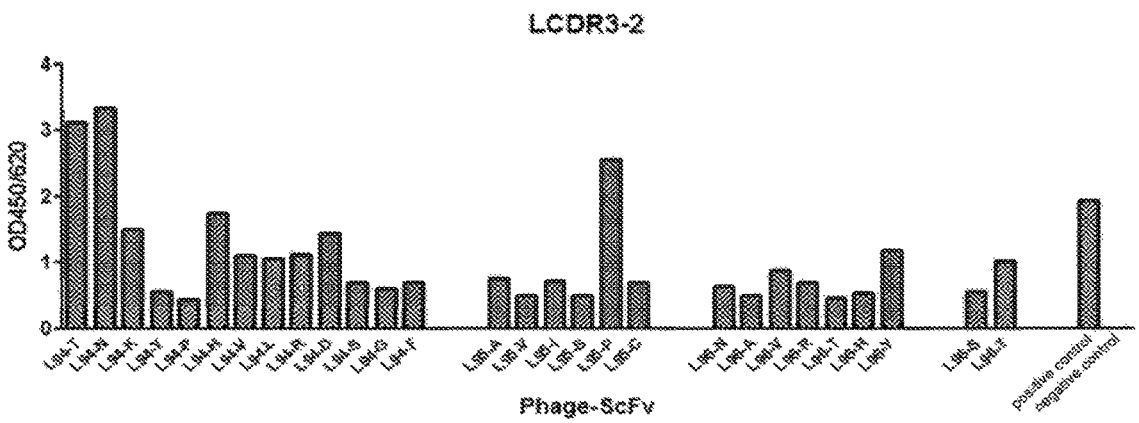
FIG. 5I
FIG. 6A

ANTIBODY AGAINST HEPATITIS B SURFACE ANTIGEN AND USE THEREOF

TECHNICAL FIELD

The invention relates to the field of molecular virology and immunology, particularly, the field concerning the treatment of Hepatitis B virus (HBV) infection. In particular, the invention relates to an antibody (in particular, a humanized antibody) against hepatitis B surface antigen (HBsAg), a nucleic acid molecule encoding the same, a method for preparing the same, and a pharmaceutical composition comprising the same. The pharmaceutical composition can be used for preventing and/or treating HBV infection or a disease associated with HBV infection (such as Hepatitis B), for neutralizing HBV virulence in a subject (such as human), or for reducing the serum level of HBV DNA and/or HBsAg in a subject. Therefore, the invention further relates to use of the antibody (particularly a humanized antibody) and a variant thereof in the manufacture of a pharmaceutical composition for preventing and/or treating HBV infection or a disease associated with HBV infection (such as Hepatitis B), for neutralizing HBV virulence in a subject (such as human), or for reducing the serum level of HBV DNA and/or HBsAg in a subject.

BACKGROUND ART

HBV infection, particularly chronic HBV infection is one of the most important public sanitation problems throughout the world (Dienstag J L. Hepatitis B virus infection. N Engl J Med 2008 Oct. 2; 359(14):1486-1500). Chronic HBV infection may cause a series of liver diseases such as Chronic hepatitis B (CHB), Liver cirrhosis (LC) and Hepatocellular carcinoma (HCC) (Liaw Y F, Chu C M. Hepatitis B virus infection. Lancet 2009 Feb. 14; 373(9663): 582-592). It is reported that there are about 2 billion persons infected by HBV, and there are about 350 million persons with chronic HBV infection in the whole world now. Among these infected persons, the risk of ultimately dying of liver diseases associated with HBV infection may reach up to 15%-25%, and more than 1 million persons die of these diseases every year in the whole world (Dienstag J L., vide supra; and Liaw Y F et al., vide supra).

Currently, the therapeutic agents for chronic HBV infection may be mainly classified into Interferons (IFNs) and nucleoside or nucleotide analogues (NAs) (Dienstag J L., vide supra; Kwon H, Lok A S. Hepatitis B therapy. Nat Rev Gastroenterol Hepatol 2011 May; 8(5): 275-284; and Liaw Y F et al., vide supra). The former includes common interferon (IFN) and Peg-interferon (Peg-IFN, also termed long acting interferon), which achieve the effect of inhibiting HBV and treating CHB mainly by enhancing the overall immunocompetence of a patient; the latter mainly includes lamivudine (LMV), adefovir dipivoxil (ADV), Entecavir (ETV), Telbivudine (LdT) and Tenofovir, which inhibit the HBV replication mainly by directly inhibiting polymerase activity of HBV. For HBV infected persons (e.g. CHB patients), said agents used alone or in combination therapy have already effectively inhibited virus replication in vivo, and greatly reduced HBV DNA level; in particular, after such a treatment for 52 weeks or longer, response rate of virological response that HBV DNA level is lower than a detection limit in patients can reach 40-80% (Kwon H et al., vide supra). However, the treatment with said agents alone or in combination cannot completely clear up HBV viruses in infected persons, and the response rate of the negative conversion of HBsAg or HBsAg serological conversion (a marker indicative of complete clearance of HBV viruses in patients) is generally lower than 5% (Kwon H et al., vide supra). Therefore, it is urgent and necessary to develop novel therapeutic methods and agents capable of more effectively clearing up HBV viruses, particularly clearing up HBsAg for HBV infected patients.

It is one of the important research directions in this field to develop new agents for treating chronic HBV infection based on immunological means. Immunotherapy of chronic HBV infection is generally performed in two manners, i.e. passive immunotherapy (corresponding to medicaments in the form of antibodies, etc.) and active immunotherapy (corresponding to medicaments in the form of vaccines, etc.). Passive immunotherapy (with antibody as an example) refers to the process of administering a therapeutic antibody to a HBV infected patient and preventing naïve hepatocytes from HBV infection by antibody-mediated virus neutralization, or clearing up viruses and infected hepatocytes in vivo by antibody-mediated immune clearance, thereby achieving a therapeutic effect. Now, anti-HBs polyclonal antibodies, obtained from serum/plasma of responder immunized with hepatitis B vaccine or rehabilitee of HBV infection, i.e. high-titer hepatitis B immunoglobulin (HBIG), have been widely applied to blockage of mother-infant vertical transmission of HBV, prevention of patient with chronic HBV infection from HBV re-infection after liver transplantation, and prevention of people accidently exposed to HBV from infection. However, the therapy concerning direct administration of HBIG to HBV-infected patients (e.g. CHB patients) has no significant therapeutic effect, and HBIG is restricted in many aspects such as relatively few sources of high-titer plasma, high cost, unstable property, and potential security problems. Active immunotherapy refers to the process of administering therapeutic vaccines (including protein vaccines, polypeptide vaccines, nucleic acid vaccines, etc.), stimulating the patient with chronic HBV infection to develop cellular immunologic response (CTL effect, etc.) or/and humoral immunologic response (antibodies, etc.) to HBV, thereby achieving the purpose of inhibiting or clearing HBV. Now, there are no agents/vaccines for active immunotherapy that are definitely effective and are useful for treating chronic HBV infection yet.

Therefore, it is urgent and necessary to develop novel therapeutic methods and agents capable of more effectively treating HBV infection for HBV infected patients.

Contents of Invention

In one aspect, the invention provides an antibody or an antigen binding fragment thereof, which can specifically bind to HBsAg, comprising:

(a) one or more (e.g. 1, 2 or 3) complementarity determining regions (CDRs) of heavy chain variable region (VH) selected from the group consisting of:

(i) VH CDR1, consisting of the following sequence: SEQ ID NO: 3, or a sequence that differs from SEQ ID NO:3 by one or several substitutions, deletions or additions (e.g. 1, 2 or 3 substitutions, deletions or additions);

(ii) VH CDR2, consisting of the following sequence: SEQ ID NO: 4, or a sequence that differs from SEQ ID NO:4 by one or several substitutions, deletions or additions (e.g. 1, 2, 3, 4, 5 or 6 substitutions, deletions or additions), and (iii) VH CDR3, consisting of the following sequence: SEQ ID NO: 5, or a sequence that differs from SEQ ID NO:5 by one or several substitutions, deletions or additions (e.g. 1, or 2 substitutions, deletions or additions);

and/or (b) one or more (e.g. 1, 2 or 3) CDRs of light chain variable region (VL) selected from the group consisting of:

(iv) VL CDR1, consisting of the following sequence: SEQ ID NO: 6, or a sequence that differs from SEQ ID NO:6 by one or several substitutions, deletions or additions (e.g. 1, 2 or 3 substitutions, deletions or additions), (v) VL CDR2, consisting of the following sequence: SEQ ID NO: 7, or a sequence that differs from SEQ ID NO:7 by one or several substitutions, deletions or additions (e.g. 1, 2, 3 or 4 substitutions, deletions or additions), and (vi) VL CDR3, consisting of the following sequence: SEQ ID NO: 8, or a sequence that differs from SEQ ID NO:8 by one or several substitutions, deletions or additions (e.g. 1, 2, 3 or 4 substitutions, deletions or additions).

In some preferred embodiments, the antibody or an antigen binding fragment thereof according to the invention comprises VH CDR1, VH CDR2 and VH CDR3 as defined above. In some preferred embodiments, the antibody or an antigen binding fragment thereof according to the invention comprises VL CDR1, VL CDR2 and VL CDR3 as defined above. In some preferred embodiments, the antibody or an antigen binding fragment thereof according to the invention comprises VH CDR1, VH CDR2, VH CDR3, VL CDR1, VL CDR2 and VL CDR3 as defined above.

In some preferred embodiments, the antibody or an antigen binding fragment thereof according to the invention is humanized. In some preferred embodiments, the antibody or an antigen binding fragment thereof according to the invention has a humanization degree of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In some preferred embodiments, the antibody or an antigen binding fragment thereof according to the invention comprises no more than 20, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 murine amino acid residues, or comprises no murine amino acid residue. In some preferred embodiments, the framework region (FR) of the antibody or an antigen binding fragment thereof according to the invention comprises no more than 20, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 murine amino acid residues, or comprises no murine amino acid residue.

In some preferred embodiments, the heavy chain variable region of the antibody according to the invention has an amino acid sequence identity of at least 80%, at least 85%, at least 90%, at least 91%, at least 92%, at least 93%, at least 94%, at least 95%, at least 96%, at least 97%, at least 98%, at least 99%, or 100% with a heavy chain variable region selected from:

heavy chain variable regions set forth in SEQ ID NOs: 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 263, 264, 265, 266, 267, 268, 269, 270, 271, 272, 273, 274, 275, 276, 277, 278 and 279.

In some preferred embodiments, the heavy chain variable region of the antibody according to the invention is selected from the heavy chain variable region set forth in any one of SEQ ID NOs: 11-92 and 263-279.

In some preferred embodiments, the light chain variable region of the antibody according to the invention has an amino acid sequence identity of at least 80%, at least 85%, at least 90%, at least 91%, at least 92%, at least 93%, at least 94%, at least 95%, at least 96%, at least 97%, at least 98%, at least 99%, or 100% with a light chain variable region selected from:

light chain variable regions set forth in SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 298, 299, 300, 301, 302, 303, 304, 305, 306, 307 and 308.

In some preferred embodiments, the light chain variable region of the antibody according to the invention is selected from the light chain variable region set forth in any one of SEQ ID NOs: 186-214 and 298-308.

In some preferred embodiments, the antibody according to the invention comprises the heavy chain variable region as defined above and the light chain variable region as defined above.

In some preferred embodiments, the antibody according to the invention comprises:

(1) VH as set forth in SEQ ID NO: 11 and VL as set forth in SEQ ID NO: 186;

(2) VH as set forth in SEQ ID NO: 16 and VL as set forth in SEQ ID NO: 187;

(3) VH as set forth in SEQ ID NO: 14 and VL as set forth in SEQ ID NO: 187;

(4) VH as set forth in SEQ ID NO: 72 and VL as set forth in SEQ ID NO: 201;

(5) VH as set forth in SEQ ID NO: 71 and VL as set forth in SEQ ID NO: 199;

(6) VH as set forth in SEQ ID NO: 17 and VL as set forth in SEQ ID NO: 187;

(7) VH as set forth in SEQ ID NO: 31 and VL as set forth in SEQ ID NO: 187;

(8) VH as set forth in SEQ ID NO: 69 and VL as set forth in SEQ ID NO: 189;

(9) VH as set forth in SEQ ID NO: 44 and VL as set forth in SEQ ID NO: 187;

(10) VH as set forth in SEQ ID NO: 73 and VL as set forth in SEQ ID NO: 202;

(11) VH as set forth in SEQ ID NO: 32 and VL as set forth in SEQ ID NO: 187;

(12) VH as set forth in SEQ ID NO: 77 and VL as set forth in SEQ ID NO: 206;

(13) VH as set forth in SEQ ID NO: 45 and VL as set forth in SEQ ID NO: 187;

(14) VH as set forth in SEQ ID NO: 74 and VL as set forth in SEQ ID NO: 209;

(15) VH as set forth in SEQ ID NO: 47 and VL as set forth in SEQ ID NO: 187;

(16) VH as set forth in SEQ ID NO: 91 and VL as set forth in SEQ ID NO: 205;

(17) VH as set forth in SEQ ID NO: 73 and VL as set forth in SEQ ID NO: 205;

(18) VH as set forth in SEQ ID NO: 36 and VL as set forth in SEQ ID NO: 187;

(19) VH as set forth in SEQ ID NO: 36 and VL as set forth in SEQ ID NO: 189;

(20) VH as set forth in SEQ ID NO: 55 and VL as set forth in SEQ ID NO: 192;

(21) VH as set forth in SEQ ID NO: 46 and VL as set forth in SEQ ID NO: 187;

(22) VH as set forth in SEQ ID NO: 74 and VL as set forth in SEQ ID NO: 202;
(23) VH as set forth in SEQ ID NO: 92 and VL as set forth in SEQ ID NO: 200;
(24) VH as set forth in SEQ ID NO: 76 and VL as set forth in SEQ ID NO: 204;
(25) VH as set forth in SEQ ID NO: 42 and VL as set forth in SEQ ID NO: 187;
(26) VH as set forth in SEQ ID NO: 48 and VL as set forth in SEQ ID NO: 187;
(27) VH as set forth in SEQ ID NO: 20 and VL as set forth in SEQ ID NO: 187;
(28) VH as set forth in SEQ ID NO: 49 and VL as set forth in SEQ ID NO: 187;
(29) VH as set forth in SEQ ID NO: 18 and VL as set forth in SEQ ID NO: 187;
(30) VH as set forth in SEQ ID NO: 24 and VL as set forth in SEQ ID NO: 187;
(31) VH as set forth in SEQ ID NO: 19 and VL as set forth in SEQ ID NO: 187;
(32) VH as set forth in SEQ ID NO: 25 and VL as set forth in SEQ ID NO: 187;
(33) VH as set forth in SEQ ID NO: 21 and VL as set forth in SEQ ID NO: 187;
(34) VH as set forth in SEQ ID NO: 27 and VL as set forth in SEQ ID NO: 187;
(35) VH as set forth in SEQ ID NO: 22 and VL as set forth in SEQ ID NO: 187;
(36) VH as set forth in SEQ ID NO: 29 and VL as set forth in SEQ ID NO: 187;
(37) VH as set forth in SEQ ID NO: 12 and VL as set forth in SEQ ID NO: 187;
(38) VH as set forth in SEQ ID NO: 30 and VL as set forth in SEQ ID NO: 187;
(39) VH as set forth in SEQ ID NO: 33 and VL as set forth in SEQ ID NO: 187;
(40) VH as set forth in SEQ ID NO: 34 and VL as set forth in SEQ ID NO: 187;
(41) VH as set forth in SEQ ID NO: 35 and VL as set forth in SEQ ID NO: 187;
(42) VH as set forth in SEQ ID NO: 23 and VL as set forth in SEQ ID NO: 187;
(43) VH as set forth in SEQ ID NO: 75 and VL as set forth in SEQ ID NO: 203;
(44) VH as set forth in SEQ ID NO: 40 and VL as set forth in SEQ ID NO: 187;
(45) VH as set forth in SEQ ID NO: 37 and VL as set forth in SEQ ID NO: 187;
(46) VH as set forth in SEQ ID NO: 13 and VL as set forth in SEQ ID NO: 187;
(47) VH as set forth in SEQ ID NO: 15 and VL as set forth in SEQ ID NO: 187;
(48) VH as set forth in SEQ ID NO: 38 and VL as set forth in SEQ ID NO: 187;
(49) VH as set forth in SEQ ID NO: 41 and VL as set forth in SEQ ID NO: 187;
(50) VH as set forth in SEQ ID NO: 39 and VL as set forth in SEQ ID NO: 187;
(51) VH as set forth in SEQ ID NO: 43 and VL as set forth in SEQ ID NO: 187;
(52) VH as set forth in SEQ ID NO: 78 and VL as set forth in SEQ ID NO: 205;
(53) VH as set forth in SEQ ID NO: 72 and VL as set forth in SEQ ID NO: 205;
(54) VH as set forth in SEQ ID NO: 26 and VL as set forth in SEQ ID NO: 187;
(55) VH as set forth in SEQ ID NO: 28 and VL as set forth in SEQ ID NO: 187;
(56) VH as set forth in SEQ ID NO: 55 and VL as set forth in SEQ ID NO: 194;
(57) VH as set forth in SEQ ID NO: 70 and VL as set forth in SEQ ID NO: 198;
(58) VH as set forth in SEQ ID NO: 55 and VL as set forth in SEQ ID NO: 195;
(59) VH as set forth in SEQ ID NO: 55 and VL as set forth in SEQ ID NO: 197;
(60) VH as set forth in SEQ ID NO: 55 and VL as set forth in SEQ ID NO: 196;
(61) VH as set forth in SEQ ID NO: 90 and VL as set forth in SEQ ID NO: 187;
(62) VH as set forth in SEQ ID NO: 51 and VL as set forth in SEQ ID NO: 188;
(63) VH as set forth in SEQ ID NO: 54 and VL as set forth in SEQ ID NO: 190;
(64) VH as set forth in SEQ ID NO: 83 and VL as set forth in SEQ ID NO: 208;
(65) VH as set forth in SEQ ID NO: 79 and VL as set forth in SEQ ID NO: 190;
(66) VH as set forth in SEQ ID NO: 85 and VL as set forth in SEQ ID NO: 190;
(67) VH as set forth in SEQ ID NO: 62 and VL as set forth in SEQ ID NO: 189;
(68) VH as set forth in SEQ ID NO: 62 and VL as set forth in SEQ ID NO: 193;
(69) VH as set forth in SEQ ID NO: 66 and VL as set forth in SEQ ID NO: 189;
(70) VH as set forth in SEQ ID NO: 66 and VL as set forth in SEQ ID NO: 193;
(71) VH as set forth in SEQ ID NO: 64 and VL as set forth in SEQ ID NO: 189;
(72) VH as set forth in SEQ ID NO: 64 and VL as set forth in SEQ ID NO: 193;
(73) VH as set forth in SEQ ID NO: 67 and VL as set forth in SEQ ID NO: 189;
(74) VH as set forth in SEQ ID NO: 67 and VL as set forth in SEQ ID NO: 193;
(75) VH as set forth in SEQ ID NO: 65 and VL as set forth in SEQ ID NO: 193;
(76) VH as set forth in SEQ ID NO: 63 and VL as set forth in SEQ ID NO: 193;
(77) VH as set forth in SEQ ID NO: 82 and VL as set forth in SEQ ID NO: 189;
(78) VH as set forth in SEQ ID NO: 82 and VL as set forth in SEQ ID NO: 193;
(79) VH as set forth in SEQ ID NO: 60 and VL as set forth in SEQ ID NO: 189;
(80) VH as set forth in SEQ ID NO: 60 and VL as set forth in SEQ ID NO: 193;
(81) VH as set forth in SEQ ID NO: 56 and VL as set forth in SEQ ID NO: 189;
(82) VH as set forth in SEQ ID NO: 56 and VL as set forth in SEQ ID NO: 193;
(83) VH as set forth in SEQ ID NO: 61 and VL as set forth in SEQ ID NO: 189;
(84) VH as set forth in SEQ ID NO: 61 and VL as set forth in SEQ ID NO: 193;
(85) VH as set forth in SEQ ID NO: 57 and VL as set forth in SEQ ID NO: 189;
(86) VH as set forth in SEQ ID NO: 57 and VL as set forth in SEQ ID NO: 193;
(87) VH as set forth in SEQ ID NO: 58 and VL as set forth in SEQ ID NO: 189;

(88) VH as set forth in SEQ ID NO: 58 and VL as set forth in SEQ ID NO: 193;
(89) VH as set forth in SEQ ID NO: 59 and VL as set forth in SEQ ID NO: 189;
(90) VH as set forth in SEQ ID NO: 59 and VL as set forth in SEQ ID NO: 193;
(91) VH as set forth in SEQ ID NO: 68 and VL as set forth in SEQ ID NO: 189;
(92) VH as set forth in SEQ ID NO: 53 and VL as set forth in SEQ ID NO: 191;
(93) VH as set forth in SEQ ID NO: 55 and VL as set forth in SEQ ID NO: 199;
(94) VH as set forth in SEQ ID NO: 55 and VL as set forth in SEQ ID NO: 200;
(95) VH as set forth in SEQ ID NO: 53 and VL as set forth in SEQ ID NO: 187;
(96) VH as set forth in SEQ ID NO: 52 and VL as set forth in SEQ ID NO: 189;
(97) VH as set forth in SEQ ID NO: 84 and VL as set forth in SEQ ID NO: 210;
(98) VH as set forth in SEQ ID NO: 84 and VL as set forth in SEQ ID NO: 212;
(99) VH as set forth in SEQ ID NO: 50 and VL as set forth in SEQ ID NO: 187;
(100) VH as set forth in SEQ ID NO: 80 and VL as set forth in SEQ ID NO: 207;
(101) VH as set forth in SEQ ID NO: 88 and VL as set forth in SEQ ID NO: 214;
(102) VH as set forth in SEQ ID NO: 52 and VL as set forth in SEQ ID NO: 189;
(103) VH as set forth in SEQ ID NO: 89 and VL as set forth in SEQ ID NO: 212;
(104) VH as set forth in SEQ ID NO: 81 and VL as set forth in SEQ ID NO: 187;
(105) VH as set forth in SEQ ID NO: 84 and VL as set forth in SEQ ID NO: 211;
(106) VH as set forth in SEQ ID NO: 86 and VL as set forth in SEQ ID NO: 190;
(107) VH as set forth in SEQ ID NO: 87 and VL as set forth in SEQ ID NO: 213;
(108) VH as set forth in SEQ ID NO: 72 and VL as set forth in SEQ ID NO: 202;
(109) VH as set forth in SEQ ID NO: 72 and VL as set forth in SEQ ID NO: 306;
(110) VH as set forth in SEQ ID NO: 72 and VL as set forth in SEQ ID NO: 200;
(111) VH as set forth in SEQ ID NO: 91 and VL as set forth in SEQ ID NO: 300;
(112) VH as set forth in SEQ ID NO: 91 and VL as set forth in SEQ ID NO: 200;
(113) VH as set forth in SEQ ID NO: 263 and VL as set forth in SEQ ID NO: 192;
(114) VH as set forth in SEQ ID NO: 264 and VL as set forth in SEQ ID NO: 205;
(115) VH as set forth in SEQ ID NO: 264 and VL as set forth in SEQ ID NO: 192;
(116) VH as set forth in SEQ ID NO: 264 and VL as set forth in SEQ ID NO: 201;
(117) VH as set forth in SEQ ID NO: 264 and VL as set forth in SEQ ID NO: 202;
(118) VH as set forth in SEQ ID NO: 265 and VL as set forth in SEQ ID NO: 205;
(119) VH as set forth in SEQ ID NO: 265 and VL as set forth in SEQ ID NO: 201;
(120) VH as set forth in SEQ ID NO: 265 and VL as set forth in SEQ ID NO: 202;
(121) VH as set forth in SEQ ID NO: 266 and VL as set forth in SEQ ID NO: 205;
(122) VH as set forth in SEQ ID NO: 266 and VL as set forth in SEQ ID NO: 192;
(123) VH as set forth in SEQ ID NO: 267 and VL as set forth in SEQ ID NO: 298;
(124) VH as set forth in SEQ ID NO: 268 and VL as set forth in SEQ ID NO: 299;
(125) VH as set forth in SEQ ID NO: 269 and VL as set forth in SEQ ID NO: 301;
(126) VH as set forth in SEQ ID NO: 270 and VL as set forth in SEQ ID NO: 302;
(127) VH as set forth in SEQ ID NO: 271 and VL as set forth in SEQ ID NO: 202;
(128) VH as set forth in SEQ ID NO: 272 and VL as set forth in SEQ ID NO: 303;
(129) VH as set forth in SEQ ID NO: 273 and VL as set forth in SEQ ID NO: 304;
(130) VH as set forth in SEQ ID NO: 274 and VL as set forth in SEQ ID NO: 305;
(131) VH as set forth in SEQ ID NO: 275 and VL as set forth in SEQ ID NO: 200;
(132) VH as set forth in SEQ ID NO: 276 and VL as set forth in SEQ ID NO: 202;
(133) VH as set forth in SEQ ID NO: 277 and VL as set forth in SEQ ID NO: 307;
(134) VH as set forth in SEQ ID NO: 278 and VL as set forth in SEQ ID NO: 308;
or
(135) VH as set forth in SEQ ID NO: 279 and VL as set forth in SEQ ID NO: 202.

In some preferred embodiments, the antibody or an antigen binding fragment thereof according to the invention can specifically bind to HBsAg, neutralize HBV virulence, and/or reduce the serum level of HBV DNA and/or HBsAg in a subject.

In some preferred embodiments, the antibody or an antigen binding fragment thereof according to the invention is selected from the group consisting of scFv, Fab, Fab', (Fab')$_2$, Fv fragment, diabody, bispecific antibody, and polyspecific antibody. Particularly preferably, the antibody or an antigen binding fragment thereof according to the invention is a scFv antibody.

In some preferred embodiments, the antibody or an antigen binding fragment thereof according to the invention is an antibody of IgG1 isotype or an antigen binding fragment thereof. For example, the antibody or an antigen binding fragment thereof according to the invention may be an antibody of IgG1, IgG2 or IgG4 isotype, or an antigen binding fragment thereof.

In another aspect, the invention provides an isolated nucleic acid molecule, comprising a nucleotide sequence encoding the antibody or an antigen binding fragment thereof according to the invention, or the heavy chain variable region and/or light chain variable region thereof.

In another aspect, the invention provides a vector (e.g. a cloning vector or an expression vector), comprising the isolated nucleic acid molecule according to the invention.

In another aspect, the invention provides a host cell, comprising the isolated nucleic acid molecule according to the invention or the vector according to the invention.

In another aspect, provided is a method for preparing the antibody or an antigen binding fragment thereof according to the invention, comprising, culturing the host cell according to the invention under a condition allowing expression of the antibody or an antigen binding fragment thereof, and recovering the antibody or an antigen binding fragment thereof from a culture of the cultured host cell.

In another aspect, the invention provides a kit, comprising the antibody or an antigen binding fragment thereof according to the invention. In a preferred embodiment, the antibody or an antigen binding fragment thereof according to the invention further comprises a detectable marker. In a preferred embodiment, the kit further comprises a second antibody, which specifically recognizes the antibody or an antigen binding fragment thereof according to the invention. Preferably, the second antibody further comprises a detectable marker. Such detectable markers, which are well known by a person skilled in the art, include, but are not limited to, radioisotope, fluorescent substance, luminescent substance, chromophoric substance and enzyme (e.g. horseradish peroxidase), etc.

In another aspect, the invention provides a method for detecting the presence or level of HBsAg protein in a sample, comprising using the antibody or an antigen binding fragment thereof according to the invention. In a preferred embodiment, the antibody or an antigen binding fragment thereof according to the invention further comprises a detectable marker. In another preferred embodiment, the method further comprises, using a second antibody carrying a detectable marker to detect the antibody or an antigen binding fragment thereof according to the invention. The method may be used for diagnostic purpose or for non-diagnostic purpose (for example, said sample is a cell sample, rather than a sample from a patient).

In another aspect, the invention provides a method for diagnosing whether a subject is infected by HBV, comprising: using the antibody or an antigen binding fragment thereof according to the invention to detect the presence of HBsAg protein in a sample from the subject. In a preferred embodiment, the antibody or an antigen binding fragment thereof according to the invention further comprises a detectable marker. In another preferred embodiment, the method further comprises, using a second antibody carrying a detectable marker to detect the antibody or an antigen binding fragment thereof according to the invention.

In another aspect, provided is use of the antibody or an antigen binding fragment thereof according to the invention in the manufacture of a kit for detecting the presence or level of HBsAg in a sample or for diagnosing whether a subject is infected by HBV.

The antibody or an antigen binding fragment thereof according to the invention can be used for preventing or treating HBV infection or a disease associated with HBV infection (such as Hepatitis B) in a subject (such as human), for neutralizing HBV virulence in vitro or in a subject (such as human), and for reducing the serum level of HBV DNA and/or HBsAg in a subject (such as human).

Therefore, in another aspect, the invention provides a pharmaceutical composition, comprising the antibody or an antigen binding fragment thereof according to the invention, and a pharmaceutically acceptable carrier and/or excipient. In a preferred embodiment, the pharmaceutical composition according to the invention may further comprise an additional pharmaceutically active agent. In a preferred embodiment, the additional pharmaceutically active agent is an agent for preventing or treating HBV infection or a disease associated with HBV infection (such as Hepatitis B), for example, interferon-type agents, such as interferon or pegylated interferon.

In another aspect, provided is use of the antibody or an antigen binding fragment thereof according to the invention or the pharmaceutical composition according to the invention in the manufacture of a medicament for preventing or treating HBV infection or a disease associated with HBV infection (such as Hepatitis B) in a subject (such as human), for neutralizing HEY virulence in vitro or in a subject (such as human), and/or for reducing the serum level of HBV DNA and/or HBsAg in a subject (such as human).

In another aspect, the invention provides a method for preventing or treating HBV infection or a disease associated with HBV infection (such as Hepatitis B) in a subject (such as human), for neutralizing HBV virulence in a subject (such as human), and/or for reducing the serum level of HBV DNA and/or HBsAg in a subject (such as human), comprising, administering to a subject in need thereof an effective amount of the antibody or an antigen binding fragment thereof according to the invention or the pharmaceutical composition according to the invention.

The medicament and pharmaceutical composition provided in the invention may be used alone or in combination, or may be used in combination with an additional pharmaceutically active agent (for example, other antiviral agents, e.g. interferon-type agents, such as interferon or pegylated interferon).

The embodiments of the invention are described in detail by reference to the following drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are obvious for a person skilled in the art.

DESCRIPTION OF THE DRAWINGS

FIGS. 1A-1B show the sequence information on 20 humanized antibodies in Example 1, wherein, FIG. 1A shows the amino acid sequences of the heavy chain variable regions of the humanized antibodies; FIG. 1B shows the amino acid sequences of the light chain variable regions of the humanized antibodies; "." means that the amino acid residue at the position is identical to the amino acid residue at the corresponding position of antibody B-S3-45.

FIG. 2 shows the map of the recombinant vector (pCGMT-scFv) encoding scFv antibody, wherein the structure of the scFv antibody is: $NH_2$-VH-linker-VL-COOH.

FIGS. 5A-5I shows the ELISA results of antigen HBsAg and the phage displaying the scFv antibody comprising a single-site mutation in CDRs, wherein, the horizontal axis represents the position and type of the single-site mutation in the scFv antibody (for example, "H31-R" means that the amino acid residue at position H31 according to Kabat numbering system is mutated to R), and the vertical axis represents the reactivity between antigen HBsAg and the phage displaying the scFv antibody comprising a single-site mutation. The experimental results in FIGS. 5A-5I show that single-site mutation can be performed to the amino acid residue in CDRs of antibody B-S3-45, without interfering the binding affinity of the antibody to antigen HBsAg.

Figures 6B, 6C, 6D:
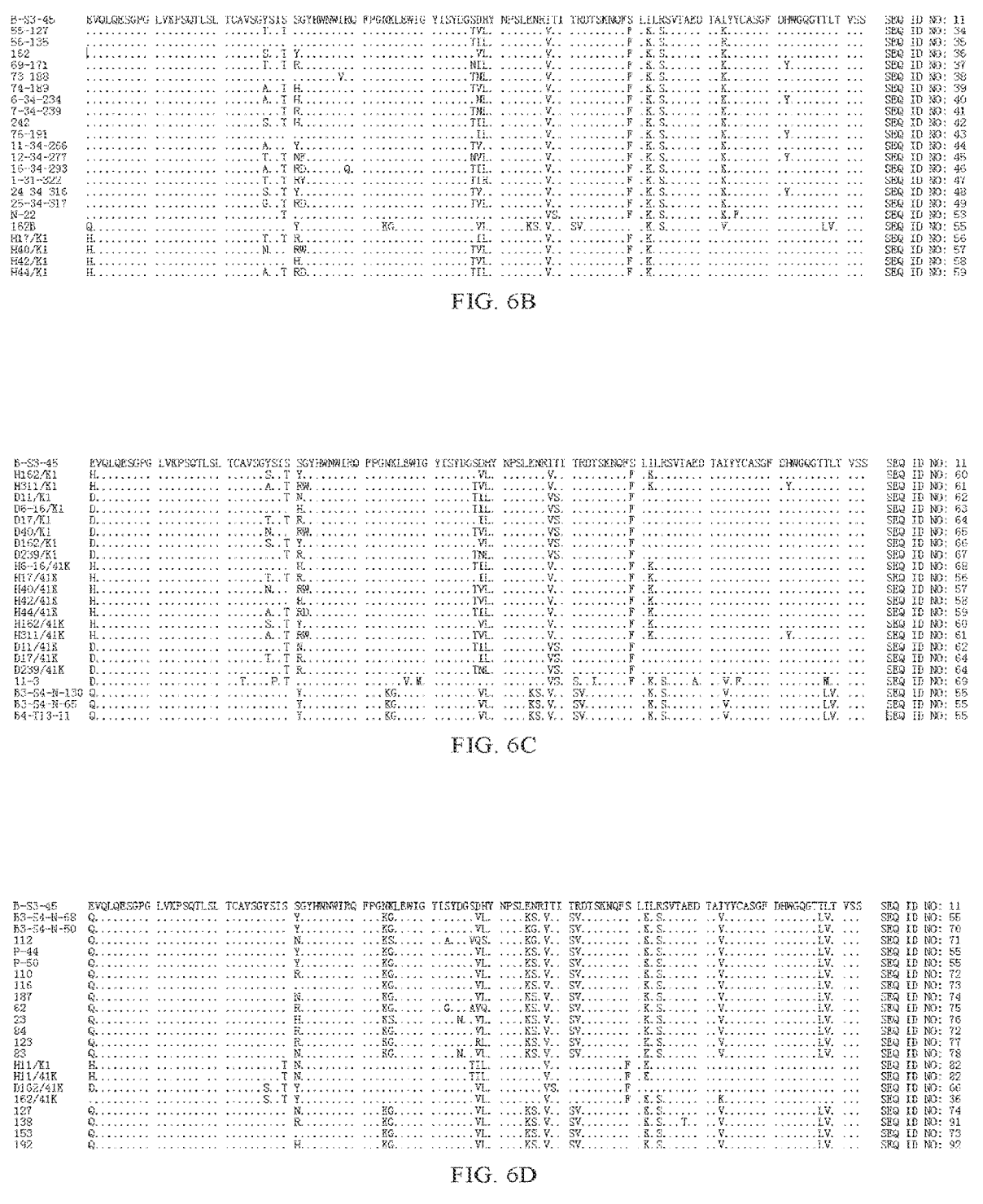
Figures 6E, 6F, 6G:
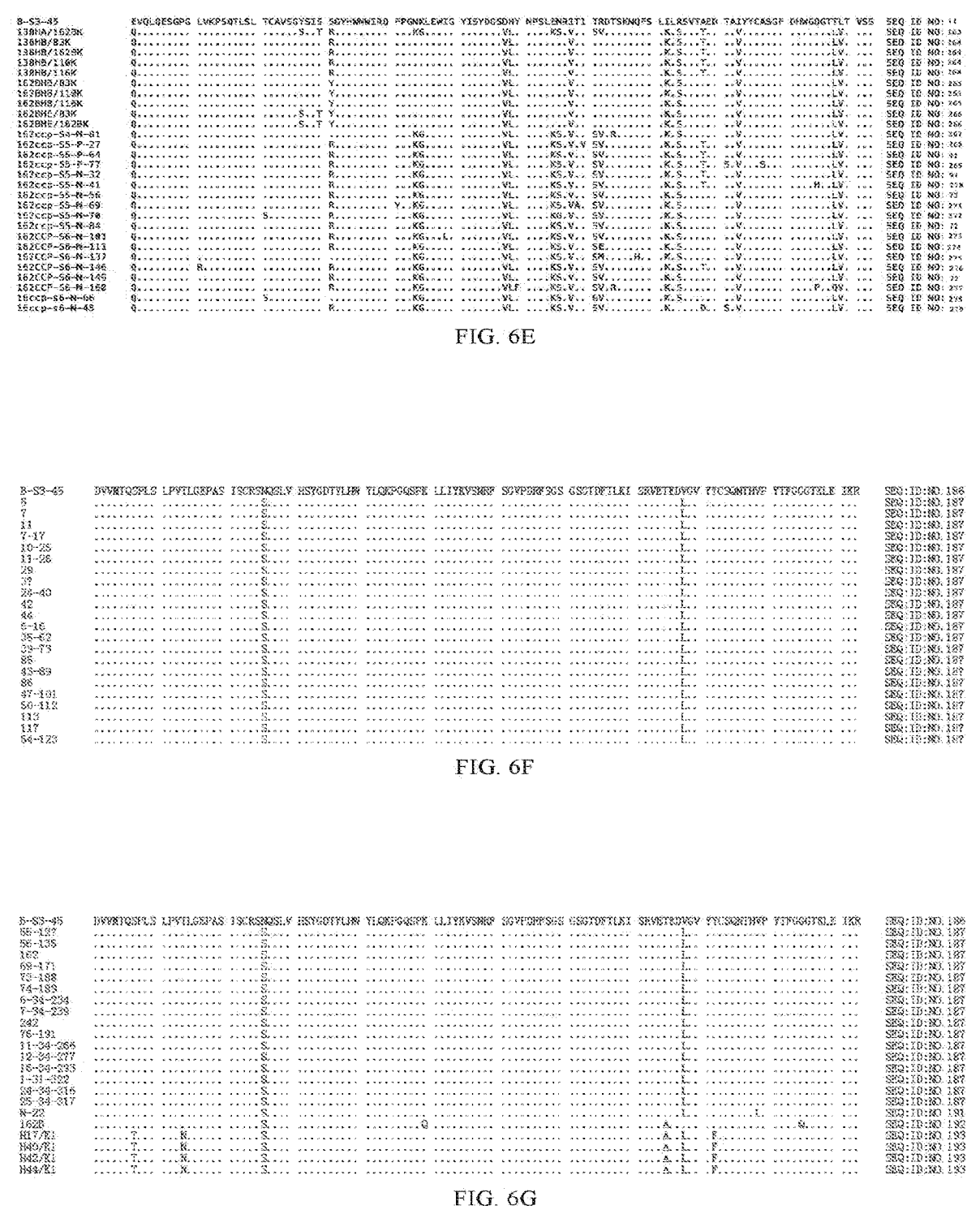
Figures 6H, 6I, 6J:
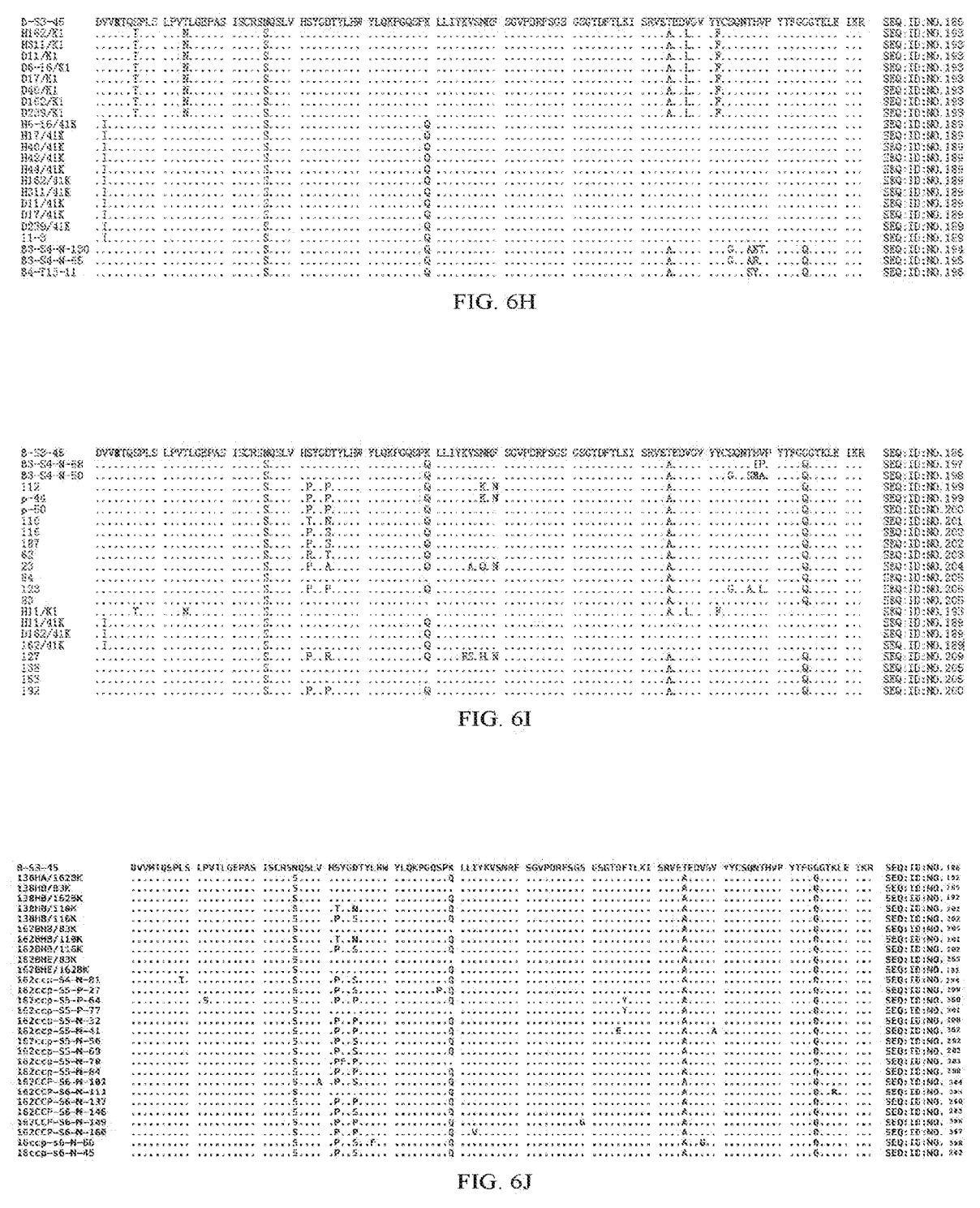

FIGS. 6A-6J show the sequence information on 115 humanized antibodies in Example 3, wherein, FIGS. 6A-6E show the amino acid sequences of the heavy chain variable regions of the humanized antibodies; FIGS. 6F-6J show the amino acid sequences of the light chain variable regions of the humanized antibodies; "." means that the amino acid residue at the position is identical to the amino acid residue at the corresponding position of antibody B-S3-45.

SEQUENCE INFORMATION

Figures 1A, 1B, 2:
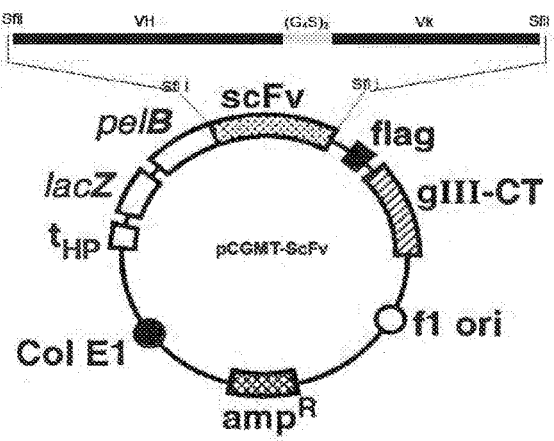

SEQ ID NO: 1
DVQLQESGPGLVKPSQSLSLTCSVTGYPITSGYHWNWIRQFPGNK

LVWMGYISYDGSDHYNPSLENRISITRDISKNQFFLILRSVTTED

TGKYFCASGFDHWGQGTTLTVSS

SEQ ID NO: 2
DVVMTQTPLSLPVSLGDQASISCRSSQSLVHSYGDTYLHWYLQKP
GQSPKLLIYKVSNRFSGVPDRFSGSGSGTDFTLKISRVETEDLGV
YFCSQNTHVPYTFGGGTKLEIKR

SEQ ID NO: 3
SGYHWN

SEQ ID NO: 4
YISYDGSDHYNPSLEN

SEQ ID NO: 5
GFDH

SEQ ID NO: 6
RSSQSLVHSYGDTYLH

SEQ ID NO: 7
KVSNRFS

SEQ ID NO: 8
SQNTHVPYT

SEQ ID NO: 9
QVQLQESGPGLVKPSQTLSLTCAVSGYSISSSNWWGWIRQPPGKG
LEWIGYIYYSGSTYYNPSLKSRVTMSVDTSKNQFSLKLSSVTAVD
TAVYYCAR

SEQ ID NO: 10
DIVMTQSPLSLPVTPGEPASISCRSSQSLLHSNGYNYLDWYLQKP
GQSPQLLIYLGSNRASGVPDRFSGSGSGTDFTLKISRVEAEDVGV
YYC

SEQ ID NO: 11
EVQLQESGPGLVKPSQTLSLTCAVSGYSTSSGYHWNWIRQFPGNK
LEWTGYISYDGSDHYNPSLENRITITRDTSKNQFSLILRSVTAED
TAIYYCASGFDHWGQGTTLTVSS

SEQ ID NO: 12
EVQLQESGPGLVKPSQTLSLTCAVSGYSTSRGYHWNWIRQFPGNK
LEWIGYISYDGSVFYNPSLENRVTITRDTSKNQFFLKLSSVTAED
TAKYYCASGFDYWGQGTTLTVSS

SEQ ID NO: 13
EVQLQESGPGLVKPSQTLSLTCAVSGYSISHGYHWNWIRQFPGNK
LEWIGYISYDGSILYNPSLENRVTITRDTSKNQFFLKLSSVTAED
TAKYYCASGFDHWGQGTTLTVSS

SEQ ID NO: 14
EVQLQESGPGLVKPSQTLSLTCAVSGYSITNGYHWNWIRQFPGNK
LEWIGYISYDGTILYNPSLENRVTITRDTSKNQFFLKLSSVTAED
TAKYYCASGFDHWGQGTTLTVSS

SEQ ID NO: 15
EVQLQESGPGLVKPSQTLSLTCAVSGTSITRGYHWNWIRQFPGNK
LEWIGYISYDGSILYNPSLENRVTITRDTSKNQFFLKLSSVTAED
TAKYYCASGFDHWGQGTTLTVSS

SEQ ID NO: 16
EVQLQESGPGLVKPSQTLSLTCAVSGTSITHGYHWNWIRQFPGNK
LEWIGYISYDGTVLYNPSLENRVTITRDTSKNQFFLKLSSVTAED
TAKYYCASGFDYWGQGTTLTVSS

SEQ ID NO: 17
EVQLQESGPGLVKPSQTLSLTCAVSGYSISSGYHWNWIRQFPGNK
LEWIGYISYDGSILYNPSLENRVTITRDTSKNQFFLKLSSVTAED
TAKYYCASGFDHWGQGTTLTVSS

SEQ ID NO: 18
EVQLQESGPGLVKPSQTLSLTCAVSGTSITRDYHWNWIRQFPGNK
LEWIGYISYDGTVLYNPSLENRVTITRDTSKNQFFLKLSSVTAED
TAKYYCASGFDYWGQGTTLTVSS

SEQ ID NO: 19
EVQLQESGPGLVKPSQTLSLTCAVSGYSISSGYHWNWIRQFPGNK
LEWIGYISYDGNVLYNPSLENRVTITRDTSKNQFFLKLSSVTAED
TAKYYCASGFDYWGQGTTLTVSS

SEQ ID NO: 20
EVQLQESGPGLVKPSQTLSLTCAVSGNSISRWYHWNWIRQFPGNK
LEWIGYISYDGTVLYNPSLENRVTITRDTSKNQFFLKLSSVTAED
TAKYYCASGFDHWGQGTTLTVSS

SEQ ID NO: 21
EVQLQESGPGLVKPSQTLSLTCAVSGYSISHGYHWNWIRQFPGNK
LEWIGYISYDGTVLYNPSLENRVTITRDTSKNQFFLKLSSVTAED
TAKYYCASGEDHWGQGTTLTVSS

SEQ ID NO: 22
EVQLQESGPGLVKPSQTLSLTCAVSGASITRDYHWNWIRQFPGNK
LEWIGYISYDGTILYNPSLENRVTITRDTSKNQFFLKLSSVTAED
TAKYYCASGFDHWGQGTTLTVSS

SEQ ID NO: 23
EVQLQESGPGLVKPSQTLSLTCAVSGYSISHGYHWNWIRQFPGNK
LEWIGYISYDGTILYNPSLENRVTITRDTSKNQFFLKLSSVTAED
TAKYYCASGFDHWGQGTTLTVSS

SEQ ID NO: 24
EVQLQESGPGLVKPSQTLSLTCAVSGASITYGYHWNWIRQFPGNK
LEWIGYISYDGSILYNPSLENRVTITRDTSKNQFFLKLSSVTAED
TAKYYCASGFDYWGQGTTLTVSS

SEQ ID NO: 25
EVQLQESGPGLVKPSQTLSLTCAVSGASITHGYHWNWIRQFPGNK
LEWIGYISYDGTSLYNPSLENRVTITRDTSKNQFFLKLSSVTAED
TAKYYCASGEDHWGQGTTLTVSS

SEQ ID NO: 26
EVQLQESGPGLVKPSQTLSLTCAVSGASITRGYHWNWIRQFPGNK
LEWIGYISYDGTVLYNPSLENRVTITRDTSKNQFFLKLSSVTAED
TAKYYCASGFDYWGQGTTLTVSS

SEQ ID NO: 27
EVQLQESGPGLVKPSQTLSLTCAVSGYSISSGYHWNWIRQFPGNK
LEWIGYISYDGTILYNPSLENRVTITRDTSKNQFFLKLSSVTAED
TAKYYCASGFDYWGQGTTLTVSS

SEQ ID NO: 28
EVQLQESGPGLVKPSQTLSLTCAVSGTSITRGYHWNWIRQFPGNK

LEWIGYISYDGSILYNPSLENRVTITRDTSKNQFFLKLSSVTAED
TAKYYCASGFDYWGQGTTLTVSS

SEQ ID NO: 29
EVQLQESGPGLVKPSQTLSLTCAVSGASITYGYHWNWIRQFPGNK
LEWIGYISYDGTILYNPSLENRVTITRDTSKNQFFLKLSSVTAED
TAKYYCASGFDTWGQGTTLTVSS

SEQ ID NO: 30
EVQLQESGPGLVKPSQTLSLTCAVSGSSITNFYHWNWIRQFPGNK
LEWIGYISYDGSVLYNPSLENRVTITRDTSKNQFFLKLSSVTAED
TAKYYCASGFDHWGQGTTLTVSS

SEQ ID NO: 31
EVQLQESGPGLVKPSQTLSLTCAVSGASITYGYHWNWIRQFPGNK
LEWIGYISYDGTILYNPSLENRVTITRDTSKNQFFLKLSSVTAED
TAKYYCASGFDHWGQGTTLTVSS

SEQ ID NO: 32
EVQLQESGPGLVKPSQTLSLTCAVSGSSITRGYHWNWIRQFPGNK
LEWIGYISYDGTILYNPSLENRVTITRDTSKNQFFLKLSSVTAED
TAKYYCASGFDHWGQGTTLTVSS

SEQ ID NO: 33
EVQLQESGPGLVKPSQTLSLTCAVSGASITHGYHWNWIRQFPGNK
LEWIGYISYDGTILYNPSLENRVTITRDTSKNQFFLKLSSVTAED
TAKYYCASGFDYWGQGTTLTVSS

SEQ ID NO: 34
EVQLQESGPGLVKPSQTLSLTCAVSGTSITSGYHWNWIRQFPGNK
LEWIGYISYDGTVLYNPSLENRVTITRDTSKNQFFLKLSSVTAED
TAKYYCASGFDHWGQGTTLTVSS

SEQ ID NO: 35
EVQLQESGPGLVKPSQTLSLTCAVSGYSISSGYHWNWIRQFPGNK
LEWIGYISYDGTILYNPSLENRVTITRDTSKNQFFLKLSSVTAED
TARYYCASGFDHWGQGTTLTVSS

SEQ ID NO: 36
EVQLQESGPGLVKPSQTLSLTCAVSGSSITYGYHWNWIRQFPGNK
LEWIGYISYDGSVLYNPSLENRVTITRDTSKNQFFLKLSSVTAED
TAKYYCASGFDHWGQGTTLTVSS

SEQ ID NO: 37
EVQLQESGPGLVKPSQTLSLTCAVSGTSITRGYHWNWIRQFPGNK
LEWIGYISYDGNILYNPSLENRVTITRDTSKNQFFLKLSSVTAED
TAKYYCASGFDYWGQGTTLTVSS

SEQ ID NO: 38
EVQLQESGPGLVKPSQTLSLTCAVSGYSISSGYHWNWVRQFPGNK
LEWIGYISYDGTNLYNPSLENRVTITRDTSKNQFFLKLSSVTAED
TAKYYCASGFDHWGQGTTLTVSS

SEQ ID NO: 39
EVQLQESGPGLVKPSQTLSLTCAVSGASITHGYHWNWIRQFPGNK
LEWIGYISYDGTVLYNPSLENRVTITRDTSKNQFFLKLSSVTAED
TAKYYCASGFDHWGQGTTLTVSS

SEQ ID NO: 40
EVQLQESGPGLVKPSQTLSLTCAVSGASITHGYHWNWIRQFPGNK
LEWIGYISYDGSNLYNPSLENRVTITRDTSKNQFFLKLSSVTAED
TAKYYCASGFDYWGQGTTLTVSS

SEQ ID NO: 41
EVQLQESGPGLVKPSQTLSLTCAVSGYSITRGYHWNWIRQFPGNK
LEWIGYISYDGTNLYNPSLENRVTITRDTSKNQFFLKLSSVTAED
TAKYYCASGFDHWGQGTTLTVSS

SEQ ID NO: 42
EVQLQESGPGLVKPSQTLSLTCAVSGSSITHGYHWNWIRQFPGNK
LEWIGYISYDGTILYNPSLENRVTITRDTSKNQFFLKLSSVTAED
TAKYYCASGFDHWGQGTTLTVSS

SEQ ID NO: 43
EVQLQESGPGLVKPSQTLSLTCAVSGYSISSGYHWNWIRQFPGNK
LEWIGYISYDGSILYNPSLENRVTITRDTSKNQFFLKLSSVTAED
TAKYYCASGFDYWGQGTTLTVSS

SEQ ID NO: 44
EVQLQESGPGLVKPSQTLSLTCAVSGASTSYGYHWNWIRQFPGNK
LEWIGYISYDGTVHYNPSLENRVTITRDTSKNQFFLKLSSVTAED
TAKYYCASGFDHWGQGTTLTVSS

SEQ ID NO: 45
EVQLQESGPGLVKPSQTLSLTCAVSGTSITNEYHWNWIRQFPGNK
LEWIGYISYDGNVLYNPSLENRVTITRDTSKNQFFLKLSSVTAED
TAKYYCASGFDYWGQGTTLTVSS

SEQ ID NO: 46
EVQLQESGPGLVKPSQTLSLTCAVSGASITRDYHWNWIQQFPGNK
LEWIGYISYDGTILYNPSLENRVTITRDTSKNQFFLKLSSVTAED
TAKYYCASGFDHWGQGTTLTVSS

SEQ ID NO: 47
EVQLQESGPGLVKPSQTLSLTCAVSGTSITRYYHWNWIRQFPGNK
LEWIGYISYDGTIRYNPSLENRVTITRDTSKNQFFLKLSSVTAED
TAKYYCASGFDHWGQGTTLTVSS

SEQ ID NO: 48
EVQLQESGPGLVKPSQTLSLTCAVSGSSITYGYHWNWIRQFPGNK
LEWIGYISYDGTVHYNPSLENRVTITRDTSKNQFFLKLSSVTAED
TAKYYCASGFDYWGQGTTLTVSS

SEQ ID NO: 49
EVQLQESGPGLVKPSQTLSLTCAVSGGSITRDYHWNWIRQFPGNK
LEWIGYISYDGTVLYNPSLENRVTITRDTSKNQFFLKLSSVTAED
TAKYYCASGFDHWGQGTTLTVSS

SEQ ID NO: 50
EVQLQESGPGLVKASQTLSLTCAVSGYSISSGYHWNWIRQLPGNK
LEWIGYISYDGSDHYNPSLENRITISRDTSKNQFFLKLRSVTAED
TAKYFCASGEDHWGQGTTLTVSS

SEQ ID NO: 51
DVQLQESGPGLVKPSQTLSLTCAVSGYPITSGYHWNWIRQFPGNK
LEWIGYISYDGSDHYNPSLENRVSITRDTSKNQFFLILRSVTAED
TAIYYCASGFDHWGQGTTLTVSS

SEQ ID NO: 52
HVQLQESGPGLVKPSQTLSLTCAVSGYSITSGYHWNWIRQFPGNK
LEWIGYISYDGSDHYNPSLENRVTITRDTSKNQFFLKLRSVTAED
TAIYYCASGFDHWGQGTTLTVSS

SEQ ID NO: 53
EVQLQESGPGLVKPSQTLSLTCAVSGYSITSGYHWNWIRQFPGNK
LEWIGYISYDGSDHYNPSLENRVSITRDTSKNQFFLKLSSVTAED
TAKYFCASGEDHWGQGTTLTVSS

SEQ ID NO: 54
EVQLQESGPGLVKPSQTLSLTCAVSGYPISSGYHWNWIRQFPGKK
LEWIGYISYDGSDHYNPSLENRVTITRDTSKNQFFLKLRSVTAED
TAIYFCASGFDHWGQGTTLTVSS

SEQ ID NO: 55
QVQLQESGPGLVKPSQTLSLTCAVSGYSISYGYHWNWIRQFPGKG
LEWIGYISYDGSVLYNPSLKSRVTISVDTSKNQFSLKLSSVTAED
TAVYYCASGEDHWGQGTLVTVSS

SEQ ID NO: 56
HVQLQESGPGLVKPSQTLSLTCAVSGTSITRGYHWNWIRQFPGNK
LEWIGYISYDGSILYNPSLENRVTITRDTSKNQFFLKLRSVTAED
TAIYYCASGFDHWGQGTTLTVSS

SEQ ID NO: 57
HVQLQESGPGLVKPSQTLSLTCAVSGNSISRWYHWNWIRQFPGNK
LEWIGYISYDGTVLYNPSLENRVTITRDTSKNQFFLKLRSVTAED
TAIYYCASGEDHWGQGTTLTVSS

SEQ ID NO: 58
HVQLQESGPGLVKPSQTLSLTCAVSGYSISHGYHWNWIRQFPGNK
LEWIGYISYDGTVLYNPSLENRVTITRDTSKNQFFLKLRSVTAED
TAIYYCASGEDHWGQGTTLTVSS

SEQ ID NO: 59
HVQLQESGPGLVKPSQTLSLTCAVSGASITRDYHWNWIRQFPGNK
LEWIGYISYDGTILYNPSLENRVTITRDTSKNQFFLKLRSVTAED
TAIYYCASGEDHWGQGTTLTVSS

SEQ ID NO: 60
HVQLQESGPGLVKPSQTLSLTCAVSGSSITYGYHWNWIRQFPGNK
LEWIGYISYDGSVLYNPSLENRVTITRDTSKNQFFLKLRSVTAED
TAIYYCASGFDHWGQGTTLTVSS

SEQ ID NO: 61
HVQLQESGPGLVKPSQTLSLTCAVSGASITRWYHWNWIRQFPGNK
LEWIGYISYDGTVLYNPSLENRVTITRDTSKNQFFLKLRSVTAED
TAIYYCASGFDYWGQGTTLTVSS

SEQ ID NO: 62
DVQLQESGPGLVKPSQTLSLTCAVSGYSITNGYHWNWIRQFPGNK
LEWIGYISYDGTILYNPSLENRVSITRDTSKNQFFLILRSVTAED
TAIYYCASGFDHWGQGTTLTVSS

SEQ ID NO: 63
DVQLQESGPGLVKPSQTLSLTCAVSGYSISHGYHWNWIRQFPGNK
LEWIGYISYDGTILYNPSLENRVSITRDTSKNQFFLILRSVTAED
TAIYYCASGFDHWGQGTTLTVSS

SEQ ID NO: 64
DVQLQESGPGLVKPSQTLSLTCAVSGTSITRGYHWNWIRQFPGNK
LEWIGYISYDGSILYNPSLENRVSITRDTSKNQFFLILRSVTAED
TAIYYCASGFDHWGQGTTLTVSS

SEQ ID NO: 65
DVQLQESGPGLVKPSQTLSLTCAVSGNSISRWYHWNWIRQFPGNK
LEWIGYISYDGTVLYNPSLENRVSITRDTSKNQFFLILRSVTAED
TAIYYCASGFDHWGQGTTLTVSS

SEQ ID NO: 66
DVQLQESGPGLVKPSQTLSLTCAVSGSSITYGYHWNWIRQFPGNK
LEWIGYISYDGSVLYNPSLENRVSITRDTSKNQFFLILRSVTAED
TAIYYCASGFDHWGQGTTLTVSS

SEQ ID NO: 67
DVQLQESGPGLVKPSQTLSLTCAVSGYSITRGYHWNWIRQFPGNK
LEWIGYISYDGTNLYNPSLENRVSITRDTSKNQFFLILRSVTAED
TAIYYCASGFDHWGQGTTLTVSS

SEQ ID NO: 68
HVQLQESGPGLVKPSQTLSLTCAVSGYSISHGYHWNWIRQFPGNK
LEWIGYISYDGTILYNPSLENRVTITRDTSKNQFFLKLRSVTAED
TAIYYCASGFDHWGQGTTLTVSS

SEQ ID NO: 69
DVQLQESGPGLVKPSQTLSLTCTVSGYPITSGYHWNWIRQFPGNK
LVWMGYISYDGSDHYNPSLENRVSIRDISKNQFFLKLSSVTAAD
TAVYFCASGFDHWGQGTMLTVSS

SEQ ID NO: 70
QVQLQESGPGLVKPSQTLSLTCAVSGYSISYGYHWNWIRQFPGKG
LEWIGYISYDGSVLYNPSLKGRVTISVDTSKNQFSLKLSSVTAED
TAVYYCASGFDHWGQGTLVTVSS

SEQ ID NO: 71
QVQLQESGPGLVKPSQTLSLTCAVSGYSISNGYHWNWIRQFPGKS
LEWIGYIAYDGVQSYNPSLKGRVTISVDTSKNQFSLKLSSVTAED
TAVYYCASGFDHWGQGTLVTVSS

SEQ ID NO: 72
QVQLQESGPGLVKPSQTLSLTCAVSGYSISRGYHWNWIRQFPGKG
LEWIGYISYDGSVLYNPSLKSRVTISVDTSKNQFSLKLSSVTAED
TAVYYCASGFDHWGQGTLVTVSS

SEQ ID NO: 73
QVQLQESGPGLVKPSQTLSLTCAVSGYSISSGYHWNWIRQFPGKG
LEWIGYISYDGSVLYNPSLKSRVTISVDTSKNQFSLKLSSVTAED
TAVYYCASGFDHWGQGTLVTVSS

SEQ ID NO: 74
QVQLQESGPGLVKPSQTLSLTCAVSGYSISNGYHWNWIRQFPGKG
LEWIGYISYDGSVLYNPSLKSRVTISVDTSKNQFSLKLSSVTAED
TAVYYCASGFDHWGQGTLVTVSS

SEQ ID NO: 75
QVQLQESGPGLVKPSQTLSLTCAVSGYSISRGYHWNWIRQFPGKG
LEWIGYIGYDGAVQYNPSLKSRVTISVDTSKNQFSLKLSSVTAED
TAVYYCASGEDHWGQGTLVTVSS

SEQ ID NO: 76
QVQLQESGPGLVKPSQTLSLTCAVSGYSISHGYHWNWIRQFPGKS
LEWIGYISYNGSVLYNPSLKSRVTISVDTSKNQFSLKLSSVTAED
TAVYYCASGFDHWGQGTLVTVSS

SEQ ID NO: 77
QVQLQESGPGLVKPSQTLSLTCAVSGYSISRGYHWNWIRQFPGKG
LEWIGYISYDGSRLYNPSLKSRVTISVDTSKNQFSLKLSSVTAED
TAVYYCASGFDHWGQGTLVTVSS

SEQ ID NO: 78
QVQLQESGPGLVKPSQTLSLTCAVSGYSISNGYHWNWIRQFPGKG
LEWIGYISYNGSVLYNPSLKSRVTISVDTSKNQFSLKLSSVTAED
TAVYYCASGFDHWGQGTLVTVSS

SEQ ID NO: 79
EVQLQESGPGLVKPSQTLSLTCAVSGYSITSGYHWNWIRQFPGKR
LEWMGYISYDGSDHYNPSLENRITITRDTSKNQFFLKLRSVTAED
TAVYYCASGFDHWGQGTTLTVSS

SEQ ID NO: 80
EVQLQESGPGLVKPSQTLSLTCAVSGYPITSGYHWNWIRQFPGNK
LEWIGYISYDGSDHYNPSLENRVSITRDTSKNQFFLKLRSVTAED
TAIYFCASGFDHWGQGTTLIVSS

SEQ ID NO: 81
EVQLQESGPGLVKPSQTLSLTCAVSGYSITSGYHWNWIRQFPGNE
LEWIGYISYDGSDHYNPSLENRITITRDTSKNQFFLKLRSVTAED
TAKYYCASGFDHWGQGTTLTVSS

SEQ ID NO: 82
HVQLQESGPGLVKPSQTLSLTCAVSGYSITNGYHWNWIRQFPGNK
LEWIGYISYDGTILYNPSLENRVTITRDTSKNQFFLKLRSVTAED
TAIYYCASGFDHWGQGTTLTVSS

SEQ ID NO: 83
EVQLQESGPGLVKPSQTLSLTCAVSGYSISSGYHWNWIRQFPGNR
LEWIGYISYDGSDHYNPSLENRVTITRDTSKNQFFLILRSVTAED
TAKYYCASGFDHWGQGTTLTVSS

SEQ ID NO: 84
EVQLQESGPGLVKPSQTLSLTCAVSGYSITSGYHWNWIRQFPGNK
LEWIGYISYDGSDHYNPSLENRVTITRDTSKNQFFLKLRSVTAED
TAKYFCASGFDHWGQGTTLTVSS

SEQ ID NO: 85
QVQLQESGPGLVKPSQTLSLTCAVSGYSISSGYHWNWIRQFPGNR
LEWMGYISYDGSDHYNPSLENRISITRDTSKNQFFLKLSSVTAED
TAKYFCASGFDHWGQGTTLTVSS

SEQ ID NO: 86
EVQLQESGPGLVKPSQTLSLTCAVSGYSITSGYHWNWIRQFPGNK
LEWIGYISYDGSDHYNPSLENRITITRDTSKNQFSLKLRSVTAED
TAVYYCASGFDHWGQGTTLTVSS

SEQ ID NO: 87
EVQLQESGPGLVKPSQTLSLTCAVSGYSITSGYHWNWIRQFPGNK
LEWIGYISYDGSDHYNPSLENRVTITRDTSKNQFFLKLSSVTAED
TAKYYCASGFDHWGQGTTLTVSS

SEQ ID NO: 88
QVQQQESGPGQVKPSQTLSLTCAVSGYPISSGYHWNWIRQFPGNK
LEWMGYISYDGSDHYNPSLENRITITRDTSKNQFFLKLRSVTAED
TAKYYCASGFDHWGQGTTLTVSS

SEQ ID NO: 89
QVQLQESGPGLVKPSQTLSLTCAVSGYSITSGYHWNWIRQFPGNK
LEWMGYISYDGSDHYNPSLENRITITRDTSKNQFFLILRSVTAED
TAIYYCASGFDHWGQGTTLTVSS

SEQ ID NO: 90
HVQLQESGPGLVKPSQTLSLTCAVSGYSISSGYHWNWIRQFPGNE
LEWIGYISYDGSDHYNPSLENRITITRDTSKNQFFLKLRSVTAED
TAKYYCASGFDHWGQGTTLTVSS

SEQ ID NO: 91
QVQLQESGPGLVKPSQTLSLTCAVSGYSISRGYHWNWIRQFPGKG
LEWIGYISYDGSVLYNPSLKSRVTISVDTSKNQFSLKLSSVTTED
TAVYYCASGFDHWGQGTLVTVSS

SEQ ID NO: 92
QVQLQESGPGLVKPSQTLSLTCAVSGYSISHGYHWNWIRQFPGKG
LEWIGYISYDGSVLYNPSLKSRVTISVDTSKNQFSLKLSSVTAED
TAVYYCASGFDHWGQGTLVTVSS

SEQ ID NO: 93
EVQLQESGPGLVKPSQTLSLTCAVSGYSIS

SEQ ID NO: 94
EVQLQESGPGLVKPSQTLSLTCAVSGYSIT

SEQ ID NO: 95
EVQLQESGPGLVKPSQTLSLTCAVSGTSIT

SEQ ID NO: 96
EVQLQESGPGLVKPSQTLSLTCAVSGNSIS

SEQ ID NO: 97
EVQLQESGPGLVKPSQTLSLTCAVSGASIT

SEQ ID NO: 98
EVQLQESGPGLVKPSQTLSLTCAVSGSSIT

SEQ ID NO: 99
EVQLQESGPGLVKPSQTLSLTCAVSGASIS

SEQ ID NO: 100
EVQLQESGPGLVKPSQTLSLTCAVSGGSIT

SEQ ID NO: 101
EVQLQESGPGLVKASQTLSLTCAVSGYSIS

DVQLQESGPGLVKPSQTLSLTCAVSGYPIT  SEQ ID NO: 102

HVQLQESGPGLVKPSQTLSLTCAVSGYSIT  SEQ ID NO: 103

EVQLQESGPGLVKPSQTLSLTCAVSGYPIS  SEQ ID NO: 104

QVQLQESGPGLVKPSQTLSLTCAVSGYSIS  SEQ ID NO: 105

HVQLQESGPGLVKPSQTLSLTCAVSGTSIT  SEQ ID NO: 106

HVQLQESGPGLVKPSQTLSLTCAVSGNSIS  SEQ ID NO: 107

HVQLQESGPGLVKPSQTLSLTCAVSGYSIS  SEQ ID NO: 108

HVQLQESGPGLVKPSQTLSLTCAVSGASIT  SEQ ID NO: 109

HVQLQESGPGLVKPSQTLSLTCAVSGSSIT  SEQ ID NO: 110

DVQLQESGPGLVKPSQTLSLTCAVSGYSIT  SEQ ID NO: 111

DVQLQESGPGLVKPSQTLSLTCAVSGYSIS  SEQ ID NO: 112

DVQLQESGPGLVKPSQTLSLTCAVSGTSIT  SEQ ID NO: 113

DVQLQESGPGLVKPSQTLSLTCAVSGNSIS  SEQ ID NO: 114

DVQLQESGPGLVKPSQTLSLTCAVSGSSIT  SEQ ID NO: 115

DVQLQESGPGLVKPSQTLSLTCTVSGYPIT  SEQ ID NO: 116

EVQLQESGPGLVKPSQTLSLTCAVSGYPIT  SEQ ID NO: 117

QVQQQESGPGQVKPSQTLSLTCAVSGYPIS  SEQ ID NO: 118

QVQLQESGPGLVKPSQTLSLTCAVSGYSIT  SEQ ID NO: 119

SGYHWN  SEQ ID NO: 120

RGYHWN  SEQ ID NO: 121

HGYHWN  SEQ ID NO: 122

NGYHWN  SEQ ID NO: 123

YGYHWN  SEQ ID NO: 124

RDYHWN  SEQ ID NO: 125

RWYHWN  SEQ ID NO: 126

NFYHWN  SEQ ID NO: 127

RYYHWN  SEQ ID NO: 128

WIRQFPGNKLEWIG  SEQ ID NO: 129

WVRQFPGNKLEWIG  SEQ ID NO: 130

WIQQFPGNKLEWIG  SEQ ID NO: 131

WIRQLPGNKLEWIG  SEQ ID NO: 132

WIRQFPGKKLEWIG  SEQ ID NO: 133

WIRQFPGKGLEWIG  SEQ ID NO: 134

WIRQFPGNKLVWMG  SEQ ID NO: 135

WIRQFPGKSLEWIG  SEQ ID NO: 136

WIRQFPGKRLEWMG  SEQ ID NO: 137

WIRQFPGNELEWIG  SEQ ID NO: 138

WIRQFPGNRLEWIG  SEQ ID NO: 139

WIRQFPGNRLEWMG  SEQ ID NO: 140

WIRQFPGNKLEWMG  SEQ ID NO: 141

YISYDGSDHYNPSLEN  SEQ ID NO: 142

YISYDGSVFYNPSLEN  SEQ ID NO: 143

YISYDGSILYNPSLEN  SEQ ID NO: 144

YISYDGTILYNPSLEN  SEQ ID NO: 145

YISYDGTVLYNPSLEN  SEQ ID NO: 146

YISYDGNVLYNPSLEN  SEQ ID NO: 147

YISYDGTSLYNPSLEN  SEQ ID NO: 148

YISYDGSVLYNPSLEN  SEQ ID NO: 149

YISYDGNILYNPSLEN  SEQ ID NO: 150

YISYDGTNLYNPSLEN  SEQ ID NO: 151

YISYDGSNLYNPSLEN  SEQ ID NO: 152

YISYDGTVHYNPSLEN  SEQ ID NO: 153

YISYDGTIRYNPSLEN  SEQ ID NO: 154

YISYDGSVLYNPSLKS  SEQ ID NO: 155

-continued

YISYDGSVLYNPSLKG
SEQ ID NO: 156

YIAYDGVQSYNPSLKG
SEQ ID NO: 157

YIGYDGAVQYNPSLKS
SEQ ID NO: 158

YISYNGSVLYNPSLKS
SEQ ID NO: 159

YISYDGSRLYNPSLKS
SEQ ID NO: 160

RITITRDTSKNQFSLILRSVTAEDTAIYYCAS
SEQ ID NO: 161

RVTITRDTSKNQFFLKLSSVTAEDTAKYYCAS
SEQ ID NO: 162

RVTITRDTSKNQFFLKLSSVTAEDTARYYCAS
SEQ ID NO: 163

RITISRDTSKNQFFLKLRSVTAEDTAKYFCAS
SEQ ID NO: 164

RVSITRDTSKNQFFLILRSVTAEDTAIYYCAS
SEQ ID NO: 165

RVTITRDTSKNQFFLKLRSVTAEDTAIYYCAS
SEQ ID NO: 166

RVSITRDTSKNQFFLKLSSVTAEDTAKYFCAS
SEQ ID NO: 167

RVTITRDTSKNQFFLKLRSVTAEDTAIYFCAS
SEQ ID NO: 168

RVTISVDTSKNQFSLKLSSVTAEDTAVYYCAS
SEQ ID NO: 169

RVSISRDISKNQFFLKLSSVTAADTAVYFCAS
SEQ ID NO: 170

RITITRDTSKNQFFLKLRSVTAEDTAVYYCAS
SEQ ID NO: 171

RVSITRDTSKNQFFLKLRSVTAEDTAIYFCAS
SEQ ID NO: 172

RITITRDTSKNQFFLKLRSVTAEDTAKYYCAS
SEQ ID NO: 173

RVTITRDTSKNQFFLILRSVTAEDTAKYYCAS
SEQ ID NO: 174

RVTITRDTSKNQFFLKLRSVTAEDTAKYYCAS
SEQ ID NO: 175

RISITRDTSKNQFFLKLSSVTAEDTAKYFCAS
SEQ ID NO: 176

RITITRDTSKNQFSLKLRSVTAEDTAVYYCAS
SEQ ID NO: 177

RITITRDTSKNQFFLILRSVTAEDTAIYYCAS
SEQ ID NO: 178

RVTISVDTSKNQFSLKLSSVTTEDTAVYYCAS
SEQ ID NO: 179

GFDH
SEQ ID NO: 180

GFDY
SEQ ID NO: 181

GFDT
SEQ ID NO: 182

WGQGTTLTVSS
SEQ ID NO: 183

WGQGTLVTVSS
SEQ ID NO: 184

WGQGTMLTVSS
SEQ ID NO: 185

SEQ ID NO: 186
DVVMTQSPLSLPVTLGEPASISCRSNQSLVHSYGDTYLHWYLQKP
GQSPKLLIYKVSNRFSGVPDRFSGSGSGTDFTLKISRVETEDVGV
YYCSQNTHVPYTFGGGTKLEIKR

SEQ ID NO: 187
DVVMTQSPLSLPVTLGEPASISCRSSQSLVHSYGDTYLHWYLQKP
GQSPKLLIYKVSNRFSGVPDRFSGSGSGTDFTLKISRVETEDLGV
YYCSQNTHVPYTFGGGTKLEIKR

SEQ ID NO: 188
DVVMTQSPLSLPVTLGEPASISCRSSQSLVHSYGDTYLHWYLQKP
GQSPKLLIYKVSNRFSGVPDRFSGSGSGTDFTLKISRVETEDVGV
YYCSQNTHVPYTFGGGTKLEIKR

SEQ ID NO: 189
DIVMTQSPLSLPVTLGEPASISCRSSQSLVHSYGDTYLHWYLQKP
GQSPQLLIYKVSNRFSGVPDRFSGSGSGTDFTLKISRVETEDVGV
YYCSQNTHVPYTFGGGTKLEIKR

SEQ ID NO: 190
DVVMTQSPLSLPVTLGEPASISCRSSQSLVHSYGDTYLHWYLQKP
GQSPQLLIYKVSNRFSGVPDRFSGSGSGTDFTLKISRVETEDLGV
YYCSQNTHVPYTFGGGTKLEIKR

SEQ ID NO: 191
DVVMTQSPLSLPVTLGEPASISCRSSQSLVHSYGDTYLHWYLQKP
GQSPKLLIYKVSNRFSGVPDRFSGSGSGTDFTLKISRVETEDLGV
YYCSQNTHLPYTFGGGTKLEIKR

SEQ ID NO: 192
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 193
DVVMTQTPLSLPVNLGEPASISCRSSQSLVHSYGDTYLHWYLQKP
GQSPKLLIYKVSNRFSGVPDRFSGSGSGTDFTLKISRVEAEDLGV
YFCSQNTHVPYTFGGGTKLEIKR

SEQ ID NO: 194
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCGQNAKTPYTFGQGTKLEIKR

SEQ ID NO: 195
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCGQNARVPYTFGQGTKLEIKR

SEQ ID NO: 196
DVVMTQSPLSLPVTLGEPASISCRSSQSLVHSYGDTYLHWYLQKP

-continued

```
GQSPQLLIYKVSNRFSGVPDRFSGSGSGTDFTLKISRVEAEDVGV
YYCSQNSYVPYTFGQGTKLEIKR

SEQ ID NO: 197
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCSQNTIPPYTFGQGTKLEIKR

SEQ ID NO: 198
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCGQNSMAPYTFGQGTKLEIKR

SEQ ID NO: 199
DVVMTQSPLSLPVTLGEPASISCRSSQSLVHPYGPTYLHWYLQKP
GQSPQLLIYKVSKRNSGVPDRFSGSGSGTDFTLKISRVEAEDVGV
YYCSQNTHVPYTFGQGTKLEIKR

SEQ ID NO: 200
DVVMTQSPLSLPVTLGEPASISCRSSQSLVHPYGPTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 201
DVVMTQSPLSLPVTLGEPASISCRSSQSLVHTYGNTYLHWYLQKP
GQSPQLLIYKVSNRFSGVPDRFSGSGSGTDFTLKISRVEAEDVGV
YYCSQNTHVPYTEGQGTKLEIKR

SEQ ID NO: 202
DVVMTQSPLSLPVTLGEPASISCRSSQSLVHPYGSTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 203
DVVMTQSPLSLPVTLGEPASISCRSSQSLVERYGTTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 204
DVVMTQSPLSLPVTLGEPASISCRSSQSLVHPYGATYLHWYLQKP
GQSPQLLIYKASQRNSGVPDRFSGSGSGTDFTLKISRVEAEDVGV
YYCSQNTHVPYTFGQGTKLEIKR

SEQ ID NO: 205
DVVMTQSPLSLPVTLGEPASISCRSSQSLVHSYGDTYLHWYLQKP
GQSPKLLIYKVSNRFSGVPDRFSGSGSGTDFTLKISRVEAEDVGV
YYCSQNTHVPYTFGQGTKLEIKR

SEQ ID NO: 206
DVVMTQSPLSLPVTLGEPASISCRSSQSLVHPYGPTYLHWYLQKP
GQSPQLLIYKVSNRFSGVPDRFSGSGSGTDFTLKISRVEAEDVGV
YYCGQNAHLPYTFGQGTKLEIKR

SEQ ID NO: 207
DIVMTQSPLSLPVTLGEPASISCRSSQSLVHSYGDTYLHWYLQKP
GQSPQLLIYKVSNRFSGVPDRFSGSGSGTDFTLKISRVETEDLGV
YFCSQNTHVPYTFGGGTKLEIKR

SEQ ID NO: 208
DIVMTQSPLSLPVTLGEQASISCRSSQSLVHSYGDTYLHWYLQKP
GQSPQLLIYKVSNRFSGVPDRFSGSGSGTDFTLKISRVETEDLGV
YFCSQNTHVPYTFGGGTKLEIKR

SEQ ID NO: 209
DVVMTQSPLSLPVTLGEPASISCRSSQSLVHPYGRTYLHWYLQKP
GQSPQLLIYRSSHRNSGVPDRFSGSGSGTDFTLKISRVEAEDVGV
YYCSQNTHVPYTFGQGTKLEIKR

SEQ ID NO: 210
DIVMTQSPLSLPVTLGEQASISCRSSQSLVHSYGDTYLHWYLQKP
GQSPKLLIYKVSNRFSGVPDRFSGSGSGTDFTLKISRVETEDLGV
YFCSQNTHVPYTFGGGTKLEIKR

SEQ ID NO: 211
DIVMTQSPLSLPVTLGEQASISCRSSQSLVHSYGDTYLHWYLQKP
GQSPKLLIYKVSNRFSGVPDRFSGSGSGTDFTLKISRVDTEDLGV
YFCSQNTHVPYTFGGGTKLEIKR

SEQ ID NO: 212
DIVMTQSPLSLPVTLGEQASISCRSSQSLVHSYGDTYLHWYLQKP
GQSPKLLIYKVSNRFSGVPDRFSGSGSGTDFTLKISRVETEDLGV
YYCSQNTHVPYTFGGGTKLEIKR

SEQ ID NO: 213
DVVMTQSPLSLPVTLGEQASISCRSSQSLVHSYGDTYLHWYLQKP
GQSPKLLIYKVSNRFSGVPDRFSGSGSGTDFTLKISRVETEDLGV
YYCSQNTHVPYTFGGGTKLEIKR

SEQ ID NO: 214
DIVMTQSPLSLPVTPGEPASISCRSSQSLVHSYGDTYLHWYLQKP
GQSPKLLIYKVSNRFSGVPDRFSGSGSGTDFTLKISRVETEDVGV
YFCSQNTHVPYTFGGGTKLEIKR

SEQ ID NO: 215
DVVMTQSPLSLPVTLGEPASISC

SEQ ID NO: 216
DIVMTQSPLSLPVTLGEPASISC

SEQ ID NO: 217
DVVMTQTPLSLPVNLGEPASISC

SEQ ID NO: 218
DIVMTQSPLSLPVTLGEQASISC

SEQ ID NO: 219
DVVMTQSPLSLPVTLGEQASISC

SEQ ID NO: 220
DIVMTQSPLSLPVTPGEPASISC

SEQ ID NO: 221
WYLQKPGQSPKLLIY

SEQ ID NO: 222
WYLQKPGQSPQLLIY

SEQ ID NO: 223
GVPDRFSGSGSGTDFTLKISRVETEDVGVYYC

SEQ ID NO: 224
GVPDRFSGSGSGTDFTLKISRVETEDLGVYYC
```

```
GVPDRFSGSGSGTDFTLKISRVEAEDVGVYYC              SEQ ID NO: 225

SEQ ID NO: 226
GVPDRFSGSGSGTDFTLKISRVEAEDLGVYFC

SEQ ID NO: 227
GVPDRFSGSGSGTDFTLKISRVETEDLGVYFC

SEQ ID NO: 228
GVPDRFSGSGSGTDFTLKISRVDTEDLGVYFC

SEQ ID NO: 229
GVPDRFSGSGSGTDFTLKISRVETEDVGVYFC

SEQ ID NO: 230
FGGGTKLEIKR

SEQ ID NO: 231
FGQGTKLEIKR

SEQ ID NO: 232
RSNQSLVHSYGDTYLH

SEQ ID NO: 233
RSSQSLVHSYGDTYLH

SEQ ID NO: 234
RSSQSLVHPYGPTYLH

SEQ ID NO: 235
RSSQSLVHTYGNTYLH

SEQ ID NO: 236
RSSQSLVHPYGSTYLH

SEQ ID NO: 237
RSSQSLVHRYGTTYLH

SEQ ID NO: 238
RSSQSLVHPYGATYLH

SEQ ID NO: 239
RSSQSLVHPYGRTYLH

SEQ ID NO: 240
KVSNRFS

SEQ ID NO: 241
KVSKRNS

SEQ ID NO: 242
KASQRNS

SEQ ID NO: 243
RSSHRNS

SEQ ID NO: 244
SQNTHVPYT

SEQ ID NO: 245
SQNTHLPYT

SEQ ID NO: 246
GQNAKTPYT

SEQ ID NO: 247
GQNARVPYT

SEQ ID NO: 248
SQNSYVPYT

SEQ ID NO: 249
SQNTIPPYT

SEQ ID NO: 250
GQNSMAPYT

SEQ ID NO: 251
GQNAHLPYT
```

SEQ ID NO: 252-262, primer sequences
(see Table 5)

SEQ ID NO: 263
QVQLQESGPGLVKPSQTLSLTCAVSGSSITRGYHWNWIRQFPGKG
LEWIGYISYDGSVLYNPSLKSRVTISVDTSKNQFSLKLSSVTTED
TAVYYCASGFDHWGQGTLVTVSS

SEQ ID NO: 264
QVQLQESGPGLVKPSQTLSLTCAVSGYSISRGYHWNWIRQFPGNK
LEWIGYISYDGSVLYNPSLENRVTITRDTSKNQFSLKLSSVTTED
TAVYYCASGFDHWGQGTLVTVSS

SEQ ID NO: 265
QVQLQESGPGLVKPSQTLSLTCAVSGYSISYGYHWNWIRQFPGNK
LEWIGYISYDGSVLYNPSLENRVTITRDTSKNQFSLKLSSVTAED
TAVYYCASGFDHWGQGTLVTVSS

SEQ ID NO: 266
QVQLQESGPGLVKPSQTLSLTCAVSGSSITYGYHWNWIRQFPGNK
LEWIGYISYDGSVLYNPSLENRVTITRDTSKNQFSLKLSSVTAED
TAVYYCASGFDHWGQGTLVTVSS

SEQ ID NO: 267
QVQLQESGPGLVKPSQTLSLTCAVSGYSISSGYHWNWIRQFPGKG
LEWIGYISYDGSVLYNPSLKSRVTISVDRSKNQFSLKLSSVTAED
TAVYYCASGFDHWGQGTLVTVSS

SEQ ID NO: 268
QVQLQESGPGLVKPSQTLSLTCAVSGYSISRGYHWNWIRQFPGKG
LEWIGYISYDGSVLYNPSLKSRVTVSVDTSKNQFSLKLSSVTTED
TAVYYCASGFDHWGQGTLVTVSS

SEQ ID NO: 269
QVQLQESGPGLVKPSQTLSLTCAVSGYSISRGYHWNWIRQFPGKG
LEWIGYISYDGSVLYNPSLKSRVTISVDTSKNQFSLKLSSVTTED
SAVYYCSSGFDHWGQGTLVTVSS

SEQ ID NO: 270
QVQLQESGPGLVKPSQTLSLTCAVSGYSISRGYHWNWIRQFPGKG
LEWIGYISYDGSVLYNPSLKSRVTISVDTSKNQFSLKLSSVTTED
TAVYYCASGFDHWGHGTLVTVSS

SEQ ID NO: 271
QVQLQESGPGLVKPSQTLSLTCAVSGYSISRGYHWNWIRQYPGKG
LEWIGYISYDGSVLYNPSLKSRVAISVDTSKNQFSLKLSSVTAED
TAVYYCASGFDHWGQGTLVTVSS

SEQ ID NO: 272
QVQLQESGPGLVKPSQTLSLSCAVSGYSISRGYHWNWIRQFPGKG
LEWIGYISYDGSVLYNPSLKGRVTISVDTSKNQFSLKLSSVTAED
TAVYYCASGFDHWGQGTLVTVSS

SEQ ID NO: 273
QVQLQESGPGLVKPSQTLSLTCAVSGYSISRGYHWNWIRQFPGKG
LEWLGYISYDGSVLYNPSLKSRVTISVDTSKNQFSLKLSSVTAED
TAVYYCASGFDHWGQGTLVTVSS

SEQ ID NO: 274
QVQLQESGPGLVKPSQTLSLTCAVSGYSISRGYHWNWIRQFPGKG
LEWIGYISYDGSVLYNPSLKSRVTISEDTSKNQFSLKLSSVTAED
TAVYYCASGFDHWGQGTLVTVSS

SEQ ID NO: 275
QVQLQESGPGLVKPSQTLSLTCAVSGYSISSGYHWNWIRQFPGKG
LEWIGYISYDGSVLYNPSLKSRVTISMDTSKNHFSLKLSSVTAED
TAVYYCASGFDHWGQGTLVTVSS

SEQ ID NO: 276
QVQLQESGPGRVKPSQTLSLTCAVSGYSISRGYHWNWIRQFPGKG
LEWIGYISYDGSVLYNPSLKSRVTISVDTSKNQFSLKLSSVTTED
TAVYYCASGFDHWGQGTLVTVSS

SEQ ID NO: 277
QVQLQESGPGLVKPSQTLSLTCAVSGYSISRGYHWNWIRQFPGKG
LEWIGYISYDGSVLFNPSLKSRVTISVDRSKNQFSLKLSSVTAED
TAVYYCASGFDHWGPGTQVTVSS

SEQ ID NO: 278
QVQLQESGPGLVKPSQTLSLSCAVSGYSISSGYHWNWIRQFPGKG
LEWIGYISYDGSVLYNPSLKSRVTIGVDTSKNQFSLKLSSVTAED
TAVYYCASGFDHWGQGTLVTVSS

SEQ ID NO: 279
QVQLQESGPGLVKPSQTLSLTCAVSGYSISRGYHWNWIRQFPGKG
LEWIGYISYDGSVLYNPSLKSRVTISVDTSKNQFSLKLRSVTDED
SAVYYCASGFDHWGQGTLVTVSS

SEQ ID NO: 280
QVQLQESGPGLVKPSQTLSLTCAVSGSSIT

SEQ ID NO: 281
QVQLQESGPGLVKPSQTLSLSCAVSGYSIS

SEQ ID NO: 282
QVQLQESGPGRVKPSQTLSLTCAVSGYSIS

SEQ ID NO: 283
WIRQYPGKGLEWIG

SEQ ID NO: 284
WIRQFPGKGLEWLG

SEQ ID NO: 285
YISYDGSVLFNPSLKS

SEQ ID NO: 286
RVTITRDTSKNQFSLKLSSVTTEDTAVYYCAS

SEQ ID NO: 287
RVTITRDTSKNQFSLKLSSVTAEDTAVYYCAS

SEQ ID NO: 288
RVTISVDRSKNQFSLKLSSVTAEDTAVYYCAS

SEQ ID NO: 289
RVTVSVDTSKNQFSLKLSSVTTEDTAVYYCAS

SEQ ID NO: 290
RVTISVDTSKNQFSLKLSSVTTEDSAVYYCSS

SEQ ID NO: 291
RVAISVDTSKNQFSLKLSSVTAEDTAVYYCAS

SEQ ID NO: 292
RVTISEDTSKNQFSLKLSSVTAEDTAVYYCAS

SEQ ID NO: 293
RVTISMDTSKNHFSLKLSSVTAEDTAVYYCAS

SEQ ID NO: 294
RVTIGVDTSKNQFSLKLSSVTAEDTAVYYCAS

SEQ ID NO: 295
RVTISVDTSKNQFSLKLRSVTDEDSAVYYCAS

SEQ ID NO: 296
WGHGTLVTVSS

SEQ ID NO: 297
WGPGTQVTVSS

SEQ ID NO: 298
DVVMTQSPISLPVTLGEPASISCRSSQSLVHPYGSTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 299
DVVMTQSPLSLPVTLGEPASISCRSSQSLVHPYGSTYLHWYLQKP
GQPPQLLIYKVSNRFSGVPDRFSGSGSGTDFTLKISRVEAEDVGV
YYCSQNTHVPYTFGQGTKLEIKR

SEQ ID NO: 300
DVVMTQSPLSLSVTLGEPASISCRSSQSLVHPYGPTYLHWYLQKP
GQSPQLLIYKVSNRFSGVPDRFSGSGSGTDYTLKISRVEAEDVGV
YYCSQNTHVPYTFGQGTKLEIKR

SEQ ID NO: 301
DVVMTQSPLSLPVTLGEPASISCRSSQSLVHSYGDTYLHWYLQKP
GQSPKLLIYKVSNRFSGVPDRFSGSGSGTDYTLKISRVEAEDVGV
YYCSQNTHVPYTFGQGTKLEIKR

SEQ ID NO: 302
DVVMTQSPLSLPVTLGEPASISCRSSQSLVHPYGPTYLHWYLQKP
GQSPQLLIYKVSNRFSGVPDRFSGSGSGTEFTLKISRVEAEDVGA
YYCSQNTHVPYTFGQGTKLEIKR

SEQ ID NO: 303
DVVMTQSPLSLPVTLGEPASISCRSSQSLVHPFGPTYLHWYLQKP
GQSPKLLIYKVSNRFSGVPDRFSGSGSGTDFTLKISRVEAEDVGV
YYCSQNTHVPYTFGQGTKLEIKR

SEQ ID NO: 304
DVVMTQSPLSLPVTLGEPASISCRSSQSLAHPYGSTYLHWYLQKP
GQSPQLLIYKVSNRFSGVPDRFSGSGSGTDFTLKISRVEAEDVGV
YYCSQNTHVPYTFGQGTKLEIKR

SEQ ID NO: 305
DVVMTQSPLSLPVTLGEPASISCRSSQSLVHSYGDTYLHWYLQKP
GQSPQLLIYKVSNRFSGVPDRFSGSGSGTDFTLKISRVEAEDVGV
YYCSQNTHVPYTFGQGTRLEIKR

SEQ ID NO: 306
DVVMTQSPLSLPVTLGEPASISCRSSQSLVHPYGPTYLHWYLQKP
GQSPQLLIYKVSNRFSGVPDRFSGGGSGTDFTLKISRVEAEDVGV
YYCSQNTHVPYTFGQGTKLEIKR

SEQ ID NO: 307
DVVMTQSPLSLPVTLGEPASISCRSSQSLVHPYGPTYLHWYLQKP

```
GQSPQLLVYKVSNRFSGVPDRFSGSGSGTDFTLKISRVEAEDVGV
YYCSQNTHVPYTFGQGTKLEIKR
                                         SEQ ID NO: 308
DVVMTQSPLSLPVTLGEPASISCRSSQSLVHPYGSTYFHWYLQKP
GQSPQLLIYKVSNRFSGVPDRFSGSGSGTDFTLKISRVEAEDGGV
YYCSQNTHVPYTFGQGTKLEIKR
                                         SEQ ID NO: 309
DVVMTQSPISLPVTLGEPASISC
                                         SEQ ID NO: 310
DVVMTQSPLSLSVTLGEPASISC
                                         SEQ ID NO: 311
WYLQKPGQPPQLLIY
                                         SEQ ID NO: 312
WYLQKPGQSPQLLVY

SEQ ID NO: 313
GVPDRFSGSGSGTDYTLKISRVEAEDVGVYYC
                                         SEQ ID NO: 314
GVPDRFSGSGSGTEFTLKISRVEAEDVGAYYC
                                         SEQ ID NO: 315
GVPDRFSGGGSGTDFTLKISRVEAEDVGVYYC
                                         SEQ ID NO: 316
GVPDRFSGSGSGTDFTLKISRVEAEDGGVYYC
                                         SEQ ID NO: 317
FGQGTRLEIKR
                                         SEQ ID NO: 318
RSSQSLVHPFGPTYLH
                                         SEQ ID NO: 319
RSSQSLAHPYGSTYLH
                                         SEQ ID NO: 320
RSSQSLVHPYGSTYFH
```

TABLE 1

The amino acid sequence Nos. of heavy chain variable regions and their CDRs and FRs of humanized antibodies

| Humanized antibody name | SEQ ID NO: | | | | | | | |
|---|---|---|---|---|---|---|---|---|
| | VH | VH-FR1 | VH-CDR1 | VH-FR2 | VH-CDR2 | VH-FR3 | VH-CDR3 | VH-FR4 |
| B-S3-45 | 11 | 93 | 120 | 129 | 142 | 161 | 180 | 183 |
| 5 | 12 | 93 | 121 | 129 | 143 | 162 | 181 | 183 |
| 7 | 13 | 93 | 122 | 129 | 144 | 162 | 180 | 183 |
| 11 | 14 | 94 | 123 | 129 | 145 | 162 | 180 | 183 |
| 7-17 | 15 | 95 | 121 | 129 | 144 | 162 | 180 | 183 |
| 10-25 | 16 | 95 | 122 | 129 | 146 | 162 | 181 | 183 |
| 11-26 | 17 | 93 | 120 | 129 | 144 | 162 | 180 | 183 |
| 29 | 18 | 95 | 125 | 129 | 146 | 162 | 181 | 183 |
| 37 | 19 | 93 | 120 | 129 | 147 | 162 | 181 | 183 |
| 24-40 | 20 | 96 | 126 | 129 | 146 | 162 | 180 | 183 |
| 42 | 21 | 93 | 122 | 129 | 146 | 162 | 180 | 183 |
| 44 | 22 | 97 | 125 | 129 | 145 | 162 | 180 | 183 |
| 6-16 | 23 | 93 | 122 | 129 | 145 | 162 | 180 | 183 |
| 35-62 | 24 | 97 | 124 | 129 | 144 | 162 | 181 | 183 |
| 39-73 | 25 | 97 | 122 | 129 | 148 | 162 | 180 | 183 |
| 85 | 26 | 97 | 121 | 129 | 146 | 162 | 181 | 183 |
| 43-89 | 27 | 93 | 120 | 129 | 145 | 162 | 181 | 183 |
| 86 | 28 | 95 | 121 | 129 | 144 | 162 | 181 | 183 |
| 47-101 | 29 | 97 | 124 | 129 | 145 | 162 | 182 | 183 |
| 50-112 | 30 | 98 | 127 | 129 | 149 | 162 | 180 | 183 |
| 113 | 31 | 97 | 124 | 129 | 145 | 162 | 180 | 183 |
| 117 | 32 | 98 | 121 | 129 | 145 | 162 | 180 | 183 |
| 54-123 | 33 | 97 | 122 | 129 | 145 | 162 | 181 | 183 |
| 55-127 | 34 | 95 | 120 | 129 | 146 | 162 | 180 | 183 |
| 56-135 | 35 | 93 | 120 | 129 | 145 | 163 | 180 | 183 |
| 162 | 36 | 98 | 124 | 129 | 149 | 162 | 180 | 183 |
| 162/41k | 36 | 98 | 124 | 129 | 149 | 162 | 180 | 183 |
| 69-171 | 37 | 95 | 121 | 129 | 150 | 162 | 181 | 183 |
| 73-188 | 38 | 93 | 120 | 130 | 151 | 162 | 180 | 183 |
| 74-189 | 39 | 97 | 122 | 129 | 146 | 162 | 180 | 183 |
| 6-34-234 | 40 | 97 | 122 | 129 | 152 | 162 | 181 | 183 |
| 7-34-239 | 41 | 94 | 121 | 129 | 151 | 162 | 180 | 183 |
| 242 | 42 | 98 | 122 | 129 | 145 | 162 | 180 | 183 |
| 76-191 | 43 | 93 | 120 | 129 | 144 | 162 | 181 | 183 |
| 11-34-266 | 44 | 99 | 124 | 129 | 153 | 162 | 180 | 183 |
| 12-34-277 | 45 | 95 | 127 | 129 | 147 | 162 | 181 | 183 |
| 16-34-293 | 46 | 97 | 125 | 131 | 145 | 162 | 180 | 183 |
| 1-31-322 | 47 | 95 | 128 | 129 | 154 | 162 | 180 | 183 |
| 24-34-316 | 48 | 98 | 124 | 129 | 153 | 162 | 181 | 183 |
| 25-34-317 | 49 | 100 | 125 | 129 | 146 | 162 | 180 | 183 |
| S-S2-25 | 50 | 101 | 120 | 132 | 142 | 164 | 180 | 183 |
| B-S2-2 | 51 | 102 | 120 | 129 | 142 | 165 | 180 | 183 |
| S-S2-41 | 52 | 103 | 120 | 129 | 142 | 166 | 180 | 183 |
| S-S2-11 | 52 | 103 | 120 | 129 | 142 | 166 | 180 | 183 |
| S-S2-10 | 53 | 94 | 120 | 129 | 142 | 167 | 180 | 183 |
| N-22 | 53 | 94 | 120 | 129 | 142 | 167 | 180 | 183 |

TABLE 1-continued

The amino acid sequence Nos. of heavy chain variable regions and their CDRs and FRs of humanized antibodies

| Humanized antibody name | SEQ ID NO: | | | | | | | |
|---|---|---|---|---|---|---|---|---|
| | VH | VH-FR1 | VH-CDR1 | VH-FR2 | VH-CDR2 | VH-FR3 | VH-CDR3 | VH-FR4 |
| B-S2-25 | 54 | 104 | 120 | 133 | 142 | 168 | 180 | 183 |
| 162B | 55 | 105 | 124 | 134 | 155 | 169 | 180 | 184 |
| B3-S4-N-130 | 55 | 105 | 124 | 134 | 155 | 169 | 180 | 184 |
| B3-S4-N-65 | 55 | 105 | 124 | 134 | 155 | 169 | 180 | 184 |
| B4-T13-11 | 55 | 105 | 124 | 134 | 155 | 169 | 180 | 184 |
| B3-S4-N-68 | 55 | 105 | 124 | 134 | 155 | 169 | 180 | 184 |
| P-44 | 55 | 105 | 124 | 134 | 155 | 169 | 180 | 184 |
| P-50 | 55 | 105 | 124 | 134 | 155 | 169 | 180 | 184 |
| H17/K1 | 56 | 106 | 121 | 129 | 144 | 166 | 180 | 183 |
| H17/41K | 56 | 106 | 121 | 129 | 144 | 166 | 180 | 183 |
| H40/K1 | 57 | 107 | 126 | 129 | 146 | 166 | 180 | 183 |
| H40/41K | 57 | 107 | 126 | 129 | 146 | 166 | 180 | 183 |
| H42/K1 | 58 | 108 | 122 | 129 | 146 | 166 | 180 | 183 |
| H42/41K | 58 | 108 | 122 | 129 | 146 | 166 | 180 | 183 |
| H44/K1 | 59 | 109 | 125 | 129 | 145 | 166 | 180 | 183 |
| H44/41K | 59 | 109 | 125 | 129 | 145 | 166 | 180 | 183 |
| H162/K1 | 60 | 110 | 124 | 129 | 149 | 166 | 180 | 183 |
| H162/41K | 60 | 110 | 124 | 129 | 149 | 166 | 180 | 183 |
| H311/K1 | 61 | 109 | 126 | 129 | 146 | 166 | 181 | 183 |
| H311/41K | 61 | 109 | 126 | 129 | 146 | 166 | 181 | 183 |
| D11/K1 | 62 | 111 | 123 | 129 | 145 | 165 | 180 | 183 |
| D11/41K | 62 | 111 | 123 | 129 | 145 | 165 | 180 | 183 |
| D6-16/K1 | 63 | 112 | 122 | 129 | 145 | 165 | 180 | 183 |
| D17/K1 | 64 | 113 | 121 | 129 | 144 | 165 | 180 | 183 |
| D17/41K | 64 | 113 | 121 | 129 | 144 | 165 | 180 | 183 |
| D40/K1 | 65 | 114 | 126 | 129 | 146 | 165 | 180 | 183 |
| D162/K1 | 66 | 115 | 124 | 129 | 149 | 165 | 180 | 183 |
| D162/41K | 66 | 115 | 124 | 129 | 149 | 165 | 180 | 183 |
| D239/K1 | 67 | 111 | 121 | 129 | 151 | 165 | 180 | 183 |
| D239/41K | 67 | 111 | 121 | 129 | 151 | 165 | 180 | 183 |
| H6-16/41K | 68 | 108 | 122 | 129 | 145 | 166 | 180 | 183 |
| 11-3 | 69 | 116 | 120 | 135 | 142 | 170 | 180 | 185 |
| B3-S4-N-50 | 70 | 105 | 124 | 134 | 156 | 169 | 180 | 184 |
| 112 | 71 | 105 | 123 | 136 | 157 | 169 | 180 | 184 |
| 110 | 72 | 105 | 121 | 134 | 155 | 169 | 180 | 184 |
| 84 | 72 | 105 | 121 | 134 | 155 | 169 | 180 | 184 |
| 116 | 73 | 105 | 120 | 134 | 155 | 169 | 180 | 184 |
| 153 | 73 | 105 | 120 | 134 | 155 | 169 | 180 | 184 |
| 187 | 74 | 105 | 123 | 134 | 155 | 169 | 180 | 184 |
| 127 | 74 | 105 | 123 | 134 | 155 | 169 | 180 | 184 |
| 62 | 75 | 105 | 121 | 134 | 158 | 169 | 180 | 184 |
| 23 | 76 | 105 | 122 | 136 | 159 | 169 | 180 | 184 |
| 123 | 77 | 105 | 121 | 134 | 160 | 169 | 180 | 184 |
| 83 | 78 | 105 | 123 | 134 | 159 | 169 | 180 | 184 |
| B-S3-2 | 79 | 94 | 120 | 137 | 142 | 171 | 180 | 183 |
| S-S2-30 | 80 | 117 | 120 | 129 | 142 | 172 | 180 | 183 |
| S-S2-47 | 81 | 94 | 120 | 138 | 142 | 173 | 180 | 183 |
| H11/K1 | 82 | 101 | 123 | 129 | 145 | 166 | 180 | 183 |
| H11/41K | 82 | 103 | 123 | 129 | 145 | 166 | 180 | 183 |
| B-S2-26 | 83 | 93 | 120 | 139 | 142 | 174 | 180 | 183 |
| S-S2-2 | 84 | 94 | 120 | 129 | 142 | 175 | 180 | 183 |
| S-S2-5 | 84 | 94 | 120 | 129 | 142 | 175 | 180 | 183 |
| S-S2-22 | 84 | 94 | 120 | 129 | 142 | 175 | 180 | 183 |
| B-S3-44 | 85 | 105 | 120 | 140 | 142 | 176 | 180 | 183 |
| S-S3-16 | 86 | 94 | 120 | 129 | 142 | 177 | 180 | 183 |
| S-S3-29 | 87 | 94 | 120 | 129 | 142 | 162 | 180 | 183 |
| S-S2-32 | 88 | 118 | 120 | 141 | 142 | 173 | 180 | 183 |
| S-S2-43 | 89 | 119 | 120 | 141 | 142 | 178 | 180 | 183 |
| B-S2-13 | 90 | 108 | 120 | 138 | 142 | 173 | 180 | 183 |
| 138 | 91 | 105 | 121 | 134 | 155 | 179 | 180 | 184 |
| 192 | 92 | 105 | 122 | 134 | 155 | 169 | 180 | 184 |
| 162ccp-S5-N-56 | 72 | 105 | 121 | 134 | 155 | 169 | 180 | 184 |
| 162ccp-S6-N-149 | 72 | 105 | 121 | 134 | 155 | 169 | 180 | 184 |
| 162ccp-S5-N-84 | 72 | 105 | 121 | 134 | 155 | 169 | 180 | 184 |
| 162ccp-S5-P-64 | 91 | 105 | 121 | 134 | 155 | 179 | 180 | 184 |
| 162ccp-S5-N-32 | 91 | 105 | 121 | 134 | 155 | 179 | 180 | 184 |
| 138HA/162BK | 263 | 280 | 121 | 134 | 155 | 179 | 180 | 184 |
| 138HB/83K | 264 | 105 | 121 | 129 | 149 | 286 | 180 | 184 |
| 138HB/162BK | 264 | 105 | 121 | 129 | 149 | 286 | 180 | 184 |
| 138HB/110K | 264 | 105 | 121 | 129 | 149 | 286 | 180 | 184 |
| 138HB/116K | 264 | 105 | 121 | 129 | 149 | 286 | 180 | 184 |
| 162BHB/83K | 265 | 105 | 124 | 129 | 149 | 287 | 180 | 184 |
| 162BHB/110K | 265 | 105 | 124 | 129 | 149 | 287 | 180 | 184 |

TABLE 1-continued

The amino acid sequence Nos. of heavy chain variable regions and their CDRs and FRs of humanized antibodies

| Humanized antibody name | SEQ ID NO: | | | | | | | |
|---|---|---|---|---|---|---|---|---|
| | VH | VH-FR1 | VH-CDR1 | VH-FR2 | VH-CDR2 | VH-FR3 | VH-CDR3 | VH-FR4 |
| 162BHB/116K | 265 | 105 | 124 | 129 | 149 | 287 | 180 | 184 |
| 162BHE/83K | 266 | 280 | 124 | 129 | 149 | 287 | 180 | 184 |
| 162BHE/162BK | 266 | 280 | 124 | 129 | 149 | 287 | 180 | 184 |
| 162ccp-S4-N-81 | 267 | 105 | 120 | 134 | 155 | 288 | 180 | 184 |
| 162ccp-S5-P-27 | 268 | 105 | 121 | 134 | 155 | 289 | 180 | 184 |
| 162ccp-S5-P-77 | 269 | 105 | 121 | 134 | 155 | 290 | 180 | 184 |
| 162ccp-S5-N-41 | 270 | 105 | 121 | 134 | 155 | 179 | 180 | 296 |
| 162ccp-S5-N-69 | 271 | 105 | 121 | 283 | 155 | 291 | 180 | 184 |
| 162ccp-S5-N-70 | 272 | 281 | 121 | 134 | 156 | 169 | 180 | 184 |
| 162ccp-S6-N-101 | 273 | 105 | 121 | 284 | 155 | 169 | 180 | 184 |
| 162ccp-S6-N-111 | 274 | 105 | 121 | 134 | 155 | 292 | 180 | 184 |
| 162ccp-S6-N-137 | 275 | 105 | 120 | 134 | 155 | 293 | 180 | 184 |
| 162ccp-S6-N-146 | 276 | 282 | 121 | 134 | 155 | 179 | 180 | 184 |
| 162ccp-S6-N-160 | 277 | 105 | 121 | 134 | 285 | 288 | 180 | 297 |
| 162ccp-S6-N-66 | 278 | 281 | 120 | 134 | 155 | 294 | 180 | 184 |
| 162ccp-S6-N-45 | 279 | 105 | 121 | 134 | 155 | 295 | 180 | 184 |

TABLE 2

The amino acid sequence Nos. of light chain variable regions and their CDRs and FRs of humanized antibodies

| Humanized antibody name | SEQ ID NO: | | | | | | | |
|---|---|---|---|---|---|---|---|---|
| | VL | VL-FR1 | VL-CDR1 | VL-FR2 | VL-CDR2 | VL-FR3 | VL-CDR3 | VL-FR4 |
| B-S3-45 | 186 | 215 | 232 | 221 | 240 | 223 | 244 | 230 |
| 5 | 187 | 215 | 233 | 221 | 240 | 223 | 244 | 230 |
| 7 | 187 | 215 | 233 | 221 | 240 | 223 | 244 | 230 |
| 11 | 187 | 215 | 233 | 221 | 240 | 223 | 244 | 230 |
| 7-17 | 187 | 215 | 233 | 221 | 240 | 223 | 244 | 230 |
| 10-25 | 187 | 215 | 233 | 221 | 240 | 223 | 244 | 230 |
| 11-26 | 187 | 215 | 233 | 221 | 240 | 223 | 244 | 230 |
| 29 | 187 | 215 | 233 | 221 | 240 | 223 | 244 | 230 |
| 37 | 187 | 215 | 233 | 221 | 240 | 223 | 244 | 230 |
| 24-40 | 187 | 215 | 233 | 221 | 240 | 223 | 244 | 230 |
| 42 | 187 | 215 | 233 | 221 | 240 | 223 | 244 | 230 |
| 44 | 187 | 215 | 233 | 221 | 240 | 223 | 244 | 230 |
| 6-16 | 187 | 215 | 233 | 221 | 240 | 223 | 244 | 230 |
| 35-62 | 187 | 215 | 233 | 221 | 240 | 223 | 244 | 230 |
| 39-73 | 187 | 215 | 233 | 221 | 240 | 223 | 244 | 230 |
| 85 | 187 | 215 | 233 | 221 | 240 | 223 | 244 | 230 |
| 43-89 | 187 | 215 | 233 | 221 | 240 | 223 | 244 | 230 |
| 86 | 187 | 215 | 233 | 221 | 240 | 223 | 244 | 230 |
| 47-101 | 187 | 215 | 233 | 221 | 240 | 224 | 244 | 230 |
| 50-112 | 187 | 215 | 233 | 221 | 240 | 224 | 244 | 230 |
| 113 | 187 | 215 | 233 | 221 | 240 | 224 | 244 | 230 |
| 117 | 187 | 215 | 233 | 221 | 240 | 224 | 244 | 230 |
| 54-123 | 187 | 215 | 233 | 221 | 240 | 224 | 244 | 230 |
| 55-127 | 187 | 215 | 233 | 221 | 240 | 224 | 244 | 230 |
| 56-135 | 187 | 215 | 233 | 221 | 240 | 224 | 244 | 230 |
| 162 | 187 | 215 | 233 | 221 | 240 | 224 | 244 | 230 |
| 69-171 | 187 | 215 | 233 | 221 | 240 | 224 | 244 | 230 |
| 73-188 | 187 | 215 | 233 | 221 | 240 | 224 | 244 | 230 |
| 74-189 | 187 | 215 | 233 | 221 | 240 | 224 | 244 | 230 |
| 6-34-234 | 187 | 215 | 233 | 221 | 240 | 224 | 244 | 230 |
| 7-34-239 | 187 | 215 | 233 | 221 | 240 | 224 | 244 | 230 |
| 242 | 187 | 215 | 233 | 221 | 240 | 224 | 244 | 230 |
| 76-191 | 187 | 215 | 233 | 221 | 240 | 224 | 244 | 230 |
| 11-34-266 | 187 | 215 | 233 | 221 | 240 | 224 | 244 | 230 |
| 12-34-277 | 187 | 215 | 233 | 221 | 240 | 224 | 244 | 230 |
| 16-34-293 | 187 | 215 | 233 | 221 | 240 | 224 | 244 | 230 |
| 1-31-322 | 187 | 215 | 233 | 221 | 240 | 224 | 244 | 230 |
| 24-34-316 | 187 | 215 | 233 | 221 | 240 | 224 | 244 | 230 |
| 25-34-317 | 187 | 215 | 233 | 221 | 240 | 224 | 244 | 230 |
| S-S2-25 | 187 | 215 | 233 | 221 | 240 | 224 | 244 | 230 |
| S-S2-10 | 187 | 215 | 233 | 221 | 221 | 224 | 244 | 230 |
| S-S2-47 | 187 | 215 | 233 | 221 | 221 | 224 | 244 | 230 |
| B-S2-13 | 187 | 215 | 233 | 221 | 221 | 224 | 244 | 230 |

TABLE 2-continued

The amino acid sequence Nos. of light chain variable regions and their CDRs and FRs of humanized antibodies

| Humanized antibody name | SEQ ID NO: | | | | | | | |
|---|---|---|---|---|---|---|---|---|
| | VL | VL-FR1 | VL-CDR1 | VL-FR2 | VL-CDR2 | VL-FR3 | VL-CDR3 | VL-FR4 |
| B-S2-2 | 188 | 215 | 233 | 221 | 240 | 223 | 244 | 230 |
| S-S2-41 | 189 | 216 | 233 | 222 | 240 | 223 | 244 | 230 |
| H6-16/41K | 189 | 216 | 233 | 222 | 240 | 223 | 244 | 230 |
| H17/41K | 189 | 216 | 233 | 222 | 240 | 223 | 244 | 230 |
| H40/41K | 189 | 216 | 233 | 222 | 240 | 223 | 244 | 230 |
| H42/41K | 189 | 216 | 233 | 222 | 240 | 223 | 244 | 230 |
| H44/41K | 189 | 216 | 233 | 222 | 240 | 223 | 244 | 230 |
| H162/41K | 189 | 216 | 233 | 222 | 240 | 223 | 244 | 230 |
| H311/41K | 189 | 216 | 233 | 222 | 240 | 223 | 244 | 230 |
| D11/41K | 189 | 216 | 233 | 222 | 240 | 223 | 244 | 230 |
| D17/41K | 189 | 216 | 233 | 222 | 240 | 223 | 244 | 230 |
| D239/41K | 189 | 216 | 233 | 222 | 240 | 223 | 244 | 230 |
| 11-3 | 189 | 216 | 233 | 222 | 240 | 223 | 244 | 230 |
| H11/41K | 189 | 216 | 233 | 222 | 240 | 223 | 244 | 230 |
| D162/41K | 189 | 216 | 233 | 222 | 240 | 223 | 244 | 230 |
| 162/41K | 189 | 216 | 233 | 222 | 240 | 223 | 244 | 230 |
| S-S2-11 | 189 | 216 | 233 | 222 | 240 | 223 | 244 | 230 |
| B-S2-25 | 190 | 215 | 233 | 222 | 240 | 224 | 244 | 230 |
| B-S3-2 | 190 | 215 | 233 | 222 | 240 | 224 | 244 | 230 |
| B-S3-44 | 190 | 215 | 233 | 222 | 240 | 224 | 244 | 230 |
| S-S3-16 | 190 | 215 | 233 | 222 | 240 | 224 | 244 | 230 |
| N-22 | 191 | 215 | 233 | 221 | 240 | 224 | 245 | 230 |
| 162B | 192 | 215 | 233 | 222 | 240 | 225 | 244 | 231 |
| H17/K1 | 193 | 217 | 233 | 221 | 240 | 226 | 244 | 230 |
| H40/K1 | 193 | 217 | 233 | 221 | 240 | 226 | 244 | 230 |
| H42/K1 | 193 | 217 | 233 | 221 | 240 | 226 | 244 | 230 |
| H44/K1 | 193 | 217 | 233 | 221 | 240 | 226 | 244 | 230 |
| H162/K1 | 193 | 217 | 233 | 221 | 240 | 226 | 244 | 230 |
| H311/K1 | 193 | 217 | 233 | 221 | 240 | 226 | 244 | 230 |
| D11/K1 | 193 | 217 | 233 | 221 | 240 | 226 | 244 | 230 |
| D6-16/K1 | 193 | 217 | 233 | 221 | 240 | 226 | 244 | 230 |
| D17/K1 | 193 | 217 | 233 | 221 | 240 | 226 | 244 | 230 |
| D40/K1 | 193 | 217 | 233 | 221 | 240 | 226 | 244 | 230 |
| D162/K1 | 193 | 217 | 233 | 221 | 240 | 226 | 244 | 230 |
| D239/K1 | 193 | 217 | 233 | 221 | 240 | 226 | 244 | 230 |
| H11/K1 | 193 | 217 | 233 | 221 | 240 | 226 | 244 | 230 |
| B3-S4-N-130 | 194 | 215 | 233 | 221 | 240 | 225 | 246 | 231 |
| B3-S4-N-65 | 195 | 215 | 233 | 221 | 240 | 225 | 247 | 231 |
| B4-T13-11 | 196 | 215 | 233 | 222 | 240 | 225 | 248 | 231 |
| B3-S4-N-68 | 197 | 215 | 233 | 222 | 240 | 225 | 249 | 231 |
| B3-84-N-50 | 198 | 215 | 233 | 222 | 240 | 225 | 250 | 231 |
| 112 | 199 | 215 | 234 | 222 | 241 | 225 | 244 | 231 |
| P-44 | 199 | 215 | 234 | 222 | 241 | 225 | 244 | 231 |
| P-50 | 200 | 215 | 234 | 222 | 240 | 225 | 244 | 231 |
| 192 | 200 | 215 | 234 | 222 | 240 | 225 | 244 | 231 |
| 110 | 201 | 215 | 235 | 222 | 240 | 225 | 244 | 231 |
| 116 | 202 | 215 | 236 | 222 | 240 | 225 | 244 | 231 |
| 187 | 202 | 215 | 236 | 222 | 240 | 225 | 244 | 231 |
| 62 | 203 | 215 | 237 | 222 | 240 | 225 | 244 | 231 |
| 23 | 204 | 215 | 238 | 722 | 242 | 225 | 244 | 231 |
| 84 | 205 | 215 | 233 | 221 | 240 | 225 | 244 | 231 |
| 83 | 205 | 215 | 233 | 221 | 240 | 225 | 244 | 231 |
| 138 | 205 | 215 | 233 | 221 | 240 | 225 | 244 | 231 |
| 153 | 205 | 215 | 233 | 221 | 240 | 225 | 244 | 231 |
| 123 | 206 | 215 | 234 | 222 | 240 | 225 | 251 | 231 |
| S-S2-30 | 207 | 216 | 233 | 222 | 240 | 227 | 244 | 230 |
| B-S2-26 | 208 | 218 | 233 | 222 | 240 | 227 | 244 | 230 |
| 127 | 209 | 215 | 239 | 222 | 243 | 225 | 244 | 231 |
| S-S2-2 | 210 | 218 | 233 | 221 | 240 | 227 | 244 | 230 |
| S-S2-5 | 211 | 218 | 233 | 221 | 240 | 228 | 244 | 230 |
| S-S2-22 | 212 | 218 | 233 | 221 | 240 | 224 | 244 | 230 |
| S-S2-43 | 212 | 218 | 233 | 221 | 240 | 224 | 244 | 230 |
| S-S3-29 | 213 | 219 | 233 | 221 | 240 | 224 | 244 | 230 |
| S-S2-32 | 214 | 220 | 233 | 221 | 240 | 229 | 244 | 230 |
| 138HA/162BK | 192 | 215 | 233 | 222 | 240 | 225 | 244 | 231 |
| 138HB/162BK | 192 | 215 | 233 | 222 | 240 | 225 | 244 | 231 |
| 162BHE/162BK | 192 | 215 | 233 | 222 | 240 | 225 | 244 | 231 |
| 162ccp-S5-N-32 | 200 | 215 | 234 | 222 | 240 | 225 | 244 | 231 |
| 162ccp-S5-N-84 | 200 | 215 | 234 | 222 | 240 | 225 | 244 | 231 |
| 162ccp-S6-N-137 | 200 | 215 | 234 | 222 | 240 | 225 | 244 | 231 |
| 138HB/110K | 201 | 215 | 235 | 222 | 240 | 225 | 244 | 231 |
| 162BHB/110K | 201 | 215 | 235 | 222 | 240 | 225 | 244 | 231 |

TABLE 2-continued

The amino acid sequence Nos. of light chain variable regions and their CDRs and FRs of humanized antibodies

| Humanized antibody name | SEQ ID NO: | | | | | | | |
|---|---|---|---|---|---|---|---|---|
| | VL | VL-FR1 | VL-CDR1 | VL-FR2 | VL-CDR2 | VL-FR3 | VL-CDR3 | VL-FR4 |
| 138HB/116K | 202 | 215 | 236 | 222 | 240 | 225 | 244 | 231 |
| 162BHB/116K | 202 | 215 | 236 | 222 | 240 | 225 | 244 | 231 |
| 162ccp-S5-N-56 | 202 | 215 | 236 | 222 | 240 | /25 | 244 | 231 |
| 162ccp-S6-N-146 | 202 | 215 | 236 | 222 | 240 | 225 | 244 | 231 |
| 162ccp-S5-N-69 | 202 | 215 | 236 | 222 | 240 | 225 | 244 | 231 |
| 162ccp-S6-N-45 | 202 | 215 | 236 | 222 | 240 | 225 | 244 | 231 |
| 138HB/83K | 205 | 215 | 233 | 221 | 240 | 225 | 244 | 231 |
| 162BHB/83K | 205 | 215 | 233 | 221 | 240 | 225 | 244 | 231 |
| 162BHE/83K | 205 | 215 | 233 | 221 | 240 | 225 | 244 | 231 |
| 162ccp-S4-N-81 | 298 | 309 | 236 | 222 | 240 | 225 | 244 | 231 |
| 162ccp-S5-P-27 | 299 | 215 | 236 | 311 | 240 | 225 | 244 | 231 |
| 162ccp-S5-P-64 | 300 | 310 | 234 | 222 | 240 | 313 | 244 | 231 |
| 162ccp-S5-P-77 | 301 | 215 | 233 | 221 | 240 | 313 | 244 | 231 |
| 162ccp-S5-N-41 | 302 | 215 | 234 | 222 | 240 | 314 | 244 | 231 |
| 162ccp-S5-N-70 | 303 | 215 | 318 | 221 | 240 | 225 | 244 | 231 |
| 162ccp-S6-N-101 | 304 | 215 | 319 | 222 | 240 | 225 | 244 | 231 |
| 162cep-S6-N-111 | 305 | 215 | 233 | 222 | 240 | 225 | 244 | 317 |
| 162ccp-S6-N-149 | 306 | 215 | 234 | 222 | 240 | 315 | 244 | 231 |
| 162ccp-S6-N-160 | 307 | 215 | 234 | 312 | 240 | 225 | 244 | 231 |
| 162ccp-S6-N-66 | 308 | 215 | 320 | 222 | 240 | 316 | 244 | 231 |

DETAILED DESCRIPTION OF THE INVENTION

Definition of Terms

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "antibody" generally refers to an immunoglobulin molecule consisting of two pairs of polypeptide chains (each pair has a light (L) chain and a heavy (H) chain). Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). A light chain constant region consists of a domain $C_L$. The constant region of an antibody can mediate the binding of an immunoglobulin to a host tissue or factor, including various cells (e.g. effector cells) of an immune system and the first component of classical complement system (C1q). $V_H$ and $V_L$ region can also be divided into hypervariable regions (called complementarity determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat, Sequences of Proteins of Immunological Interest (National Institutes of Health, Bethesda, Md. (1987 and 1991)), or Chothia & Lesk (1987) J. Mol. Biol. 196:901-917; Chothia et al., (1989) Nature 342:878-883.

As used herein, the term "complementarity determining region" or "CDR" refers to the amino acid residues responsible for antigen binding in antibody variable region, which generally comprises residues 24-34 {LCDR1}, 50-56 {LCDR2}, 89-97 {LCDR3} in light chain variable region and residues 31-35 {HCDR1}, 50-65 {HCDR2}, 95-102 {HCDR3} in heavy chain variable region (see, for example, Kabat et al., Sequences of Proteins of Immunological Interest, the fifth edition, Public Health Service, National Institutes of Health, Bethesda, Md. (1991)), or residues 26-32 {L1}, 50-52 {L2}, 91-96 {L3} in light chain variable region and residues 26-32 {H1}, 53-55 {H2}, 96-101 {H3} in heavy chain variable region (see, Chothia and Lesk J. Mol. Biol. 196: 901-917 (1987)).

As used herein, the term "framework region" or "FR" residues refers to the amino acid residues other than the CDR residues as defined above, in antibody variable region.

The term "antibody" is not restricted by any specific method for producing antibodies. For example, antibodies can include recombinant antibodies, monoclonal antibodies and polyclonal antibodies. Antibodies may be of different antibody isotypes, for example, IgG (e.g. IgG1, IgG2, IgG3 or IgG4 subtype), IgA1, IgA2, IgD, IgE or IgM antibody.

As used herein, the term "antigen binding fragment" refers to polypeptides comprising fragments of a full-length antibody, which retain the ability of specifically binding to an antigen that the full-length antibody specifically binds to, and/or compete with the full-length antibody for binding to the same antigen, also known as "antigen binding portion". Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')$_2$, Fd, Fv, dAb and complementarity determining region (CDR) fragments, single chain antibody (e.g. scFv), chimeric antibody, diabody and such polypeptides that comprise at least part of antibody sufficient to confer the specific antigen binding ability on the polypeptides.

As used herein, the term "Fd fragment" refers to an antibody fragment consisting of $V_H$ and $C_H1$ domain; the term "dAb fragment" refers to an antibody fragment consisting of VH domain (Ward et al., Nature 341:544 546 (1989)); the term "Fab fragment" refers to an antibody fragment consisting of VL, VH, CL and CH1 domain; the term "F(ab')$_2$ fragment" refers to an antibody fragment comprising two Fab fragments linked to each other via disulphide bridge(s) on hinge region.

As used herein, the term "Fv fragment" refers to an antibody fragment consisting of $V_L$ and $V_H$ domain of a single arm of an antibody. Fv fragment is generally taken as the minimum antibody fragment which can form a complete antigen-binding site. It is generally believed that six CDRs confer antigen binding specificity to an antibody. However, even if one variable region (for example, Fd fragment, merely comprising three CDRs specific to antigen) can also recognize and bind antigen, though with an affinity lower than that of an complete binding site.

Under some conditions, antigen binding fragments of an antibody are single chain antibodies (e.g. scFv), wherein $V_L$ and $V_H$ domain are paired to form a monovalent molecule via a linker that enables them to produce a single polypeptide chain (see, for example, Bird et al., Science 242:423-426 (1988) and Huston et al., Proc. Natl. Acad. Sci. USA 85:5879-5883 (1988)). Such scFv molecules generally have a common structure: $NH_2$-$V_L$-linker-$V_H$-COOH or $NH_2$-$V_H$-linker-$V_L$-COOH. Suitable linkers in the prior art consist of repeated amino acid sequence of GGGGS or variants thereof. For example, a linker having an amino acid sequence (GGGGS)$_4$ may be used, and its variants may also be used (Holliger et al., (1993), Proc. Natl. Acad. Sci. USA 90: 6444-6448). Other linkers that may be used in the invention are described by Alfthan et al., (1995), Protein Eng. 8:725-731, Choi et al., (2001), Eur. J. Immunol. 31: 94-106, Hu et al., (1996), Cancer Res. 56:3055-3061, Kipriyanov et al., (1999), J. Mol. Biol. 293:41-56 and Roovers et al., (2001), Cancer Immunol.

As used herein, the term "single chain antibody-Fc" or "scFv-Fc" refers to an engineered antibody formed by linking scFv to Fc fragment of an antibody. As used herein, the term "Fc fragment" refers to an antibody fragment formed by linking the second and third constant regions of the first heavy chain to the second and third constant regions of the second heavy chain via disulfide bond. Fc fragment of antibody has a variety of functions, but is not involved in antigen binding.

Under some conditions, antigen binding fragments of an antibody may be diabodies, i.e. divalent antibodies, wherein $V_H$ and $V_T$, domain are expressed on a single polypeptide chain, however, the linker used is too short to allow the pairing of the two domains on the same chain, the domains have to be paired with the complementary domains on another chain to produce two antigen binding sites (see, for example, Holliger P. et al., Proc. Natl. Acad. Sci. USA 90:6444-6448 (1993), and Poljak R. J. et al., Structure 2:1121-1123 (1994)).

Antigen binding fragments (e.g. the antibody fragments as described above) of an antibody may be obtained from a given antibody (e.g. the monoclonal antibody provided in the invention) by conventional techniques known by a person skilled in the art (e.g. recombinant DNA technique or enzymatic or chemical cleavage methods), and may be screened for specificity in the same manner by which intact antibodies are screened.

In the invention, unless specified definitely, when the term "antibody" is mentioned, it includes not only intact antibodies, but also antigen binding fragments of the antibodies.

As used herein, the terms "mAb" and "monoclonal antibody" refer to an antibody or a fragment of an antibody from a population of highly homologous antibody molecules, i.e. a population of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. Monoclonal antibodies are generally obtained by hybridoma technique reported by Kohler et al. for the first time (Nature, 256:495, 1975), and can also be obtained by recombinant DNA technique (see, for example, U.S. Pat. No. 4,816,567).

For example, monoclonal antibodies may be prepared as follows. Firstly, mice or other suitable host animals are immunized by injection of immunogen (if necessary, adjuvants are added). The injection means of immunogens or adjuvants generally are subcutaneous multi-point injection or intraperitoneal injection. Pre-conjugation of immunogens to some known proteins (e.g. serum albumin or soybean trypsin inhibitor) may promote immunogenicity of antigens in a host. Adjuvants may be Freund's adjuvant or MPL-TDM, etc. After immunization of animal, lymphocytes secreting antibodies that specifically bind to immunogen are produced in the animal. In addition, the lymphocytes may also be obtained by means of in vitro immunization. Lymphocytes of interest are collected and are fused to myeloma cells using a suitable fusion agent (such as PEG), thereby getting hybridoma cells (Goding, Monoclonal Antibodies: Principles and Practice, pp. 59-103, Academic Press, 1996). The hybridoma cells prepared above are seeded to a suitable culture medium and grow in the medium, and the culture medium preferably comprises one or more substances capable of inhibiting growth of unfused, parent myeloma cells. For example, in the case of parent myeloma cells deficient in hypoxanthine guanine phosphoribosyl transferase (HGPRT or HPRT), growth of HGPRT-deficient cells is inhibited by the addition of substances such as hypoxanthine, aminopterin and thymidine (HAT culture medium) to the culture medium. Preferred myeloma cells should have a high fusion rate, stable ability of secreting antibodies, be sensitive to HAT culture medium, and the like. The first choice of myeloma cells is murine myeloma, such as MOP-21 or MC-11 mouse tumor derived cell line (THE Salk Institute Cell Distribution Center, San Diego, Calif. USA), and SP-2/0 or X63-Ag8-653 cell line (American Type Culture Collection, Rockville, Md. USA). In addition, human myeloma and human-mouse heterogeneous myeloma cell lines may be used to prepare human monoclonal antibodies (Kozbor, J. Immunol., 133: 3001 (1984); Brodeur et al., Monoclonal Antibody Production Techniques and Applications, pp. 51-63, Marcel Dekker, Inc., New York, 1987). Culture media for growing hybridoma cells are used to detect the generation of monoclonal antibodies against specific antigens. The following methods may be used to determine the binding specificity of monoclonal antibodies produced by hybridoma cells, immunoprecipitation or in vitro binding assays, such as Radioimmunoassay (RIA) and enzyme linked immunosorbent assay (ELISA). For example, Scatchard assay described in Munson et al., Anal. Biochem. 107: 220 (1980) may be used to determine the affinity of monoclonal antibodies. After determining the specificity, affinity and reactivity of antibodies produced by hybridomas, cell lines of interest may be subcloned by the standard limiting dilution method described in Goding, Monoclonal Antibodies: Principles and Practice, pp. 59-103, Academic Press, 1996. A suitable culture medium may be DMEM or RPMI-1640, etc. In addition, hybridoma cells may grow in a form of ascites tumor in animal bodies. By using traditional methods for purifying immunoglobulins, such as Protein A agarose gel, hydroxyapatite chromatography, gel electrophoresis, dialysis and affinity chromatography, monoclonal antibodies secreted by subclone cells may be isolated from cell culture, ascites or serum.

Monoclonal antibodies may also be obtained by genetic engineering recombinant techniques. The nucleic acid primers that specifically bind to genes of MAb heavy chain and light chain are subjected to PCR amplification, to obtain the DNA molecules encoding MAb heavy chain and light chain from hybridoma cells. The DNA molecules obtained are inserted into an expression vector, host cells (e.g. E. coli cells, COS cells, CHO cells, or other myeloma cells that do not produce immunoglobulin) are transfected with them and are cultured under suitable conditions to obtain antibodies of interest by recombinant expression.

As used herein, the terms "antigenic epitope" and "epitope" refer to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g. an antibody) are present linearly along the primary amino acid sequence of the protein. In a conformational epitope, the interaction sites span over amino acid residues that separate the interaction sites from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens. High-throughput methods for obtaining antibodies binding to the same epitope, which are based on their cross-competition, are described in an international patent application WO 03/48731.

As used herein, the term "specifically bind" or "specifically binding" refers to the binding of two molecules in a non-random manner, such as the reaction between an antibody and the antigen it directs to. In some embodiments, an antibody that specifically binds to an antigen (or an antibody specific for an antigen) refers to an antibody that binds to the antigen with an affinity ($K_D$) of less than about $10^{-5}$ M, e.g. of less than about $10^{-6}$ M, $10^{-7}$ M, $10^{-8}$ M, $10^{-9}$ M or $10^{-10}$ M or less.

As used herein, the term "$K_D$" refers to a dissociation constant of a specific antibody-antigen interaction, which is used to describe the binding affinity of an antibody to an antigen. The smaller the dissociation constant, the more tightly bound the antibody is, and the higher the affinity between antibody and antigen. Generally, an antibody (e.g. the antibody according to the invention) binds to an antigen (e.g. HBsAg) with a $K_D$ of less than about $10^{-5}$ M, e.g. less than about $10^{-6}$ M, $10^{-7}$ M, $10^{-8}$ M, $10^{-9}$ M or $10^{-10}$ M or less, determined by, for example, surface plasmon resonance (SPR) in BIACORE device.

As used herein, the term "immunogenicity" refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response in which antibody or sensitized T lymphocyte can be formed in immune system of an organism after stimulation of an antigen. When a heterologous antibody is applied to a subject, the immunogenicity of the heterologous antibody is unwanted in the subject. Such immunogenicity can lead to the rejection of the heterologous antibody by the immune system/immune cell of the subject, thereby resulting in reduced efficacy of the heterologous antibody in the subject or unwanted side effects in the subject. Therefore, before administered to a human subject, a heterologous antibody (e.g. a murine antibody) generally needs to be engineered to reduce its immunogenicity as much as possible.

As used herein, the term "chimeric antibody" refers to such an antibody wherein a part of its light chain and/or heavy chain is derived from an antibody (which may be originated from a specific species or belongs to a specific antibody type or subtype), and the other part of its light chain and/or heavy chain is derived from another antibody (which may be originated from an identical or different species or belongs to an identical or different antibody type or subtype), provided that the antibody still retains the activity of binding to the antigen of interest (U.S. Pat. No. 4,816,567 to Cabilly et al.; Morrison et al., Proc. Natl. Acad. Sci. USA, 81: 6851-6855 (1984)). For example, the term "chimeric antibody" may include such an antibody (e.g. human-murine chimeric antibody), wherein the heavy chain and light chain variable region of the antibody are from a first antibody (e.g. a murine antibody), while the heavy chain and light chain constant region of the antibody are from a second antibody (e.g. a human antibody).

As used herein, the term "humanized antibody" refers to an antibody or antibody fragment in which all the CDR regions or a part of CDR regions of human immunoglobulin (receptor antibody) are replaced with the CDR regions of a non-human antibody (donor antibody). A humanized antibody generally retains the expected properties including, but not limited to antigen specificity, affinity, reactivity, virus-neutralizing ability and/or virus-cleaning ability, etc. A donor antibody may be a mouse, rat, rabbit or non-human primate antibody having the expected properties (e.g. antigen specificity, affinity, reactivity, virus-neutralizing ability and/or virus-clearing ability).

Since a humanized antibody can not only retain the expected properties of a non-human donor antibody (e.g. a murine antibody), but also effectively reduce the immunogenicity of the non-human donor antibody (e.g. a murine antibody) in a human subject, it is particularly favorable. However, due to the matching problem between CDRs of a donor antibody and FRs of a receptor antibody, the expected property (e.g. antigen specificity, affinity, reactivity, virus-neutralizing ability and/or virus-clearing ability) of a humanized antibody is generally lower than that of a non-human donor antibody (e.g. a murine antibody). Therefore, in order to make a humanized antibody retain the properties (including antigen specificity, affinity, reactivity, virus-neutralizing ability and/or virus-clearing ability) of a donor antibody as much as possible, in some cases, some amino acid residues in the framework regions (FRs) of the humanized antibody are substituted with the corresponding amino acid residues of the non-human donor antibody.

In addition, in order to further enhance the humanization degree to reduce the immunogenicity resulted from non-human amino acid residues as much as possible, in some cases, some amino acid residues of CDRs derived from a donor antibody in a humanized antibody can be substituted, for example, with the corresponding amino acid residues in CDRs of human immunoglobulin, or other amino acid residues.

In addition, in order to further improve or optimize the properties of a humanized antibody, some amino acid residues in the heavy chain and light chain variable region of a humanized antibody, can also be substituted, for example, with the amino acid residues that are neither from a receptor antibody nor from a donor antibody.

Although researchers in the art have conducted deep research on humanization of antibodies, and have made some progress (see, for example, Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000)), no detailed guidance is provided in the prior art, with respect to how to sufficiently humanize a certain donor antibody to enable the resultant humanized antibody to have a humanization degree as high as possible while retaining the expected properties of the donor antibody as much as possible. Those skilled in the art have to investigate, explore and engineer a particular donor antibody, and have to pay a lot of creative work to obtain a humanized antibody that not only has a high humanization degree (e.g. a humanization degree of at least 80%, at least 85%, at least 90%, at least 91%, at least 92%, at least 93%, at least 94%, at least 95%, at least 96%, at least 97%, at least 98%, at least 99%, or 100%), but also retains the expected properties of the donor antibody.

In the present application, the inventors first developed a murine antibody (its heavy chain and light chain variable region are set forth in SEQ ID NO: 1 and 2, respectively) having good properties: the murine antibody can not only specifically recognize/bind HBsAg, neutralize HBV virulence, but also reduce the serum level of HBV DNA and/or HBsAg in a subject, and effectively clear HBV and HBV-infected cells in vivo. Therefore, the murine antibody has potential in preventing and treating HBV infection and a disease associated with HBV infection (such as Hepatitis B).

On the basis of this, the inventor further paid a lot of creative work to study and engineer the murine antibody deeply, and therefore developed the humanized antibodies of the murine antibody: the humanized antibodies according to the invention not only have a very high humanization degree (a humanization degree of up to 97%), but also have substantively the same (or even better) expected properties (including, but not limited to, HBsAg binding activity, HBV-neutralizing activity, activity of clearing HBV DNA or HBsAg in vivo, or activity of clearing HBV and HBV-infected cells in vivo, etc.) as the murine antibody and human-murine chimeric antibody (which has completely identical heavy chain and light chain variable region as the murine antibody).

Therefore, the antibody according to the invention (particularly a humanized antibody) can be very favorable, as it can retain the functions and properties of the parent murine antibody, and therefore have potential in preventing and treating HBV infection and a disease associated with HBV infection (such as Hepatitis B); moreover, the antibody can have a very high humanization degree (a humanization degree of up to 97%), and therefore can be administered to a human subject safely, without raising an immunogenic response. The antibody according to the invention (particularly a humanized antibody) can have important clinical value.

In the present application, the expected properties of the antibody according to the invention include the activity of specifically binding to HBsAg, activity of neutralizing HBV, activity of clearing HBV DNA or HBsAg in vivo, and/or activity of clearing HBV and HBV-infected cells in vivo. The humanized antibody according to the invention can retain one or more of the expected properties of the parent murine antibody, preferably retain all the above-mentioned expected properties of the parent murine antibody.

In the present application, the parent murine antibody and humanized antibody according to the invention are further engineered, for example, some amino acid residues in their CDRs and FRs are subjected to substitutions (for example, conservative substitution). Such substitutions can, for example, (1) reduce sensitivity of antibodies to proteolysis; (2) reduce susceptibility of antibodies to oxidization; (3) change (e.g. enhance) antigen binding affinity of antibodies; (4) change (e.g. enhance) HBV-neutralizing activity of antibodies; (5) change (e.g. enhance) HBV-clearing activity of antibodies; (6) further enhance humanization degree of antibodies to reduce immunogenicity of antibodies; or (7) change other biochemical characteristics or functional properties of antibodies; but still retain the expected properties of antibodies. Such substitutions can be present in CDRs and/or FRs, and can be a single amino acid substitution or multiple amino acid substitutions.

As used herein, the term "humanization degree" is an index indicating the number of non-human amino acid residues in a humanized antibody. The humanization degree of a humanized antibody can be calculated by, for example, the following formula: humanization degree=(number of amino acids in FR−number of non-human amino acids in FR)/number of amino acids in FR×100%.

As used herein, the term "neutralizing antibody" refers to an antibody or an antigen binding fragment thereof that can significantly reduce or completely inhibit the virulence (e.g. ability of infecting cells) of a target virus. In general, a neutralizing antibody can recognize and bind to a target virus, and prevent the target virus from entering/infecting the cell in a subject. The antibody according to the invention is a neutralizing antibody.

However, it should be understood that in the present application, the virus-neutralizing ability of an antibody is not directly equivalent to the virus-clearing ability of an antibody. As used herein, "neutralizing virus" means that the virulence of a target virus is neutralized (i.e. the virulence of a target virus is significantly reduced or completely inhibited) by inhibiting the target virus from entering/infecting the cell of a subject. As used herein, "clearing virus" means that a target virus (no matter it infects a cell or not) is eliminated from an organism, and therefore the organism turns toward the state before infection by the virus (e.g. the serological test result of virus turns negative). Therefore, in general, neutralizing antibodies do not necessarily have virus-clearing ability. However, in the present application, the inventor surprisingly found that the antibodies according to the invention can not only neutralize HBV, but also clear virus (i.e. can clear HBV DNA and/or HBsAg in vivo, clear HBV and HBV-infected cells in vivo), and therefore have important clinical value.

As used herein, the term "isolated" refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprises multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, prokaryotic cell such as *E. coli* or *Bacillus subtilis*, and fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the terms "conservative substitution" and "conservative amino acid substitution" refer to amino acid substitutions which would not disadvantageously affect or change the expected properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

The 20 conventional amino acids involved herein are expressed in accordance with routine methods. See, for example, Immunology-A Synthesis (2nd Edition, E. S. Golub and D. R. Gren, Eds., Sinauer Associates, Sunderland, Mass. (1991)), which is incorporated herein by reference. In the invention, the terms "polypeptide" and "protein" have the same meanings, and can be used interchangeably. Moreover, in the invention, amino acids are generally expressed as one-letter codes and three-letter codes. For example, alanine may be expressed as A or Ala. In addition, as used herein, the term "monoclonal antibody" and "mAb" have the same meanings, and can be used interchangeably; the terms "polyclonal antibody" and "pAb" have the same meanings, and can be used interchangeably.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to a pH adjuster, a surfactant, an adjuvant, an ionic strength enhancer, a diluent, an osmotic pressure-controlling agent, an absorption delaying agent, and a preservative. For example, the pH adjuster includes, but is not limited to, phosphate buffer. The surfactant includes, but is not limited to, cationic, anionic, or non-ionic surfactant, e.g. Tween-80. The ionic strength enhancer includes, but is not limited to, sodium chloride. The preservative includes, but is not limited to a variety of antibacterial agents and antifungal agents, such as paraben, chlorobutanol, phenol, and sorbic acid. The osmotic pressure-controlling agent includes, but is not limited to sugar, NaCl and analogs thereof. The absorption delaying agent includes, but is not limited to monostearate and gelatin.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium *parvum*, lipopolysaccharide, cytokines, and the like. Freund's adjuvant is the most commonly used adjuvant in animal experiments now. Aluminum hydroxide adjuvant is more commonly used in clinical trials.

As used herein, the term "prevention/preventing" refers to a method that is carried out in order to suppress or delay the occurrence of a disease, a disorder or a symptom (such as HBV infection or a disease associated with HBV infection) in a subject. As used herein, the term "treatment/treating" refers to a method that is carried out in order to obtain a beneficial or desired clinical outcome. For the purpose of the invention, the beneficial or desired clinical outcome includes, but is not limited to, easing symptom, narrowing the scope of disease, stabilizing (i.e. not aggravating) the state of disease, delaying or slowing the progress of disease, and alleviating symptoms (either partially or completely), no matter detectable or not detectable. In addition, "treatment" also refers to a prolonged survival period compared to the expected survival period (if no treatment is accepted). In the present application, the antibody according to the invention has the ability of neutralizing HBV, and therefore can be used to prevent/protect an unaffected subject or a cell thereof from infection by HBV. In addition, the antibody according to the invention has the ability of clearing HBV (i.e. able to clear HBV DNA and/or HBsAg in vivo, clear HBV and cells infected by HBV in vivo), and therefore can be used to treat HBV infection or a disease associated with HBV infection in an infected subject.

As used herein, the term "subject" refers to mammal, for example, primate mammal, such as human.

As used herein, the term "an effective amount" refers to an amount that is sufficient to achieve or at least partially achieve the expected effect. For example, an amount effective for preventing a disease (such as HBV infection or diseases associated with HBV infection) refers to an amount effective for preventing, suppressing, or delaying the occurrence of a disease (such as HBV infection or diseases associated with HBV infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

Antibodies According to the Invention

In the present application, the inventor first developed a murine antibody (its heavy chain and light chain variable region are set forth in SEQ ID NO: 1 and 2, respectively) having good properties: the murine antibody can not only specifically recognize/bind HBsAg, but also neutralize HBV virulence, reduce the serum level of HBV DNA and/or HBsAg in a subject, and effectively clear HBV and HBV-infected cells in vivo. Therefore, the murine antibody has potential in preventing and treating HBV infection and a disease associated with HBV infection (such as Hepatitis B).

On the basis of this, the inventor further paid a lot of creative work to study and engineer the murine antibody deeply, and therefore developed the humanized antibody of the murine antibody: the humanized antibody according to the invention can not only have a very high humanization degree (a humanization degree of up to 97%), but also have substantively the same (or even better) expected properties (including, but not limited to, HBsAg binding activity, HBV-neutralizing activity, activity of clearing HBV DNA or HBsAg in vivo, or activity of clearing HBV and HBV-infected cells in vivo, etc.) as the murine antibody and human-murine chimeric antibody (heavy chain and light chain variable region of which is completely identical to that of the murine antibody).

Therefore, the antibody according to the invention (particularly a humanized antibody) is very favorable as it retains the functions and properties of its parent murine antibody, and therefore has potential in preventing and treating HBV infection and a disease associated with HBV infection (such as Hepatitis B); moreover, it has a very high humanization degree (a humanization degree of up to 97%), and therefore can be administered to a human subject safely, without raising an immunogenic response. The antibody according to the invention (particularly a humanized antibody) has important clinical value.

Therefore, in one aspect, the invention provides an antibody or an antigen binding fragment thereof, which can specifically bind to HBsAg, comprising:

(a) one or more (e.g. 1, 2 or 3) complementarity determining regions (CDRs) of heavy chain variable region (VH) selected from the group consisting of:

(i) VH CDR1, consisting of the following sequence: SEQ ID NO: 3, or a sequence that differs from SEQ ID NO:3 by one or several substitutions, deletions or additions (e.g. 1, 2 or 3 substitutions, deletions or additions);

(ii) VH CDR2, consisting of the following sequence: SEQ ID NO: 4, or a sequence that differs from SEQ ID NO:4 by one or several substitutions, deletions or additions (e.g. 1, 2, 3, 4, 5 or 6 substitutions, deletions or additions), and (iii) VH CDR3, consisting of the following sequence: SEQ ID NO: 5, or a sequence that differs from SEQ ID NO:5 by one or several substitutions, deletions or additions (e.g. 1, or 2 substitutions, deletions or additions);

and/or (b) one or more (e.g. 1, 2 or 3) CDRs of light chain variable region (VL) selected from the group consisting of:

(iv) VL CDR1, consisting of the following sequence: SEQ ID NO: 6, or a sequence that differs from SEQ ID NO:6 by one or several substitutions, deletions or additions (e.g. 1, 2 or 3 substitutions, deletions or additions), (v) VL CDR2, consisting of the following sequence: SEQ ID NO: 7, or a sequence that differs from SEQ ID NO:7 by one or several substitutions, deletions or additions (e.g. 1, 2, 3 or 4 substitutions, deletions or additions), and (vi) VL CDR3, consisting of the following sequence: SEQ ID NO: 8, or a sequence that differs from SEQ ID NO:8 by one or several substitutions, deletions or additions (e.g. 1, 2, 3 or 4 substitutions, deletions or additions).

In some preferred embodiments, the antibody or an antigen binding fragment thereof according to the invention comprises VH CDR1, VH CDR2 and VH CDR3 as defined above. In some preferred embodiments, the antibody or an antigen binding fragment thereof according to the invention comprises VL CDR1, VL CDR2 and VL CDR3 as defined above. In some preferred embodiments, the antibody or an antigen binding fragment thereof according to the invention comprises VH CDR1, VH CDR2, VH CDR3, VL CDR1, VL CDR2 and VL CDR3 as defined above.

In some preferred embodiments, VH CDR1 of the antibody or an antigen binding fragment thereof according to the invention is SEQ ID NO: 3, or differs from SEQ ID NO: 3 by one or more substitutions (e.g. 1, 2 or 3 substitutions) selected from the group consisting of:

(01) R, Y, H, or N at H31;
(02) Y, F, W, or D at H32;
(03) N, or L at H34;
(04) Y, H, or P at H35; and
(05) I, S, P, G, or H at H35A;

wherein, the amino acid positions mentioned in (01)-(05) are numbered according to Kabat numbering system.

In some preferred embodiments, VH CDR1 of the antibody or an antigen binding fragment thereof according to the invention is SEQ ID NO: 3, or differs from SEQ ID NO: 3 by one or more substitutions (e.g. 1 or 2 substitutions) selected from the group consisting of:

(01) R, Y, H, or N (preferably, R or Y) at H31; and
(02) Y, F, W, or D (preferably, W or D) at H32;

wherein, the amino acid positions mentioned in (01)-(02) are numbered according to Kabat numbering system.

In some preferred embodiments, VH CDR1 of the antibody or an antigen binding fragment thereof according to the invention is SEQ ID NO: 3, or differs from SEQ ID NO: 3 by one or more substitutions (e.g. 1 or 2 substitutions) selected from the group consisting of:

(01) R or Y at H31; and
(02) W at H32;

wherein, the amino acid positions mentioned in (01)-(02) are numbered according to Kabat numbering system.

In some preferred embodiments, the VH CDR1 of the antibody or an antigen binding fragment thereof according to the invention has a sequence selected from the group consisting of:

SGYHWN; (SEQ ID NO: 3)

RGYHWN; (SEQ ID NO: 121)

HGYHWN; (SEQ ID NO: 122)

NGYHWN; (SEQ ID NO: 123)

RDYHWN; (SEQ ID NO: 125)

RWYHWN; (SEQ ID NO: 126)

YGYHWN; (SEQ ID NO: 124)

NFYHWN; (SEQ ID NO: 127)
and

RYYHWN. (SEQ ID NO: 128)

In some preferred embodiments, the sequence of the VH CDR1 of the antibody or an antigen binding fragment thereof according to the invention is selected from the group consisting of:

SGYHWN; (SEQ ID NO: 3)

RWYHWN; (SEQ ID NO: 126)

HGYHWN; (SEQ ID NO: 122)

YGYHWN; (SEQ ID NO: 124)

RGYHWN; (SEQ ID NO: 121)

NGYHWN; (SEQ ID NO: 123)
and

RDYHWN. (SEQ ID NO: 125)

In some preferred embodiments, the sequence of the VH CDR1 of the antibody or an antigen binding fragment thereof according to the invention is selected from the group consisting of:

SGYHWN; (SEQ ID NO: 3)

RWYHWN; (SEQ ID NO: 126)

YGYHWN; (SEQ ID NO: 124)
and

RGYHWN. (SEQ ID NO: 121)

In some preferred embodiments, VH CDR2 of the antibody or an antigen binding fragment thereof according to the invention is SEQ ID NO: 4, or differs from SEQ ID NO: 4 by one or more substitutions (e.g. 1, 2, 3, 4, 5 or 6 substitutions) selected from the group consisting of:

(06) R, G, L, F, S, or V at H50;
(07) V, M, L, T, F, or C at H51;
(08) D, A, G, V, F, or P at H52;
(09) P, N, S, E, L, F, K, or I at H53;

(10) V, T, N, L, A, S, I, or F at H54;
(11) I, H, S, F, C, E, L, or V at H55;
(12) N, A, M, L, Q, G, F, T, P, V, or R at H56;
(13) any naturally occurring amino acid at H57;
(14) S, T, F, W, Y, V, G, E, L, Q, or R at H58;
(15) S, A, L, or D at H61;
(16) G, E, or R at H62;
(17) H, or F at H63;
(18) L, A, I, T, G, K, or V at H64; and
(19) G, R, S, W, H, D, A, or Y at H65;
wherein, the amino acid positions mentioned in (06)-(19) are numbered according to Kabat numbering system.

In some preferred embodiments, VH CDR2 of the antibody or an antigen binding fragment thereof according to the invention is SEQ ID NO: 4, or differs from SEQ ID NO: 4 by one or more substitutions (e.g. 1, 2, 3, 4, 5 or 6 substitutions) selected from the group consisting of:
(08) A, or G at H52;
(09) N at H54;
(12) N, A, T, or V at H56;
(13) V, I, S, N, Q, or R at H57;
(14) S, F, L, Q, or R at H58;
(18) K at H64; and
(19) G, or S at H65;
wherein, the amino acid positions mentioned above are numbered according to Kabat numbering system.

In some preferred embodiments, VH CDR2 of the antibody or an antigen binding fragment thereof according to the invention is SEQ ID NO: 4, or differs from SEQ ID NO: 4 by one or more substitutions (e.g. 1, 2 or 3 substitutions) selected from the group consisting of:
(12) T at H56;
(13) V, I, or N (preferably V or N) at H57; and
(14) L at H58;
wherein, the amino acid positions mentioned above are numbered according to Kabat numbering system.

In some preferred embodiments, the VH CDR2 of the antibody or an antigen binding fragment thereof according to the invention has a sequence selected from the group consisting of:

```
                                  (SEQ ID NO: 4)
YISYDGSDHYNPSLEN;

(SEQ ID NO: 143)
YISYDGSVFYNPSLEN;

(SEQ ID NO: 144)
YISYDGSILYNPSLEN;

(SEQ ID NO: 145)
YISYDGTILYNPSLEN;

(SEQ ID NO: 146)
YISYDGTVLYNPSLEN;

(SEQ ID NO: 147)
YISYDGNVLYNPSLEN;

(SEQ ID NO: 148)
YISYDGTSLYNPSLEN;

(SEQ ID NO: 149)
YISYDGSVLYNPSLEN;

(SEQ ID NO: 150)
YISYDGNILYNPSLEN;

(SEQ ID NO: 151)
YISYDGTNLYNPSLEN;
```

-continued
```
                                  (SEQ ID NO: 152)
YISYDGSNLYNPSLEN;

(SEQ ID NO: 153)
YISYDGTVHYNPSLEN;

(SEQ ID NO: 154)
YISYDGTIRYNPSLEN;

(SEQ ID NO: 155)
YISYDGSVLYNPSLKS;

(SEQ ID NO: 156)
YISYDGSVLYNPSLKG;

(SEQ ID NO: 157)
YIAYDGVQSYNPSLKG;

(SEQ ID NO: 158)
YIGYDGAVQYNPSLKS;

(SEQ ID NO: 159)
YISYNGSVLYNPSLKS;

(SEQ ID NO: 160)
YISYDGSRLYNPSLKS;
and
                                  (SEQ ID NO: 285)
YISYDGSVLFNPSLKS
```

In some preferred embodiments, the sequence of the VH CDR2 of the antibody or an antigen binding fragment thereof according to the invention is selected from the group consisting of:

```
                                  (SEQ ID NO: 4)
YISYDGSDHYNPSLEN;

(SEQ ID NO: 146)
YISYDGTVLYNPSLEN;

(SEQ ID NO: 145)
YISYDGTILYNPSLEN;

(SEQ ID NO: 149)
YISYDGSVLYNPSLEN;

(SEQ ID NO: 151)
YISYDGTNLYNPSLEN;
and
                                  (SEQ ID NO: 144)
YISYDGSILYNPSLEN.
```

In some preferred embodiments, the sequence of the VH CDR2 of the antibody or an antigen binding fragment thereof according to the invention is selected from the group consisting of:

```
                                  (SEQ ID NO: 4)
YISYDGSDHYNPSLEN;

(SEQ ID NO: 146)
YISYDGTVLYNPSLEN;

(SEQ ID NO: 149)
YISYDGSVLYNPSLEN;
and
                                  (SEQ ID NO: 151)
YISYDGTNLYNPSLEN.
```

In some preferred embodiments, VH CDR3 of the antibody or an antigen binding fragment thereof according to the invention is SEQ ID NO: 5, or differs from SEQ ID NO: 5 by one or more substitutions (e.g. 1 or 2 substitutions) selected from the group consisting of:
(20) N at H101; and
(21) Y, R, S, T, A, L, or I at H102;
wherein, the amino acid positions mentioned in (20)-(21) are numbered according to Kabat numbering system.

In some preferred embodiments, VH CDR3 of the antibody or an antigen binding fragment thereof according to the invention is SEQ ID NO: 5, or differs from SEQ ID NO: 5 by Y or T (preferably, Y) at H102.

In some preferred embodiments, the VH CDR3 of the antibody or an antigen binding fragment thereof according to the invention has a sequence selected from the group consisting of:

```
                                            (SEQ ID NO: 5)
           GFDH;

(SEQ ID NO: 181)
           GFDY;
           and (SEQ ID NO: 182)
           GFDT.
```

In some preferred embodiments, VL CDR1 of the antibody or an antigen binding fragment thereof according to the invention is SEQ ID NO: 6, or differs from SEQ ID NO: 6 by one or more substitutions (e.g. 1, 2 or 3 substitutions) selected from the group consisting of:
(22) H, L, W, S, T, or C at L24;
(23) L, V, P, or N at L25;
(24) G, E, V, Y, A, N, or D at L26;
(25) T, R, H, M, Y, V, or A at L27;
(26) Q, or F at L27A;
(27) E, F, N, W, G, or L at L27C;
(28) L, V, G, W, Y, S, F, or N at L27D;
(29) P, R, V, T, or M at L27E;
(30) F, W, G, D, A, E, R, L, S, V, or K at L28;
(31) F, I, Y, D, V, or L at L29;
(32) E, S, C, F, R, A, Q, L, P, N, M, or T at L30;
(33) I, V, Q, F, M, A, C, R, S, or L at L31;
(34) W, F, G, or L at L32;
(35) R, V, F, S, M, A, P, or Y at L33; and
(36) F, N, R, Q, or G at L34;
wherein, the amino acid positions mentioned in (22)-(36) are numbered according to Kabat numbering system.

In some preferred embodiments, VL CDR1 of the antibody or an antigen binding fragment thereof according to the invention is SEQ ID NO: 6, or differs from SEQ ID NO: 6 by one or more substitutions (e.g. 1 or 2 substitutions) selected from the group consisting of:
(29) P, R, or T at L27E; and
(32) S, R, A, P, N, or T at L30;
wherein, the amino acid positions mentioned above are numbered according to Kabat numbering system.

In some preferred embodiments, the VL CDR1 of the antibody or an antigen binding fragment thereof according to the invention has a sequence selected from the group consisting of:

```
                                            (SEQ ID NO: 6)
           RSSQSLVHSYGDTYLH;

(SEQ ID NO: 232)
           RSNQSLVHSYGDTYLH;

(SEQ ID NO: 234)
           RSSQSLVHPYGPTYLH;

(SEQ ID NO: 235)
           RSSQSLVHTYGNTYLH;

(SEQ ID NO: 236)
           RSSQSLVHPYGSTYLH;

(SEQ ID NO: 237)
           RSSQSLVHRYGTTYLH;

(SEQ ID NO: 238)
           RSSQSLVHPYGATYLH;

(SEQ ID NO: 239)
           RSSQSLVHPYGRTYLH;

(SEQ ID NO: 318)
           RSSQSLVHPFGPTYLH;

(SEQ ID NO: 319)
           RSSQSLAHPYGSTYLH;
           and (SEQ ID NO: 320)
           RSSQSLVHPYGSTYFH.
```

In some preferred embodiments, the sequence of the VL CDR1 of the antibody or an antigen binding fragment thereof according to the invention is SEQ ID NO: 6.

In some preferred embodiments, VL CDR2 of the antibody or an antigen binding fragment thereof according to the invention is SEQ ID NO: 7, or differs from SEQ ID NO: 7 by one or more substitutions (e.g. 1, 2, 3 or 4 substitutions) selected from the group consisting of:
(37) N, R, F, S, T, or L at L50;
(38) C, A, N, D, S, or L at L51;
(39) L, V, M, W, A, or F at L52;
(40) C, H, K, R, P, Q, or S at L53;
(41) I, F, N, M, or L at L54;
(42) R, N, or C at L55; and
(43) L, F, W, T, K, R, or Q at L56;
wherein, the amino acid positions mentioned in (37)-(43) are numbered according to Kabat numbering system.

In some preferred embodiments, VL CDR2 of the antibody or an antigen binding fragment thereof according to the invention is SEQ ID NO: 7, or differs from SEQ ID NO: 7 by one or more substitutions (e.g. 1, 2, 3 or 4 substitutions) selected from the group consisting of:
(37) R at L50;
(38) A or S at L51;
(40) H, K, or Q at L53; and
(42) N at L55;
wherein, the amino acid positions mentioned above are numbered according to Kabat numbering system.

In some preferred embodiments, the VL CDR2 of the antibody or an antigen binding fragment thereof according to the invention has a sequence selected from the group consisting of:

```
                                            (SEQ ID NO: 7)
           KVSNRFS;

(SEQ ID NO: 241)
           KVSKRNS;

(SEQ ID NO: 242)
           KASQRNS;
           and
```

-continued

RSSHRNS;  (SEQ ID NO: 243)

In some preferred embodiments, the sequence of the VL CDR2 of the antibody or an antigen binding fragment thereof according to the invention is SEQ ID NO: 7.

In some preferred embodiments, VL CDR3 of the antibody or an antigen binding fragment thereof according to the invention is SEQ ID NO: 8, or differs from SEQ ID NO: 8 by one or more substitutions (e.g. 1, 2, 3 or 4 substitutions) selected from the group consisting of:

(44) L, G, N, T, or V at L89;
(45) H, or S at L90;
(46) A, S, or P at L92;
(47) A, S, K, R, L, T, Y, F, W, N, M, V, I, or E at L93;
(48) T, N, D, K, F, Y, P, H, L, R, S, A, or G at L94;
(49) A, I, S, C, or V at L95;
(50) N, A, V, R, T, or H at L96; and
(51) S at L97;

wherein, the amino acid positions mentioned in (44)-(51) are numbered according to Kabat numbering system;

In some preferred embodiments, VL CDR3 of the antibody or an antigen binding fragment thereof according to the invention is SEQ ID NO: 8, or differs from SEQ ID NO: 8 by one or more substitutions (e.g. 1, 2, 3 or 4 substitutions) selected from the group consisting of:

(44) G at L89;
(46) A, or S at L92;
(47) K, R, Y, M, or I at L93; and
(48) T, P, L, or A at L94;

wherein, the amino acid positions mentioned above are numbered according to Kabat numbering system;

Preferably, the VL CDR3 is SEQ ID NO: 8, or differs from SEQ ID NO: 8 by L at L94.

In some preferred embodiments, the VL CDR3 of the antibody or an antigen binding fragment thereof according to the invention has a sequence selected from the group consisting of:

SQNTHVPYT;  (SEQ ID NO: 8)

SQNTHLPYT;  (SEQ ID NO: 245)

GQNAKTPYT;  (SEQ ID NO: 246)

GQNARVPYT;  (SEQ ID NO: 247)

SQNSYVPYT;  (SEQ ID NO: 248)

SQNTIPPYT;  (SEQ ID NO: 249)

GQNSMAPYT;  (SEQ ID NO: 250)
and

GQNAHLPYT.  (SEQ ID NO: 251)

In some preferred embodiments, the sequence of the VL CDR3 of the antibody or an antigen binding fragment thereof according to the invention is selected from the group consisting of:

SQNTHVPYT;  (SEQ ID NO: 8)
and

SQNTHLPYT.  (SEQ ID NO: 245)

In some preferred embodiments, the antibody or an antigen binding fragment thereof according to the invention comprises a VL comprising, a combination of VL CDR1, VL CDR2 and VL CDR3 selected from any one of the following (1)-(16):

|      | VL-CDR1 (SEQ ID NO:) | VL-CDR2 (SEQ ID NO:) | VL-CDR3 (SEQ ID NO:) |
|------|------|------|------|
| (1)  | 232 | 240 | 244 |
| (2)  | 233 | 240 | 244 |
| (3)  | 233 | 240 | 245 |
| (4)  | 233 | 240 | 246 |
| (5)  | 233 | 240 | 247 |
| (6)  | 233 | 240 | 248 |
| (7)  | 233 | 240 | 249 |
| (8)  | 233 | 240 | 250 |
| (9)  | 234 | 240 | 244 |
| (10) | 234 | 240 | 251 |
| (11) | 234 | 241 | 244 |
| (12) | 235 | 240 | 244 |
| (13) | 236 | 240 | 244 |
| (14) | 237 | 240 | 244 |
| (15) | 238 | 242 | 244 |
| (16) | 239 | 243 | 244 |

In some preferred embodiments, the antibody or an antigen binding fragment thereof according to the invention comprises a VL comprising:

(a) VL CDR1 as set forth in RSSQSLVHSYGDTYLH (SEQ ID NO: 6); VL CDR2 as set forth in KVSNRFS (SEQ ID NO: 7); and, VL CDR3 as set forth in SQNTHVPYT (SEQ ID NO: 8);

(b) VL CDR1 as set forth in RSSQSLVHSYGDTYLH (SEQ ID NO: 6); VL CDR2 as set forth in KVSNRFS (SEQ ID NO: 7); and, VL CDR3 as set forth in SQNTHLPYT (SEQ ID NO: 245);

(c) VL CDR1 as set forth in RSNQSLVHSYGDTYLH (SEQ ID NO: 232); VL CDR2 as set forth in KVSNRFS (SEQ ID NO: 7); and, VL CDR3 as set forth in SQNTHVPYT (SEQ ID NO: 8);

(d) VL CDR1 as set forth in RSSQSLVHSYGDTYLH (SEQ ID NO: 6); VL CDR2 as set forth in KVSNRFS (SEQ ID NO: 7); and, VL CDR3 as set forth in GQNAKTPYT (SEQ ID NO: 246);

(e) VL CDR1 as set forth in RSSQSLVHSYGDTYLH (SEQ ID NO: 6); VL CDR2 as set forth in KVSNRFS (SEQ ID NO: 7); and, VL CDR3 as set forth in GQNARVPYT (SEQ ID NO: 247);

(f) VL CDR1 as set forth in RSSQSLVHSYGDTYLH (SEQ ID NO: 6); VL CDR2 as set forth in KVSNRFS (SEQ ID NO: 7); and, VL CDR3 as set forth in SQNSYVPYT (SEQ ID NO: 248);

(g) VL CDR1 as set forth in RSSQSLVHSYGDTYLH (SEQ ID NO: 6); VL CDR2 as set forth in KVSNRFS (SEQ ID NO: 7); and, VL CDR3 as set forth in SQNTIPPYT (SEQ ID NO: 249);

(h) VL CDR1 as set forth in RSSQSLVHSYGDTYLH (SEQ ID NO: 6); VL CDR2 as set forth in KVSNRFS (SEQ ID NO: 7); and, VL CDR3 as set forth in GQNSMAPYT (SEQ ID NO: 250);

(i) VL CDR1 as set forth in RSSQSLVHPYGPTYLH (SEQ ID NO: 234); VL CDR2 as set forth in KVSKRNS (SEQ ID NO: 241); and, VL CDR3 as set forth in SQNTHVPYT (SEQ ID NO: 8);

(j) VL CDR1 as set forth in RSSQSLVHPYGPTYLH (SEQ ID NO: 234); VL CDR2 as set forth in KVSNRFS (SEQ ID NO: 7); and, VL CDR3 as set forth in SQNTHVPYT (SEQ ID NO: 8);

(k) VL CDR1 as set forth in RSSQSLVHTYGNTYLH (SEQ ID NO: 235); VL CDR2 as set forth in KVSNRFS (SEQ ID NO: 7); and, VL CDR3 as set forth in SQNTHVPYT (SEQ ID NO: 8);

(l) VL CDR1 as set forth in RSSQSLVHPYGSTYLH (SEQ ID NO: 236); VL CDR2 as set forth in KVSNRFS (SEQ ID NO: 7); and, VL CDR3 as set forth in SQNTHVPYT (SEQ ID NO: 8);

(m) VL CDR1 as set forth in RSSQSLVHRYGTTYLH (SEQ ID NO: 237); VL CDR2 as set forth in KVSNRFS (SEQ ID NO: 7); and, VL CDR3 as set forth in SQNTHVPYT (SEQ ID NO: 8);

(n) VL CDR1 as set forth in RSSQSLVHPYGATYLH (SEQ ID NO: 238); VL CDR2 as set forth in KASQRNS (SEQ ID NO: 242); and, VL CDR3 as set forth in SQNTHVPYT (SEQ ID NO: 8);

(o) VL CDR1 as set forth in RSSQSLVHPYGPTYLH (SEQ ID NO: 234); VL CDR2 as set forth in KVSNRFS (SEQ ID NO: 7); and, VL CDR3 as set forth in GQNAHLPYT (SEQ ID NO: 251); or (p) VL CDR1 as set forth in RSSQSLVHPYGRTYLH (SEQ ID NO: 239); VL CDR2 as set forth in RSSHRNS (SEQ ID NO: 243); and, VL CDR3 as set forth in SQNTHVPYT (SEQ ID NO: 8).

In some preferred embodiments, the VL of the antibody or an antigen binding fragment thereof according to the invention comprises: VL CDR1 as set forth in RSSQSLVHSYGDTYLH (SEQ ID NO: 6); VL CDR2 as set forth in KVSNRFS (SEQ ID NO: 7); and, VL CDR3 as set forth in SQNTHVPYT (SEQ ID NO: 8) or SQNTHLPYT (SEQ ID NO: 245) (preferably, VL CDR3 as set forth in SQNTHVPYT (SEQ ID NO: 8)).

In some preferred embodiments, the antibody or an antigen binding fragment thereof according to the invention comprises a VH comprising, a combination of VH CDR1, VH CDR2 and VH CDR3 selected from any one of the following (1)-(48):

|      | VH-CDR1 (SEQ ID NO:) | VH-CDR2 (SEQ ID NO:) | VH-CDR3 (SEQ ID NO:) |
|------|----------------------|----------------------|----------------------|
| (1)  | 120 | 142 | 180 |
| (2)  | 120 | 144 | 180 |
| (3)  | 120 | 144 | 181 |
| (4)  | 120 | 145 | 180 |
| (5)  | 120 | 145 | 181 |
| (6)  | 120 | 146 | 180 |
| (7)  | 120 | 147 | 181 |
| (8)  | 120 | 151 | 180 |
| (9)  | 120 | 155 | 180 |
| (10) | 121 | 143 | 181 |
| (11) | 121 | 144 | 180 |
| (12) | 121 | 144 | 181 |
| (13) | 121 | 145 | 180 |
| (14) | 121 | 146 | 181 |
| (15) | 121 | 150 | 181 |
| (16) | 121 | 151 | 180 |
| (17) | 121 | 155 | 180 |
| (18) | 121 | 158 | 180 |
| (19) | 121 | 160 | 180 |
| (20) | 122 | 144 | 180 |
| (21) | 122 | 145 | 180 |
| (22) | 122 | 145 | 181 |
| (23) | 122 | 146 | 180 |
| (24) | 122 | 146 | 181 |
| (25) | 122 | 148 | 180 |
| (26) | 122 | 152 | 181 |
| (27) | 122 | 155 | 180 |
| (28) | 122 | 159 | 180 |
| (29) | 123 | 145 | 180 |
| (30) | 123 | 155 | 180 |
| (31) | 123 | 157 | 180 |
| (32) | 123 | 159 | 180 |
| (33) | 124 | 144 | 181 |
| (34) | 124 | 145 | 180 |
| (35) | 124 | 145 | 182 |
| (36) | 124 | 149 | 180 |
| (37) | 124 | 153 | 180 |
| (38) | 124 | 153 | 181 |
| (39) | 124 | 155 | 180 |
| (40) | 124 | 156 | 180 |
| (41) | 125 | 145 | 180 |
| (42) | 125 | 146 | 180 |
| (43) | 125 | 146 | 181 |
| (44) | 126 | 146 | 180 |
| (45) | 126 | 146 | 181 |
| (46) | 127 | 147 | 181 |
| (47) | 127 | 149 | 180 |
| (48) | 128 | 154 | 180 |

In some preferred embodiments, the antibody or an antigen binding fragment thereof according to the invention comprises a VH comprising:

(a) VH CDR1 as set forth in SGYHWN (SEQ ID NO: 3); VH CDR2 as set forth in YISYDGSDHYNPSLEN (SEQ ID NO: 4); and, VH CDR3 as set forth in GFDH (SEQ ID NO: 5);

(b) VH CDR1 as set forth in RGYHWN (SEQ ID NO: 121); VH CDR2 as set forth in YISYDGSVFYNPSLEN (SEQ ID NO: 143); and, VH CDR3 as set forth in GFDY (SEQ ID NO: 181);

(c) VH CDR1 as set forth in HGYHWN (SEQ ID NO: 122); VH CDR2 as set forth in YISYDGSILYNPSLEN (SEQ ID NO: 144); and, VH CDR3 as set forth in GFDH (SEQ ID NO: 5);

(d) VH CDR1 as set forth in NGYHWN (SEQ ID NO: 123); VH CDR2 as set forth in YISYDGTILYNPSLEN (SEQ ID NO: 145); and, VH CDR3 as set forth in GFDH (SEQ ID NO: 5);

(e) VH CDR1 as set forth in RGYHWN (SEQ ID NO: 121); VH CDR2 as set forth in YISYDGSILYNPSLEN (SEQ ID NO: 144); and, VH CDR3 as set forth in GFDH (SEQ ID NO: 5);

(f) VH CDR1 as set forth in HGYHWN (SEQ ID NO: 122); VH CDR2 as set forth in YISYDGTVLYNPSLEN (SEQ ID NO: 146); and, VH CDR3 as set forth in GFDY (SEQ ID NO: 181);

(g) VH CDR1 as set forth in SGYHWN (SEQ ID NO: 3); VH CDR2 as set forth in YISYDGSILYNPSLEN (SEQ ID NO: 144); and, VH CDR3 as set forth in GFDH (SEQ ID NO: 5);

(h) VH CDR1 set forth in RDYHWN (SEQ ID NO: 125); VH CDR2 as set forth in YISYDGTVLYNPSLEN (SEQ ID NO: 146); and, VH CDR3 as set forth in GFDY (SEQ ID NO: 181);

(i) VH CDR1 as set forth in SGYHWN (SEQ ID NO: 3); VH CDR2 as set forth in YISYDGNVLYNPSLEN (SEQ ID NO: 147); and, VH CDR3 as set forth in GFDY (SEQ ID NO: 181);

(j) VH CDR1 as set forth in RWYHWN (SEQ ID NO: 126); VH CDR2 as set forth in YISYDGTVLYNPSLEN (SEQ ID NO: 146); and, VH CDR3 as set forth in GFDH (SEQ ID NO: 5);

(k) VH CDR1 as set forth in HGYHWN (SEQ ID NO: 122); VH CDR2 as set forth in YISYDGTVLYNPSLEN (SEQ ID NO: 146); and, VH CDR3 as set forth in GFDH (SEQ ID NO: 5);

(l) VH CDR1 set forth in RDYHWN (SEQ ID NO: 125); VH CDR2 as set forth in YISYDGTILYNPSLEN (SEQ ID NO: 145); and, VH CDR3 as set forth in GFDH (SEQ ID NO: 5);

(m) VH CDR1 as set forth in HGYHWN (SEQ ID NO: 122); VH CDR2 as set forth in YISYDGTILYNPSLEN (SEQ ID NO: 145); and, VH CDR3 as set forth in GFDH (SEQ ID NO: 5);

(n) VH CDR1 as set forth in YGYHWN (SEQ ID NO: 124); VH CDR2 as set forth in YISYDGSILYNPSLEN (SEQ ID NO: 144); and, VH CDR3 as set forth in GFDY (SEQ ID NO: 181);

(o) VH CDR1 as set forth in HGYHWN (SEQ ID NO: 122); VH CDR2 as set forth in YISYDGTSLYNPSLEN (SEQ ID NO: 148); and, VH CDR3 as set forth in GFDH (SEQ ID NO: 5);

(p) VH CDR1 as set forth in RGYHWN (SEQ ID NO: 121); VH CDR2 as set forth in YISYDGTVLYNPSLEN (SEQ ID NO: 146); and, VH CDR3 as set forth in GFDY (SEQ ID NO: 181);

(q) VH CDR1 as set forth in SGYHWN (SEQ ID NO: 3); VH CDR2 as set forth in YISYDGTILYNPSLEN (SEQ ID NO: 145); and, VH CDR3 as set forth in GFDY (SEQ ID NO: 181);

(r) VH CDR1 as set forth in RGYHWN (SEQ ID NO: 121); VH CDR2 as set forth in YISYDGSILYNPSLEN (SEQ ID NO: 144); and, VH CDR3 as set forth in GFDY (SEQ ID NO: 181);

(s) VH CDR1 as set forth in YGYHWN (SEQ ID NO: 124); VH CDR2 as set forth in YISYDGTILYNPSLEN (SEQ ID NO: 145); and, VH CDR3 as set forth in GFDT (SEQ ID NO: 182);

(t) VH CDR1 as set forth in NFYHWN (SEQ ID NO: 127); VH CDR2 as set forth in YISYDGSVLYNPSLEN (SEQ ID NO: 149); and, VH CDR3 as set forth in GFDH (SEQ ID NO: 5);

(u) VH CDR1 as set forth in YGYHWN (SEQ ID NO: 124); VH CDR2 as set forth in YISYDGTILYNPSLEN (SEQ ID NO: 145); and, VH CDR3 as set forth in GFDH (SEQ ID NO: 5);

(v) VH CDR1 as set forth in RGYHWN (SEQ ID NO: 121); VH CDR2 as set forth in YISYDGTILYNPSLEN (SEQ ID NO: 145); and, VH CDR3 as set forth in GFDH (SEQ ID NO: 5);

(w) VH CDR1 as set forth in HGYHWN (SEQ ID NO: 122); VH CDR2 as set forth in YISYDGTILYNPSLEN (SEQ ID NO: 145); and, VH CDR3 as set forth in GFDY (SEQ ID NO: 181);

(x) VH CDR1 as set forth in SGYHWN (SEQ ID NO: 3); VH CDR2 as set forth in YISYDGTVLYNPSLEN (SEQ ID NO: 146); and, VH CDR3 as set forth in GFDH (SEQ ID NO: 5);

(y) VH CDR1 as set forth in SGYHWN (SEQ ID NO: 3); VH CDR2 as set forth in YISYDGTILYNPSLEN (SEQ ID NO: 145); and, VH CDR3 as set forth in GFDH (SEQ ID NO: 5);

(z) VH CDR1 as set forth in YGYHWN (SEQ ID NO: 124); VH CDR2 as set forth in YISYDGSVLYNPSLEN (SEQ ID NO: 149); and, VH CDR3 as set forth in GFDH (SEQ ID NO: 5);

(aa) VH CDR1 as set forth in RGYHWN (SEQ ID NO: 121); VH CDR2 as set forth in YISYDGNILYNPSLEN (SEQ ID NO: 150); and, VH CDR3 as set forth in GFDY (SEQ ID NO: 181);

(ab) VH CDR1 as set forth in SGYHWN (SEQ ID NO: 3); VH CDR2 as set forth in YISYDGTNLYNPSLEN (SEQ ID NO: 151); and, VH CDR3 as set forth in GFDH (SEQ ID NO: 5);

(ac) VH CDR1 as set forth in HGYHWN (SEQ ID NO: 122); VH CDR2 as set forth in YISYDGSNLYNPSLEN (SEQ ID NO: 152); and, VH CDR3 as set forth in GFDY (SEQ ID NO: 181);

(ad) VH CDR1 as set forth in RGYHWN (SEQ ID NO: 121); VH CDR2 as set forth in YISYDGTNLYNPSLEN (SEQ ID NO: 151); and, VH CDR3 as set forth in GFDH (SEQ ID NO: 5);

(ae) VH CDR1 as set forth in HGYHWN (SEQ ID NO: 122); VH CDR2 as set forth in YISYDGTILYNPSLEN (SEQ ID NO: 145); and, VH CDR3 as set forth in GFDH (SEQ ID NO: 5);

(af) VH CDR1 as set forth in SGYHWN (SEQ ID NO: 3); VH CDR2 as set forth in YISYDGSILYNPSLEN (SEQ ID NO: 144); and, VH CDR3 as set forth in GFDY (SEQ ID NO: 181);

(ag) VH CDR1 as set forth in YGYHWN (SEQ ID NO: 124); VH CDR2 as set forth in YISYDGTVHYNPSLEN (SEQ ID NO: 153); and, VH CDR3 as set forth in GFDH (SEQ ID NO: 5);

(ah) VH CDR1 as set forth in NFYHWN (SEQ ID NO: 127); VH CDR2 as set forth in YISYDGNVLYNPSLEN (SEQ ID NO: 147); and, VH CDR3 as set forth in GFDY (SEQ ID NO: 181);

(ai) VH CDR1 as set forth in RYYHWN (SEQ ID NO: 128); VH CDR2 as set forth in YISYDGTIRYNPSLEN (SEQ ID NO: 154); and, VH CDR3 as set forth in GFDH (SEQ ID NO: 5);

(aj) VH CDR1 as set forth in YGYHWN (SEQ ID NO: 124); VH CDR2 as set forth in YISYDGTVHYNPSLEN (SEQ ID NO: 153); and, VH CDR3 as set forth in GFDY (SEQ ID NO: 181);

(ak) VH CDR1 set forth in RDYHWN (SEQ ID NO: 125); VH CDR2 as set forth in YISYDGTVLYNPSLEN (SEQ ID NO: 146); and, VH CDR3 as set forth in GFDH (SEQ ID NO: 5);

(al) VH CDR1 as set forth in YGYHWN (SEQ ID NO: 124); VH CDR2 as set forth in YISYDGSVLYNPSLKS (SEQ ID NO: 155); and, VH CDR3 as set forth in GFDH (SEQ ID NO: 5);

(am) VH CDR1 as set forth in RWYHWN (SEQ ID NO: 126); VH CDR2 as set forth in YISYDGTVLYNPSLEN (SEQ ID NO: 146); and, VH CDR3 as set forth in GFDY (SEQ ID NO: 181);

(an) VH CDR1 as set forth in YGYHWN (SEQ ID NO: 124); VH CDR2 as set forth in YISYDGSVLYNPSLKG (SEQ TD NO: 156); and, VH CDR3 as set forth in GFDH (SEQ TD NO: 5);

(ao) VH CDR1 as set forth in NGYHWN (SEQ ID NO: 123); VH CDR2 as set forth in YIAYDGVQSYNPSLKG (SEQ ID NO: 157); and, VH CDR3 as set forth in GFDH (SEQ ID NO: 5);

(ap) VH CDR1 as set forth in RGYHWN (SEQ ID NO: 121); VH CDR2 as set forth in YISYDGSVLYNPSLKS (SEQ ID NO: 155); and, VH CDR3 as set forth in GFDH (SEQ ID NO: 5);

(aq) VH CDR1 as set forth in SGYHWN (SEQ ID NO: 3); VH CDR2 as set forth in YISYDGSVLYNPSLKS (SEQ ID NO: 155); and, VH CDR3 as set forth in GFDH (SEQ ID NO: 5);

(ar) VH CDR1 as set forth in NGYHWN (SEQ ID NO: 123); VH CDR2 as set forth in YISYDGSVLYNPSLKS (SEQ ID NO: 155); and, VH CDR3 as set forth in GFDH (SEQ ID NO: 5);

(as) VH CDR1 as set forth in RGYHWN (SEQ ID NO: 121); VH CDR2 as set forth in YIGYDGAVQYNPSLKS (SEQ ID NO: 158); and, VH CDR3 as set forth in GFDH (SEQ ID NO: 5);

(at) VH CDR1 as set forth in HGYHWN (SEQ ID NO: 122); VH CDR2 as set forth in YISYNGSVLYNPSLKS (SEQ ID NO: 159); and, VH CDR3 as set forth in GFDH (SEQ ID NO: 5);

(au) VH CDR1 as set forth in RGYHWN (SEQ ID NO: 121); VH CDR2 as set forth in YISYDGSRLYNPSLKS (SEQ ID NO: 160); and, VH CDR3 as set forth in GFDH (SEQ ID NO: 5); or (av) VH CDR1 as set forth in NGYHWN (SEQ ID NO: 123); VH CDR2 as set forth in YISYNGSVLYNPSLKS (SEQ ID NO: 159); and, VH CDR3 as set forth in GFDH (SEQ ID NO: 5).

In some preferred embodiments, the VH of the antibody or an antigen binding fragment thereof according to the invention comprises VH CDR3 as set forth in GFDH (SEQ ID NO: 5), and, VH CDR1 and VH CDR2 selected from:

(a) VH CDR1 as set forth in SGYHWN (SEQ ID NO: 3) and VH CDR2 as set forth in YISYDGSDHYNPSLEN (SEQ ID NO: 4);

(d) VH CDR1 as set forth in NGYHWN (SEQ ID NO: 123) and VH CDR2 as set forth in YISYDGTILYNPSLEN (SEQ ID NO: 145);

(e) VH CDR1 as set forth in RGYHWN (SEQ ID NO: 121) and VH CDR2 as set forth in YISYDGSILYNPSLEN (SEQ ID NO: 144);

(j) VH CDR1 as set forth in RWYHWN (SEQ ID NO: 126) and VH CDR2 as set forth in YISYDGTVLYNPSLEN (SEQ ID NO: 146);

(k) VH CDR1 as set forth in HGYHWN (SEQ ID NO: 122) and VH CDR2 as set forth in YISYDGTVLYNPSLEN (SEQ ID NO: 146);

(l) VH CDR1 set forth in RDYHWN (SEQ ID NO: 125) and VH CDR2 as set forth in YISYDGTILYNPSLEN (SEQ ID NO: 145);

(m) VH CDR1 as set forth in HGYHWN (SEQ ID NO: 122) and VH CDR2 as set forth in YISYDGTILYNPSLEN (SEQ ID NO: 145);

(z) VH CDR1 as set forth in YGYHWN (SEQ ID NO: 124) and VH CDR2 as set forth in YISYDGSVLYNPSLEN (SEQ ID NO: 149); or (ad) VH CDR1 as set forth in RGYHWN (SEQ ID NO: 121) and VH CDR2 as set forth in YISYDGTNLYNPSLEN (SEQ ID NO: 151).

In some preferred embodiments, VH CDR1, VH CDR2 and/or VH CDR3 comprised in the antibody or an antigen binding fragment thereof according to the invention are selected from VH CDR1, VH CDR2 and VH CDR3 comprised in any one of SEQ ID NOs: 11-92 and 263-279, respectively. In some preferred embodiments, VL CDR1, VL CDR2 and/or VL CDR3 comprised in the antibody or an antigen binding fragment thereof according to the invention are selected from VL CDR1, VL CDR2 and VL CDR3 comprised in any one of SEQ ID NOs: 186-214 and 298-308.

In some preferred embodiments, as compared to an antibody wherein VH is SEQ ID NO: 1 and VL is SEQ ID NO: 2, the antibody or an antigen binding fragment thereof according to the invention comprises only 1, 2, 3, 4, 5 or 6 substitutions in VH CDR1-3 and VL CDR1-3. In some preferred embodiments, as compared to an antibody wherein VH is SEQ ID NO: 1 and VL is SEQ ID NO: 2, the antibody or an antigen binding fragment thereof according to the invention comprises only 1 substitution in VH CDR1-3 and VL CDR1-3.

In some preferred embodiments, the antibody or an antigen binding fragment thereof according to the invention comprises VH CDR1, VH CDR2 and VH CDR3 as defined above. In some preferred embodiments, the antibody or an antigen binding fragment thereof according to the invention comprises VL CDR1, VL CDR2 and VL CDR3 as defined above. In some preferred embodiments, the antibody or an antigen binding fragment thereof according to the invention comprises VH CDR1, VH CDR2, VH CDR3, VL CDR1, VL CDR2 and VL CDR3 as defined above. In some preferred embodiments, the antibody or an antigen binding fragment thereof according to the invention comprises 6 CDRs from heavy chain and light chain variable regions of an antibody selected from:

| Antibody name | Heavy chain variable region (SEQ ID NO:) | Light chain variable region (SEQ ID NO:) |
| --- | --- | --- |
| B-S3-45 | 11 | 186 |
| 10-25 | 16 | 187 |
| 11 | 14 | 187 |
| 110 | 72 | 201 |
| 112 | 71 | 199 |
| 11-26 | 17 | 187 |
| 113 | 31 | 187 |
| 11-3 | 69 | 189 |
| 11-34-266 | 44 | 187 |
| 116 | 73 | 202 |
| 117 | 32 | 187 |
| 123 | 77 | 206 |
| 12-34-277 | 45 | 187 |
| 127 | 74 | 209 |
| 1-31-322 | 47 | 187 |
| 138 | 91 | 205 |
| 153 | 73 | 205 |
| 162 | 36 | 187 |
| 162/41k | 36 | 189 |
| 162B | 55 | 192 |
| 16-34-293 | 46 | 187 |
| 187 | 74 | 202 |
| 192 | 92 | 200 |
| 23 | 76 | 204 |
| 242 | 42 | 187 |
| 24-34-316 | 48 | 187 |
| 24-40 | 20 | 187 |
| 25-34-317 | 49 | 187 |
| 29 | 18 | 187 |
| 35-62 | 24 | 187 |
| 37 | 19 | 187 |
| 39-73 | 25 | 187 |
| 42 | 21 | 187 |
| 43-89 | 27 | 187 |
| 44 | 22 | 187 |
| 47-101 | 29 | 187 |
| 5 | 12 | 187 |
| 50-112 | 30 | 187 |
| 54-123 | 33 | 187 |
| 55-127 | 34 | 187 |
| 56-135 | 35 | 187 |
| 6-16 | 23 | 187 |

-continued

| Antibody name | Heavy chain variable region (SEQ ID NO:) | Light chain variable region (SEQ ID NO:) |
|---|---|---|
| 62 | 75 | 203 |
| 6-34-234 | 40 | 187 |
| 69-171 | 37 | 187 |
| 7 | 13 | 187 |
| 7-17 | 15 | 187 |
| 73-188 | 38 | 187 |
| 7-34-239 | 41 | 187 |
| 74-189 | 39 | 187 |
| 76-191 | 43 | 187 |
| 83 | 78 | 205 |
| 84 | 72 | 205 |
| 85 | 26 | 187 |
| 86 | 28 | 187 |
| B3-S4-N-130 | 55 | 194 |
| B3-S4-N-50 | 70 | 198 |
| B3-S4-N-65 | 55 | 195 |
| B3-S4-N-68 | 55 | 197 |
| B4-T13-11 | 55 | 196 |
| B-S2-13 | 90 | 187 |
| B-S2-2 | 51 | 188 |
| B-S2-25 | 54 | 190 |
| B-S2-26 | 83 | 208 |
| B-S3-2 | 79 | 190 |
| B-S3-44 | 85 | 190 |
| D11/41K | 62 | 189 |
| D11/K1 | 62 | 193 |
| D162/41K | 66 | 189 |
| D162/K1 | 66 | 193 |
| D17/41K | 64 | 189 |
| D17/K1 | 64 | 193 |
| D239/41K | 67 | 189 |
| D239/K1 | 67 | 193 |
| D40/K1 | 65 | 193 |
| D6-16/K1 | 63 | 193 |
| H11/41K | 82 | 189 |
| H11/K1 | 82 | 193 |
| H162/41K | 60 | 189 |
| H162/K1 | 60 | 193 |
| H17/41K | 56 | 189 |
| H17/K1 | 56 | 193 |
| H311/41K | 61 | 189 |
| H311/K1 | 61 | 193 |
| H40/41K | 57 | 189 |
| H40/K1 | 57 | 193 |
| H42/41K | 58 | 189 |
| H42/K1 | 58 | 193 |
| H44/41K | 59 | 189 |
| H44/K1 | 59 | 193 |
| H6-16/41K | 68 | 189 |
| N-22 | 53 | 191 |
| P-44 | 55 | 199 |
| P-50 | 55 | 200 |
| S-S2-10 | 53 | 187 |
| S-S2-11 | 52 | 189 |
| S-S2-2 | 84 | 210 |
| S-S2-22 | 84 | 212 |
| S-S2-25 | 50 | 187 |
| S-S2-30 | 80 | 207 |
| S-S2-32 | 88 | 214 |
| S-S2-41 | 52 | 189 |
| S-S2-43 | 89 | 212 |
| S-S2-47 | 81 | 187 |
| S-S2-5 | 84 | 211 |
| S-S3-16 | 86 | 190 |
| S-S3-29 | 87 | 213 |
| 162ccp-S5-N-56 | 72 | 202 |
| 162ccp-S6-N-149 | 72 | 306 |
| 162ccp-S5-N-84 | 72 | 200 |
| 162ccp-S5-P-64 | 91 | 300 |
| 162ccp-S5-N-32 | 91 | 200 |
| 138HA/162BK | 263 | 192 |
| 138HB/83K | 264 | 205 |
| 138HB/162BK | 264 | 192 |
| 138HB/110K | 264 | 201 |
| 138HB/116K | 264 | 202 |
| 162BHB/83K | 265 | 205 |
| 162BHB/110K | 265 | 201 |
| 162BHB/116K | 265 | 202 |
| 162BHE/83K | 266 | 205 |
| 162BHE/162BK | 266 | 192 |
| 162ccp-S4-N-81 | 267 | 298 |
| 162ccp-S5-P-27 | 268 | 299 |
| 162ccp-S5-P-77 | 269 | 301 |
| 162ccp-S5-N-41 | 270 | 302 |
| 162ccp-S5-N-69 | 271 | 202 |
| 162ccp-S5-N-70 | 272 | 303 |
| 162ccp-S6-N-101 | 273 | 304 |
| 162ccp-S6-N-111 | 274 | 305 |
| 162ccp-S6-N-137 | 275 | 200 |
| 162ccp-S6-N-146 | 276 | 202 |
| 162ccp-S6-N-160 | 277 | 307 |
| 162ccp-S6-N-66 | 278 | 308 |
| 162ccp-S6-N-45 | 279 | 202 |

In some preferred embodiments, the antibody or an antigen binding fragment thereof according to the invention is humanized. In some preferred embodiments, the antibody or an antigen binding fragment thereof according to the invention has a humanization degree of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In some preferred embodiments, the antibody or an antigen binding fragment thereof according to the invention comprises no more than 20, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 murine amino acid residues, or comprises no murine amino acid residue. In some preferred embodiments, the FR of the antibody or an antigen binding fragment thereof according to the invention comprises no more than 20, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 murine amino acid residues, or comprises no murine amino acid residue.

In some preferred embodiments, the antibody or an antigen binding fragment thereof according to the invention comprises:

(a) one or more (e.g. 1, 2, 3 or 4) framework regions (FRs) of heavy chain variable region (VH) selected from the group consisting of:

(i) VH FR1, consisting of the following sequence: EVQLQESGPGLVKPSQTLSLTCAVSGYSIS (SEQ ID NO: 93), or a sequence that differs from SEQ ID NO: 93 by one or several substitutions, deletions or additions (e.g. 1, 2, 3 or 4 substitutions, deletions or additions);

(ii) VH FR2, consisting of the following sequence: WIRQFPGNKLEWIG (SEQ ID NO: 129), or a sequence that differs from SEQ ID NO: 129 by one or several substitutions, deletions or additions (e.g. 1, 2 or 3 substitutions, deletions or additions);

(iii) VH FR3, consisting of the following sequence: RITITRDTSKNQFSLILRSVTAEDTAIYYCAS (SEQ ID NO: 161), or a sequence that differs from SEQ ID NO: 161 by one or several substitutions, deletions or additions (e.g. 1, 2, 3, 4, 5, 6, 7, 8, 9, or 10 substitutions, deletions or additions); and (iv) VH FR4, consisting of the following sequence: WGQGTTLTVSS (SEQ ID NO: 183), or a sequence that differs from SEQ ID NO: 183 by one or several substitutions, deletions or additions (e.g. 1, or 2 substitutions, deletions or additions);

and/or (b) one or more (e.g. 1, 2, 3 or 4) framework regions (FRs) of light chain variable region (VL) selected from the group consisting of:

(v) VL FR1, consisting of the following sequence: DVVMTQSPLSLPVTLGEPASISC (SEQ ID NO: 215), or a sequence that differs from SEQ ID NO: 215 by one or several substitutions, deletions or additions (e.g. 1, 2 or 3 substitutions, deletions or additions);

(vi) VL FR2, consisting of the following sequence: WYLQKPGQSPKLLIY (SEQ ID NO: 221), or a sequence that differs from SEQ ID NO: 221 by one or several substitutions, deletions or additions (e.g. 1, or 2 substitutions, deletions or additions);

(vii) VL FR3, consisting of the following sequence: GVPDRFSGSGSGTDFTLKISRVETEDVGVYYC (SEQ ID NO: 223), or a sequence that differs from SEQ TD NO: 223 by one or several substitutions, deletions or additions (e.g. 1, 2 or 3 substitutions, deletions or additions); and (viii) VL FR4, consisting of the following sequence: FGGGTKLEIKR (SEQ ID NO: 230), or a sequence that differs from SEQ ID NO: 230 by one or several substitutions, deletions or additions (e.g. 1, or 2 substitutions, deletions or additions).

In some preferred embodiments, the antibody or an antigen binding fragment thereof according to the invention comprises VH FR1, VH FR2, VH FR3 and VH FR4 as defined above. In some preferred embodiments, the antibody or an antigen binding fragment thereof according to the invention comprises VL FR1, VL FR2, VL FR3 and VL FR4 as defined above. In some preferred embodiments, the antibody or an antigen binding fragment thereof according to the invention comprises VH FR1, VH FR2, VH FR3, VH FR4, VL FR1, VL FR2, VL FR3 and VL FR4 as defined above.

In some preferred embodiments, VH FR1 of the antibody or an antigen binding fragment thereof according to the invention is SEQ TD NO: 93, or differs from SEQ ID NO: 93 by one or more substitutions (e.g. 1, 2, 3 or 4 substitutions) selected from the group consisting of:

(01) Q, H, or D at H1;
(02) Q at H4;
(03) Q at H11;
(04) A at H14;
(05) T at H23;
(06) T, N, A, S, or G at H27;
(07) P at H28; and
(08) T at H30;

wherein, the amino acid positions mentioned in (01)-(08) are numbered according to Kabat numbering system.

In some preferred embodiments, VH FR1 of the antibody or an antigen binding fragment thereof according to the invention is SEQ ID NO: 93, or differs from SEQ ID NO: 93 by one or more substitutions (e.g. 1, 2, 3 or 4 substitutions) selected from the group consisting of:

(01) H or D at H1;
(04) A at H14;
(05) T at H23;
(06) T, N, A, or S at H27;
(07) P at H28; and
(08) T at H30;

wherein, the amino acid positions mentioned above are numbered according to Kabat numbering system.

In some preferred embodiments, VH FR1 of the antibody or an antigen binding fragment thereof according to the invention is SEQ ID NO: 93, or differs from SEQ ID NO: 93 by one or more substitutions (e.g. 1, 2, 3 or 4 substitutions) selected from the group consisting of:

(01) D at H1;
(04) A at H14;
(05) T at H23;
(06) N or S at H27;
(07) P at H28; and
(08) T at H30;

wherein, the amino acid positions mentioned above are numbered according to Kabat numbering system.

In some preferred embodiments, the VH FR1 of the antibody or an antigen binding fragment thereof according to the invention has a sequence selected from the group consisting of:

```
                                        (SEQ ID NO: 93)
EVQLQESGPGLVKPSQTLSLTCAVSGYSIS;

(SEQ ID NO: 94)
EVQLQESGPGLVKPSQTLSLTCAVSGYSIT;

(SEQ ID NO: 95)
EVQLQESGPGLVKPSQTLSLTCAVSGTSIT;

(SEQ ID NO: 96)
EVQLQESGPGLVKPSQTLSLTCAVSGNSIS;

(SEQ ID NO: 97)
EVQLQESGPGLVKPSQTLSLTCAVSGASIT;

(SEQ ID NO: 98)
EVQLQESGPGLVKPSQTLSLTCAVSGSSIT;

(SEQ ID NO: 99)
EVQLQESGPGLVKPSQTLSLTCAVSGASIS;

(SEQ ID NO: 100)
EVQLQESGPGLVKPSQTLSLTCAVSGGSIT;

(SEQ ID NO: 101)
EVQLQESGPGLVKASQTLSLTCAVSGYSIS;

(SEQ ID NO: 102)
DVQLQESGPGLVKPSQTLSLTCAVSGYPIT;

(SEQ ID NO: 103)
HVQLQESGPGLVKPSQTLSLTCAVSGYSIT;

(SEQ ID NO: 104)
EVQLQESGPGLVKPSQTLSLTCAVSGYPIS;

(SEQ ID NO: 105)
QVQLQESGPGLVKPSQTLSLTCAVSGYSIS;

(SEQ ID NO: 106)
HVQLQESGPGLVKPSQTLSLTCAVSGTSIT;

(SEQ ID NO: 107)
HVQLQESGPGLVKPSQTLSLTCAVSGNSIS;

(SEQ ID NO: 108)
HVQLQESGPGLVKPSQTLSLTCAVSGYSIS;

(SEQ ID NO: 109)
HVQLQESGPGLVKPSQTLSLTCAVSGASIT;

(SEQ ID NO: 110)
HVQLQESGPGLVKPSQTLSLTCAVSGSSIT;
```

(SEQ ID NO: 111)
DVQLQESGPGLVKPSQTLSLTCAVSGYSIT;

(SEQ ID NO: 112)
DVQLQESGPGLVKPSQTLSLTCAVSGYSIS;

(SEQ ID NO: 113)
DVQLQESGPGLVKPSQTLSLTCAVSGTSIT;

(SEQ ID NO: 114)
DVQLQESGPGLVKPSQTLSLTCAVSGNSIS;

(SEQ ID NO: 115)
DVQLQESGPGLVKPSQTLSLTCAVSGSSIT;

(SEQ ID NO: 117)
EVQLQESGPGLVKPSQTLSLTCAVSGYPIT;

(SEQ ID NO: 116)
DVQLQESGPGLVKPSQTLSLTCTVSGYPIT;

(SEQ ID NO: 118)
QVQQQESGPGQVKPSQTLSLTCAVSGYPIS;
and (SEQ ID NO: 119)
QVQLQESGPGLVKPSQTLSLTCAVSGYSIT.

In some preferred embodiments, the sequence of the VH FR1 of the antibody or an antigen binding fragment thereof according to the invention is selected from the group consisting of:

(SEQ ID NO: 93)
EVQLQESGPGLVKPSQTLSLTCAVSGYSIS;

(SEQ ID NO: 96)
EVQLQESGPGLVKPSQTLSLTCAVSGNSIS;

(SEQ ID NO: 98)
EVQLQESGPGLVKPSQTLSLTCAVSGSSIT;

(SEQ ID NO: 94)
EVQLQESGPGLVKPSQTLSLTCAVSGYSIT;

(SEQ ID NO: 102)
DVQLQESGPGLVKPSQTLSLTCAVSGYPIT;

(SEQ ID NO: 117)
EVQLQESGPGLVKPSQTLSLTCAVSGYPIT;

(SEQ ID NO: 101)
EVQLQESGPGLVKASQTLSLTCAVSGYSIS;

(SEQ ID NO: 104)
EVQLQESGPGLVKPSQTLSLTCAVSGYPIS;

(SEQ ID NO: 103)
HVQLQESGPGLVKPSQTLSLTCAVSGYSIT;

(SEQ ID NO: 106)
HVQLQESGPGLVKPSQTLSLTCAVSGTSIT;

(SEQ ID NO: 107)
HVQLQESGPGLVKPSQTLSLTCAVSGNSIS;

(SEQ ID NO: 108)
HVQLQESGPGLVKPSQTLSLTCAVSGYSIS;

(SEQ ID NO: 110)
HVQLQESGPGLVKPSQTLSLTCAVSGSSIT;

(SEQ ID NO: 111)
DVQLQESGPGLVKPSQTLSLTCAVSGYSIT;

(SEQ ID NO: 115)
DVQLQESGPGLVKPSQTLSLTCAVSGSSIT;

(SEQ ID NO: 116)
DVQLQESGPGLVKPSQTLSLTCTVSGYPIT;
and (SEQ ID NO: 109)
HVQLQESGPGLVKPSQTLSLTCAVSGASIT.

In some preferred embodiments, the sequence of the VH FR1 of the antibody or an antigen binding fragment thereof according to the invention is selected from the group consisting of:

(SEQ ID NO: 93)
EVQLQESGPGLVKPSQTLSLTCAVSGYSIS;

(SEQ ID NO: 96)
EVQLQESGPGLVKPSQTLSLTCAVSGNSIS;

(SEQ ID NO: 98)
EVQLQESGPGLVKPSQTLSLTCAVSGSSIT;

(SEQ ID NO: 94)
EVQLQESGPGLVKPSQTLSLTCAVSGYSIT;

(SEQ ID NO: 117)
EVQLQESGPGLVKPSQTLSLTCAVSGYPIT;

(SEQ ID NO: 101)
EVQLQESGPGLVKASQTLSLTCAVSGYSIS;

(SEQ ID NO: 104)
EVQLQESGPGLVKPSQTLSLTCAVSGYPIS;
and (SEQ ID NO: 116)
DVQLQESGPGLVKPSQTLSLTCTVSGYPIT.

In some preferred embodiments, VH FR2 of the antibody or an antigen binding fragment thereof according to the invention is SEQ ID NO: 129, or differs from SEQ ID NO: 129 by one or more substitutions (e.g. 1, 2 or 3 substitutions) selected from the group consisting of:
(09) V at H37;
(10) Q at H38;
(11) L at H40;
(12) K at H43;
(13) R, S, E, or G at H44;
(14) V at H46; and
(15) M at H48;
wherein, the amino acid positions mentioned in (09)-(15) are numbered according to Kabat numbering system.

In some preferred embodiments, VH FR2 of the antibody or an antigen binding fragment thereof according to the invention is SEQ ID NO: 129, or differs from SEQ ID NO: 129 by one or more substitutions (e.g. 1, 2 or 3 substitutions) selected from the group consisting of:
(11) L at H40;
(12) K at H43;
(13) R or E at H44;
(14) V at H46; and
(15) M at H48;
wherein, the amino acid positions mentioned above are numbered according to Kabat numbering system.

In some preferred embodiments, the VH FR2 of the antibody or an antigen binding fragment thereof according to the invention has a sequence selected from the group consisting of:

(SEQ ID NO: 129)
WIRQFPGNKLEWIG;

WVRQFPGNKLEWIG; (SEQ ID NO: 130)

WIQQFPGNKLEWIG; (SEQ ID NO: 131)

WIRQLPGNKLEWIG; (SEQ ID NO: 132)

WIRQFPGKKLEWIG; (SEQ ID NO: 133)

WIRQFPGKGLEWIG; (SEQ ID NO: 134)

WIRQFPGNKLVWMG; (SEQ ID NO: 135)

WIRQFPGKSLEWIG; (SEQ ID NO: 136)

WIRQFPGKRLEWMG; (SEQ ID NO: 137)

WIRQFPGNELEWIG; (SEQ ID NO: 138)

WIRQFPGNRLEWIG; (SEQ ID NO: 139)

WIRQFPGNRLEWMG; and (SEQ ID NO: 140)

WIRQFPGNKLEWMG. (SEQ ID NO: 141)

In some preferred embodiments, VH FR3 of the antibody or an antigen binding fragment thereof according to the invention is SEQ ID NO: 161, or differs from SEQ ID NO: 161 by one or more substitutions (e.g. 1, 2, 3, 4, 5, 6, 7, 8, 9, or 10 substitutions) selected from the group consisting of:
(16) V at H67;
(17) S at H68;
(18) S at H70;
(19) V at H71;
(20) I at H73;
(21) F at H79;
(22) K at H81;
(23) S at H82A;
(24) T at H84;
(25) A at H85;
(26) V or K at H89; and
(27) F at H91;
wherein, the amino acid positions mentioned in (16)-(27) are numbered according to Kabat numbering system.

In some preferred embodiments, the VH FR3 of the antibody or an antigen binding fragment thereof according to the invention has a sequence selected from the group consisting of:

RITITRDTSKNQFSLILRSVTAEDTAIYYCAS; (SEQ ID NO: 161)

RVTITRDTSKNQFFLKLSSVTAFDTAKYYCAS; (SEQ ID NO: 162)

RVTITRDTSKNQFFLKLSSVTAFDTARYYCAS; (SEQ ID NO: 163)

RITISRDTSKNQFFLKLRSVTAEDTAKYFCAS; (SEQ ID NO: 164)

RVSITRDTSKNQFFLILRSVTAEDTAIYYCAS; (SEQ ID NO: 165)

RVTITRDTSKNQFFLKLRSVTAEDTAIYYCAS; (SEQ ID NO: 166)

RVSITRDTSKNQFFLKLSSVTAEDTAKYFCAS; (SEQ ID NO: 167)

RVTITRDTSKNQFFLKLRSVTAEDTAIYFCAS; (SEQ ID NO: 168)

RVTISVDTSKNQFSLKLSSVTAEDTAVYYCAS; (SEQ ID NO: 169)

RVSISRDISKNQFFLKLSSVTAADTAVYFCAS; (SEQ ID NO: 170)

RITITRDTSKNQFFLKLRSVTAEDTAVYYCAS; (SEQ ID NO: 171)

RVSITRDTSKNQFFLKLRSVTAEDTAIYFCAS; (SEQ ID NO: 172)

RITITRDTSKNQFFLKLRSVTAEDTAKYYCAS; (SEQ ID NO: 173)

RVTITRDTSKNQFFLILRSVTAEDTAKYYCAS; (SEQ ID NO: 174)

RVTITRDTSKNQFFLKLRSVTAEDTAKYYCAS; (SEQ ID NO: 175)

RISITRDTSKNQFFLKLSSVTAEDTAKYFCAS; (SEQ ID NO: 176)

RITITRDTSKNQFSLKLRSVTAEDTAVYYCAS; (SEQ ID NO: 177)

RITITRDTSKNQFFLILRSVTAEDTAIYYCAS; and (SEQ ID NO: 178)

RVTISVDTSKNQFSLKLSSVTTEDTAVYYCAS. (SEQ ID NO: 179)

In some preferred embodiments, VH FR4 of the antibody or an antigen binding fragment thereof according to the invention is SEQ ID NO: 183, or differs from SEQ ID NO: 183 by one or more substitutions (e.g. 1 or 2 substitutions) selected from the group consisting of:
(28) L or M at H108; and
(29) V at H109;
wherein, the amino acid positions mentioned in (28)-(29) are numbered according to Kabat numbering system.

In some preferred embodiments, VH FR4 of the antibody or an antigen binding fragment thereof according to the invention is SEQ ID NO: 183, or differs from SEQ ID NO: 183 by M at H108.

In some preferred embodiments, the VH FR4 of the antibody or an antigen binding fragment thereof according to the invention has a sequence selected from the group consisting of:

WGQGTTLTVSS; (SEQ ID NO: 183)

WGQGTLVTVSS; and (SEQ ID NO: 184)

WGQGTMLTVSS. (SEQ ID NO: 185)

In some preferred embodiments, the sequence of the VH FR4 of the antibody or an antigen binding fragment thereof according to the invention is selected from the group consisting of WGQGTTLTVSS (SEQ ID NO: 183); and WGQGTMLTVSS (SEQ ID NO: 185).

In some preferred embodiments, VL FR1 of the antibody or an antigen binding fragment thereof according to the invention is SEQ ID NO: 215, or differs from SEQ ID NO: 215 by one or more substitutions (e.g. 1, 2 or 3 substitutions) selected from the group consisting of:

(30) I at L2;
(31) T at L7;
(32) N at L14;
(33) P at L15; and
(34) Q at L18;

wherein, the amino acid positions mentioned in (30)-(34) are numbered according to Kabat numbering system.

In some preferred embodiments, VL FR1 of the antibody or an antigen binding fragment thereof according to the invention is SEQ ID NO: 215, or differs from SEQ ID NO: 215 by one or more substitutions (e.g. 1 or 2 substitutions) selected from the group consisting of:

(30) I at L2;
(31) T at L7; and
(32) N at L14;

wherein, the amino acid positions mentioned above are numbered according to Kabat numbering system.

In some preferred embodiments, VL FR1 of the antibody or an antigen binding fragment thereof according to the invention is SEQ ID NO: 215, or differs from SEQ ID NO: 215 by one or more substitutions (e.g. 1 or 2 substitutions) selected from the group consisting of:

(30) I at L2; and
(34) Q at L18;

wherein, the amino acid positions mentioned above are numbered according to Kabat numbering system.

In some preferred embodiments, the VL FR1 of the antibody or an antigen binding fragment thereof according to the invention has a sequence selected from the group consisting of:

DVVMTQSPLSLPVTLGEPASISC; (SEQ ID NO: 215)

DIVMTQSPLSLPVTLGEPASISC; (SEQ ID NO: 216)

DVVMTQTPLSLPVNLGEPASISC; (SEQ ID NO: 217)

DIVMTQSPLSLPVTLGEQASISC; (SEQ ID NO: 218)

DVVMTQSPLSLPVTLGEQASISC; (SEQ ID NO: 219)
and

DIVMTQSPLSLPVTPGEPASISC. (SEQ ID NO: 220)

In some preferred embodiments, VL FR2 of the antibody or an antigen binding fragment thereof according to the invention is SEQ ID NO: 221, or differs from SEQ ID NO: 221 by the following substitution: (35) Q at L45, wherein, the amino acid position mentioned in (35) is numbered according to Kabat numbering system.

In some preferred embodiments, the VL FR2 of the antibody or an antigen binding fragment thereof according to the invention has a sequence selected from the group consisting of:

WYLQKPGQSPKLLIY; (SEQ ID NO: 221)
and

WYLQKPGQSPQLLIY. (SEQ ID NO: 222)

In some preferred embodiments, VL FR3 of the antibody or an antigen binding fragment thereof according to the invention is SEQ ID NO: 223, or differs from SEQ ID NO: 223 by one or more substitutions (e.g. 1, 2 or 3 substitutions) selected from the group consisting of:

(36) D at L79;
(37) A at L80;
(38) L at L83; and
(39) F at L87;

wherein, the amino acid positions mentioned in (36)-(39) are numbered according to Kabat numbering system.

In some preferred embodiments, VL FR3 of the antibody or an antigen binding fragment thereof according to the invention is SEQ ID NO: 223, or differs from SEQ ID NO: 223 by one or more substitutions (e.g. 1, 2 or 3 substitutions) selected from the group consisting of:

(37) A at L80;
(38) L at L83; and
(39) F at L87;

wherein, the amino acid positions mentioned in (37)-(39) are numbered according to Kabat numbering system.

In some preferred embodiments, VL FR3 of the antibody or an antigen binding fragment thereof according to the invention is SEQ ID NO: 223, or differs from SEQ ID NO: 223 by one or more substitutions (e.g. 1 or 2 substitutions) selected from the group consisting of:

(38) L at L83; and
(39) F at L87;

wherein, the amino acid positions mentioned in (38)-(39) are numbered according to Kabat numbering system.

In some preferred embodiments, the VL FR3 of the antibody or an antigen binding fragment thereof according to the invention has a sequence selected from the group consisting of:

GVPDRFSGSGSGTDFTLKISRVETEDVGVYYC; (SEQ ID NO: 223)

GVPDRFSGSGSGTDFTLKISRVETEDLGVYYC; (SEQ ID NO: 224)

GVPDRFSGSGSGTDFTLKISRVEAEDVGVYYC; (SEQ ID NO: 225)

GVPDRFSGSGSGTDFTLKISRVEAEDLGVYFC; (SEQ ID NO: 226)

GVPDRFSGSGSGTDFTLKISRVETEDLGVYFC; (SEQ ID NO: 227)

GVPDRFSGSGSGTDFTLKISRVDTEDLGVYFC; (SEQ ID NO: 228)
and

GVPDRFSGSGSGTDFTLKISRVETEDVGVYFC. (SEQ ID NO: 229)

In some preferred embodiments, the sequence of the VL FR3 of the antibody or an antigen binding fragment thereof according to the invention is selected from the group consisting of:

```
                                       (SEQ ID NO: 223)
GVPDRFSGSGSGTDFTLKISRVETEDVGVYYC;

(SEQ ID NO: 224)
GVPDRFSGSGSGTDFTLKISRVETEDLGVYYC;

(SEQ ID NO: 227)
GVPDRFSGSGSGTDFTLKISRVETEDLGVYFC;
and (SEQ ID NO: 226)
GVPDRFSGSGSGTDFTLKISRVEAEDLGVYFC.
```

In some preferred embodiments, the sequence of the VL FR3 of the antibody or an antigen binding fragment thereof according to the invention is selected from the group consisting of:

```
                                       (SEQ ID NO: 223)
GVPDRFSGSGSGTDFTLKISRVETEDVGVYYC;

(SEQ ID NO: 224)
GVPDRFSGSGSGTDFTLKISRVETEDLGVYYC;
and (SEQ ID NO: 227)
GVPDRFSGSGSGTDFTLKISRVETEDLGVYFC.
```

In some preferred embodiments, VL FR4 of the antibody or an antigen binding fragment thereof according to the invention is SEQ ID NO: 230, or differs from SEQ ID NO: 230 by the following substitution: (40) Q at L100, wherein, the amino acid position mentioned in (40) is numbered according to Kabat numbering system.

In some preferred embodiments, the VL FR4 of the antibody or an antigen binding fragment thereof according to the invention has a sequence selected from the group consisting of:

```
                                       (SEQ ID NO: 230)
FGGGTKLEIKR,
and (SEQ ID NO: 231)
FGQGTKLEIKR.
```

In some preferred embodiments, the sequence of the VL FR4 of the antibody or an antigen binding fragment thereof according to the invention is FGGGTKLEIKR (SEQ ID NO: 230).

In some preferred embodiments, the antibody or an antigen binding fragment thereof according to the invention comprises a VL comprising, a combination of VL FR1, VL FR2, VL FR3 and VL FR4, selected from any one of the following (1)-(14):

| | VL-FR1 (SEQ ID NO:) | VL-FR2 (SEQ ID NO:) | VL-FR3 (SEQ ID NO:) | VL-FR4 (SEQ ID NO:) |
|---|---|---|---|---|
| (1) | 215 | 221 | 223 | 230 |
| (2) | 215 | 221 | 224 | 230 |
| (3) | 215 | 221 | 225 | 231 |
| (4) | 215 | 222 | 224 | 230 |
| (5) | 215 | 222 | 225 | 231 |
| (6) | 216 | 222 | 223 | 230 |
| (7) | 216 | 222 | 227 | 230 |
| (8) | 217 | 221 | 226 | 230 |
| (9) | 218 | 221 | 224 | 230 |
| (10) | 218 | 221 | 227 | 230 |
| (11) | 218 | 221 | 228 | 230 |
| (12) | 218 | 222 | 227 | 230 |
| (13) | 219 | 221 | 224 | 230 |
| (14) | 220 | 221 | 229 | 230 |

In some preferred embodiments, the antibody or an antigen binding fragment thereof according to the invention comprises a VL comprising:

(a) VL FR1 as set forth in DVVMTQSPLSLPVTLGEPASISC (SEQ ID NO: 215); VL FR2 as set forth in WYLQKPGQSPKLLIY (SEQ ID NO: 221); VL FR3 as set forth in GVPDRFSGSGSGTDFTLKISRVETEDVGVYYC (SEQ ID NO: 223); and, VL FR4 as set forth in FGGGTKLEIKR (SEQ ID NO: 230);

(b) VL FR1 as set forth in DVVMTQSPLSLPVTLGEPASISC (SEQ ID NO: 215); VL FR2 as set forth in WYLQKPGQSPKLLIY (SEQ ID NO: 221); VL FR3 as set forth in GVPDRFSGSGSGTDFTLKISRVETEDLGVYYC (SEQ ID NO: 224); and, VL FR4 as set forth in FGGGTKLEIKR (SEQ ID NO: 230);

(c) VL FR1 as set forth in DIVMTQSPLSLPVTLGEPASISC (SEQ ID NO: 216); VL FR2 as set forth in WYLQKPGQSPQLLIY (SEQ ID NO: 222); VL FR3 as set forth in GVPDRFSGSGSGTDFTLKISRVETEDVGVYYC (SEQ ID NO: 223); and, VL FR4 as set forth in FGGGTKLEIKR (SEQ ID NO: 230);

(d) VL FR1 as set forth in DVVMTQSPLSLPVTLGEPASISC (SEQ ID NO: 215); VL FR2 as set forth in WYLQKPGQSPQLLIY (SEQ ID NO: 222); VL FR3 as set forth in GVPDRFSGSGSGTDFTLKISRVETEDLGVYYC (SEQ ID NO: 224); and, VL FR4 as set forth in FGGGTKLEIKR (SEQ ID NO: 230);

(e) VL FR1 as set forth in DVVMTQSPLSLPVTLGEPASISC (SEQ ID NO: 215); VL FR2 as set forth in WYLQKPGQSPQLLIY (SEQ ID NO: 222); VL FR3 as set forth in GVPDRFSGSGSGTDFTLKISRVEAEDVGVYYC (SEQ ID NO: 225); and, VL FR4 as set forth in FGQGTKLEIKR (SEQ ID NO: 231);

(f) VL FR1 as set forth in DVVMTQTPLSLPVNLGEPASISC (SEQ TD NO: 217); VL FR2 as set forth in WYLQKPGQSPKLLIY (SEQ ID NO: 221); VL FR3 as set forth in GVPDRFSGSGSGTDFTLKISRVEAEDLGVYFC (SEQ ID NO: 226); and, VL FR4 as set forth in FGGGTKLEIKR (SEQ ID NO: 230);

(g) VL FR1 as set forth in DVVMTQSPLSLPVTLGEPASISC (SEQ ID NO: 215); VL FR2 as set forth in WYLQKPGQSPKLLIY (SEQ ID NO: 221); VL FR3 as set forth in GVPDRFSGSGSGTDFTLKISRVEAEDVGVYYC (SEQ ID NO: 225); and, VL FR4 as set forth in FGQGTKLEIKR (SEQ ID NO: 231);

(h) VL FR1 as set forth in DIVMTQSPLSLPVTLGEPASISC (SEQ ID NO: 216); VL FR2 as set forth in WYLQKPGQSPQLLIY (SEQ ID NO: 222); VL FR3 as set forth in GVPDRFSGSGSGTDFTLKISRVETEDLGVYFC (SEQ ID NO: 227); and, VL FR4 as set forth in FGGGTKLEIKR (SEQ ID NO: 230);

(i) VL FR1 as set forth in DIVMTQSPLSLPVTLGEQASISC (SEQ ID NO: 218); VL FR2 as set forth in WYLQKPGQSPQLLIY (SEQ ID NO: 222); VL FR3 as set forth in GVPDRFSGSGSGTDFTLKISRVETEDLGVYFC (SEQ ID NO: 227); and, VL FR4 as set forth in FGGGTKLEIKR (SEQ ID NO: 230);

(j) VL FR1 as set forth in DIVMTQSPLSLPVTLGEQASISC (SEQ ID NO: 218); VL FR2 as set forth in WYLQK- PGQSPKLLIY (SEQ ID NO: 221); VL FR3 as set forth in GVPDRFSGSGSGTDFTLKISRVETEDLGVYFC (SEQ ID NO: 227); and, VL FR4 as set forth in FGGGTKLEIKR (SEQ ID NO: 230);

(k) VL FR1 as set forth in DIVMTQSPLSLPVTLGEQASISC (SEQ ID NO: 218); VL FR2 as set forth in WYLQKPGQSPKLLIY (SEQ ID NO: 221); VL FR3 as set forth in GVPDRFSGSGSGTDFTLKISRVDTEDLGVYFC (SEQ ID NO: 228); and, VL FR4 as set forth in FGGGTKLEIKR (SEQ ID NO: 230);

(l) VL FR1 as set forth in DIVMTQSPLSLPVTLGEQASISC (SEQ ID NO: 218); VL FR2 as set forth in WYLQKPGQSPKLLIY (SEQ ID NO: 221); VL FR3 as set forth in GVPDRFSGSGSGTDFTLKISRVETEDLGVYYC (SEQ ID NO: 224); and, VL FR4 as set forth in FGGGTKLEIKR (SEQ ID NO: 230);

(m) VL FR1 as set forth in DVVMTQSPLSLPVTLGEQASISC (SEQ ID NO: 219); VL FR2 as set forth in WYLQKPGQSPKLLIY (SEQ ID NO: 221); VL FR3 as set forth in GVPDRFSGSGSGTDFTLKISRVETEDLGVYYC (SEQ ID NO: 224); and, VL FR4 as set forth in FGGGTKLEIKR (SEQ ID NO: 230); or (n) VL FR1 as set forth in DIVMTQSPLSLPVTPGEPASISC (SEQ ID NO: 220); VL FR2 as set forth in WYLQKPGQSPKLLIY (SEQ ID NO: 221); VL FR3 as set forth in GVPDRFSGSGSGTDFTLKISRVETEDVGVYFC (SEQ ID NO: 229); and, VL FR4 as set forth in FGGGTKLEIKR (SEQ ID NO: 230).

In some preferred embodiments, the VL of the antibody or an antigen binding fragment thereof according to the invention comprises VL FR4 as set forth in FGGGTKLEIKR (SEQ ID NO: 230); and, VL FR1, VL FR2 and VL FR3 selected from the group consisting of:

(b) VL FR1 as set forth in DVVMTQSPLSLPVTLGEPASISC (SEQ ID NO: 215); VL FR2 as set forth in WYLQKPGQSPKLLIY (SEQ ID NO: 221); VL FR3 as set forth in GVPDRFSGSGSGTDFTLKISRVETEDLGVYYC (SEQ ID NO: 224);

(c) VL FR1 as set forth in DIVMTQSPLSLPVTLGEPASISC (SEQ ID NO: 216); VL FR2 as set forth in WYLQKPGQSPQLLIY (SEQ ID NO: 222); VL FR3 as set forth in GVPDRFSGSGSGTDFTLKISRVETEDVGVYYC (SEQ ID NO: 223);

(d) VL FR1 as set forth in DVVMTQSPLSLPVTLGEPASISC (SEQ ID NO: 215); VL FR2 as set forth in WYLQKPGQSPQLLIY (SEQ ID NO: 222); VL FR3 as set forth in GVPDRFSGSGSGTDFTLKISRVETEDLGVYYC (SEQ ID NO: 224);

(f) VL FR1 as set forth in DVVMTQTPLSLPVNLGEPASISC (SEQ ID NO: 217); VL FR2 as set forth in WYLQKPGQSPKLLIY (SEQ ID NO: 221); VL FR3 as set forth in GVPDRFSGSGSGTDFTLKISRVEAEDLGVYFC (SEQ ID NO: 226);

(h) VL FR1 as set forth in DIVMTQSPLSLPVTLGEPASISC (SEQ ID NO: 216); VL FR2 as set forth in WYLQKPGQSPQLLIY (SEQ ID NO: 222); VL FR3 as set forth in GVPDRFSGSGSGTDFTLKISRVETEDLGVYFC (SEQ ID NO: 227); and (i) VL FR1 as set forth in DIVMTQSPLSLPVTLGEQASISC (SEQ ID NO: 218); VL FR2 as set forth in WYLQKPGQSPQLLIY (SEQ ID NO: 222); VL FR3 as set forth in GVPDRFSGSGSGTDFTLKISRVETEDLGVYFC (SEQ ID NO: 227).

In some preferred embodiments, the antibody or an antigen binding fragment thereof according to the invention comprises a VH comprising, a combination of VH FR1, VH FR2, VH FR3 and VH FR4 selected from any one of the following (1)-(41):

| | VH-FR1 (SEQ ID NO:) | VH-FR2 (SEQ ID NO:) | VH-FR3 (SEQ ID NO:) | VH-FR4 (SEQ ID NO:) |
|---|---|---|---|---|
| (1) | 93 | 129 | 161 | 183 |
| (2) | 93 | 129 | 162 | 183 |
| (3) | 93 | 129 | 163 | 183 |
| (4) | 93 | 130 | 162 | 183 |
| (5) | 93 | 139 | 174 | 183 |
| (6) | 94 | 129 | 162 | 183 |
| (7) | 94 | 129 | 167 | 183 |
| (8) | 94 | 129 | 175 | 183 |
| (9) | 94 | 129 | 177 | 183 |
| (10) | 94 | 137 | 171 | 183 |
| (11) | 94 | 138 | 173 | 183 |
| (12) | 95 | 129 | 162 | 183 |
| (13) | 96 | 129 | 162 | 183 |
| (14) | 97 | 129 | 162 | 183 |
| (15) | 97 | 131 | 162 | 183 |
| (16) | 98 | 129 | 162 | 183 |
| (17) | 99 | 129 | 162 | 183 |
| (18) | 100 | 129 | 162 | 183 |
| (19) | 101 | 132 | 164 | 183 |
| (20) | 102 | 129 | 165 | 183 |
| (21) | 103 | 129 | 166 | 183 |
| (22) | 104 | 133 | 168 | 183 |
| (23) | 105 | 134 | 169 | 184 |
| (24) | 105 | 134 | 179 | 184 |
| (25) | 105 | 136 | 169 | 184 |
| (26) | 105 | 140 | 176 | 183 |
| (27) | 106 | 129 | 166 | 183 |
| (28) | 107 | 129 | 166 | 183 |
| (29) | 108 | 129 | 166 | 183 |
| (30) | 108 | 138 | 173 | 183 |
| (31) | 109 | 129 | 166 | 183 |
| (32) | 110 | 129 | 166 | 183 |
| (33) | 111 | 129 | 165 | 183 |
| (34) | 112 | 129 | 165 | 183 |
| (35) | 113 | 129 | 165 | 183 |
| (36) | 114 | 129 | 165 | 183 |
| (37) | 115 | 129 | 165 | 183 |
| (38) | 116 | 135 | 170 | 185 |
| (39) | 117 | 129 | 172 | 183 |
| (40) | 118 | 141 | 173 | 183 |
| (41) | 119 | 141 | 178 | 183 |

In some preferred embodiments, the antibody or an antigen binding fragment thereof according to the invention comprises a VH comprising:

(a) VH FR1 as set forth in EVQLQESGPGLVKPSQTLSLTCAVSGYSIS (SEQ ID NO: 93); VH FR2 as set forth in WIRQFPGNKLEWIG (SEQ ID NO: 129); VH FR3 as set forth in RITITRDTSKNQFSLILRSVTAFDTAIYYCAS (SEQ ID NO: 161); and, VH FR4 as set forth in WGQGTTLTVSS (SEQ ID NO: 183);

(b) VH FR1 as set forth in EVQLQESGPGLVKPSQTLSLTCAVSGYSIS (SEQ ID NO: 93); VH FR2 as set forth in WIRQFPGNKLEWIG (SEQ ID NO: 129); VH FR3 as set forth in RVTITRDTSKNQFFLKLSSVTAEDTAKYYCAS (SEQ ID NO: 162); and, VH FR4 as set forth in WGQGTTLTVSS (SEQ ID NO: 183);

(c) VH FR1 as set forth in EVQLQESGPGLVKPSQTLSLTCAVSGYSIS (SEQ ID NO: 93); VH FR2 as set forth in WIRQFPGNKLEWIG (SEQ ID NO: 129); VH FR3 as set forth in RVTITRDTSKNQFFLKLSSVTAEDTARYYCAS (SEQ ID NO: 163); and, VH FR4 as set forth in WGQGTTLTVSS (SEQ ID NO: 183);

(d) VH FR1 as set forth in EVQLQESGPGLVKPSQTLSLTCAVSGYSIS (SEQ ID NO: 93); VH FR2 as set forth in WVRQFPGNKLEWIG (SEQ ID NO: 130); VH FR3 as set forth in RVTITRDTSKNQFFLKLSSVTAED- TAKYYCAS (SEQ ID NO: 162); and, VH FR4 as set forth in WGQGTTLTVSS (SEQ ID NO: 183);

(e) VH FR1 as set forth in EVQLQESGPGLVKP-SQTLSLTCAVSGYSIS (SEQ ID NO: 93); VH FR2 as set forth in WIRQFPGNRLEWIG (SEQ ID NO: 139); VH FR3 as set forth in RVTITRDTSKNQFFLILRSVTAEDTAKYY-CAS (SEQ ID NO: 174); and, VH FR4 as set forth in WGQGTTLTVSS (SEQ ID NO: 183);

(f) VH FR1 as set forth in EVQLQESGPGLVKP-SQTLSLTCAVSGYSIT (SEQ ID NO: 94); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(g) VH FR1 as set forth in EVQLQESGPGLVKP-SQTLSLTCAVSGYSIT (SEQ ID NO: 94); VH FR2 as set forth in WIRQFPGNKLEWIG (SEQ ID NO: 129); VH FR3 as set forth in RVSITRDTSKNQFFLKLSSVTAEDTAKY-FCAS (SEQ ID NO: 167); and, VH FR4 as set forth in WGQGTTLTVSS (SEQ ID NO: 183);

(h) VH FR1 as set forth in EVQLQESGPGLVKP-SQTLSLTCAVSGYSIT (SEQ ID NO: 94); VH FR2 as set forth in WIRQFPGKRLEWMG (SEQ ID NO: 137); VH FR3 as set forth in RITITRDTSKNQFFLKLRSVTAED-TAVYYCAS (SEQ ID NO: 171); and, VH FR4 as set forth in WGQGTTLTVSS (SEQ ID NO: 183);

(i) VH FR1 as set forth in EVQLQESGPGLVKP-SQTLSLTCAVSGYSIT (SEQ ID NO: 94); VH FR2 as set forth in WIRQFPGNELEWIG (SEQ ID NO: 138); VH FR3 as set forth in RITITRDTSKNQFFLKLRSVTAEDTAKYY-CAS (SEQ ID NO: 173); and, VH FR4 as set forth in WGQGTTLTVSS (SEQ ID NO: 183);

(j) VH FR1 as set forth in EVQLQESGPGLVKP-SQTLSLTCAVSGYSIT (SEQ ID NO: 94); VH FR2 as set forth in WIRQFPGNKLEWIG (SEQ ID NO: 129); VH FR3 as set forth in RVSITRDTSKNQFFLKLSSVTAEDTAKY-FCAS (SEQ ID NO: 167); and, VH FR4 as set forth in WGQGTTLTVSS (SEQ ID NO: 183);

(k) VH FR1 as set forth in EVQLQESGPGLVKP-SQTLSLTCAVSGTSIT (SEQ ID NO: 95); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(l) VH FR1 as set forth in EVQLQESGPGLVKP-SQTLSLTCAVSGNSIS (SEQ ID NO: 96); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(m) VH FR1 as set forth in EVQLQESGPGLVKP-SQTLSLTCAVSGASIT (SEQ ID NO: 97); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(n) VH FR1 as set forth in EVQLQESGPGLVKP-SQTLSLTCAVSGASIT (SEQ ID NO: 97); VH FR2 as set forth in WIQQFPGNKLEWIG (SEQ ID NO: 131); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(o) VH FR1 as set forth in EVQLQESGPGLVKP-SQTLSLTCAVSGSSIT (SEQ ID NO: 98); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(p) VH FR1 as set forth in EVQLQESGPGLVKP-SQTLSLTCAVSGASIS (SEQ ID NO: 99); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(q) VH FR1 as set forth in EVQLQESGPGLVKP-SQTLSLTCAVSGGSIT (SEQ ID NO: 100); VH FR2 as set forth in WIRQFPGNKLEWIG (SEQ ID NO: 129); VH FR3 as set forth in RVTITRDTSKNQFFLKLSSVTAED-TAKYYCAS (SEQ ID NO: 162); and, VH FR4 as set forth in WGQGTTLTVSS (SEQ ID NO: 183);

(r) VH FR1 as set forth in EVQLQES-GPGLVKASQTLSLTCAVSGYSIS (SEQ ID NO: 101); VH FR2 as set forth in WIRQLPGNKLEWIG (SEQ ID NO: 132); VH FR3 as set forth in RITISRDTSKNQFFLKLRS-VTAEDTAKYFCAS (SEQ ID NO: 164); and, VH FR4 as set forth in WGQGTTLTVSS (SEQ ID NO: 183);

(s) VH FR1 as set forth in EVQLQESGPGLVKP-SQTLSLTCAVSGYPIS (SEQ ID NO: 104); VH FR2 as set forth in WIRQFPGKKLEWIG (SEQ ID NO: 133); VH FR3 as set forth in RVTITRDTSKNQFFLKLRSVTAEDTAIYF-CAS (SEQ ID NO: 168); and, VH FR4 as set forth in WGQGTTLTVSS (SEQ ID NO: 183);

(t) VH FR1 as set forth in EVQLQESGPGLVKP-SQTLSLTCAVSGYPIT (SEQ ID NO: 117); VH FR2 as set forth in WIRQFPGNKLEWIG (SEQ ID NO: 129); VH FR3 as set forth in RVSITRDTSKNQFFLKLRSVTAEDTAIYF-CAS (SEQ ID NO: 172); and, VH FR4 as set forth in WGQGTTLTVSS (SEQ ID NO: 183);

(u) VH FR1 as set forth in HVQLQESGPGLVKP-SQTLSLTCAVSGTSIT (SEQ ID NO: 106); VH FR2 as set forth in WIRQFPGNKLEWIG (SEQ ID NO: 129); VH FR3 as set forth in RVTITRDTSKNQFFLKLRSVTAEDTAIYY-CAS (SEQ ID NO: 166); and, VH FR4 as set forth in WGQGTTLTVSS (SEQ ID NO: 183);

(v) VH FR1 as set forth in HVQLQESGPGLVKP-SQTLSLTCAVSGYSIS (SEQ ID NO: 108); VH FR2 as set forth in WIRQFPGNKLEWIG (SEQ ID NO: 129); VH FR3 as set forth in RVTITRDTSKNQFFLKLRSVTAEDTAIYY-CAS (SEQ ID NO: 166); and, VH FR4 as set forth in WGQGTTLTVSS (SEQ ID NO: 183);

(w) VH FR1 as set forth in HVQLQESGPGLVKP-SQTLSLTCAVSGASIT (SEQ ID NO: 109); VH FR2 as set forth in WIRQFPGNKLEWIG (SEQ ID NO: 129); VH FR3 as set forth in RVTITRDTSKNQFFLKLRSVTAEDTAIYY-CAS (SEQ ID NO: 166); and, VH FR4 as set forth in WGQGTTLTVSS (SEQ ID NO: 183);

(x) VH FR1 as set forth in HVQLQESGPGLVKP-SQTLSLTCAVSGYSIT (SEQ ID NO: 103); VH FR2 as set forth in WIRQFPGNKLEWIG (SEQ ID NO: 129); VH FR3 as set forth in RVTITRDTSKNQFFLKLRSVTAEDTAIYY-CAS (SEQ ID NO: 166); and, VH FR4 as set forth in WGQGTTLTVSS (SEQ ID NO: 183);

(y) VH FR1 as set forth in HVQLQESGPGLVKP-SQTLSLTCAVSGNSIS (SEQ TD NO: 107); VH FR2 as set forth in WIRQFPGNKLEWIG (SEQ ID NO: 129); VH FR3 as set forth in RVTITRDTSKNQFFLKLRSVTAEDTAIYY-CAS (SEQ ID NO: 166); and, VH FR4 as set forth in WGQGTTLTVSS (SEQ ID NO: 183);

(z) VH FR1 as set forth in HVQLQESGPGLVKP-SQTLSLTCAVSGSSIT (SEQ ID NO: 110); VH FR2 as set forth in WIRQFPGNKLEWIG (SEQ ID NO: 129); VH FR3 as set forth in RVTITRDTSKNQFFLKLRSVTAEDTAIYY- CAS (SEQ ID NO: 166); and, VH FR4 as set forth in WGQGTTLTVSS (SEQ ID NO: 183);

(aa) VH FR1 as set forth in QVQLQESGPGLVKPSQTLSLTCAVSGYSIS (SEQ ID NO: 105); VH FR2 as set forth in WIRQFPGKGLEWIG (SEQ ID NO: 134); VH FR3 as set forth in RVTISVDTSKNQFSLKLSSVTAEDTAVYYCAS (SEQ ID NO: 169); and, VH FR4 as set forth in WGQGTLVTVSS (SEQ ID NO: 184);

(ab) VH FR1 as set forth in QVQLQESGPGLVKPSQTLSLTCAVSGYSIS (SEQ ID NO: 105); VH FR2 as set forth in WIRQFPGKSLEWIG (SEQ ID NO: 136); VH FR3 as set forth in RVTISVDTSKNQFSLKLSSVTAEDTAVYYCAS (SEQ ID NO: 169); and, VH FR4 as set forth in WGQGTLVTVSS (SEQ ID NO: 184);

(ac) VH FR1 as set forth in DVQLQESGPGLVKPSQTLSLTCAVSGYSIT (SEQ ID NO: 111); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183);

(ad) VH FR1 as set forth in DVQLQESGPGLVKPSQTLSLTCTVSGYPIT (SEQ ID NO: 116); VH FR2 as set forth in WIRQFPGNKLVWMG (SEQ ID NO: 135); VH FR3 as set forth in RVSISRDISKNQFFLKLSSVTAADTAVYFCAS (SEQ ID NO: 170); and, VH FR4 as set forth in WGQGTMLTVSS (SEQ ID NO: 185);

(ae) VH FR1 as set forth in DVQLQESGPGLVKPSQTLSLTCAVSGYPIT (SEQ ID NO: 102); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183);

(af) VH FR1 as set forth in DVQLQESGPGLVKPSQTLSLTCAVSGYSIS (SEQ ID NO: 112); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183);

(ag) VH FR1 as set forth in DVQLQESGPGLVKPSQTLSLTCAVSGTSIT (SEQ ID NO: 113); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183);

(ah) VH FR1 as set forth in DVQLQESGPGLVKPSQTLSLTCAVSGNSIS (SEQ ID NO: 114); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183); or (ai) VH FR1 as set forth in DVQLQESGPGLVKPSQTLSLTCAVSGSSIT (SEQ ID NO: 115); VH FR2 as set forth in WIRQFPGNKLEWIG (SEQ ID NO: 129); VH FR3 as set forth in RVSITRDTSKNQFFLILRSVTAEDTAIYYCAS (SEQ ID NO: 165); and, VH FR4 as set forth in WGQGTTLTVSS (SEQ ID NO: 183).

In some preferred embodiments, the VH of the antibody or an antigen binding fragment thereof according to the invention comprises:

(1) VH FR2 as set forth in WIRQFPGNKLEWIG (SEQ ID NO: 129), VH FR4 as set forth in WGQGTTLTVSS (SEQ ID NO: 183), and, (1a) VH FR3 as set forth in RVTITRDTSKNQFFLKLSSVTAEDTAKYYCAS (SEQ ID NO: 162), and VH FR1 selected from the group consisting of:
EVQLQESGPGLVKPSQTLSLTCAVSGYSIS (SEQ ID NO: 93);
EVQLQESGPGLVKPSQTLSLTCAVSGSSIT (SEQ ID NO: 98);
EVQLQESGPGLVKPSQTLSLTCAVSGYSIT (SEQ ID NO: 94); and
EVQLQESGPGLVKPSQTLSLTCAVSGNSIS (SEQ ID NO: 96); or (1b) VH FR3 as set forth in RVTITRDTSKNQFFLKLRSVTAEDTAIYYCAS (SEQ ID NO: 166), and VH FR1 selected from the group consisting of:
HVQLQESGPGLVKPSQTLSLTCAVSGYSIT (SEQ ID NO: 103);
HVQLQESGPGLVKPSQTLSLTCAVSGTSIT (SEQ ID NO: 106);
HVQLQESGPGLVKPSQTLSLTCAVSGNSIS (SEQ ID NO: 107);
HVQLQESGPGLVKPSQTLSLTCAVSGYSIS (SEQ ID NO: 108);
HVQLQESGPGLVKPSQTLSLTCAVSGYSIT (SEQ ID NO: 110);
HVQLQESGPGLVKPSQTLSLTCAVSGYSIT (SEQ ID NO: 103); and
HVQLQESGPGLVKPSQTLSLTCAVSGASIT (SEQ ID NO: 109); or (1c) VH FR3 as set forth in RVSITRDTSKNQFFLILRSVTAEDTAIYYCAS (SEQ ID NO: 165), and VH FR1 selected from the group consisting of:
DVQLQESGPGLVKPSQTLSLTCAVSGYSIT (SEQ ID NO: 111);
DVQLQESGPGLVKPSQTLSLTCAVSGSSIT (SEQ ID NO: 115); and
DVQLQESGPGLVKPSQTLSLTCAVSGYPIT (SEQ ID NO: 102); or (1d) VH FR1 as set forth in EVQLQESGPGLVKPSQTLSLTCAVSGYSIS (SEQ ID NO: 93), and VH FR3 as set forth in RITITRDTSKNQFSLILRSVTAEDTAIYYCAS (SEQ ID NO: 161); or (1e) VH FR1 as set forth in EVQLQESGPGLVKPSQTLSLTCAVSGYSIT (SEQ ID NO: 94), and VH FR3 as set forth in RVSITRDTSKNQFFLKLSSVTAEDTAKYFCAS (SEQ ID NO: 167); or (1f) VH FR1 as set forth in EVQLQESGPGLVKPSQTLSLTCAVSGYPIT (SEQ ID NO: 117), and VH FR3 as set forth in RVSITRDTSKNQFFLKLRSVTAEDTAIYFCAS (SEQ ID NO: 172); or (2) VH FR4 as set forth in WGQGTTLTVSS (SEQ ID NO: 183), VH FR1, VH FR2 and VH FR3 selected from the group consisting of:

(2a) VH FR1 as set forth in EVQLQESGPGLVKPSQTLSLTCAVSGYSIT (SEQ ID NO: 94); VH FR2 as set forth in WIRQFPGKRLEWMG (SEQ ID NO: 137); and VH FR3 as set forth in RITITRDTSKNQFFLKLRSVTAEDTAVYYCAS (SEQ ID NO: 171);

(2b) VH FR1 as set forth in EVQLQESGPGLVKPSQTLSLTCAVSGYSIT (SEQ ID NO: 94); VH FR2 as set forth in WIRQFPGNELEWIG (SEQ ID NO: 138); and VH FR3 as set forth in RITITRDTSKNQFFLKLRSVTAEDTAKYYCAS (SEQ ID NO: 173);

(2c) VH FR1 as set forth in EVQLQESGPGLVKASQTLSLTCAVSGYSIS (SEQ ID NO: 101); VH FR2 as set forth in WIRQLPGNKLEWIG (SEQ ID NO: 132); and VH FR3 as set forth in RITISRDTSKNQFFLKLRSVTAEDTAKYFCAS (SEQ ID NO: 164);

(2d) VH FR1 as set forth in EVQLQESGPGLVKPSQTLSLTCAVSGYPIS (SEQ ID NO: 104); VH FR2 as set forth in WIRQFPGKKLEWIG (SEQ ID NO:

133); and VH FR3 as set forth in RVTITRDTSKNQF-FLKLRSVTAEDTAIYFCAS (SEQ ID NO: 168); or
(3) VH FR1 as set forth in DVQLQESGPGLVKP-SQTLSLTCTVSGYPIT (SEQ ID NO: 116); VH FR2 as set forth in WIRQFPGNKLVWMG (SEQ ID NO: 135); VH FR3 as set forth in RVSISRDISKNQFFLKLSSVTAAD-TAVYFCAS (SEQ ID NO: 170); and, VH FR4 as set forth in WGQGTMLTVSS (SEQ ID NO: 185).

In some preferred embodiments, the VH of the antibody or an antigen binding fragment thereof according to the invention comprises:
(1) VH FR2 as set forth in WIRQFPGNKLEWIG (SEQ ID NO: 129), VH FR4 as set forth in WGQGTTLTVSS (SEQ ID NO: 183), and,
  (1a) VH FR3 as set forth in RVTITRDTSKNQFFLKLSS-VTAEDTAKYYCAS (SEQ ID NO: 162), and VH FR1 selected from the group consisting of:
EVQLQESGPGLVKPSQTLSLTCAVSGSSIT (SEQ ID NO: 98);
EVQLQESGPGLVKPSQTLSLTCAVSGYSIT (SEQ ID NO: 94); and
EVQLQESGPGLVKPSQTLSLTCAVSGNSIS (SEQ ID NO: 96); or
  (1b) VH FR1 as set forth in EVQLQESGPGLVKP-SQTLSLTCAVSGYSIS (SEQ ID NO: 93), and VH FR3 as set forth in RITITRDTSKNQFSLILRSVTAE-DTATYYCAS (SEQ ID NO: 161); or
  (1c) VH FR1 as set forth in EVQLQESGPGLVKP-SQTLSLTCAVSGYSIT (SEQ ID NO: 94), VH FR3 as set forth in RVSITRDTSKNQFFLKLSSVTAED-TAKYFCAS (SEQ ID NO: 167); or
  (1d) VH FR1 as set forth in EVQLQESGPGLVKP-SQTLSLTCAVSGYPIT (SEQ ID NO: 117), and VH FR3 as set forth in RVSITRDTSKNQFFLKLRSV-TAEDTAIYFCAS (SEQ ID NO: 172); or
(2) VH FR4 as set forth in WGQGTTLTVSS (SEQ ID NO: 183), and VH FR1, VH FR2 and VH FR3 selected from the group consisting of:
  (2a) VH FR1 as set forth in EVQLQESGPGLVKP-SQTLSLTCAVSGYSIT (SEQ ID NO: 94); VH FR2 as set forth in WIRQFPGKRLEWMG (SEQ ID NO: 137); and VH FR3 as set forth in RITITRDTSKNQFFLKL-RSVTAEDTAVYYCAS (SEQ ID NO: 171);
  (2b) VH FR1 as set forth in EVQLQESGPGLVKP-SQTLSLTCAVSGYSIT (SEQ ID NO: 94); VH FR2 as set forth in WIRQFPGNELEWIG (SEQ ID NO: 138); and VH FR3 as set forth in RITITRDTSKNQFFLKL-RSVTAEDTAKYYCAS (SEQ ID NO: 173);
  (2c) VH FR1 as set forth in EVQLQES-GPGLVKASQTLSLTCAVSGYSIS (SEQ ID NO: 101); VH FR2 as set forth in WIRQLPGNKLEWIG (SEQ ID NO: 132); and VH FR3 as set forth in RITISRDTSKNQFFLKLRSVTAEDTAKYFCAS (SEQ TD NO: 164);
  (2d) VH FR1 as set forth in EVQLQESGPGLVKP-SQTLSLTCAVSGYPIS (SEQ ID NO: 104); VH FR2 as set forth in WIRQFPGKKLEWIG (SEQ ID NO: 133); and VH FR3 as set forth in RVTITRDTSKNQF-FLKLRSVTAEDTAIYFCAS (SEQ ID NO: 168);
  (2e) VH FR1 as set forth in EVQLQESGPGLVKP-SQTLSLTCAVSGYSIS (SEQ ID NO: 93); VH FR2 as set forth in WIRQFPGNRLEWIG (SEQ ID NO: 139); and VH FR3 as set forth in RVTITRDTSKNQFFLIL-RSVTAEDTAKYYCAS (SEQ ID NO: 174); or
(3) VH FR1 as set forth in DVQLQESGPGLVKP-SQTLSLTCTVSGYPIT (SEQ ID NO: 116); VH FR2 as set forth in WIRQFPGNKLVWMG (SEQ ID NO: 135); VH FR3 as set forth in RVSISRDISKNQFFLKLSSVTAAD-TAVYFCAS (SEQ ID NO: 170); and, VH FR4 as set forth in WGQGTMLTVSS (SEQ ID NO: 185).

In some preferred embodiments, the antibody or an antigen binding fragment thereof according to the invention comprises VH FR1, VH FR2, VH FR3 and VH FR4 as defined above. In some preferred embodiments, the antibody or an antigen binding fragment thereof according to the invention comprises VL FR1, VL FR2, VL FR3 and VL FR4 as defined above. In some preferred embodiments, the antibody or an antigen binding fragment thereof according to the invention comprises VH FR1, VH FR2, VH FR3, VH FR4, VL FR1, VL FR2, VL FR3 and VL FR4 as defined above.

In some preferred embodiments, the heavy chain variable region framework region (FR1-4) of the antibody according to the invention has a sequence identity of at least 80%, at least 85%, at least 90%, at least 95%, at least 96%, at least 97%, at least 98%, at least 99% or 100% with the heavy chain variable region framework region (FR1-4) comprised in any one (such as SEQ ID NO: 11) of SEQ ID NOs: 11-92 and 263-279. In some preferred embodiments, the light chain variable region framework region (FR1-4) of the antibody according to the invention has a sequence identity of at least 80%, at least 85%, at least 90%, at least 95%, at least 96%, at least 97%, at least 98%, at least 99% or 100% with the light chain variable region framework region (FR1-4) comprised in any one (such as SEQ ID NO: 186) of SEQ ID NOs: 186-214 and 298-308. In some preferred embodiments, the antibody according to the invention comprises, a heavy chain variable region framework region (FR1-4) having a sequence identity of at least 80%, at least 85%, at least 90%, at least 95%, at least 96%, at least 97%, at least 98%, at least 99% or 100% with a heavy chain variable region framework region (FR1-4) comprised in any one (such as SEQ ID NO: 11) of SEQ ID NOs: 11-92 and 263-279, and a light chain variable region framework region (FR1-4) having a sequence identity of at least 80%, at least 85%, at least 90%, at least 95%, at least 96%, at least 97%, at least 98%, at least 99% or 100% with a light chain variable region framework region (FR1-4) comprised in any one (such as SEQ ID NO: 186) of SEQ ID NOs: 186-214 and 298-308.

In some preferred embodiments, the antibody or an antigen binding fragment thereof according to the invention comprises 8 FRs from heavy chain and light chain variable regions of an antibody selected from:

| Antibody name | VH (SEQ ID NO:) | VL (SEQ ID NO:) |
|---|---|---|
| B-S3-45 | 11 | 186 |
| 10-25 | 16 | 187 |
| 11 | 14 | 187 |
| 110 | 72 | 201 |
| 112 | 71 | 199 |
| 11-26 | 17 | 187 |
| 113 | 31 | 187 |
| 11-3 | 69 | 189 |
| 11-34-266 | 44 | 187 |
| 116 | 73 | 202 |
| 117 | 32 | 187 |
| 123 | 77 | 206 |
| 12-34-277 | 45 | 187 |
| 127 | 74 | 209 |
| 1-31-322 | 47 | 187 |
| 138 | 91 | 205 |
| 153 | 73 | 205 |
| 162 | 36 | 187 |
| 162/41k | 36 | 189 |

| Antibody name | VH (SEQ ID NO:) | VL (SEQ ID NO:) |
|---|---|---|
| 162B | 55 | 192 |
| 16-34-293 | 46 | 187 |
| 187 | 74 | 202 |
| 192 | 92 | 200 |
| 23 | 76 | 204 |
| 242 | 42 | 187 |
| 24-34-316 | 48 | 187 |
| 24-40 | 20 | 187 |
| 25-34-317 | 49 | 187 |
| 29 | 18 | 187 |
| 35-62 | 24 | 187 |
| 37 | 19 | 187 |
| 39-73 | 25 | 187 |
| 42 | 21 | 187 |
| 43-89 | 27 | 187 |
| 44 | 22 | 187 |
| 47-101 | 29 | 187 |
| 5 | 12 | 187 |
| 50-112 | 30 | 187 |
| 54-123 | 33 | 187 |
| 55-127 | 34 | 187 |
| 56-135 | 35 | 187 |
| 6-16 | 23 | 187 |
| 62 | 75 | 203 |
| 6-34-234 | 40 | 187 |
| 69-171 | 37 | 187 |
| 7 | 13 | 187 |
| 7-17 | 15 | 187 |
| 73-188 | 38 | 187 |
| 7-34-239 | 41 | 187 |
| 74-189 | 39 | 187 |
| 76-191 | 43 | 187 |
| 83 | 78 | 205 |
| 84 | 72 | 205 |
| 85 | 26 | 187 |
| 86 | 28 | 187 |
| B3-S4-N-130 | 55 | 194 |
| B3-S4-N-50 | 70 | 198 |
| B3-S4-N-65 | 55 | 195 |
| B3-S4-N-68 | 55 | 197 |
| B4-T13-11 | 55 | 196 |
| B-S2-13 | 90 | 187 |
| B-S2-2 | 51 | 188 |
| B-S2-25 | 54 | 190 |
| B-S2-26 | 83 | 208 |
| B-S3-2 | 79 | 190 |
| B-S3-44 | 85 | 190 |
| D11/41K | 62 | 189 |
| D11/K1 | 62 | 193 |
| D162/41K | 66 | 189 |
| D162/K1 | 66 | 193 |
| D17/41K | 64 | 189 |
| D17/K1 | 64 | 193 |
| D239/41K | 67 | 189 |
| D239/K1 | 67 | 193 |
| D40/K1 | 65 | 193 |
| D6-16/K1 | 63 | 193 |
| H11/41K | 82 | 189 |
| H11/K1 | 82 | 193 |
| H162/41K | 60 | 189 |
| H162/K1 | 60 | 193 |
| H17/41K | 56 | 189 |
| H17/K1 | 56 | 193 |
| H311/41K | 61 | 189 |
| H311/K1 | 61 | 193 |
| H40/41K | 57 | 189 |
| H40/K1 | 57 | 193 |
| H42/41K | 58 | 189 |
| H42/K1 | 58 | 193 |
| H44/41K | 59 | 189 |
| H44/K1 | 59 | 193 |
| H6-16/41K | 68 | 189 |
| N-22 | 53 | 191 |
| P-44 | 55 | 199 |
| P-50 | 55 | 200 |
| S-S2-10 | 53 | 187 |
| S-S2-11 | 52 | 189 |
| S-S2-2 | 84 | 210 |
| S-S2-22 | 84 | 212 |
| S-S2-25 | 50 | 187 |
| S-S2-30 | 80 | 207 |
| S-S2-32 | 88 | 214 |
| S-S2-41 | 52 | 189 |
| S-S2-43 | 89 | 212 |
| S-S2-47 | 81 | 187 |
| S-S2-5 | 84 | 211 |
| S-S3-16 | 86 | 190 |
| S-S3-29 | 87 | 213 |
| 162ccp-S5-N-56 | 72 | 202 |
| 162ccp-S6-N-149 | 72 | 306 |
| 162ccp-S5-N-84 | 72 | 200 |
| 162ccp-S5-P-64 | 91 | 300 |
| 162ccp-S5-N-32 | 91 | 200 |
| 138HA/162BK | 263 | 192 |
| 138HB/83K | 264 | 205 |
| 138HB/162BK | 264 | 192 |
| 138HB/110K | 264 | 201 |
| 138HB/116K | 264 | 202 |
| 162BHB/83K | 265 | 205 |
| 162BHB/110K | 265 | 201 |
| 162BHB/116K | 265 | 202 |
| 162BHE/83K | 266 | 205 |
| 162BHE/162BK | 266 | 192 |
| 162ccp-S4-N-81 | 267 | 298 |
| 162ccp-S5-P-27 | 268 | 299 |
| 162ccp-S5-P-77 | 269 | 301 |
| 162ccp-S5-N-41 | 270 | 302 |
| 162ccp-S5-N-69 | 271 | 202 |
| 162ccp-S5-N-70 | 272 | 303 |
| 162ccp-S6-N-101 | 273 | 304 |
| 162ccp-S6-N-111 | 274 | 305 |
| 162ccp-S6-N-137 | 275 | 200 |
| 162ccp-S6-N-146 | 276 | 202 |
| 162ccp-S6-N-160 | 277 | 307 |
| 162ccp-S6-N-66 | 278 | 308 |
| 162ccp-S6-N-45 | 279 | 202 |

In some preferred embodiments, the heavy chain variable region of the antibody or an antigen binding fragment thereof according to the invention comprises VH FR1, VH CDR1, VH FR2, VH CDR2, VH FR3, VH CDR3 and VH FR4 as defined above. In some preferred embodiments, the light chain variable region of the antibody or an antigen binding fragment thereof according to the invention comprises VL FR1, VL CDR1, VL FR2, VL CDR2, VL FR3, VL CDR3 and VL FR4 as defined above. In some preferred embodiments, the heavy chain variable region of the antibody or an antigen binding fragment thereof according to the invention comprises VH FR1, VH CDR1, VH FR2, VH CDR2, VH FR3, VH CDR3 and VH FR4 as defined above; and, the light chain variable region comprises VL FR1, VL CDR1, VL FR2, VL CDR2, \TL FR3, VL CDR3 and VL FR4 as defined above.

In some preferred embodiments, the heavy chain variable region of the antibody or an antigen binding fragment thereof according to the invention has an amino acid sequence identity of at least 80%, at least 85%, at least 90%, at least 91%, at least 92%, at least 93%, at least 94%, at least 95%, at least 96%, at least 97%, at least 98%, at least 99%, or 100% with a heavy chain variable region selected from the group consisting of:

heavy chain variable regions set forth in SEQ ID NOs: 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 263, 264, 265, 266, 267, 268, 269, 270, 271, 272, 273, 274, 275, 276, 277, 278 and 279.

In some preferred embodiments, the heavy chain variable region of the antibody or an antigen binding fragment thereof according to the invention is selected from a heavy chain variable region set forth in any one of SEQ ID NOs: 11-92 and 263-279.

In some preferred embodiments, the light chain variable region of the antibody or an antigen binding fragment thereof according to the invention has an amino acid sequence identity of at least 80%, at least 85%, at least 90%, at least 91%, at least 92%, at least 93%, at least 94%, at least 95%, at least 96%, at least 97%, at least 98%, at least 99%, or 100% with a light chain variable region selected from the group consisting of:

light chain variable regions set forth in SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 298, 299, 300, 301, 302, 303, 304, 305, 306, 307 and 308.

In some preferred embodiments, the light chain variable region of the antibody or an antigen binding fragment thereof according to the invention is selected from a light chain variable region set forth in any one of SEQ ID NOs: 186-214 and 298-308.

In some preferred embodiments, the heavy chain variable region comprised in the antibody according to the invention has a sequence identity of at least 80%, at least 85%, at least 90%, at least 91%, at least 92%, at least 93%, at least 94%, at least 95%, at least 96%, at least 97%, at least 98%, at least 99%, or 100% with SEQ ID NO: 11. In some preferred embodiments, the light chain variable region comprised in the antibody according to the invention has a sequence identity of at least 80%, at least 85%, at least 90%, at least 91%, at least 92%, at least 93%, at least 94%, at least 95%, at least 96%, at least 97%, at least 98%, at least 99%, or 100% with SEQ ID NO: 186. In some preferred embodiments, the antibody according to the invention comprises a heavy chain variable region and a light chain variable region, wherein the heavy chain variable region has a sequence identity of at least 80%, at least 85%, at least 90%, at least 91%, at least 92%, at least 93%, at least 94%, at least 95%, at least 96%, at least 97%, at least 98%, at least 99%, or 100% with SEQ ID NO: 11, and the light chain variable region has a sequence identity of at least 80%, at least 85%, at least 90%, at least 91%, at least 92%, at least 93%, at least 94%, at least 95%, at least 96%, at least 97%, at least 98%, at least 99%, or 100% with SEQ ID NO: 186.

In some preferred embodiments, the antibody according to the invention comprises the heavy chain variable region as defined above and the light chain variable region as defined above.

In some preferred embodiments, the antibody according to the invention comprises a heavy chain variable region and a light chain variable region comprised in an antibody selected from:

| Antibody name | VH (SEQ ID NO:) | VL (SEQ ID NO:) |
|---|---|---|
| B-S3-45 | 11 | 186 |
| 10-25 | 16 | 187 |
| 11 | 14 | 187 |
| 110 | 72 | 201 |
| 112 | 71 | 199 |
| 11-26 | 17 | 187 |
| 113 | 31 | 187 |
| 11-3 | 69 | 189 |
| 11-34-266 | 44 | 187 |
| 116 | 73 | 202 |
| 117 | 32 | 187 |
| 123 | 77 | 206 |
| 12-34-277 | 45 | 187 |
| 127 | 74 | 209 |
| 1-31-322 | 47 | 187 |
| 138 | 91 | 205 |
| 153 | 73 | 205 |
| 162 | 36 | 187 |
| 162/41k | 36 | 189 |
| 162B | 55 | 192 |
| 16-34-293 | 46 | 187 |
| 187 | 74 | 202 |
| 192 | 92 | 200 |
| 23 | 76 | 204 |
| 242 | 42 | 187 |
| 24-34-316 | 48 | 187 |
| 24-40 | 20 | 187 |
| 25-34-317 | 49 | 187 |
| 29 | 18 | 187 |
| 35-62 | 24 | 187 |
| 37 | 19 | 187 |
| 39-73 | 25 | 187 |
| 42 | 21 | 187 |
| 43-89 | 27 | 187 |
| 44 | 22 | 187 |
| 47-101 | 29 | 187 |
| 5 | 12 | 187 |
| 50-112 | 30 | 187 |
| 54-123 | 33 | 187 |
| 55-127 | 34 | 187 |
| 56-135 | 35 | 187 |
| 6-16 | 23 | 187 |
| 62 | 75 | 203 |
| 6-34-234 | 40 | 187 |
| 69-171 | 37 | 187 |
| 7 | 13 | 187 |
| 7-17 | 15 | 187 |
| 73-188 | 38 | 187 |
| 7-34-239 | 41 | 187 |
| 74-189 | 39 | 187 |
| 76-191 | 43 | 187 |
| 83 | 78 | 205 |
| 84 | 72 | 205 |
| 85 | 26 | 187 |
| 86 | 28 | 187 |
| B3-S4-N-130 | 55 | 194 |
| B3-S4-N-50 | 70 | 198 |
| B3-S4-N-65 | 55 | 195 |
| B3-S4-N-68 | 55 | 197 |
| B4-T13-11 | 55 | 196 |
| B-S2-13 | 90 | 187 |
| B-S2-2 | 51 | 188 |
| B-S2-25 | 54 | 190 |
| B-S2-26 | 83 | 208 |
| B-S3-2 | 79 | 190 |
| B-S3-44 | 85 | 190 |
| D11/41K | 62 | 189 |
| D11/K1 | 62 | 193 |
| D162/41K | 66 | 189 |
| D162/K1 | 66 | 193 |
| D17/41K | 64 | 189 |
| D17/K1 | 64 | 193 |
| D239/41K | 67 | 189 |
| D239/K1 | 67 | 193 |
| D40/K1 | 65 | 193 |
| D6-16/K1 | 63 | 193 |
| H11/41K | 82 | 189 |
| H11/K1 | 82 | 193 |
| H162/41K | 60 | 189 |
| H162/K1 | 60 | 193 |
| H17/41K | 56 | 189 |
| H17/K1 | 56 | 193 |
| H311/41K | 61 | 189 |
| H311/K1 | 61 | 193 |
| H40/41K | 57 | 189 |

-continued

| Antibody name | VH (SEQ ID NO:) | VL (SEQ ID NO:) |
|---|---|---|
| H40/K1 | 57 | 193 |
| H42/41K | 58 | 189 |
| H42/K1 | 58 | 193 |
| H44/41K | 59 | 189 |
| H44/K1 | 59 | 193 |
| H6-16/41K | 68 | 189 |
| N-22 | 53 | 191 |
| P-44 | 55 | 199 |
| P-50 | 55 | 200 |
| S-S2-10 | 53 | 187 |
| S-S2-11 | 52 | 189 |
| S-S2-2 | 84 | 210 |
| S-S2-22 | 84 | 212 |
| S-S2-25 | 50 | 187 |
| S-S2-30 | 80 | 207 |
| S-S2-32 | 88 | 214 |
| S-S2-41 | 52 | 189 |
| S-S2-43 | 89 | 212 |
| S-S2-47 | 81 | 187 |
| S-S2-5 | 84 | 211 |
| S-S3-16 | 86 | 190 |
| S-S3-29 | 87 | 213 |
| 162ccp-S5-N-56 | 72 | 202 |
| 162ccp-S6-N-149 | 72 | 306 |
| 162ccp-S5-N-84 | 72 | 200 |
| 162ccp-S5-P-64 | 91 | 300 |
| 162ccp-S5-N-32 | 91 | 200 |
| 138HA/162BK | 263 | 192 |
| 138HB/83K | 264 | 205 |
| 138HB/162BK | 264 | 192 |
| 138HB/110K | 264 | 201 |
| 138HB/116K | 264 | 202 |
| 162BHB/83K | 265 | 205 |
| 162BHB/110K | 265 | 201 |
| 162BHB/116K | 265 | 202 |
| 162BHE/83K | 266 | 205 |
| 162BHE/162BK | 266 | 192 |
| 162ccp-S4-N-81 | 267 | 298 |
| 162ccp-S5-P-27 | 268 | 299 |
| 162ccp-S5-P-77 | 269 | 301 |
| 162ccp-S5-N-41 | 270 | 302 |
| 162ccp-S5-N-69 | 271 | 202 |
| 162ccp-S5-N-70 | 272 | 303 |
| 162ccp-S6-N-101 | 273 | 304 |
| 162ccp-S6-N-111 | 274 | 305 |
| 162ccp-S6-N-137 | 275 | 200 |
| 162ccp-S6-N-146 | 276 | 202 |
| 162ccp-S6-N-160 | 277 | 307 |
| 162ccp-S6-N-66 | 278 | 308 |
| 162ccp-S6-N-45 | 279 | 202 |

In some preferred embodiments, the antibody according to the invention comprises:

(1) VH as set forth in SEQ ID NO: 11 and VL as set forth in SEQ ID NO: 186;
(2) VH as set forth in SEQ ID NO: 16 and VL as set forth in SEQ ID NO: 187;
(3) VH as set forth in SEQ ID NO: 14 and VL as set forth in SEQ ID NO: 187;
(4) VH as set forth in SEQ ID NO: 72 and VL as set forth in SEQ ID NO: 201;
(5) VH as set forth in SEQ ID NO: 71 and VL as set forth in SEQ ID NO: 199;
(6) VH as set forth in SEQ ID NO: 17 and VL as set forth in SEQ ID NO: 187;
(7) VH as set forth in SEQ ID NO: 31 and VL as set forth in SEQ ID NO: 187;
(8) VH as set forth in SEQ ID NO: 69 and VL as set forth in SEQ ID NO: 189;
(9) VH as set forth in SEQ ID NO: 44 and VL as set forth in SEQ ID NO: 187;
(10) VH as set forth in SEQ ID NO: 73 and VL as set forth in SEQ ID NO: 202;
(11) VH as set forth in SEQ ID NO: 32 and VL as set forth in SEQ ID NO: 187;
(12) VH as set forth in SEQ ID NO: 77 and VL as set forth in SEQ ID NO: 206;
(13) VH as set forth in SEQ ID NO: 45 and VL as set forth in SEQ ID NO: 187;
(14) VH as set forth in SEQ ID NO: 74 and VL as set forth in SEQ ID NO: 209;
(15) VH as set forth in SEQ ID NO: 47 and VL as set forth in SEQ ID NO: 187;
(16) VH as set forth in SEQ ID NO: 91 and VL as set forth in SEQ ID NO: 205;
(17) VH as set forth in SEQ ID NO: 73 and VL as set forth in SEQ ID NO: 205;
(18) VH as set forth in SEQ ID NO: 36 and VL as set forth in SEQ ID NO: 187;
(19) VH as set forth in SEQ ID NO: 36 and VL as set forth in SEQ ID NO: 189;
(20) VH as set forth in SEQ ID NO: 55 and VL as set forth in SEQ ID NO: 192;
(21) VH as set forth in SEQ ID NO: 46 and VL as set forth in SEQ ID NO: 187;
(22) VH as set forth in SEQ ID NO: 74 and VL as set forth in SEQ ID NO: 202;
(23) VH as set forth in SEQ ID NO: 92 and VL as set forth in SEQ ID NO: 200;
(24) VH as set forth in SEQ ID NO: 76 and VL as set forth in SEQ ID NO: 204;
(25) VH as set forth in SEQ ID NO: 42 and VL as set forth in SEQ ID NO: 187;
(26) VH as set forth in SEQ ID NO: 48 and VL as set forth in SEQ ID NO: 187;
(27) VH as set forth in SEQ ID NO: 20 and VL as set forth in SEQ ID NO: 187;
(28) VH as set forth in SEQ ID NO: 49 and VL as set forth in SEQ ID NO: 187;
(29) VH as set forth in SEQ ID NO: 18 and VL as set forth in SEQ ID NO: 187;
(30) VH as set forth in SEQ ID NO: 24 and VL as set forth in SEQ ID NO: 187;
(31) VH as set forth in SEQ ID NO: 19 and VL as set forth in SEQ ID NO: 187;
(32) VH as set forth in SEQ ID NO: 25 and VL as set forth in SEQ ID NO: 187;
(33) VH as set forth in SEQ ID NO: 21 and VL as set forth in SEQ ID NO: 187;
(34) VH as set forth in SEQ ID NO: 27 and VL as set forth in SEQ ID NO: 187;
(35) VH as set forth in SEQ ID NO: 22 and VL as set forth in SEQ ID NO: 187;
(36) VH as set forth in SEQ ID NO: 29 and VL as set forth in SEQ ID NO: 187;
(37) VH as set forth in SEQ ID NO: 12 and VL as set forth in SEQ ID NO: 187;
(38) VH as set forth in SEQ ID NO: 30 and VL as set forth in SEQ ID NO: 187;
(39) VH as set forth in SEQ ID NO: 33 and VL as set forth in SEQ ID NO: 187;
(40) VH as set forth in SEQ ID NO: 34 and VL as set forth in SEQ ID NO: 187;
(41) VH as set forth in SEQ ID NO: 35 and VL as set forth in SEQ ID NO: 187;
(42) VH as set forth in SEQ ID NO: 23 and VL as set forth in SEQ ID NO: 187;
(43) VH as set forth in SEQ ID NO: 75 and VL as set forth in SEQ ID NO: 203;

(44) VH as set forth in SEQ ID NO: 40 and VL as set forth in SEQ ID NO: 187;
(45) VH as set forth in SEQ ID NO: 37 and VL as set forth in SEQ ID NO: 187;
(46) VH as set forth in SEQ ID NO: 13 and VL as set forth in SEQ ID NO: 187;
(47) VH as set forth in SEQ ID NO: 15 and VL as set forth in SEQ ID NO: 187;
(48) VH as set forth in SEQ ID NO: 38 and VL as set forth in SEQ ID NO: 187;
(49) VH as set forth in SEQ ID NO: 41 and VL as set forth in SEQ ID NO: 187;
(50) VH as set forth in SEQ ID NO: 39 and VL as set forth in SEQ ID NO: 187;
(51) VH as set forth in SEQ ID NO: 43 and VL as set forth in SEQ ID NO: 187;
(52) VH as set forth in SEQ ID NO: 78 and VL as set forth in SEQ ID NO: 205;
(53) VH as set forth in SEQ ID NO: 72 and VL as set forth in SEQ ID NO: 205;
(54) VH as set forth in SEQ ID NO: 26 and VL as set forth in SEQ ID NO: 187;
(55) VH as set forth in SEQ ID NO: 28 and VL as set forth in SEQ ID NO: 187;
(56) VH as set forth in SEQ ID NO: 55 and VL as set forth in SEQ ID NO: 194;
(57) VH as set forth in SEQ ID NO: 70 and VL as set forth in SEQ ID NO: 198;
(58) VH as set forth in SEQ ID NO: 55 and VL as set forth in SEQ ID NO: 195;
(59) VH as set forth in SEQ ID NO: 55 and VL as set forth in SEQ ID NO: 197;
(60) VH as set forth in SEQ ID NO: 55 and VL as set forth in SEQ ID NO: 196;
(61) VH as set forth in SEQ ID NO: 90 and VL as set forth in SEQ ID NO: 187;
(62) VH as set forth in SEQ ID NO: 51 and VL as set forth in SEQ ID NO: 188;
(63) VH as set forth in SEQ ID NO: 54 and VL as set forth in SEQ ID NO: 190;
(64) VH as set forth in SEQ ID NO: 83 and VL as set forth in SEQ ID NO: 208;
(65) VH as set forth in SEQ ID NO: 79 and VL as set forth in SEQ ID NO: 190;
(66) VH as set forth in SEQ ID NO: 85 and VL as set forth in SEQ ID NO: 190;
(67) VH as set forth in SEQ ID NO: 62 and VL as set forth in SEQ ID NO: 189;
(68) VH as set forth in SEQ ID NO: 62 and VL as set forth in SEQ ID NO: 193;
(69) VH as set forth in SEQ ID NO: 66 and VL as set forth in SEQ ID NO: 189;
(70) VH as set forth in SEQ ID NO: 66 and VL as set forth in SEQ ID NO: 193;
(71) VH as set forth in SEQ ID NO: 64 and VL as set forth in SEQ ID NO: 189;
(72) VH as set forth in SEQ ID NO: 64 and VL as set forth in SEQ ID NO: 193;
(73) VH as set forth in SEQ ID NO: 67 and VL as set forth in SEQ ID NO: 189;
(74) VH as set forth in SEQ ID NO: 67 and VL as set forth in SEQ ID NO: 193;
(75) VH as set forth in SEQ ID NO: 65 and VL as set forth in SEQ ID NO: 193;
(76) VH as set forth in SEQ ID NO: 63 and VL as set forth in SEQ ID NO: 193;
(77) VH as set forth in SEQ ID NO: 82 and VL as set forth in SEQ ID NO: 189;
(78) VH as set forth in SEQ ID NO: 82 and VL as set forth in SEQ ID NO: 193;
(79) VH as set forth in SEQ ID NO: 60 and VL as set forth in SEQ ID NO: 189;
(80) VH as set forth in SEQ ID NO: 60 and VL as set forth in SEQ ID NO: 193;
(81) VH as set forth in SEQ ID NO: 56 and VL as set forth in SEQ ID NO: 189;
(82) VH as set forth in SEQ ID NO: 56 and VL as set forth in SEQ ID NO: 193;
(83) VH as set forth in SEQ ID NO: 61 and VL as set forth in SEQ ID NO: 189;
(84) VH as set forth in SEQ ID NO: 61 and VL as set forth in SEQ ID NO: 193;
(85) VH as set forth in SEQ ID NO: 57 and VL as set forth in SEQ ID NO: 189;
(86) VH as set forth in SEQ ID NO: 57 and VL as set forth in SEQ ID NO: 193;
(87) VH as set forth in SEQ ID NO: 58 and VL as set forth in SEQ ID NO: 189;
(88) VH as set forth in SEQ ID NO: 58 and VL as set forth in SEQ ID NO: 193;
(89) VH as set forth in SEQ ID NO: 59 and VL as set forth in SEQ ID NO: 189;
(90) VH as set forth in SEQ ID NO: 59 and VL as set forth in SEQ ID NO: 193;
(91) VH as set forth in SEQ ID NO: 68 and VL as set forth in SEQ ID NO: 189;
(92) VH as set forth in SEQ ID NO: 53 and VL as set forth in SEQ ID NO: 191;
(93) VH as set forth in SEQ ID NO: 55 and VL as set forth in SEQ ID NO: 199;
(94) VH as set forth in SEQ ID NO: 55 and VL as set forth in SEQ ID NO: 200;
(95) VH as set forth in SEQ ID NO: 53 and VL as set forth in SEQ ID NO: 187;
(96) VH as set forth in SEQ ID NO: 52 and VL as set forth in SEQ ID NO: 189;
(97) VH as set forth in SEQ ID NO: 84 and VL as set forth in SEQ ID NO: 210;
(98) VH as set forth in SEQ ID NO: 84 and VL as set forth in SEQ ID NO: 212;
(99) VH as set forth in SEQ ID NO: 50 and VL as set forth in SEQ ID NO: 187;
(100) VH as set forth in SEQ ID NO: 80 and VL as set forth in SEQ ID NO: 207;
(101) VH as set forth in SEQ ID NO: 88 and VL as set forth in SEQ ID NO: 214;
(102) VH as set forth in SEQ ID NO: 52 and VL as set forth in SEQ ID NO: 189;
(103) VH as set forth in SEQ ID NO: 89 and VL as set forth in SEQ ID NO: 212;
(104) VH as set forth in SEQ ID NO: 81 and VL as set forth in SEQ ID NO: 187;
(105) VH as set forth in SEQ ID NO: 84 and VL as set forth in SEQ ID NO: 211;
(106) VH as set forth in SEQ ID NO: 86 and VL as set forth in SEQ ID NO: 190;
(107) VH as set forth in SEQ ID NO: 87 and VL as set forth in SEQ ID NO: 213;
(108) VH as set forth in SEQ ID NO: 72 and VL as set forth in SEQ ID NO: 202;
(109) VH as set forth in SEQ ID NO: 72 and VL as set forth in SEQ ID NO: 306;

(110) VH as set forth in SEQ ID NO: 72 and VL as set forth in SEQ ID NO: 200;
(111) VH as set forth in SEQ ID NO: 91 and VL as set forth in SEQ ID NO: 300;
(112) VH as set forth in SEQ ID NO: 91 and VL as set forth in SEQ ID NO: 200;
(113) VH as set forth in SEQ ID NO: 263 and VL as set forth in SEQ ID NO: 192;
(114) VH as set forth in SEQ ID NO: 264 and VL as set forth in SEQ ID NO: 205;
(115) VH as set forth in SEQ ID NO: 264 and VL as set forth in SEQ ID NO: 192;
(116) VH as set forth in SEQ ID NO: 264 and VL as set forth in SEQ ID NO: 201;
(117) VH as set forth in SEQ ID NO: 264 and VL as set forth in SEQ ID NO: 202;
(118) VH as set forth in SEQ ID NO: 265 and VL as set forth in SEQ ID NO: 205;
(119) VH as set forth in SEQ ID NO: 265 and VL as set forth in SEQ ID NO: 201;
(120) VH as set forth in SEQ ID NO: 265 and VL as set forth in SEQ ID NO: 202;
(121) VH as set forth in SEQ ID NO: 266 and VL as set forth in SEQ ID NO: 205;
(122) VH as set forth in SEQ ID NO: 266 and VL as set forth in SEQ ID NO: 192;
(123) VH as set forth in SEQ ID NO: 267 and VL as set forth in SEQ ID NO: 298;
(124) VH as set forth in SEQ ID NO: 268 and VL as set forth in SEQ ID NO: 299;
(125) VH as set forth in SEQ ID NO: 269 and VL as set forth in SEQ ID NO: 301;
(126) VH as set forth in SEQ ID NO: 270 and VL as set forth in SEQ ID NO: 302;
(127) VH as set forth in SEQ ID NO: 271 and VL as set forth in SEQ ID NO: 202;
(128) VH as set forth in SEQ ID NO: 272 and VL as set forth in SEQ ID NO: 303;
(129) VH as set forth in SEQ ID NO: 273 and VL as set forth in SEQ ID NO: 304;
(130) VH as set forth in SEQ ID NO: 274 and VL as set forth in SEQ ID NO: 305;
(131) VH as set forth in SEQ ID NO: 275 and VL as set forth in SEQ ID NO: 200;
(132) VH as set forth in SEQ ID NO: 276 and VL as set forth in SEQ ID NO: 202;
(133) VH as set forth in SEQ ID NO: 277 and VL as set forth in SEQ ID NO: 307;
(134) VH as set forth in SEQ ID NO: 278 and VL as set forth in SEQ ID NO: 308;
or
(135) VH as set forth in SEQ ID NO: 279 and VL as set forth in SEQ ID NO: 202.

The antibody according to the invention may be obtained by genetic engineering recombinant techniques. For example, a DNA molecule of genes encoding a heavy chain and a light chain of the antibody according to the invention can be obtained by chemical synthesis or PCR amplification. The DNA molecule obtained can be inserted into an expression vector, and then be transfected into a host cell (such as E. coli cell, simian primate COS cell, CHO cell, or other myeloma cell that do not produce immunoglobulin. Then, the transfected host cell can be cultured under specific conditions to express the antibody according to the invention.

The antibody according to the invention has a high specificity and affinity for HBsAg protein. For example, the antibody according to the invention bind to HBsAg with a KD value of below $1 \times 10^{-5}$ M; preferably, with a KD value of below $1 \times 10^{-6}$ M; more preferably, with a KD value of below $1 \times 10^{-7}$ M; most preferably, with a KD value of below $1 \times 10^{-8}$ M.

The antibody according to the invention can be a traditional Y-shaped antibody that comprises two heavy chains and two light chains. In addition, the antibody according to the invention can also be Fab fragment, Fab', F(ab)$_2$, Fv, or other fragments of the traditional Y-shaped antibody, which retain affinity for HBsAg protein, and can bind to HBsAg protein with affinity higher or lower than that of the traditional Y-shaped antibody.

The antigen binding fragment according to the invention can be obtained by hydrolysis of an intact antibody molecule (see Morimoto et al., J. Biochem. Biophys. Methods 24:107-117 (1992) and Brennan et al., Science 229:81 (1985)). In addition, these antigen binding fragments can also be produced directly by recombinant host cells (reviewed in Hudson, Curr. Opin. Immunol. 11: 548-557 (1999); Little et al., Immunol. Today, 21: 364-370 (2000)). For example, Fab' fragment can be obtained directly from E. coli cell; and Fab' fragment can be chemically coupled to form F(ab')$_2$ fragment (Carter et al., Bio/Technology, 10: 163-167 (1992)). In addition, Fv, Fab or F(ab')$_2$ fragment can also be isolated directly from a culture of a recombinant host cell. A person skilled in the art well knows other technologies for preparing the antigen binding fragment.

Therefore, in some preferred embodiments, the antibody or an antigen binding fragment thereof according to the invention is selected from the group consisting of scFv, Fab, Fab', (Fab')$_2$, Fv fragment, diabody, bispecific antibody, and polyspecific antibody. Particularly preferably, the antibody or an antigen binding fragment thereof according to the invention is scFv antibody.

In some preferred embodiments, the antibody or an antigen binding fragment thereof according to the invention can specifically bind to HBsAg, neutralize HBV virulence, and/or reduce the serum level of HBV DNA and/or HBsAg in a subject.

In some preferred embodiments, the antibody or an antigen binding fragment thereof according to the invention is an antibody of IgG isotype or an antigen binding fragment thereof. For example, the antibody or an antigen binding fragment thereof according to the invention may be an antibody of IgG1, IgG2 or IgG4 isotype or an antigen binding fragment thereof.

Chimeric Antibodies

In another aspect, a fusion antibody or an immunoadhesin can be prepared, for example, the antibody or an antigen binding fragment thereof according to the invention can be linked to another polypeptide. In some preferred embodiments, a fusion antibody comprises the heavy chain variable region and light chain variable region of the antibody according to the invention. In some preferred embodiments, a fusion antibody comprises VH domain and VL domain of the antibody according to the invention; wherein, the VH domain is linked to a first polypeptide, and the VL domain is linked to a second polypeptide.

Derivatized Antibodies

The antibody or an antigen binding fragment thereof according to the invention can be derivatized, for example, linked to another molecule (e.g. another polypeptide or protein). In general, the derivatization (such as labeling) of an antibody or an antigen binding fragment thereof would not affect its binding to HBsAg adversely. Therefore, the antibody or an antigen binding fragment thereof according to the invention is also intended to include such derivatized forms. For example, the antibody or an antigen binding fragment thereof according to the invention can be functionally linked (by chemical coupling, genetic fusion, non-covalent linkage or other means) to one or more other molecular groups, such as another antibody (e.g. forming a bispecific antibody), a detection agent, a medicinal agent, and/or a protein or polypeptide capable of mediating associate of the antibody or an antigen binding fragment thereof with another molecule (such as an avidin or a polyhistidine-tag).

One type of derivatized antibody (such as bispecific antibody) is produced by crosslinking two or more antibodies (which belong to the same type or not). Suitable cross-linking agents include, for example, heterbifunctional cross-linking agent, comprising two different reactive groups separated by a suitable spacer (such as m-maleimidoben-zoyl-N-hydroxylsuccinimide ester); and, homobifunctional crosslinking agent (disuccinimidyl suberate). Such cross-linking agents may be purchased from Pierce Chemical Company, Rockford, II.

Another type of derivatized antibody is a labelled antibody. For example, the antibody or an antigen binding fragment thereof according to the invention can be linked to a useful detection agent. Such detection agents include, for example, fluorescent compounds such as fluorescein, fluorescein isothiocyanate, rhodamine, dansyl chloride, phycoerythrin, lanthanide phosphor, and so on. In addition, an antibody can also be labelled by enzyme, such as horseradish peroxidase, beta-galactosidase, luciferase, alkaline phosphatase, glucose oxidase, and so on. When an antibody is labelled by enzyme, a reagent, which can be utilized by the enzyme to produce a discernible signal or reaction product, can be added to detect the labelled antibody. For example, when horseradish peroxidase is used to label an antibody, hydrogen peroxide and diaminobenzidine can be added to produce a detectable chromogenic reaction product so as to determine the presence or amount of the labelled antibody. In addition, an antibody can also be labelled by a biotin. In this case, the presence or amount of the labelled antibody can be determined by indirectly determining the binding of avidin. In addition, an antibody can also be labelled by a tag which can be recognized by a second reporter molecule (such as leucine zipper pair sequences, metal-binding domain, epitope tag, and so on). In some particular embodiments, a label can be linked to an antibody via a spacer arm of a different length, to reduce potential steric hindrance.

In addition, the antibody or an antigen binding fragment thereof according to the invention can also be derivatized with a chemical group, such as polyethylene glycol (PEG), methyl or ethyl, or saccharide group. These groups can be used to improve the biological properties of the antibody, such as increasing serum half-life.

Nucleic Acid Molecule, Vector and Host Cell

In another aspect, the invention provides an isolated nucleic acid molecule, comprising a nucleotide sequence encoding the antibody or an antigen binding fragment thereof according to the invention, or its heavy chain variable region and/or light chain variable region. In some preferred embodiments, the isolated nucleic acid molecule according to the invention encodes the antibody or an antigen binding fragment thereof according to the invention, or its heavy chain variable region and/or light chain variable region.

In another aspect, the invention provides a vector (e.g. a cloning vector or an expression vector), comprising the isolated nucleic acid molecule according to the invention. In some preferred embodiments, the vector according to the invention is, for example, a plasmid, a cosmid, a phage, etc. In some preferred embodiments, the vector can express the antibody or an antigen binding fragment thereof according to the invention in a subject (for example, mammal, such as human).

In another aspect, the invention provides a host cell, comprising the isolated nucleic acid molecule according to the invention or the vector according to the invention. Such host cells include, but are not limited to, prokaryotic cell such as E. coli cell, and eukaryotic cell such as yeast cell, insect cell, plant cell and animal cell (e.g. mammalian cell, such as mouse cell and human cell). The cell according to the invention may be a cell line, such as 293T cell.

In another aspect, provided is a method for preparing the antibody or an antigen binding fragment thereof according to the invention, comprising, culturing the host cell according to the invention under a condition allowing expression of the antibody or an antigen binding fragment thereof, and recovering the antibody or an antigen binding fragment thereof from a culture of the cultured host cell.

Diagnostic Method and Kit

The antibody or an antigen binding fragment thereof according to the invention can specifically bind to HBsAg, and therefore can be used for detecting the presence or level of HBsAg protein in a sample, and can be used for diagnozing whether a subject is infected by HBV.

Thus, in another aspect, the invention provides a kit comprising the antibody or an antigen binding fragment thereof according to the invention. In a preferred embodiment, the antibody or an antigen binding fragment thereof according to the invention further comprises a detectable marker. In a preferred embodiment, the kit further comprises a second antibody, which specifically recognizes the antibody or an antigen binding fragment thereof according to the invention. Preferably, the second antibody further comprises a detectable marker.

In accordance with the methods described above, the antibody or an antigen binding fragment thereof or the second antibody according to the invention can be labeled. For example, the antibody or an antigen binding fragment thereof according to the invention can be labeled with a detectable marker. Such detectable markers, which are well known by a person skilled in the art, include, but are not limited to, radioisotope, fluorescent substance, luminescent substance, chromophoric substance and enzyme (e.g. horseradish peroxidase), etc. In addition, such detectable markers further include, for example, radioisotope, such as $^{125}$I; fluorescent substance, such as fluorescein, fluorescein isothiocyanate, rhodamine, 5-dimethylamino-1-naphthalenesulfonyl chloride, phycoerythrin, and lanthanide phosphor; enzyme capable of producing a discernible signal or reaction product, such as horseradish peroxidase, β-galactosidase, luciferase, alkaline phosphatase, and glucose oxidase; a tag that can be recognized by a second reporter molecule, such as biotin, avidin, leucine zipper pair sequence, metal-binding domain, and epitope tag. In some particular embodiments, a detection agent (e.g. a tag) can be linked to an antibody via a linker of a different length, to reduce potential steric hindrance.

In another aspect, the invention provides a method for detecting the presence or level of HBsAg protein in a sample, comprising using the antibody or an antigen binding fragment thereof according to the invention. In a preferred embodiment, the antibody or an antigen binding fragment thereof according to the invention further comprises a detectable marker. In another preferred embodiment, the method further comprises, using a second antibody carrying a detectable marker to detect the antibody or an antigen binding fragment thereof according to the invention. The method may be used for diagnostic purpose or for non-diagnostic purpose (for example, said sample is a cell sample, rather than a sample from a patient).

In another aspect, the invention provides a method for diagnosing whether a subject is infected by HBV, comprising: using the antibody or an antigen binding fragment thereof according to the invention to detect the presence of HBsAg protein in a sample from the subject. In a preferred embodiment, the antibody or an antigen binding fragment thereof according to the invention further comprises a detectable marker. In another preferred embodiment, the method further comprises, using a second antibody carrying a detectable marker to detect the antibody or an antigen binding fragment thereof according to the invention.

In another aspect, provided is use of the antibody or an antigen binding fragment thereof according to the invention in the manufacture of a kit for detecting the presence or level of HBsAg in a sample or for diagnosing whether a subject is infected by HBV.

Therapeutic Methods and Pharmaceutical Compositions

The antibody or an antigen binding fragment thereof according to the invention can be used for preventing or treating HBV infection or a disease associated with HBV infection (such as Hepatitis B) in a subject (such as human), for neutralizing HBV virulence in vitro or in a subject (such as human), and for reducing the serum level of HBV DNA and/or HBsAg in a subject (such as human).

Thus, in another aspect, the invention provides a pharmaceutical composition, comprising the antibody or an antigen binding fragment thereof according to the invention, and a pharmaceutically acceptable carrier and/or excipient. In a preferred embodiment, the pharmaceutical composition according to the invention may further comprise an additional pharmaceutically active agent. In a preferred embodiment, the additional pharmaceutically active agent is an agent for preventing or treating HBV infection or a disease associated with HBV infection (such as Hepatitis B), for example, other antiviral agents, e.g. interferon-type agents, such as interferon or pegylated interferon.

In another aspect, provided is use of the antibody or an antigen binding fragment thereof according to the invention or the pharmaceutical composition according to the invention in the manufacture of a medicament for preventing or treating HBV infection or a disease associated with HBV infection (such as Hepatitis B) in a subject (such as human), for neutralizing HBV virulence in vitro or in a subject (such as human), and/or for reducing the serum level of HBV DNA and/or HBsAg in a subject (such as human).

In another aspect, the invention provides a method for preventing or treating HBV infection or a disease associated with HBV infection (such as Hepatitis B) in a subject, for neutralizing HBV virulence in a subject (such as human), and/or for reducing the serum level of HBV DNA and/or HBsAg in a subject (such as human), comprising administering to a subject in need thereof an effective amount of the antibody or an antigen binding fragment thereof according to the invention, or the pharmaceutical composition according to the invention.

The antibody or an antigen binding fragment thereof according to the invention or the pharmaceutical composition according to the invention may be administered by traditional routes, including but not limited to, oral, buccal, sublingual, intraocular, topical, parenteral, rectal, intravaginal, intracisternal, inguinal, intravesical, topical (such as, powder, ointment or drop), or nasal route. The antibody or an antigen binding fragment thereof according to the invention can be administered by multiple routes known in the art. However, for many therapeutic uses, the preferred administration route/way is parenteral administration (such as intravenous injection, subcutaneous injection, intraperitoneal injection, and intramuscular injection). A person skilled in the art understands that the administration route/way can be changed depending on expected purpose. In a preferred embodiment, the antibody or an antigen binding fragment thereof according to the invention is administered by intravenous infusion or injection.

The antibody or an antigen binding fragment thereof according to the invention or the pharmaceutical composition according to the invention can be prepared in multiple dosage forms, such as liquid, semisolid, and solid forms, for example, solution (e.g. injection), dispersion or suspension, tablet, powder, granule, emulsion, pill, syrup, powder, liposome, capsule and suppository. Preferred dosage form depends on the expected administration route and therapeutic use.

For example, one preferred dosage form is an injection. Such an injection may be a sterile injectable solution. For example, a sterile injectable solution can be prepared by the following method: a necessary dose of the antibody or an antigen binding fragment thereof according to the invention is incorporated into a suitable solvent, and optionally, other expected ingredients (including, but not limited to, a pH regulator, a surfactant, an adjuvant, an ionic strength enhancer, an isotonic agent, a preservative, a diluent, or any combination thereof) are incorporated simultaneously, and then filtered sterilization is carried out. In addition, the sterile injectable solution can be prepared into a sterile powder (for example, by vacuum drying or freeze drying) for the convenience of storage and use. Such sterile powder can be dispersed in a suitable vehicle before use, such as sterile pyrogen-free water.

Another preferred dosage form is a dispersion. A dispersion can be prepared by the following method: the antibody or an antigen binding fragment thereof according to the invention is incorporated in a sterile vehicle comprising a basic dispersion medium and optionally, other expected ingredients (including, but not limited to, a pH regulator, a surfactant, an adjuvant, an ionic strength enhancer, an isotonic agent, a preservative, a diluent, or any combination thereof). In addition, an absorption delaying agent can also be incorporated in a dispersion, such as monostearate salt and gelatin, in order to obtain an expected pharmacokinetic property.

Another preferred dosage form is an oral solid dosage form, including capsule, tablet, powder, granule, and the like. Such a solid dosage form generally comprises at least one of: (a) inert drug excipient (or vehicle), such as sodium citrate and calcium phosphate; (b) filler, such as starch, lactose, sucrose, mannose and silicic acid; (c) binder, such as carboxymethyl cellulose, alginate, gelatin, polyvinylpyrrolidone, sucrose and arabic gum; (d) wetting agent, such as glycerol; (e) disintegrating agent, such as agar, calcium carbonate, potato or tapioca starch; (f) retarder, such as olefin; (g) absorption enhancer, such as quaternary ammonium compound; (h) humectant, such as cetyl alcohol and glyceryl monostearate; (i) adsorbent, such as kaolin and bentonite; (j) lubricant, such as talc, calcium stearate, magnesium stearate, solid polyethylene glycol, sodium dodecyl sulfate, or any combination thereof. In the case of tablet and capsule dosage forms, a buffer can also be comprised.

In addition, a release rate modifier (i.e. an agent capable of changing drug release rate) may also be added to an oral solid dosage form, in order to obtain a modified release or pulsed release dosage form. Such a release rate modifier includes, but is not limited to carboxypropyl methylcellulose, methylcellulose, carboxymethyl cellulose sodium, ethyl cellulose, cellulose acetate, polyethylene oxide, xanthan gum, isoacrylic amino copolymer, hydrogenated flavoring oil, carnauba wax, paraffin, cellulose acetate phthalate, carboxypropyl methylcellulose phthalate, methacrylic acid copolymer, or any combination thereof. A modified release or pulsed release dosage form may comprise one or a group of release rate modifiers.

Another preferred dosage form is an oral liquid dosage form, including emulsion, solution, suspension, syrup, and the like. In addition to active ingredients, such an oral liquid dosage form may further comprise inert solvents commonly used in the art, for example water or other solvents, such as ethyl alcohol, isopropanol, propylene glycol, 1,3-butylene glycol, oil (such as cotton seed oil, peanut oil, corn oil, olive oil, flavoring oil and sesame oil), glycerol, polyethylene glycol and sorbitan fatty acid ester, and any combination thereof. In addition to these inert solvents, such an oral liquid dosage form may further comprise humectant, emulsifying agent, suspending agent, sweetening agent, flavoring agent, fragrant agent, and the like.

In addition, the antibody or an antigen binding fragment thereof according to the invention may be present in a unit dosage form in a pharmaceutical composition, for the convenience of administration. The pharmaceutical composition according to the invention should be sterile, and stable under the conditions of manufacture and storage conditions.

The medicament and pharmaceutical composition provided in the invention may be used alone or in combination, or may be used in combination with an additional pharmaceutically active agent (for example, other antiviral agents, e.g. interferon-type agents, such as interferon or pegylated interferon). In some preferred embodiments, the antibody or an antigen binding fragment thereof according to the invention is used in combination with other antiviral agent(s), in order to prevent and/or treat a disease associated with HBV infection. The antibody or an antigen binding fragment thereof according to the invention and such antiviral agent(s) can be administered simultaneously, separately or sequentially. Such antiviral agent(s) include, but are not limited to, interferon-type agents, ribavirin, adamantane, hydroxyurea, IL-2, L-12 and pentacarboxy cytosolic acid, etc.

The pharmaceutical composition according to the invention may comprise "a therapeutically effective amount" or "a prophylactically effective amount" of the antibody or an antigen binding fragment thereof according to the invention. "A prophylactically effective amount" refers to an amount that is sufficient to prevent, suppress or delay the development of a disease (such as HBV infection or a disease associated with HBV infection). "A therapeutically effective amount" refers to an amount that is sufficient to cure or at least partially suppress a disease and its complications in a patient with the disease. The therapeutically effective amount of the antibody or an antigen binding fragment thereof according to the invention may vary depending on the following factors: the severity of a disease to be treated, general state of the immune system in a patient, general conditions of a patient such as age, weight and gender, administration modes of drugs, additional therapies used simultaneously, and the like.

A dosage regimen can be adjusted to provide an optimal desired effect (for example, a therapeutic or prophylactic effect). For example, a single dose may be administered, or multiple doses may be administered within a period of time, or the dose can be proportionally reduced or increased as indicated by the exigencies of the therapeutic situation.

For the antibody or antigen binding fragment thereof according to the invention, an exemplary and non-limiting range for a therapeutically or prophylactically effective amount is from 0.025 to 50 mg/kg, more preferably from 0.1 to 50 mg/kg, more preferably 0.1-25 mg/kg, 0.1-10 mg/kg. It should be noticed that a dose can vary depending on the type and severity of a disease to be treated. In addition, a person skilled in the art understands that for any specific patient, specific dosage regimen should be adjusted over time depending on the patient's need and the professional evaluation made by a doctor; the dose range provided here is only provided for the purpose of exemplification, rather than defining the use or scope of the pharmaceutical composition according to the invention.

Beneficial Effects of the Invention

As compared with the prior art, the technical solutions of the invention have the following beneficial effects.

(1) The antibody according to the invention can not only specifically recognize/bind HBsAg, but also neutralize HBV virulence, reduce the serum level of HBV DNA and/or HBsAg in a subject, and effectively clear HBV and HBV-infected cells in vivo. Therefore, the antibody according to the invention has potential in preventing and treating HBV infection and a disease associated with HBV infection (such as Hepatitis B).

(2) The antibody according to the invention (particularly a humanized antibody) retain the functions and properties of the parent murine antibody, and therefore has potential in preventing and treating HBV infection and a disease associated with HBV infection (such as Hepatitis B); moreover, it has a very high humanization degree (a humanization degree of up to 97%), and therefore can be administered to a human subject safely, without raising an immunogenic response. The antibody according to the invention (particularly humanized antibody) has an important clinical value.

Specific Modes for Carrying Out the Invention

The invention is illustrated by reference to the following examples which are intended to exemplify the invention, rather than limiting the protection scope of the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, $3^{rd}$ Edition, John Wiley & Sons, Inc., 1995; restriction enzymes are used under the conditions recommended by manufacturers of the products. Those skilled in the art understand that the examples are used for illustrating the present invention, and are not intended to limit the protection scope of the present invention.

Example 1: Mouse Monoclonal Antibody 6D11 Specifically Binding to HBsAg and Humanization Thereof 1.1: Characterization of Monoclonal Antibody 6D11

In accordance with conventional immunological methods, mouse monoclonal antibody 6D11 specifically binding to HBsAg (hereinafter referred to as 6D11-mAb or mAb) was prepared. The mouse monoclonal antibody 6D11 has the amino acid sequence of heavy chain variable region set forth in SEQ ID NO: 1, and the amino acid sequence of light chain variable region set forth in SEQ ID NO: 2.

SEQ ID NO: 1
DVQLQESGPGLVKPSQSLSLTCSVTGYPITSGYHWNWIRQFPGNKLVWMG
YISYDGSDHYNPSLENRISITRDISKNQFFLILRSVTTEDTGKYFCASGF
DHWGQGTTLTVSS

SEQ ID NO: 2
DVVMTQTPLSLPVSLGDQASISCRSSQSLVHSYGDTYLHWYLQKPGQSPK
LLIYKVSNRFSGVPDRFSGSGSGTDFTLKISRVETEDLGVYFCSQNTHVP
YTEGGGTKLEIKR

Furthermore, by using the method described by Kabat et al. (Kabat et al., Sequences of Proteins of Immunological Interest, 5th edition, Public Health Service, National Institutes of Health, Bethesda, Md. (1991), pages 647-669), the CDR sequences of mouse monoclonal antibody 6D11 were identified. The amino acid sequences of CDRs of the heavy chain and light chain variable regions of mouse monoclonal antibody 6D11 were shown in Table 3 (SEQ ID NO: 3-8).

TABLE 3

Amino acid sequences of CDRs of the heavy chain and light chain variable regions of antibody 6D11

| | | |
|---|---|---|
| VH CDR1 | SGYHWN | SEQ ID NO: 3 |
| VH CDR2 | YISYDGSDHYNPSLEN | SEQ ID NO: 4 |
| VH CDR3 | GFDH | SEQ ID NO: 5 |
| VL CDR1 | RSSQSLVHSYGDTYLH | SEQ ID NO: 6 |
| VL CDR2 | KVSNRFS | SEQ ID NO: 7 |
| VL CDR3 | SQNTHVPYT | SEQ ID NO: 8 |

In addition, the gene sequences encoding the heavy chain and light chain variable regions of mouse monoclonal antibody 6D11 were linked to the gene sequences encoding the heavy chain and light chain constant regions of human antibody, respectively, and the recombinant expression was performed in CHO cells, so as to obtain chimeric antibody 6D11-cAb (hereinafter referred to as cAb for short).

It was surprisingly found that mouse monoclonal antibody 6D11-mAb and chimeric antibody 6D11-cAb could not only specifically bind/recognize HBsAg, but also reduce the serum level of HBV DNA and/or HBsAg in a subject, and effectively clear HBV and HBV-infected cells in vivo (for the experimental data on 6D11-mAb and 6D11-cAb, please refer to FIGS. 7-9). Therefore, both the mouse monoclonal antibody 6D11-mAb and chimeric antibody 6D11-cAb have potential in the treatment of HBV infection or a disease associated with HBV infection (such as Hepatitis B) in a subject.

1.2: Selection and Optimization of Human Antibody Template for Humanization of Antibody 6D11-mAb In order to reduce the immunogenicity of a heterologous antibody when administered to a human subject, mouse monoclonal antibody 6D11-mAb had to be humanized by CDR grafting. Although an antibody contacts and recognizes an antigen mainly via CDRs, some residues in FRs of an antibody might also be involved in antigen-antibody interaction and affect the steric conformation of CDRs. Therefore, after FRs of a murine antibody are replaced by FRs of a human antibody, generally the steric conformation of the CDRs from the murine antibody may change, resulting in a significant reduction in affinity of the humanized antibody for recognizing/binding antigen, or even loss of antigen binding ability of the humanized antibody (Ge Yan, Strategy Analysis and Application Study on Humanized Antibody Preparation [J]. Foreign Medical Sciences (Section of Immunology), 2004, 27(5): 271). Therefore, during humanization of a murine antibody, it is very important to select a human antibody template that can match CDRs of the murine antibody.

On the basis of a great deal of analysis and experimentation, the inventor surprisingly found that it was particularly advantageous to use human germ line gene sequences 4-28-02 (SEQ ID NO: 9) and 2D-28-01 (SEQ ID NO: 10) as the human antibody template for accepting CDRs of 6D11-mAb. In particular, human germ line gene sequences 4-28-02 (SEQ ID NO: 9) and 2D-28-01 (SEQ ID NO: 10) can match well with the heavy chain and light chain CDRs of 6D11-mAb, and can retain the antigen binding affinity of 6D11-mAb to the largest extent. The particular sequences of human germ line gene sequences 4-28-02 (SEQ ID NO: 9) and 2D-28-01 (SEQ ID NO: 10) can also be found in public database such as NCBI, Kabat and GenBank.

The heavy chain and light chain CDRs of mouse monoclonal antibody 6D11-mAb were grafted onto FRs of the template for humanization (i.e. human germ line gene sequences 4-28-02 (SEQ ID NO: 9) and 2D-28-01 (SEQ ID NO: 10)). Furthermore, based on the sequence analysis in combination with past humanization experience, a series of back mutations were performed to the amino acid residues in FRs of the template for humanization, so as to enable the humanized antibody to retain the antigen binding ability of the murine antibody as much as possible. 20 humanized antibodies were obtained in total. The names as well as the VH and VL information of the 20 humanized antibodies were shown in FIGS. 1A-1B, wherein, FIG. 1A showed the amino acid sequences of the heavy chain variable regions of the humanized antibodies; FIG. 1B showed the amino acid sequences of the light chain variable regions of the humanized antibodies; and "." means that the amino acid residue at the position is identical to the amino acid residue at the corresponding position of antibody B-53-45. In addition, the amino acid sequence Nos. of heavy chain variable region, light chain variable region, as well as heavy chain and light chain FRs (FR1-FR4) and CDRs (CDR1-CDR3) of the 20 humanized antibodies were summarized in Table 1 and Table 2.

1.3: Construction of Humanized scFv Antibodies Derived from 6D11-mAb

The genes encoding the 20 humanized antibodies were used as templates, and by using splicing overlapping extension-PCR (SOE-PCR), 20 gene fragments encoding the humanized scFv antibodies derived from 6D11-mAb were obtained. The structure of scFv antibody was $NH_2$—VH-linker-VL-COOH, wherein the sequence of the linker may be $(G_4S)_3$. Following are the conditions used in PCR: pre-denaturation at 95° C. for 5 min; 8 cycles (denaturation at 95° C. for 30 s, annealing at 57° C. for 30 s, extension at 72° C. for 30 s); and reaction at 72° C. for 10 min. The amplification products were analyzed by agarose gel electrophoresis, and recovered/purified by using DNA Purification Kit (TianGen, DP214-03), so as to obtain the 20 gene fragments H-K encoding humanized scFv antibodies derived from 6D11-mAb. Each of the gene fragments H-K was cleaved by enzyme SfiI, and then ligated to the vector pCGMT (from Scripps, Making chemistry selectable by linking it to infectivity) at a molar ratio of 10:1 (gene fragment: vector). By electroporation under the conditions of 25 μF, 2.5 KV and 200Ω, the ligation product was transformed into competent E. coli ER2738. The transformed E. coli was incubated in SOC medium for 45 min, and then 200 μL bacterial liquid was spread on LB plate (containing 100 g/L ampicillin+tetracycline+2 g/mL glucose), and was left standing at 37° C. overnight. A single bacterial colony was picked from the plate, and sequenced to ensure that the sequence of the recombinant vector encoding the scFv antibody was correct. The map of the recombinant vector (pCGMT-scFv) encoding scFv antibody was shown in FIG. 2.

1.4: Detection of Humanized scFv Antibodies

The positive single bacterial colonies obtained in the previous step were cultured in a 2×YT medium containing ampicillin (100 g/L) and glucose (2 g/mL) until OD=0.6, followed by superinfection with M13KO7. 2 h later, 100 g/L kanamycin was added, and the incubation was continued at 37° C. for 2 h. Then, the culture was centrifuged at 4000 rpm for 10 min, the supernatant was discarded, and the cell pellets were collected. The cell pellets were re-suspended in a culture medium containing ampicillin and kanamycin (100 g/L), and cultured at 30° C. under shaking overnight. Later, the culture was centrifuged at 12000 rpm for 10 min, the bacteria and supernatant were collected, and stored at 4° C. for assay.

Figure 3:
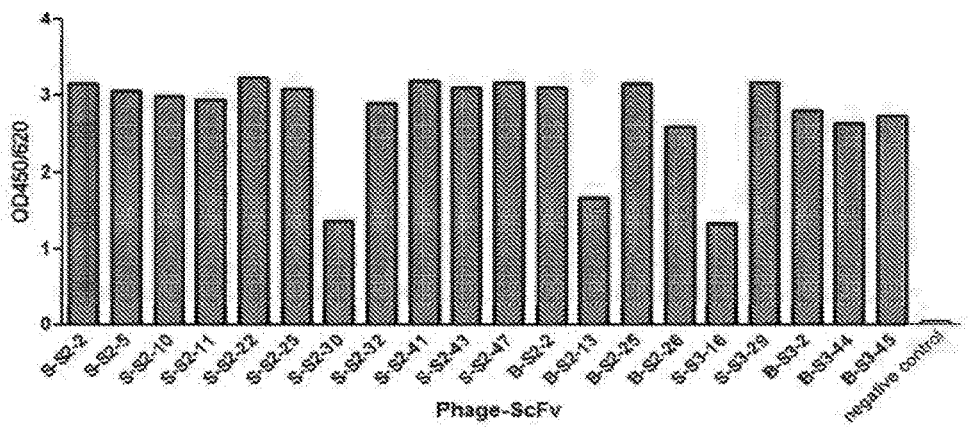
FIG. 3 shows the ELISA result of the phage displaying scFv antibody and antigen HBsAg. The result showed that the phages displaying the scFv antibody according to the invention had reactivity as measured by ELISA; all of the 20 humanized scFv antibodies constructed could bind to antigen HBsAg.

To each well of the ELISA plate coated with HBsAg (3 μg/mL) antigen, 100 μL supernatant to be tested was added, and incubated at 37° C. for 1 h. Later, the ELISA place was washed with PBST for 5 times, and 100 μL anti M13-HRP diluted at 1:5000 was then added, and incubated at 37° C. for 30 min. Later, the ELISA place was washed with PBST for 5 times, and the substrate TMB solution was added. 15 min after reaction, $H_2SO_4$ was added to stop the color development, and the $OD_{450/620}$ value was read. M13KO7 was used as negative control. ELISA result was shown in FIG. 3. The result in FIG. 3 showed that all the phages displaying these scFv antibodies had reactivity as measured by ELISA, and all of the 20 constructed humanized scFv antibodies could bind to antigen HBsAg.

In addition, the humanization degree of the 20 humanized antibodies was calculated in accordance with the following formula:

Humanization degree=(number of amino acid numbers in FR−number of murine amino acids reserved in FR)/number of amino acids in FR×100%.

The result showed that the 20 humanized antibodies had a humanization degree of between 91.12% and 88.17%, and the number of murine amino acids reserved in FR and the humanization degree were shown in Table 4.

TABLE 4

Sequence analysis of humanized antibodies

| Antibody name | Number of murine amino acid reserved in FR | Humanization degree | Antibody name | Number of murine amino acid reserved in FR | Humanization degree |
|---|---|---|---|---|---|
| S-S2-2 | 19 | 88.76% | S-S2-30 | 20 | 88.17% |
| S-S2-5 | 20 | 88.17% | S-S2-22 | 18 | 89.35% |
| S-S2-10 | 19 | 88.76% | S-S2-25 | 19 | 88.76% |
| S-S2-41 | 15 | 91.12% | S-S2-32 | 19 | 88.76% |
| B-S3-2 | 17 | 89.94% | S-S2-43 | 20 | 88.17% |
| B-S3-44 | 18 | 89.35% | S-S2-47 | 19 | 88.76% |
| B-S3-45 | 17 | 89.94% | B-S2-2 | 20 | 88.17% |
| S-S3-16 | 16 | 90.53% | B-S2-13 | 18 | 89.35% |
| S-S3-29 | 18 | 89.35% | B-S2-25 | 17 | 89.94% |
| S-S2-11 | 15 | 91.12% | B-S2-26 | 18 | 89.35% |

Example 2: Single-Site Substitution of Amino Acids in CDRs of Humanized Antibody B-S3-45

The amino acid at each site of 6 CDRs of humanized antibody B-S3-45 was subjected to single-site substitution with the 20 naturally-occurring amino acids, respectively. The cloning methods described in Example 1.3 and 1.4 were used to obtain recombinant vectors expressing phage antibodies, wherein the phage antibodies had a single-site mutation in CDRs, as compared to B-S3-45. Degenerate primers were used to introduce an amino acid substitution at a mutation site.

Figure 4:
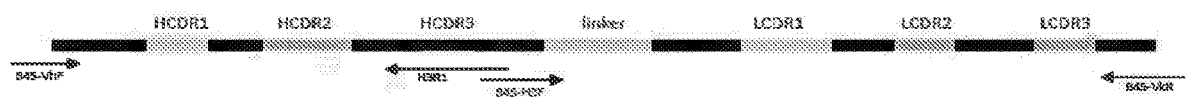
FIG. 4 shows the schematic representation of PCR strategy for single-site mutation of the first amino acid residue (H95) of HCDR3 of antibody B-S3-45.
Figure 5A:
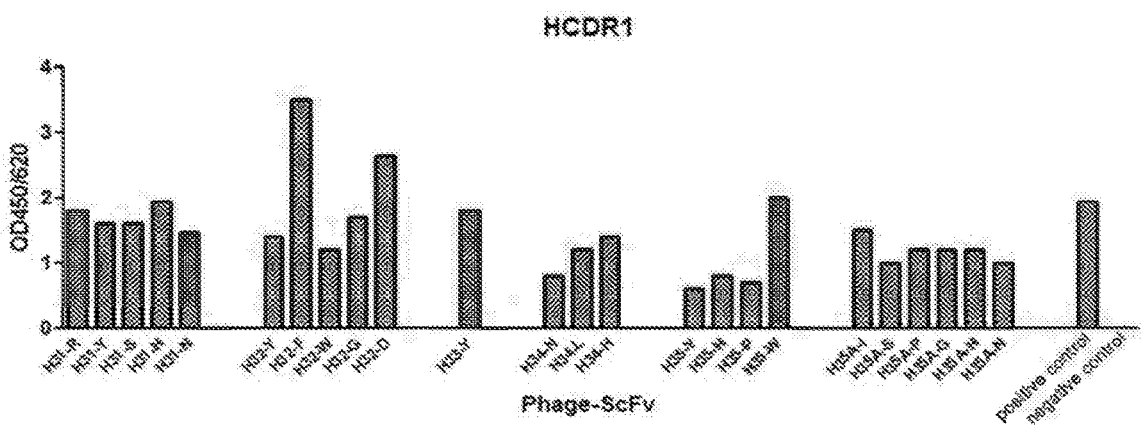
Figure 5B:
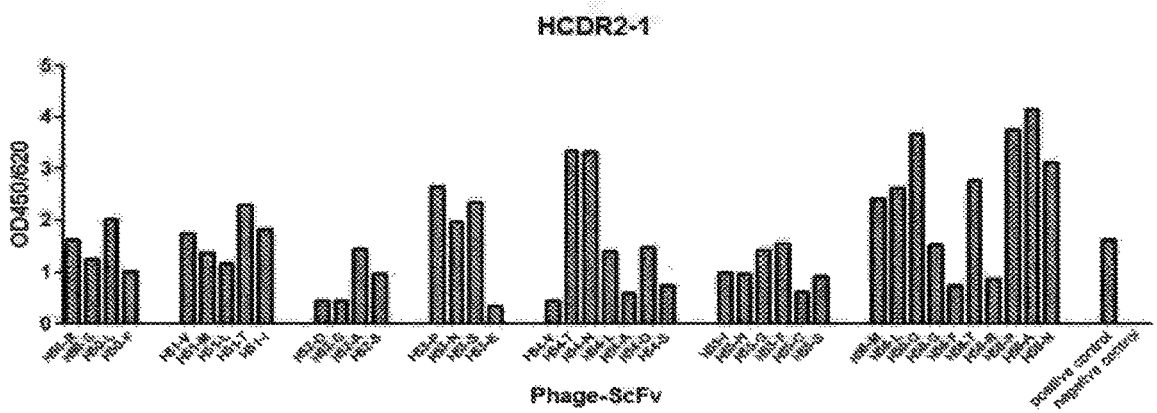
Figure 5C:
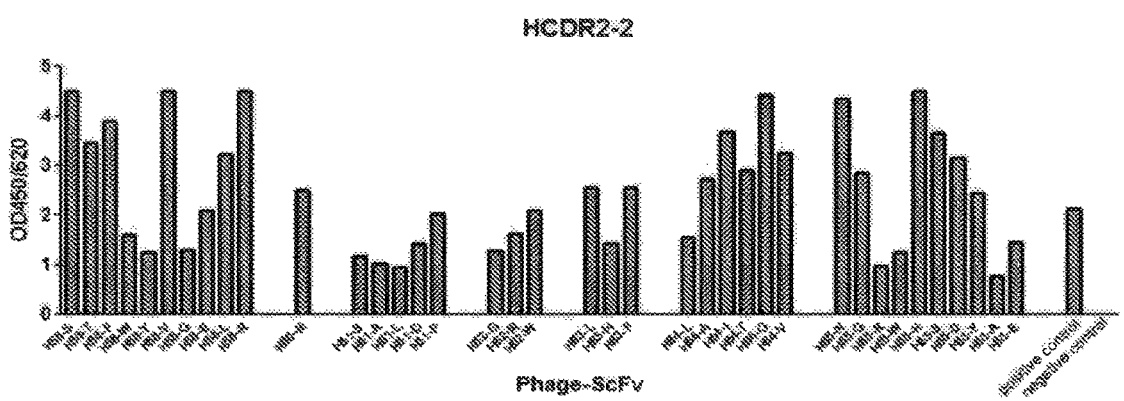
Figure 5D:
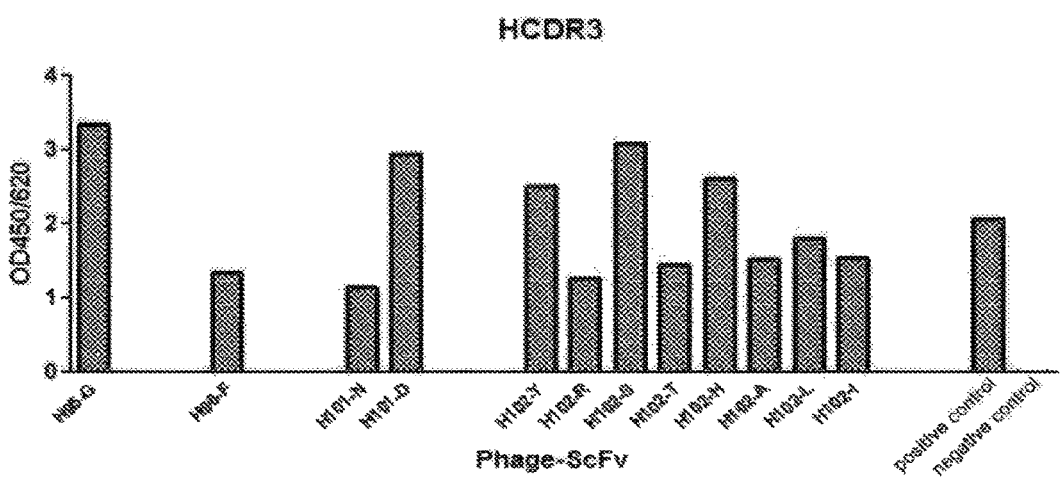
Figure 5E:
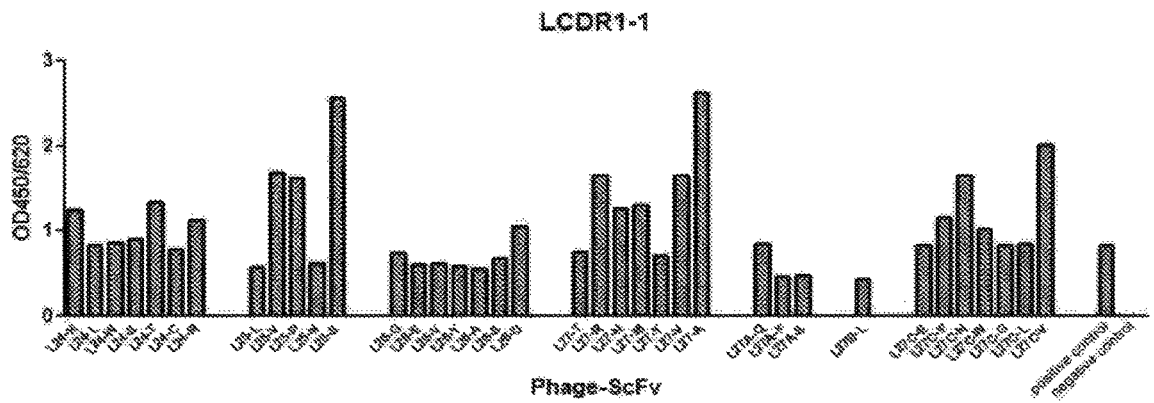
Figure 5F:
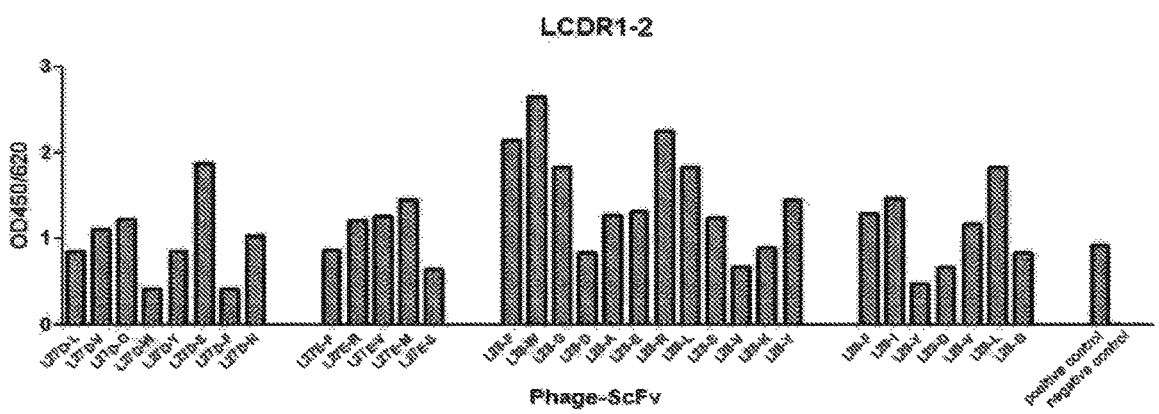
Figure 5G:
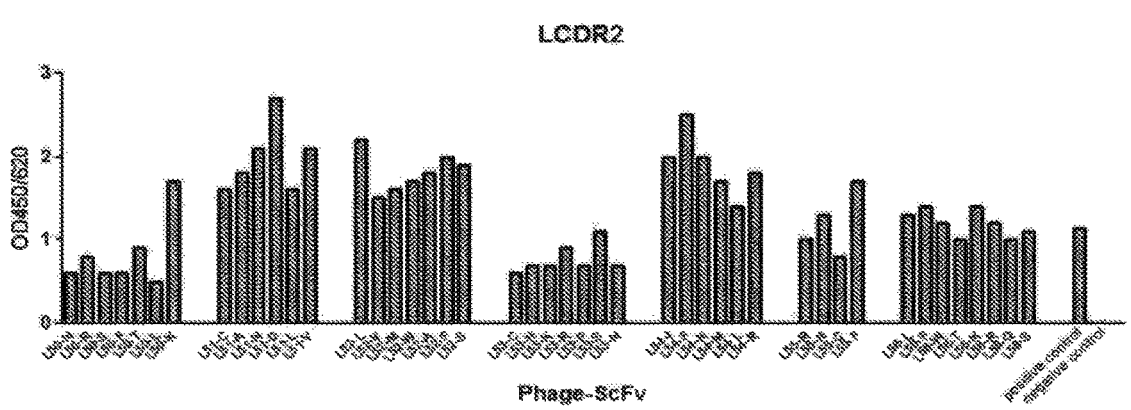

Substitution of the first amino acid of the heavy chain variable region CDR3 (HCDR3) was taken as an example, oligonucleotide primers H3R1 and B45-H3F (the sequences of which were shown in Table 5) were designed, the annealing positions of the primers in the genes encoding humanized antibody B-S3-45 were shown in FIG. 4. The PCR method was as follows: B-S3-45 coding gene was used as template, and the upstream and downstream fragments were amplified by the primer pair B45-VhF/H3R1 and B45-H3F/B45-VkR, respectively; by splicing overlapping extension-PCR, the fragments were ligated together, and B45-VhF/B45-VkR were used as upstream and downstream primers respectively for amplification, to obtain the entire scFv gene fragment having a single-site mutation occurred at the first amino acid position of HCDR3.

TABLE 5

Primer sequences

| Primer name | SEQ ID NO | Primer sequence |
|---|---|---|
| H3R1 | 252 | 5'-GACTGTGAGAGTTGTGCCTTGGCCCCAGTGGTCAAAVNNACTCGCACAGTAATATATGG |
| B45-H3F | 253 | 5'-GCACAACTCTCACAGTCTCCTCACTGAGGTGGCGGATCTGGAGG |
| B45-VhF | 254 | 5'-GTTATTACTCGTGGCCCAGCCGGCCATGGCAGAGGTGCAGCTGCAGGAGTC |

TABLE 5-continued

Primer sequences

| Primer name | SEQ ID NO | Primer sequence |
|---|---|---|
| B45-VkR | 255 | 5'-GTCGACCAGGCCCCGAGGCCCCGTTTTATTTCCAGCTTGGTCCCCCTCC<br>5'-ACGGATCTCTAGCGAATTCATGGGAAGGCTTACTTCTTCATTCCTGCTACTGA |
| PTT5-VHF2 | 256 | TTGTCC |
| 6D11-PTT5-VHR | 257 | 5'-TGGGCCCTTGAAGCTTGCTGAGGAGACTGTGAGAGTTG |
| PTT5-CH-R | 258 | 5'-TTTTCCTTTTGCGGCCGCTTATTTACCCGGAGACAGGGAGAGG |
| PTT5-VKF2 | 259 | 5'-CGGATCTCTAGCGAATTCATGTCTGTGCCAACTCAGGTCCTGGGGTTGCTGCTGCTGTG |
| 6D11-PTT5-VKR | 260 | 5'-ACAGATGGTGCAGCCACAGTCCGTTTTATTTCCAGCTTGG |
| PTT5-CK-F | 261 | 5'-ACTGTGGCTGCACCATCTGTCTTCATCTTCCCG |
| PTT5-CK-R | 262 | 5'-AAACGGGCCCTCTAGATTAACACTCTCCCCTGTTGAAGCTCTTTGTGACGGG |

The obtained scFv gene fragments H-K were cleaved by enzyme SfiI, and then ligated to the vector pCGMT at a molar ratio of 10:1 (gene fragment: vector), respectively. The recombinant vector comprising a single-site mutation was electro-transformed into ER2738 cell. Then, the transformed E. coli was spread on LB plate (containing 100 g/L ampicillin+tetracycline+2 g/mL glucose), and was left standing at 37° C. overnight. A single bacterial colony was selected from the plate, and sequenced, to ensure that the sequence of the recombinant vector encoding the scFv antibody comprising a single-site mutation was correct. Then, in accordance with the method described in Example 1, the reactivity between the scFv antibody comprising a single-site mutation with antigen HBsAg, was determined, wherein the phage displaying antibody B-S3-45 was used as positive control.

The ELISA results were shown in FIGS. 5A-5I, wherein, the horizontal axis represents the position and type of a single-site mutation in the scFv antibody (for example, "H31-R" means that the amino acid residue at position H31 according to Kabat numbering system is mutated to R), and the vertical axis represents the reactivity between a phage displaying scFv antibody comprising a single-site mutation and antigen HBsAg. The experimental results in FIGS. 5A-5I showed that a single-site mutation could be performed to the amino acid residue in CDRs of antibody B-S3-45, without interfering the binding affinity of the antibody to antigen HBsAg.

In addition, all the single-site mutations involved in FIGS. 5A-5I were summarized in Table 6, in order to determine the amino acid positions where mutation can be tolerated in CDRs of antibody B-S3-45, as well as the types of the amino acid residues that could be substituted in said positions.

TABLE 6

Single-site mutations of amino acid residues in CDRs of antibody B-S3-45

| No.* | Original amino acid | Type of amino acid for substitution | No.* | Original amino acid | Type of ammo acid for substitution |
|---|---|---|---|---|---|
| HCDR1 | | | LCDR1 | | |
| H31 | S | R, Y, S, H, N | L24 | R | H, L, W, S, T, C, R |
| H32 | G | Y, F, W, G, D | L25 | S | L, V, P, N, S |
| H33 | Y | Y | L26 | N | G, E, V, Y, A, S, D, N |
| H34 | H | N, L, H | L27 | Q | T, R, H, M, Y, V, A, Q |
| H35 | W | Y, H, P, W | L27A | S | Q, F, S |
| H35A | N | I, S, P, G, H, N | L27B | L | L |
| HCDR2 | | | L27C | V | E, F, N, W, G, L, V |
| H50 | Y | R, G, L, F, S, V, Y | L27D | H | L, V, G, W, Y, S, F, N, H |
| H51 | I | V, M, L, T, F, C, I | L27E | S | P, R, V, M, S |
| H52 | S | D, A, G, V, F, P, S | L28 | Y | F, W, G, D, A, E, R, L, S, V, K, Y |
| H53 | Y | P, N, S, E, L, F, K, I, Y | L29 | G | F, I, Y, D, V, L, G |
| H54 | D | V, T, N, L, A, S, I, F, D | L30 | D | E, S, C, F, R, A, Q, L, P, N, M, T, D |
| H55 | G | I, H, S, F, C, E, L, V, G | | | |
| H56 | S | N, A, M, L, Q, G, F, T, P, R, S | L31 | T | L, V, Q, F, M, A, C, R, S, L, T |
| | | | L32 | Y | W, F, G, L, Y |
| H57 | D | X | L33 | L | R, V, F, S, M, A, P, Y, L |

TABLE 6-continued

Single-site mutations of amino acid residues in CDRs of antibody B-S3-45

| No.ˣ | Original amino acid | Type of amino acid for substitution | No.ˣ | Original amino acid | Type of ammo acid for substitution |
|---|---|---|---|---|---|
| H58 | H | S, T, F, W, Y, V, G, E, L, R, H | L34 | H | F, N, R, Q, G, H |
| | | | | | LCDR2 |
| H59 | Y | Y | L50 | K | N, R, F, S, T, L, K |
| H60 | N | N | L51 | V | C, A, N, L, V |
| H61 | P | S, A, L, D, P | L52 | S | L, V, M, W, A, F, S |
| H62 | S | G, E, R, S | L53 | N | C, H, K, R, S, N |
| H63 | L | H, F, L | L54 | R | L, F, N, M, L, R |
| H64 | E | L, A, I, T, G, V, E | L55 | F | R, N, C, F |
| H65 | N | G, R, S, W, H, D, A, Y, N | L56 | S | L, F, W, T, K, R, Q, S |
| | | HCDR3 | | | LCDR3 |
| H95 | G | G | L89 | S | L, G, N, T, V, S |
| H96 | F | F | L90 | Q | H, S, Q |
| H101 | D | N, D | L91 | N | N |
| H102 | H | Y, R, S, T, A, L, L, H | L92 | T | A, S, P, T |
| | | | L93 | II | A, S, K, R, L, T, Y, F, W, N, M, V, I, E, H |
| | | | L94 | V | T, N, D, K, F, Y, P, H, L, R, S, G, V |
| | | | L95 | P | A, I, S, C, V, P |
| | | | L96 | Y | N, A, V, R, T, H, Y |
| | | | L97 | T | S, T |

ˣThe amino acid residue positions mentioned above are numbered in accordance with Kabat numbering system; "X" represents any amino acid of the 20 naturally-occurring amino acids.

Example 3: Optimization and Engineering of Humanized Antibody B-S3-45

Since FRs of a humanized antibody further comprised about 10% murine amino acid residues (see Table 4), and the amino acid residues in CDRs were substantively murine, when administered to a human subject, the humanized antibody would cause immunological rejection to some extent. In order to reduce such immunological rejection as much as possible, and make a humanized antibody to retain the functions and properties of its parent murine antibody (i.e. antigen binding activity, virus-neutralizing activity, and ability of clearing HBV DNA and HBsAg) as much as possible, humanized antibody B-S3-45 was further optimized and engineered.

In brief, based on the amino acid sequence of humanized antibody B-S3-45, the positions where amino acid residues can be substituted in CDRs and the types of amino acid residues for substitution identified in Example 2, as well as the alignment result from NCBI BLAST, the inventor introduced different combinations of amino acid mutations in FRs and CDRs of humanized antibody B-S3-45, and designed 115 new humanized antibodies. The amino acid sequences of the heavy chain variable regions and light chain variable regions of the 115 humanized antibodies were shown in FIGS. 6A-6J, wherein, FIGS. 6A-6E showed the amino acid sequences of the heavy chain variable regions of the humanized antibodies, FIGS. 6F-6J showed the amino acid sequences of the light chain variable regions of the humanized antibodies; and "." means that the amino acid residue at the position is identical to the amino acid residue at the corresponding position of antibody B-S3-45. In addition, the amino acid sequence Nos. of the heavy chain variable region, light chain variable region, and light chain and heavy chain FRs (FR1-FR4) and CDRs (CDR1-CDR3) of the 115 humanized antibodies were also summarized in Table 1 and Table 2.

Among the 115 humanized antibodies, Antibodies 162B, B3-S4-N-130, B3-S4-N-65, B4-T13-11, B3-S4-N-68, P-44, P-50, B3-S4-N-50, 112, 110, 84, 116, 153, 187, 127, 62, 23, 123, 83, 138, and 192 had a humanization degree of 97%, the FR region of which only kept 4 murine amino acid residues.

The eukaryotic expression and antigen binding activity of the 115 humanized antibodies and 10 antibodies randomly selected from the 20 humanized antibodies in Example 1, were determined.

3.1: Construction of Recombinant Vectors for Eukaryotic Expression

Construction of recombinant vector expressing heavy chain: by virtue of EcoRI enzyme cleavage site (GAATTC) and HindIII enzyme cleavage site (AAGCTT), the gene sequence encoding heavy chain variable region was inserted into the already constructed heavy chain expression vector pTT5-CH (comprising a sequence encoding heavy chain constant region of human antibody). In brief, by using splicing overlapping extension-PCR (SOE-PCR) method, the gene fragments of the heavy chain variable regions of the 125 humanized antibodies were obtained. PCR amplification products were recovered and purified by gel electrophoresis. Later, the recovered PCR amplification product (the product of the first round PCR) was used as template, and the primers PTT5-VHF2/6D11-PTT5-VHR (the sequences of which were shown in Table 5) were used to perform a second round PCR, to obtain the second PCR amplification product (comprising the entire VH gene and a sequence encoding signal peptide). The second PCR amplification product was recovered by DNA Extraction Kit (TIANGEN). And then the second PCR amplification product and the vector PTT5-CH were subjected to double enzyme digestion by two restriction endonucleases EcoRI and HindIII. T4 ligase (NEB) was used to ligate the cleavage products of the two enzymes, so as to obtain the recombinant vector expressing heavy chain, VH+CH+pTT5. Condition used in the ligation reaction is: ligation at 16° C. for 4 h. The recombinant vector VH+CH+ pTT5 was transformed into E. coli strain 5α. The transformed E. coli was then spread onto LB plate, and was left standing at 37° C. overnight. A single bacterial colony was picked from the plate, and sequenced, to ensure that the sequence of the recombinant vector VH+CH+pTT5 was correct.

Construction of recombinant vector expressing light chain: by virtue of EcoRI enzyme cleavage site (GAATTC) and XbaI enzyme cleavage site (TCTAGA), the gene sequence encoding light chain variable region and light chain constant region was inserted into the light chain expression vector pTT5. In brief, by using splicing overlapping extension-PCR (SOE-PCR) method, the gene fragments of the light chain variable regions of the 125 humanized antibodies were obtained. PCR amplification products were recovered and purified by gel electrophoresis. Later, the recovered PCR amplification product (the produce of the first round PCR) was used as template, and the primers, PTT5-VKF2/6D11-PTT5-VKR (the sequences of which were shown in Table 5) were used to perform a second round PCR, to obtain the second PCR amplification product (comprising the entire VK gene and a sequence encoding signal peptide). The second PCR amplification product was recovered by DNA Extraction Kit (TIANGEN). The vector comprising the light chain constant region gene was used as template, and the primers PTT5-CK-F/PTT5-CK-R (the sequences of which were shown in Table 5, wherein the primer PTT5-CK-R comprises XbaI enzyme cleavage site) were used to perform PCR amplification, to obtain the light chain constant region gene CK. The light chain constant region gene CK was recovered and purified by gel electrophoresis. Later, by using splicing overlapping extension-PCR method, the second PCR amplification product was ligated to the light chain constant region gene CK, to form an entire light chain gene VK+CK. The primers PTT5-VKF2 and PTT5-CK-R were used to amplify gene VK+CK. The gene VK+CK and the vector pTT5 were subjected to double enzyme digestion by two restriction endonucleases EcoRI and XbaI. The cleavage products of the gene VK+CK were recovered by DNA Extraction Kit (TIANGEN), and the cleavage product of the vector pTT5 was recovered by gel electrophoresis. T4 ligase (NEB) was used to ligate the cleavage products of the gene VK+CK and the vector pTT5 together, thereby obtaining the recombinant vector expressing light chain, VK+CK+pTT5. Condition used in the ligation reaction is: ligation at 16° C. for 4 h. The recombinant vector VK+CK+pTT5 was transformed into E. coli strain 5α. The transformed E. coli was then spread onto LB plate, and was left standing at 37° C. overnight. A single bacterial colony was picked from the plate, and was sequenced to ensure that the sequence of the recombinant vector VK+CK+pTT5 was correct.

3.2: Eukaryotic Expression of Humanized Antibodies

The recombinant vectors VH+CH+pTT5 and VK+CK+pTT5 were used to co-transfect CHO—S suspension cells (at a cell density of about $2 \times 10^6$ cells/ml). The transfected cells were cultured in a $CO_2$ incubator at 32° C. for 7 d, and the cell supernatant was then collected for antibody purification. According to the instructions of manufacturer, IgG antibodies in the supernatant were purified by protein A column. The purified IgG antibodies were analyzed by SDS-PAGE, to determine the purify of IgG antibodies.

3.3: Determination of the Antigen Binding Activity of Humanized Antibodies

Figure 7A:
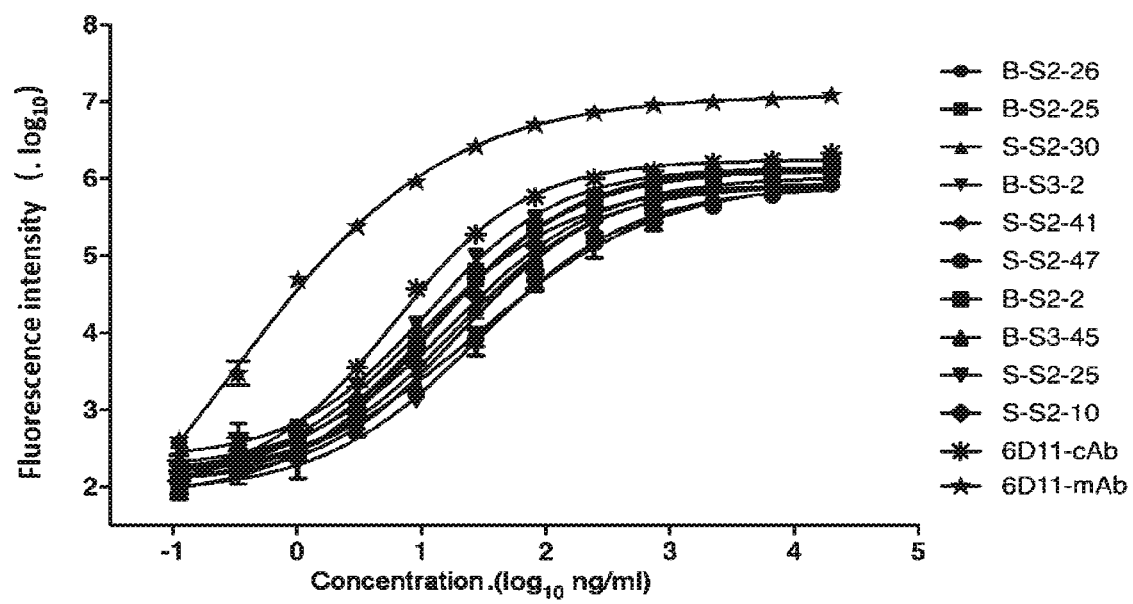
FIGS. 7A-7W show the ELISA results on the binding activity of 125 humanized antibodies to antigen HBsAg, wherein, the horizontal axis represents antibody concentration ($\log_{10}$ ng/ml), and the vertical axis represents fluorescence intensity ($\log_{10}$ RLU). The results show that all the tested humanized antibodies had good antigen binding activity, and were superior to 6D11-mAb and 6D11-cAb, or at least comparable to 6D11-mAb and 6D11-cAb in terms of affinity for antigen HBsAg.
Figure 7B:
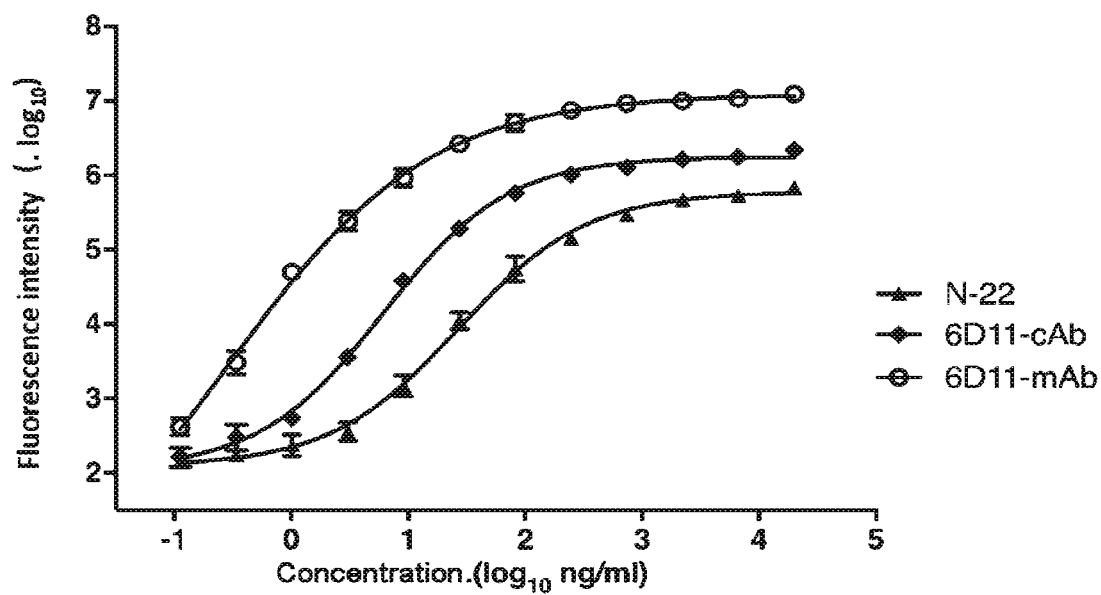
Figure 7C:
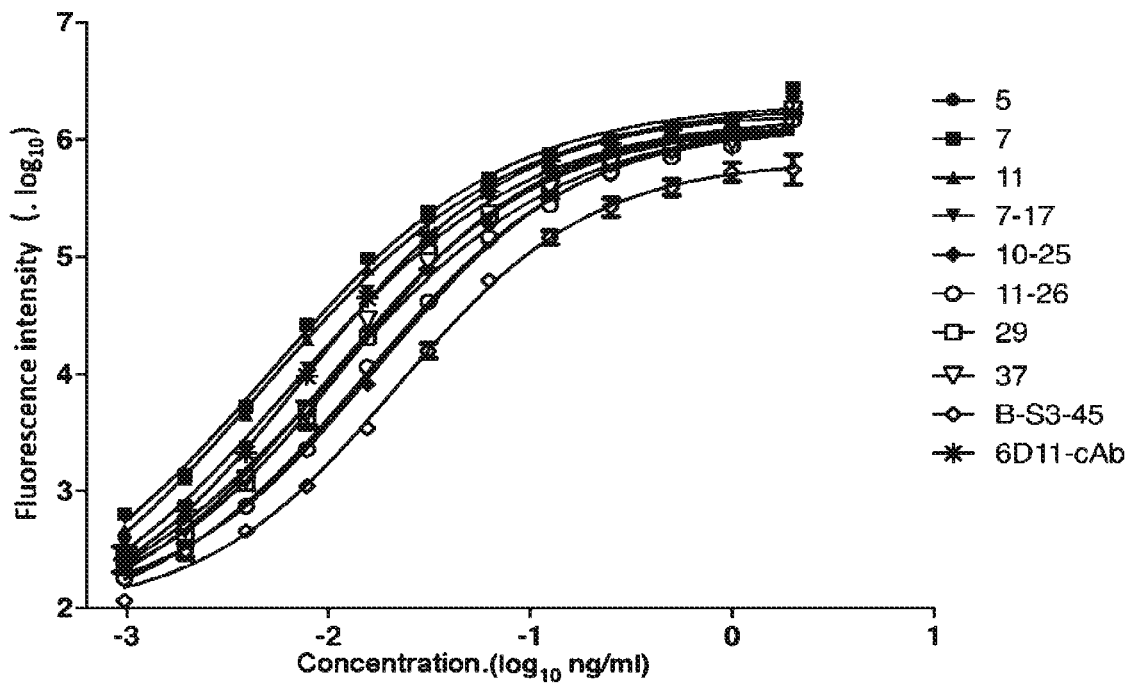
Figure 7D:
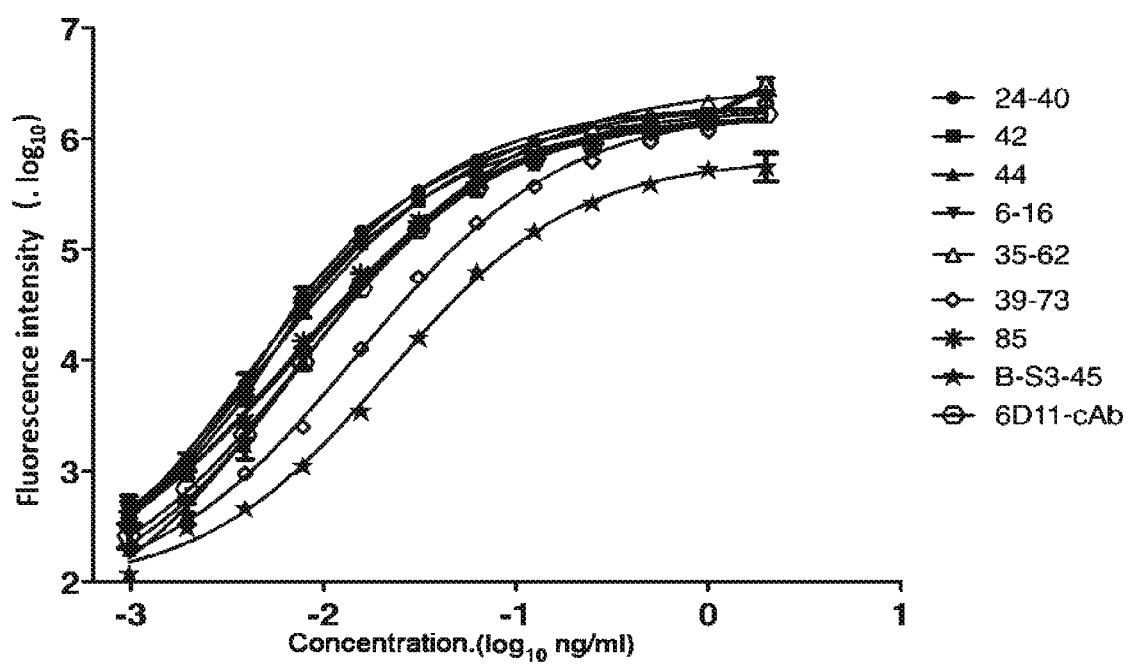
Figure 7E:
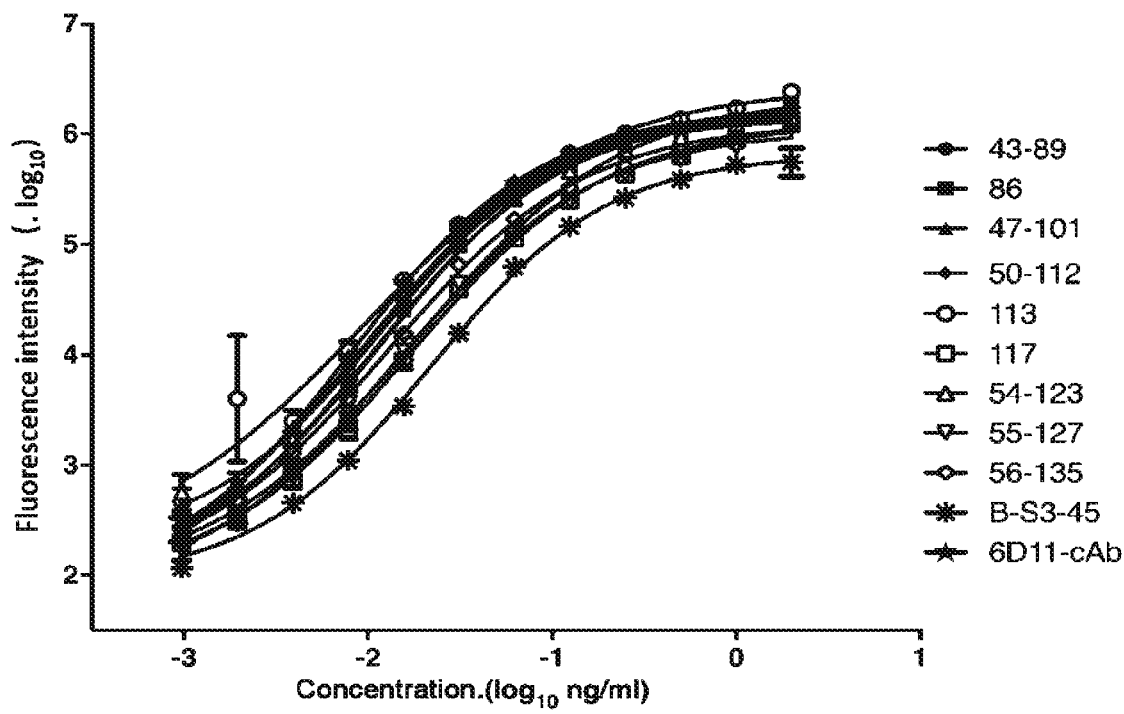
Figure 7F:
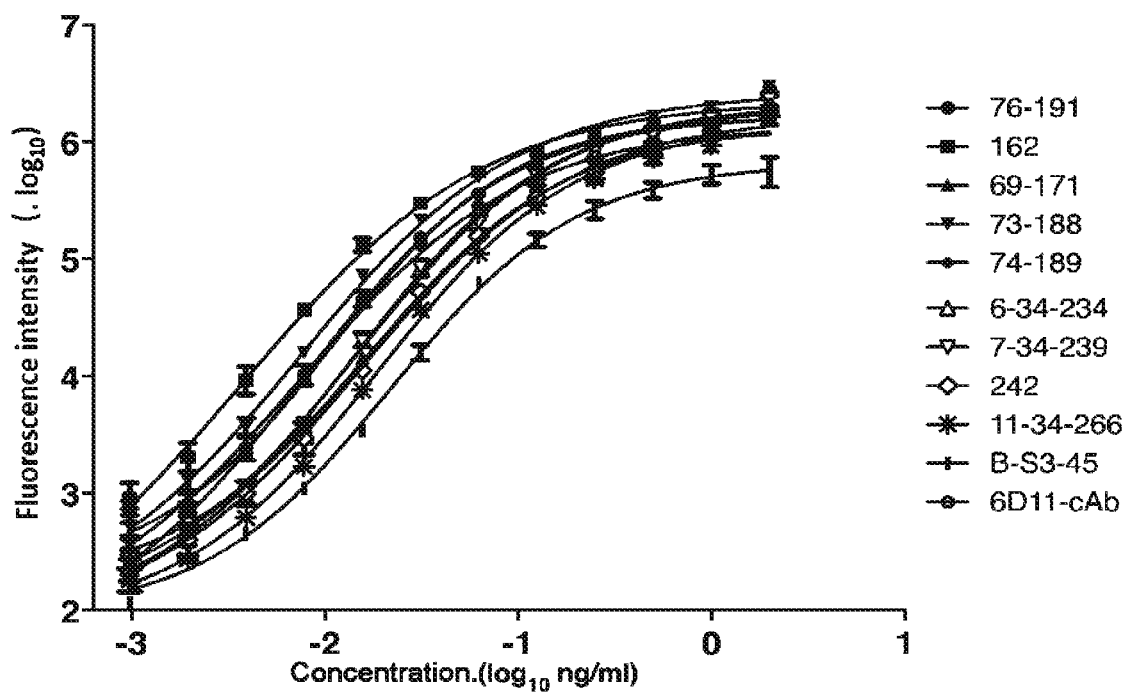
Figure 7G:
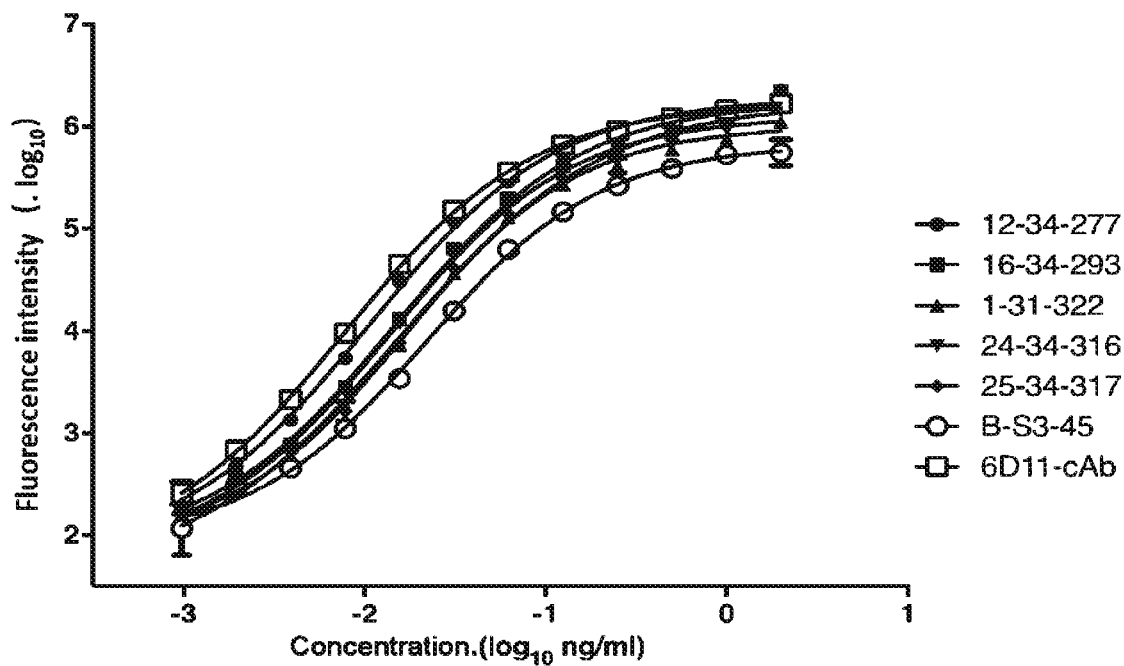
Figure 7H:
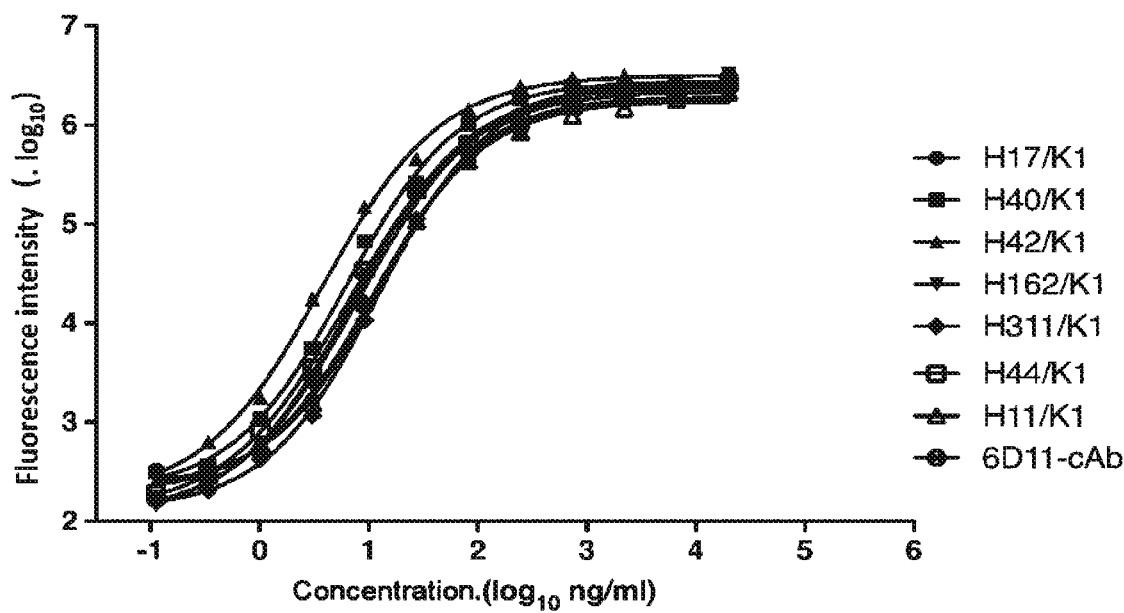
Figure 7I:
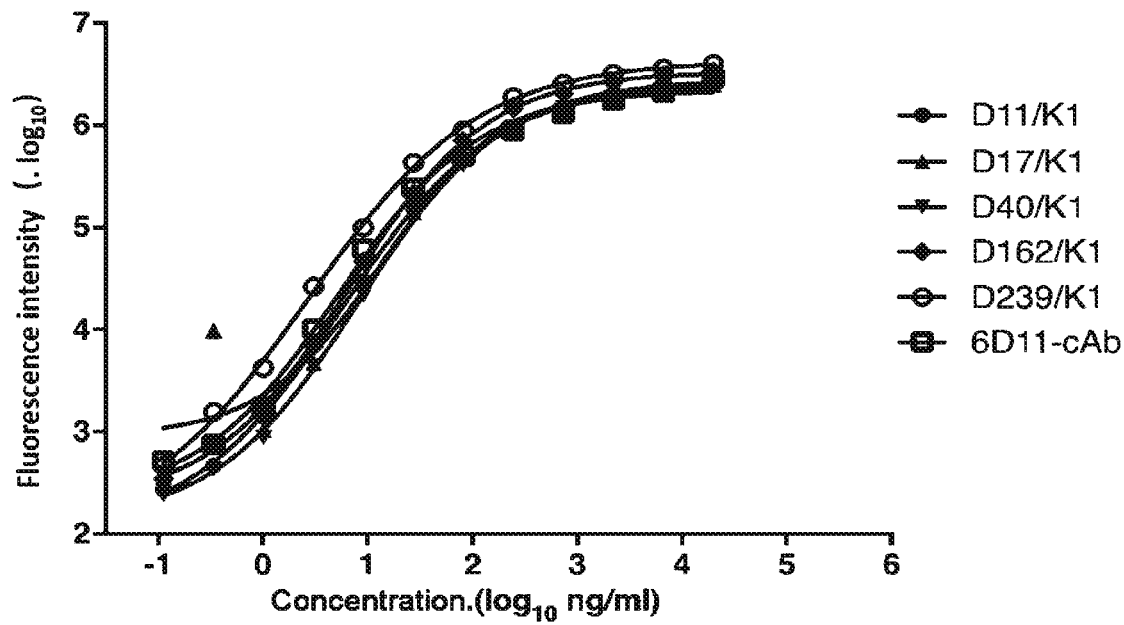
Figure 7J:
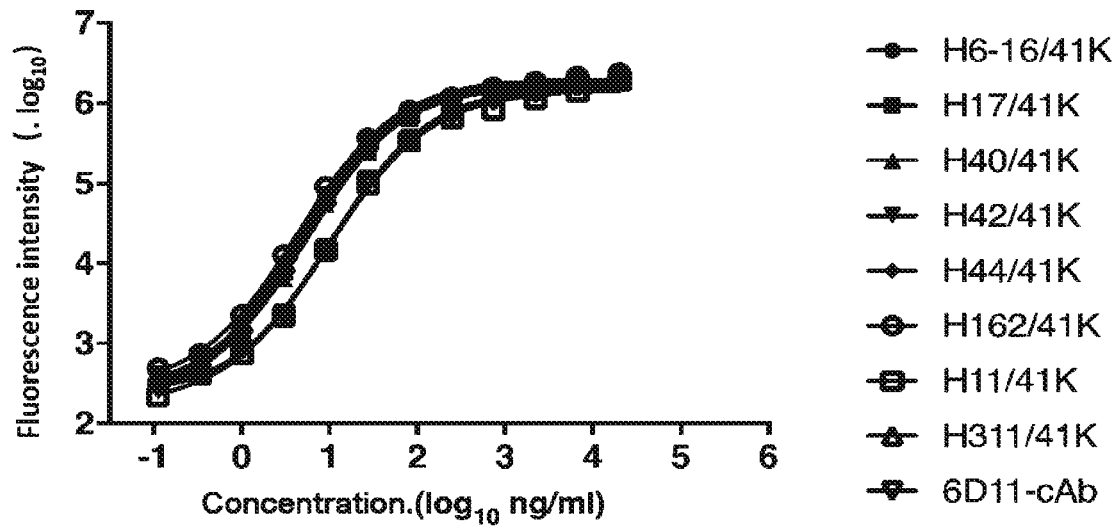
Figure 7K:
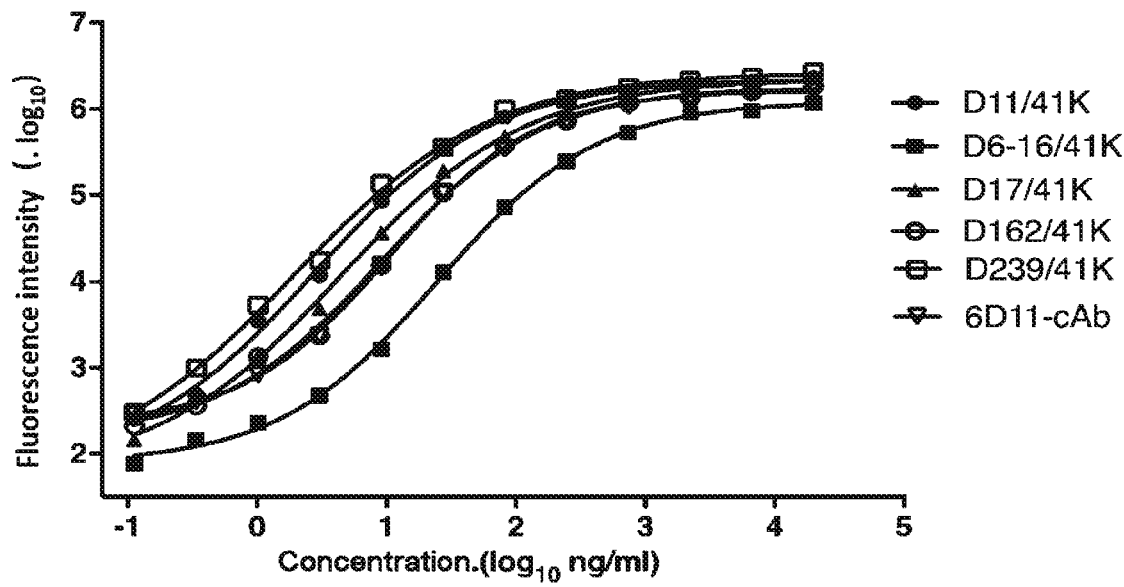
Figure 7L:
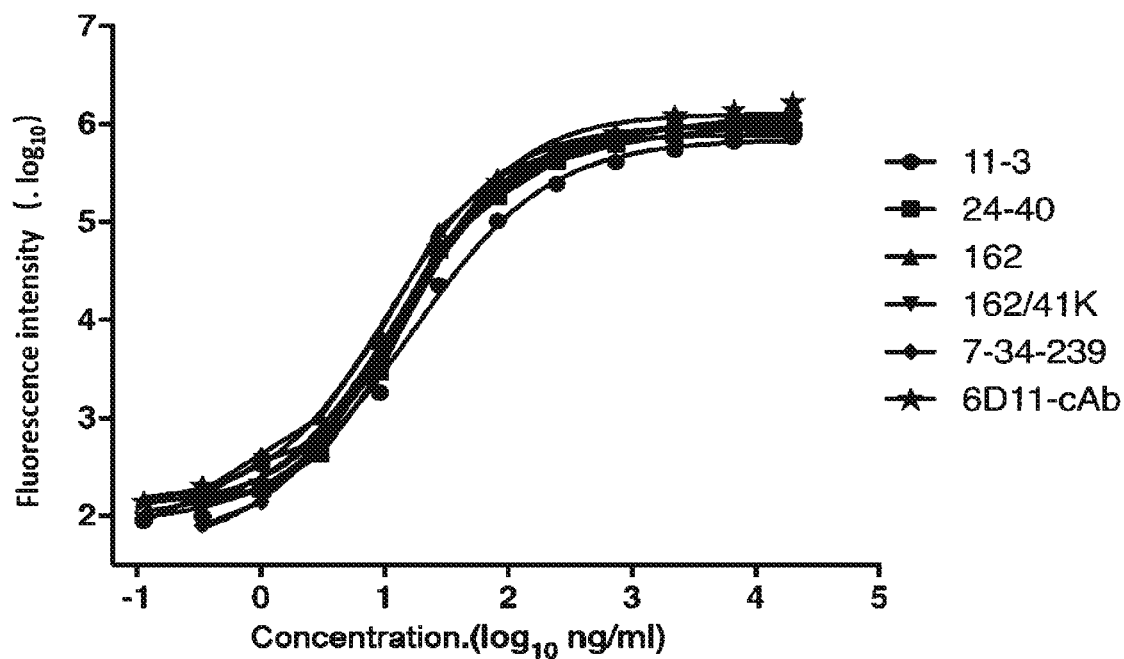
Figure 7M:
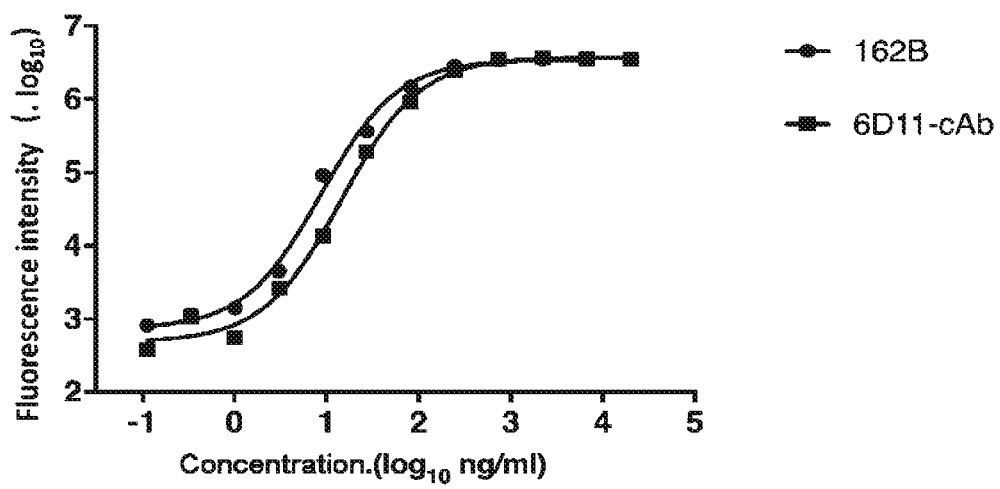
Figure 7N:
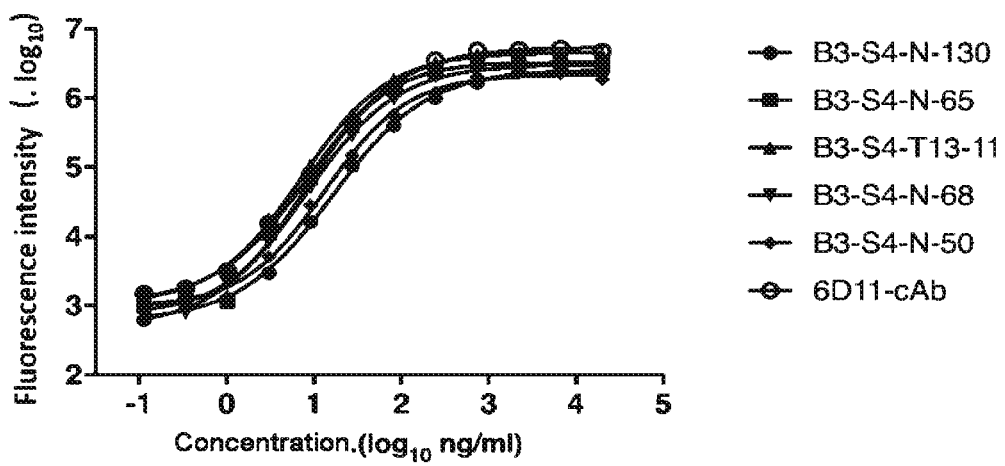
Figure 7O:
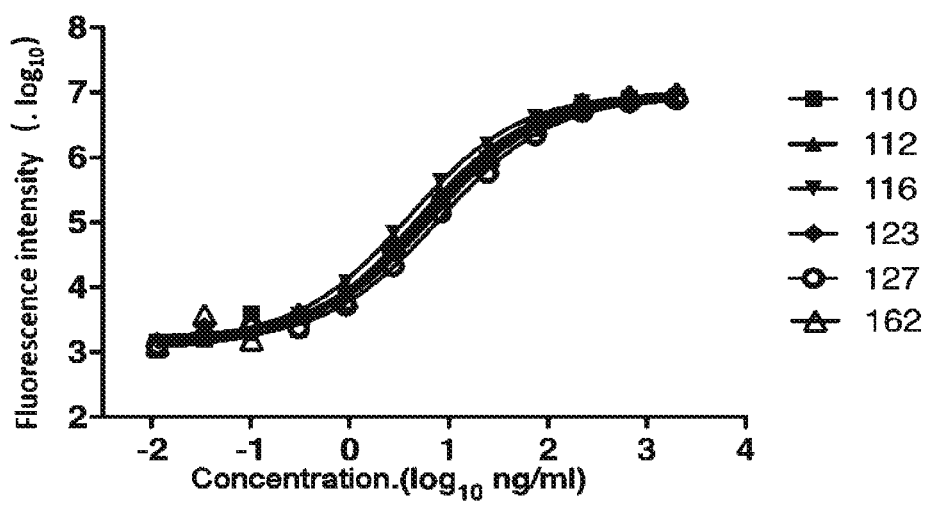
Figure 7P:
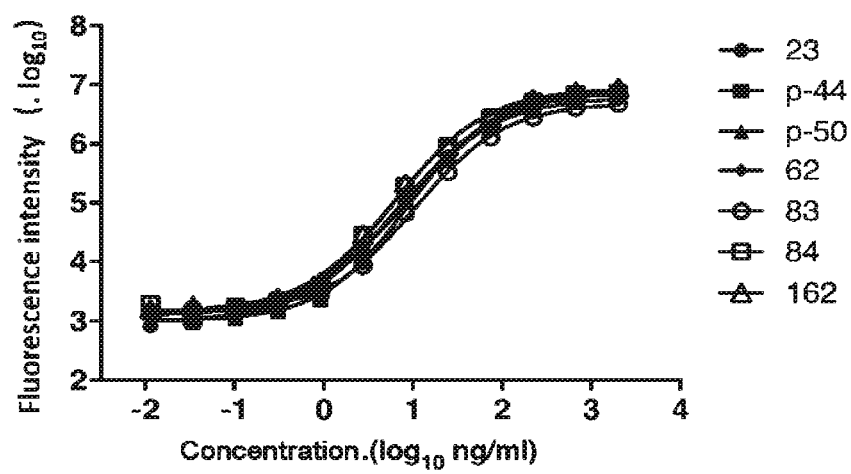
Figure 7Q:
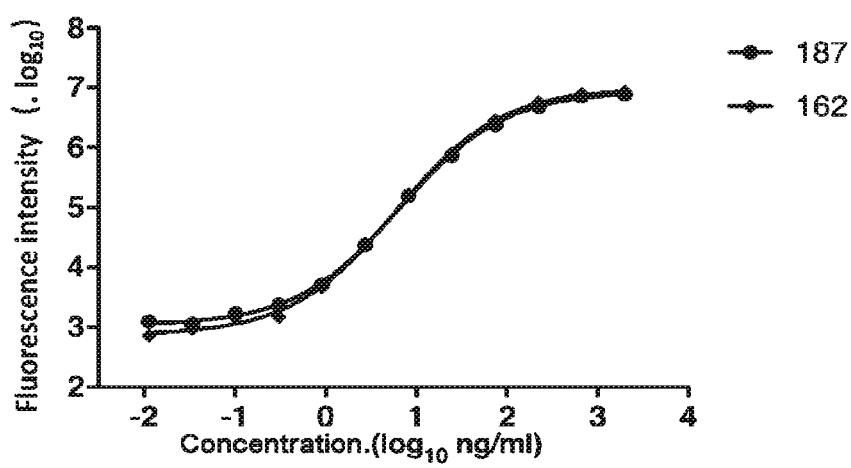
Figure 7R:
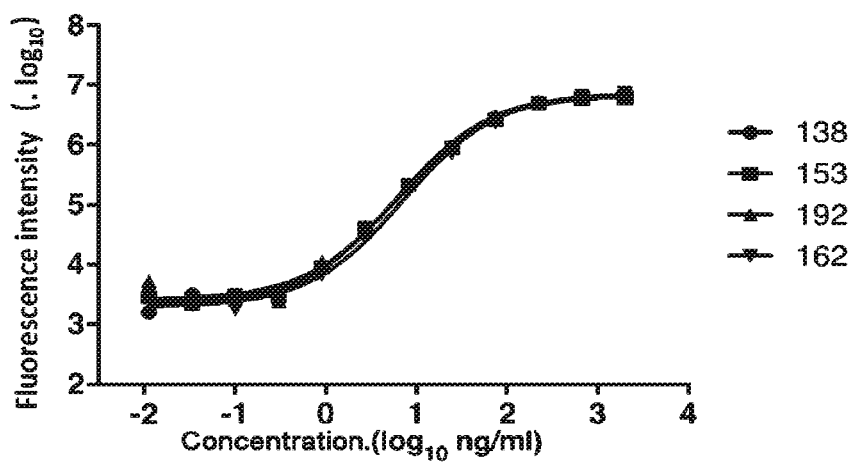
Figure 7S:
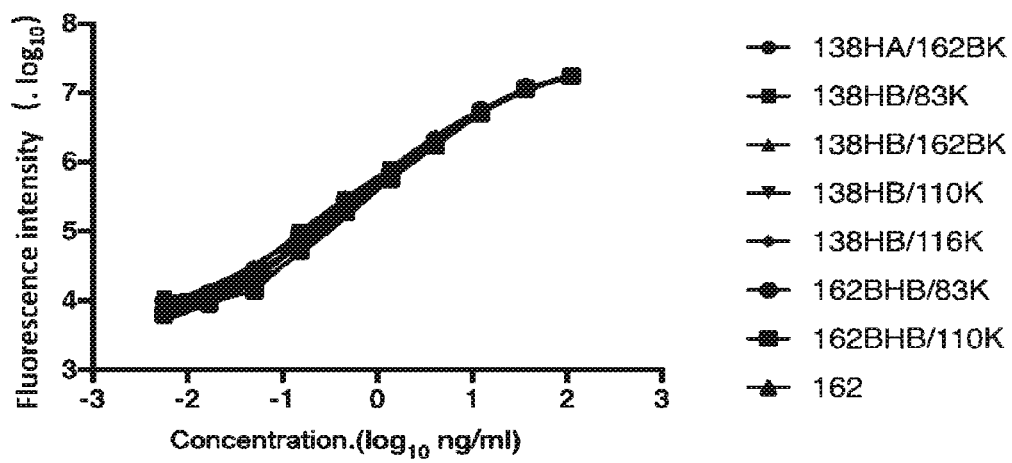
Figure 7T:
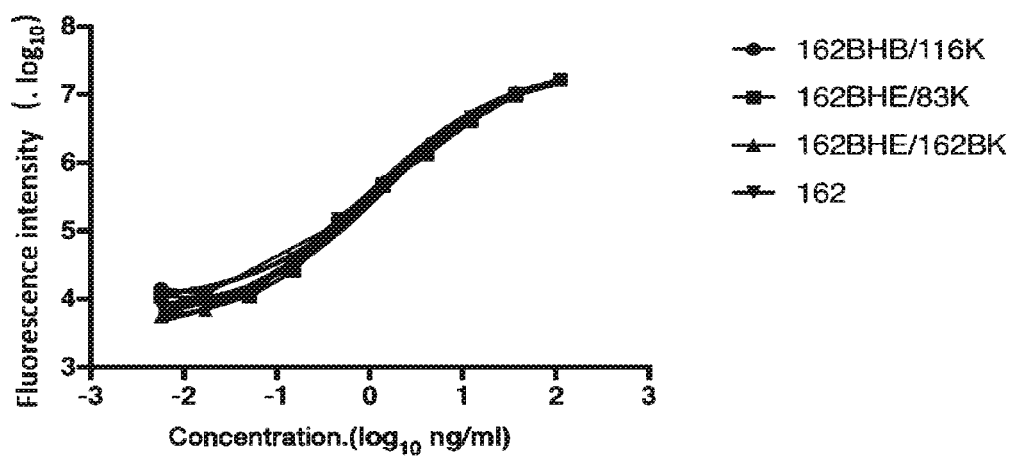
Figure 7U:
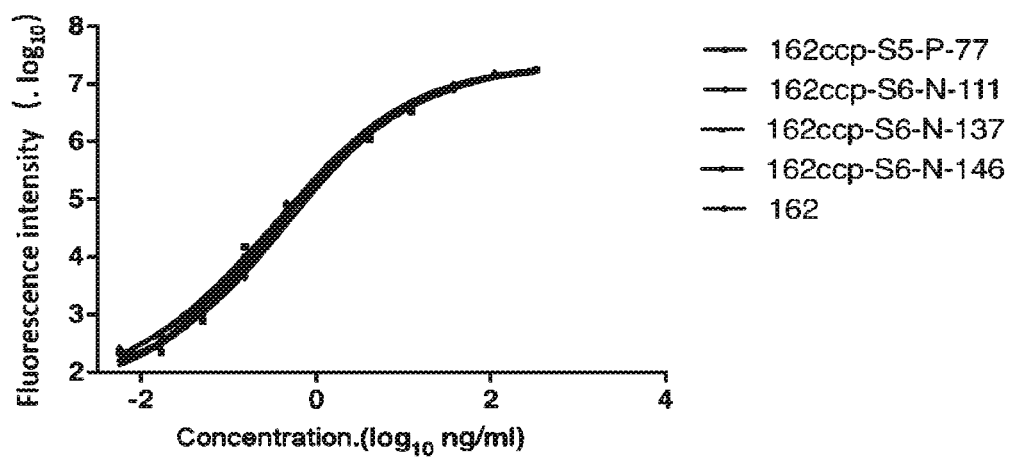
Figure 7V:
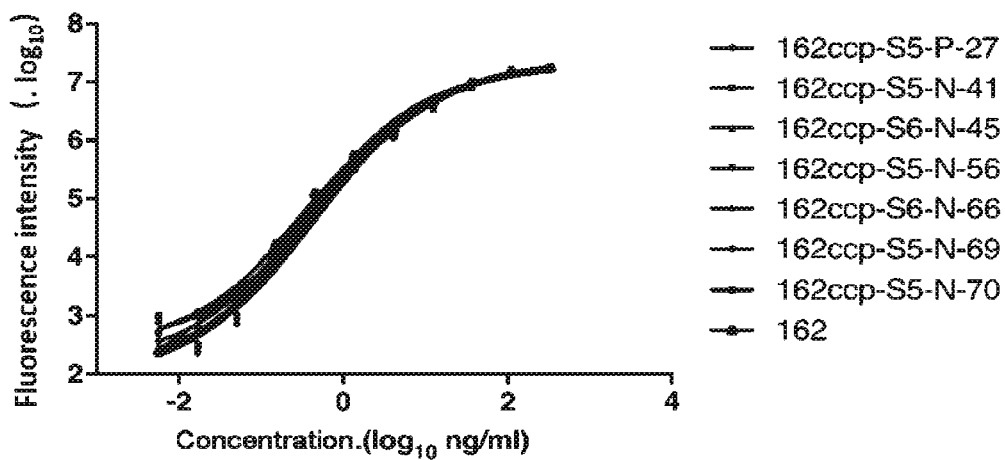
Figure 7W:
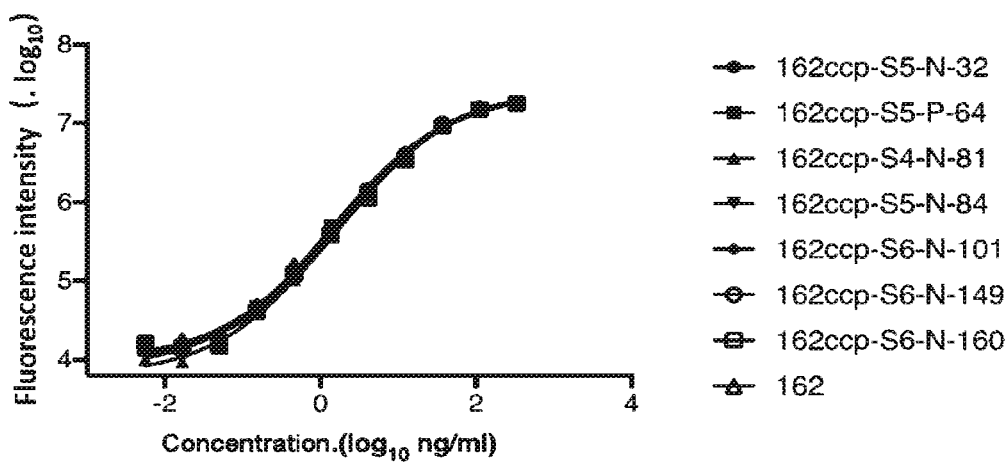
Figure 8A:
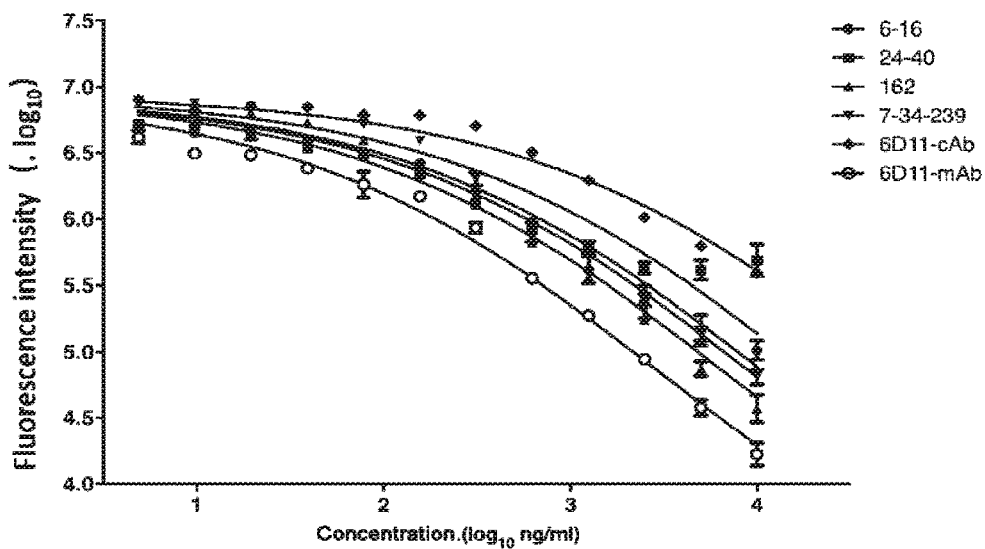
FIGS. 8A-8G show the results on HBV-neutralizing activity of 36 humanized antibodies, wherein, the horizontal axis represents antibody concentration ($\log_{10}$ ng/ml), and the vertical axis represents fluorescence intensity ($\log_{10}$ RLU). The results show that all the tested humanized antibodies had good virus-neutralizing activity, and were superior to the chimeric antibody 6D11-cAb in terms of HBV-neutralizing activity, and some neutralizing antibodies were even comparable to 6D11-mAb in terms of neutralizing activity.
Figure 8B:
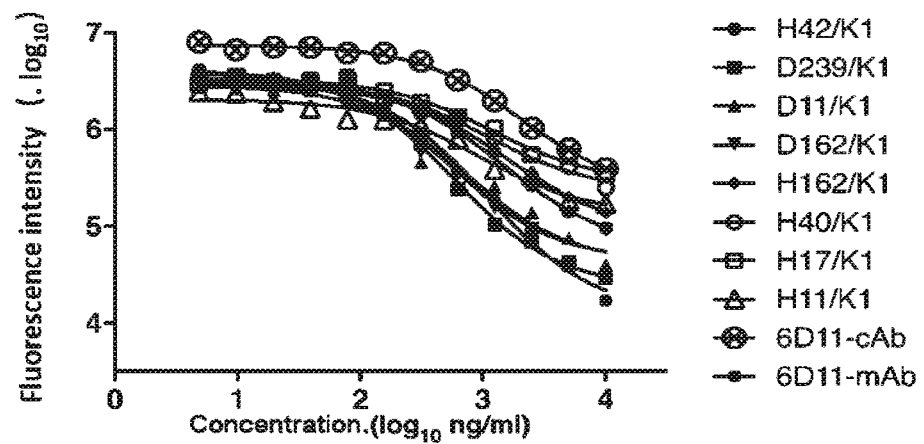
Figure 8C:
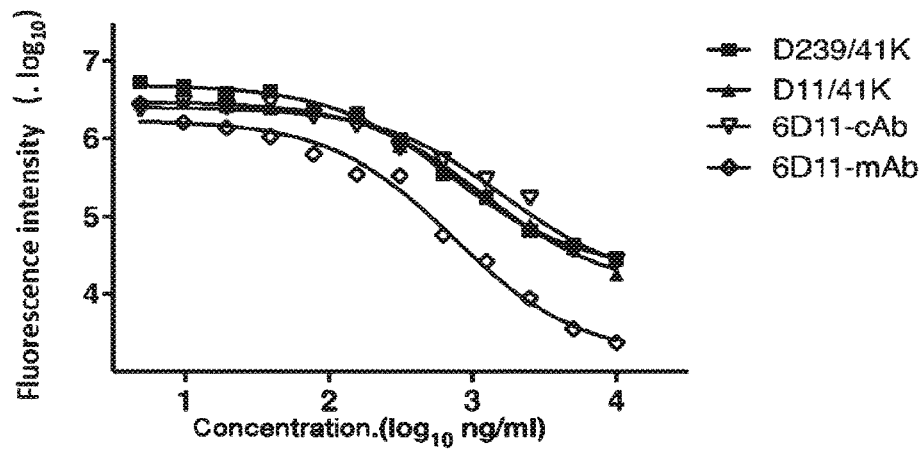
Figure 8D:
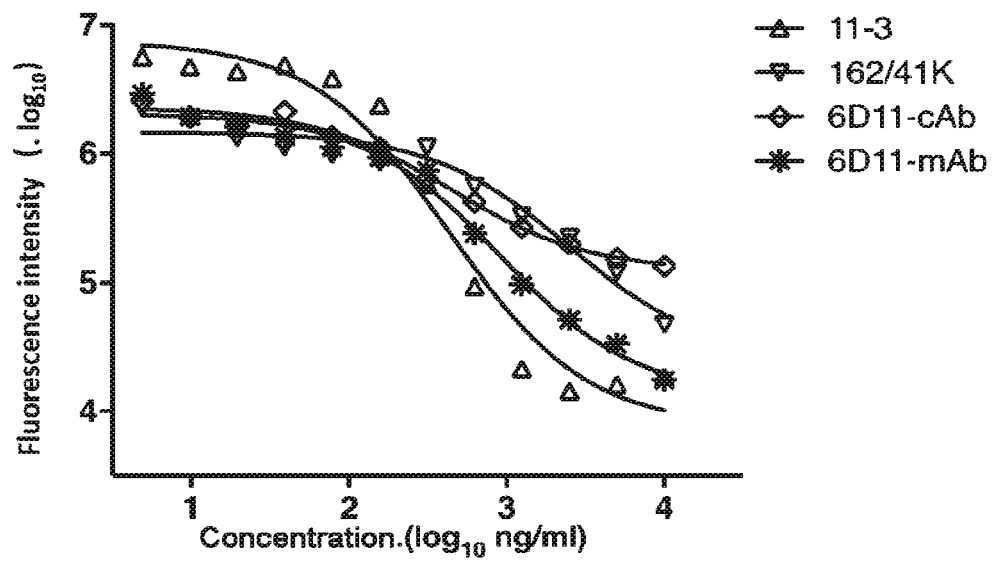
Figure 8E:
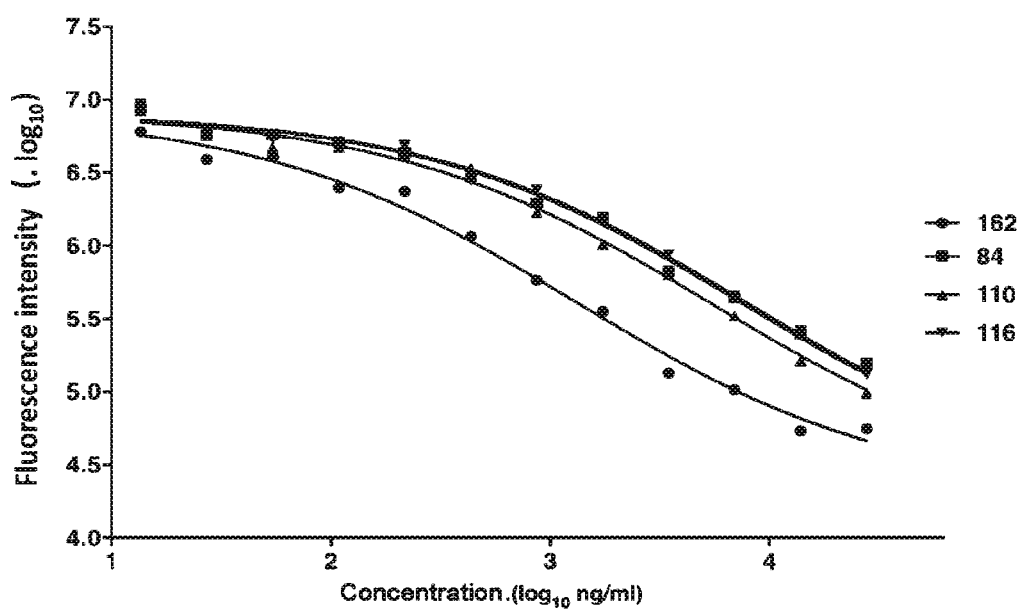
Figure 8F:
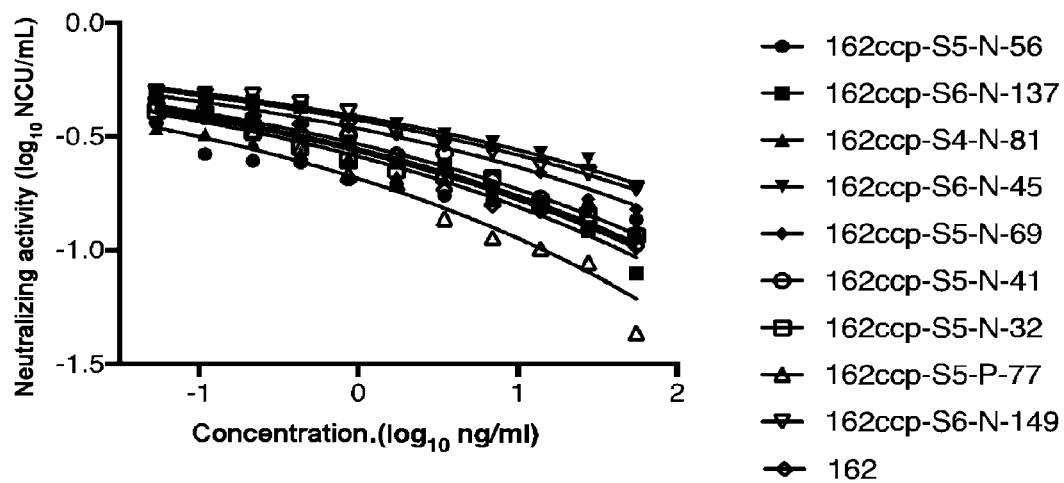
Figure 8G:
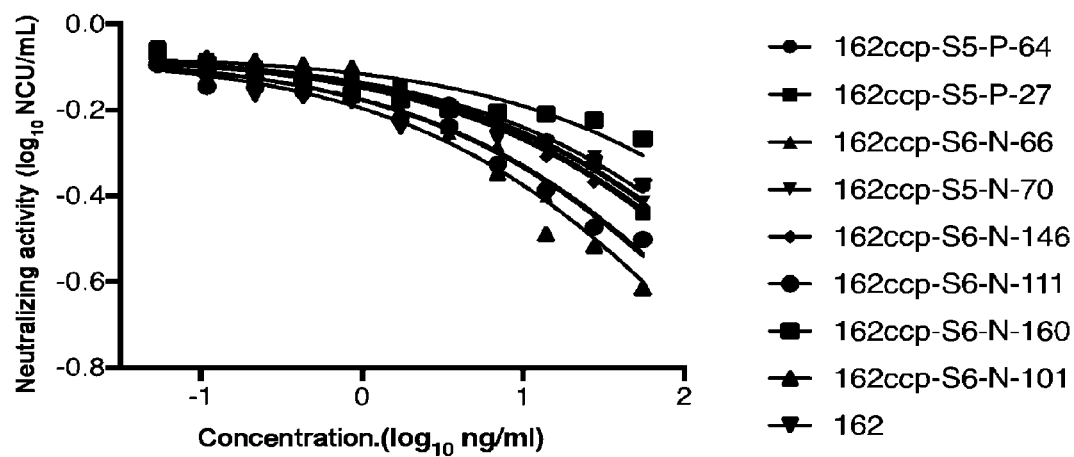

The HBsAg-binding activity of humanized antibodies was determined by chemiluminescence method. In brief, firstly, BCA Protein Quantification kit was used to determine the concentration of the purified antibodies, and all the antibodies were diluted to a concentration of 200 μg/mL. Later, the antibodies were 3-fold serially diluted with 20% NBS, starting from 20 μg/mL, to obtain 12 concentrations in total. The diluted antibodies were then added to the chemiluminescent plate coated with 2 μg/mL HBsAg, and incubated at 37° C. for 1 h. MAH-HRP enzyme-labeled secondary antibody was then added, and incubated for 30 min. After incubation, the plate was washed, a luminescent solution was added, and the light intensity was determined. The data was analyzed by GraphPad Prism, and the results were shown in FIGS. 7A-7W. The results in FIGS. 7A-7W showed that all the tested humanized antibodies had good antigen binding activity, and were superior to 6D11-mAb and 6D11-cAb, or at least comparable to 6D11-mAb and 6D11-cAb in terms of affinity for antigen HBsAg. These results showed that the humanized antibodies according to the invention could not only had a very high humanization degree (of up to 97%), and reduce the possibility of immunological rejection, but also substantively retain the antigen binding activity of the parent murine antibody, or even show higher antigen binding activity than the parent murine antibody. Such technical effects were significant and unexpected.

The heavy chain and light chain CDR sequences of humanized antibodies having good HBsAg-binding activity were analyzed. The analysis results were summarized in Tables 7A-7B.

TABLE 7A

Heavy chain CDR sequences of humanized antibodies having good HBsAg-binding activity

| SEQ ID NO: | VH-CDR1 | SEQ ID NO: | VH-CDR2 | SEQ ID NO: | VH-CDR3 |
|---|---|---|---|---|---|
| 120 | SGYHWN | 142 | YISYDGSDHYNPSLEN | 180 | GFDH |
| 121 | RGYHWN | 143 | YISYDGSVFYNPSLEN | 181 | GEDY |
| 122 | HGYHWN | 144 | YISYDGSILYNPSLEN | 182 | GFDT |
| 123 | NGYHWN | 145 | YISYDGTILYNPSLEN | | |
| 124 | YGYHWN | 146 | YISYDGTVLYNPSLEN | | |
| 125 | RDYHWN | 147 | YISYDGNVLYNPSLEN | | |
| 126 | RWYHWN | 148 | YISYDGTSLYNPSLEN | | |
| 127 | NFYHWN | 149 | YISYDGSVLYNPSLEN | | |
| 128 | RYYHWN | 150 | YISYDGNILYNPSLEN | | |
| | | 151 | YISYDGTNLYNPSLEN | | |
| | | 152 | YISYDGSNLYNPSLEN | | |
| | | 153 | YISYDGTVHYNPSLEN | | |
| | | 154 | YISYDGTIRYNPSLEN | | |
| | | 155 | YISYDGSVLYNPSLKS | | |
| | | 156 | YISYDGSVLYNPSLKG | | |
| | | 157 | YIAYDGVQSYNPSLKG | | |
| | | 158 | YIGYDGAVQYNPSLKS | | |
| | | 159 | YISYNGSVLYNPSLKS | | |
| | | 160 | YISYDGSRLYNPSLKS | | |

TABLE 7A-continued

Heavy chain CDR sequences of humanized antibodies having good HBsAg-binding activity

| SEQ ID NO: | VH-CDR1 | SEQ ID NO: | VH-CDR2 | SEQ ID NO: | VH-CDR3 |
|---|---|---|---|---|---|
| | | 285 | YISYDGSVLFNPSLKS | | |

TABLE 7B

Light chain CDR sequences of humanized antibodies having good HBsAg-binding activity

| SEQ ID NO: | VK-CDR1 | SEQ ID NO: | VK-CDR2 | SEQ ID NO: | VK-CDR3 |
|---|---|---|---|---|---|
| 232 | RSNQSLVHSYGDTYLH | 240 | KVSNRFS | 244 | SQNTHVPYT |
| 233 | RSSQSLVHSYGDTYLH | 241 | KVSKRNS | 245 | SQNTHLPYT |
| 234 | RSSQSLVHPYGPTYLH | 242 | KASQRNS | 246 | GQNAKTPYT |
| 235 | RSSQSLVHTYGNTYLH | 243 | RSSHRNS | 247 | GQNARVPYT |
| 236 | RSSQSLVHPYGSTYLH | | | 248 | SQNSYVPYT |
| 237 | RSSQSLVHRYGTTYLH | | | 249 | SQNTIPPYT |
| 238 | RSSQSLVHPYGATYLH | | | 250 | GQNSMAPYT |
| 239 | RSSQSLVHPYGRTYLH | | | 251 | GQNAHLPYT |
| 318 | RSSQSLVHPFGPTYLH | | | | |
| 319 | RSSQSLAHPYGSTYLH | | | | |
| 320 | RSSQSLVHPYGSTYFH | | | | |

Example 4: Determination of Neutralizing Activity of Humanized Antibodies

Mouse monoclonal antibody 6D11-mAb could specifically bind to HBV viral particles, block the adsorption of HBV to the already differentiated HepaRG cells, and inhibit HBV invasion into cells, which resulted in the loss in infection capability of HBV. In the absence of neutralizing antibodies, HBV invaded the differentiated HepaRG cell, and was replicated in the cell, thereby resulting in a high level of HBV antigen (HBeAg) in a sample. On the contrary, in the presence of neutralizing antibodies, the invasion and replication of HBV would be attenuated or completely suppressed, thereby resulting in a low level of HBV antigen (HBeAg) in the sample. Therefore, by determining the level of HBV antigen (HBeAg), different humanized antibodies can be determined for their ability of neutralizing HBV.

HepaAD38 cells were cells capable of controlled expression of HBV, prepared by the laboratory. When HepaAD38 cells need to be proliferated without expressing HBV, tetracycline can be added to a culture medium in order to inhibit the transcription and replication of HBV. When the expression of HBV is needed, a culture medium free of tetracycline can be used in order to initiate the transcription and replication of HBV. The culture supernatant derived from HepaAD38 cells were brought in contact with the differentiated HepaRG cells. The result showed that the culture supernatant contained HBV, and could effective infect the differentiated HepaRG cells.

By using the HepaRG/HBV infection model, humanized antibodies were evaluated for their ability of neutralizing/blocking HBV infection with an MOI of 100. The humanized antibodies were subjected to 2-fold serial dilution, starting from 10 μg/mL, to obtain 10 concentrations in total. In a virus solution for infecting cells, a specified concentration of a humanized antibody was added in advance, and the virus solution was then used to infect HepaRG cells. 7 days after infection, the supernatant of the cell culture was taken to determine its HBeAg level (an important index indicating the success of HBV infection). The method was as follows.

(1) Coating: an anti-HBeAg monoclonal antibody was diluted in 20 mM PB7.4, at a final concentration of 2 μg/mL. To a 96-well plate, the diluted anti-HBeAg monoclonal antibody (100 μl/well) was added, and incubated at 4° C. overnight. The materials used were purchased from Beijing Wantai Biological Pharmacy Enterprise Co., LTD.

(2) Washing: 96-well microplate was washed with PBST once, and then remove the wash.

(3) Blocking: a blocking solution was added to the 96-well microplate, at 200 μL per well. The blocking solution was purchased from Beijing Wantai Biological Pharmacy Enterprise Co., LTD.

(4) Incubation: a test sample was added at 100 μL/well, and incubated at 37° C. for 60 min.

(5) Washing: 96-well microplate was washed with PBST for five times.

(6) Incubation: horseradish peroxidase-labelled anti-HBeAg antibody (100 μl/well) was added, and incubated at 37° C. for 30 min. The materials were purchased from Beijing Wantai Biological Pharmacy Enterprise Co., LTD.

(7) Washing: 96-well microplate was washed with PBST for five times.

(8) Color development: chemiluminescent reagent luminol was added (100 μl/well).

(9) Plate reading: values were read by using Chemiluminescent ELISA instrument.

In the Example, the neutralizing ability of the following humanized antibodies were determined: 24-40, 6-16, 162, 7-34-239, H11/K1, H17/K1, H40/K1, H42/K1, H162/K1, D11/K1, D162/K1, D239/K1, 11-3, D11/41K, 162/41k, D239/41K, 84, 110, 116, 162ccp-S5-N-56, 162ccp-S6-N-149, 162ccp-S5-P-64, 162ccp-S5-N-32, 162ccp-S4-N-81, 162ccp-S5-P-27, 162ccp-S5-P-77, 162ccp-S5-N-41, 162ccp-S5-N-69, 162ccp-S5-N-70, 162ccp-S6-N-101, 162ccp-S6-N-111, 162ccp-S6-N-137, 162ccp-S6-N-146, 162ccp-S6-N-160, 162ccp-S6-N-66 and 162ccp-S6-N-45.

The experimental results were shown in FIGS. 8A-8G. The results in FIGS. 8A-8G showed that humanized antibodies 24-40, 6-16, 162, 7-34-239, H11/K1, H17/K1, H40/K1, H42/K1, H162/K1, D11/K1, D162/K1, D239/K1, 11-3, D11/41K, 162/41k, D239/41K, 84, 110, 116, 162ccp-S5-N-56, 162ccp-S6-N-149, 162ccp-S5-P-64, 162ccp-S5-N-32, 162ccp-S4-N-81, 162ccp-S5-P-27, 162ccp-S5-P-77, 162ccp-S5-N-41, 162ccp-S5-N-69, 162ccp-S5-N-70, 162ccp-S6-N-101, 162ccp-S6-N-111, 162ccp-S6-N-137, 162ccp-S6-N-146, 162ccp-S6-N-160, 162ccp-S6-N-66 and 62ccp-S6-N-45 had good virus-neutralizing activity, and were superior to chimeric antibody 6D11-cAb in terms of HBV-neutralizing activity, and some of the neutralizing antibodies were even comparable to 6D11-mAb in terms of neutralizing activity. These results showed that the humanized antibodies according to the invention could not only have a very high humanization degree (up to 97%), reduce the possibility of immunological rejection, but also exhibit higher virus-neutralizing activity than chimeric antibody 6D11-cAb. Such technical effects were significant and unexpected.

The humanized antibodies having good virus-neutralizing activity were also analyzed for their heavy chain and light chain CDR sequences. The analytic results were summarized in Tables 8A-8B.

TABLE 8A

The heavy chain CDR sequences of the humanized antibodies having good virus-neutralizing activity

| SEQ ID NO: | VH-CDR1 | SEQ ID NO: | VH-CDR2 | SEQ ID NO: | VH-CDR3 |
|---|---|---|---|---|---|
| 126 | RWYHWN | 146 | YISYDGTVLYNPSLEN | 180 | GFDH |
| 122 | HGYHWN | 145 | YISYDGTILYNPSLEN | | |
| 124 | YGYHWN | 149 | YISYDGSVLYNPSLEN | | |
| 121 | RGYHWN | 151 | YISYDGTNLYNPSLEN | | |
| 123 | NGYHWN | 144 | YISYDGSILYNPSLEN | | |
| 120 | SGYHWN | 142 | YISYDGSDHYNPSLEN | | |
| | | 155 | YISYDGSVLYNPSLKS | | |
| | | 156 | YISYDGSVLYNPSLKG | | |
| | | 285 | YISYDGSVLFNPSLKS | | |

TABLE 8B

The light chain CDR sequences of the humanized antibodies having good virus-neutralizing activity

| SEQ ID NO: | VK-CDR1 | SEQ ID NO: | VK-CDR2 | SEQ ID NO: | VK-CDR3 |
|---|---|---|---|---|---|
| 233 | RSSQSLVHSYGDTYLH | 240 | KVSNRFS | 244 | SQNTHVPYT |
| 235 | RSSQSLVHTYGNTYLH | | | | |
| 236 | RSSQSLVHPYGSTYLH | | | | |
| 234 | RSSQSLVHPYGPTYLH | | | | |
| 318 | RSSQSLVHPFGPTYLH | | | | |
| 319 | RSSQSLAHPYGSTYLH | | | | |
| 320 | RSSQSLVHPYGSTYFH | | | | |

Example 5: Evaluation of the Therapeutic Effects of Humanized Antibodies in Animal HBV transgenic mice were used to evaluate the virus-clearing ability of humanized antibodies in animal. The virus-clearing ability directly reflected the potential of the antibodies as drugs. The purified humanized antibody at a specified concentration was filtrated with a 0.22 μm filter, to ensure a sterile state. A single dose of 10 mg/kg of the humanized antibody was administered to HBV transgenic mice by means of tail vein injection. Later, at a specified time, blood was collected from retro-orbital venous plexus, to obtain the blood samples of the mice. HBsAg level in mouse serum was quantitatively determined.

5.1: Quantitative Determination of HBsAg (1) Preparation of a reaction plate: the anti-HBsAg mouse monoclonal antibody HBs-45E9 was diluted with 1×PB buffer to 2 μg/mL, and then added to ELISA plate. The plate was coated at 2-8° C. for 16-24 h, and then coated at 37° C. for 2 h. Later, the plate was washed with PBST once. After washing, to each well, 200 μL blocking solution was added, and the plate was blocked at 37° C. for 2 h. Later, the blocking solution was discarded, and the plate was dried and packaged in a vacuum aluminum foil bag, and stored at 2-8° C. for use.

(2) Sample dilution: the collected mouse serum was diluted with PBS solution containing 20% new-born calf serum, at 1:30 and 1:150, for quantitative determination.

(3) Sample denaturation: 15 μL diluted serum sample was sufficiently mixed with 7.5 μL denaturing buffer (15% SDS, dissolved in 20 mM PB7.4), and incubated at 37° C. for 1 h. Later, 90 μL neutralizing buffer (4% CHAPS, dissolved in 20 mM PB7.4) was added, and mixed sufficiently.

(4) Sample reaction: 100 μL denatured serum sample was added to the well of a reaction plate, and incubated at 37° C. for 1 h. The plate was then washed with PBST for 5 times.

(5) Reaction with an enzyme-labelled antibody: HBs-A6A7-HRP reaction solution (100 μL/well) was added to the well of the reaction plate, and then incubated at 37° C. for 1 h. The plate was then washed with PB ST for 5 times.

(6) Luminescent reaction and measurement: a luminescent substrate solution (100 μL/well) was added to the well of the reaction plate, and light intensity was measured.

(7) Determination of HBsAg concentration in a serum sample to be tested: standards with known concentrations of HBsAg were used in parallel experiments. Based on the determined results of standards, a standard curve was plotted (i.e. a linear regression analysis on the measured light intensity and the HBsAg concentration of standards was performed). Then, the HBsAg concentration in a serum sample to be tested could be calculated by the standard curve.

In the Example, the following humanized antibodies were tested for their virus-clearing ability in animal: 24-40, 7-34-239, 162, 11-3, 162/41K, 116, 110 and 138. The experimental results were shown in FIGS. 9A-9B.

Figure 9A:
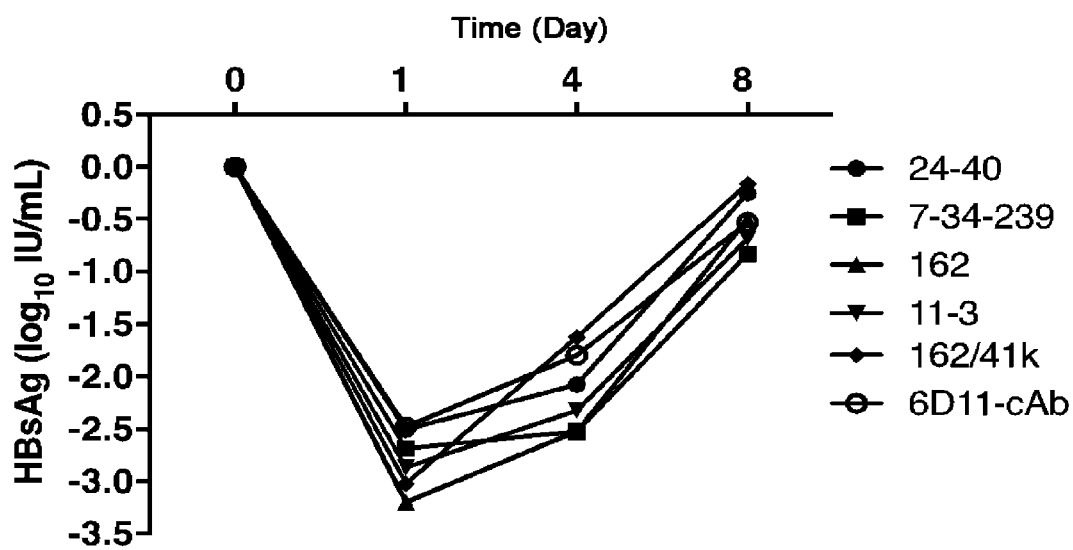
FIGS. 9A-9B show changes in the serum level of HBsAg in mice treated with different humanized antibodies, wherein, the horizontal axis represents the number of days after injection of humanized antibody, and the vertical axis represents the HBsAg level (log 10 IU/ml) in mouse serum. The results show that all the tested humanized antibodies had good virus-clearing ability in animal, and were superior to chimeric antibody 6D11-cAb in terms of the ability of clearing HBsAg in animal.
Figure 9B:
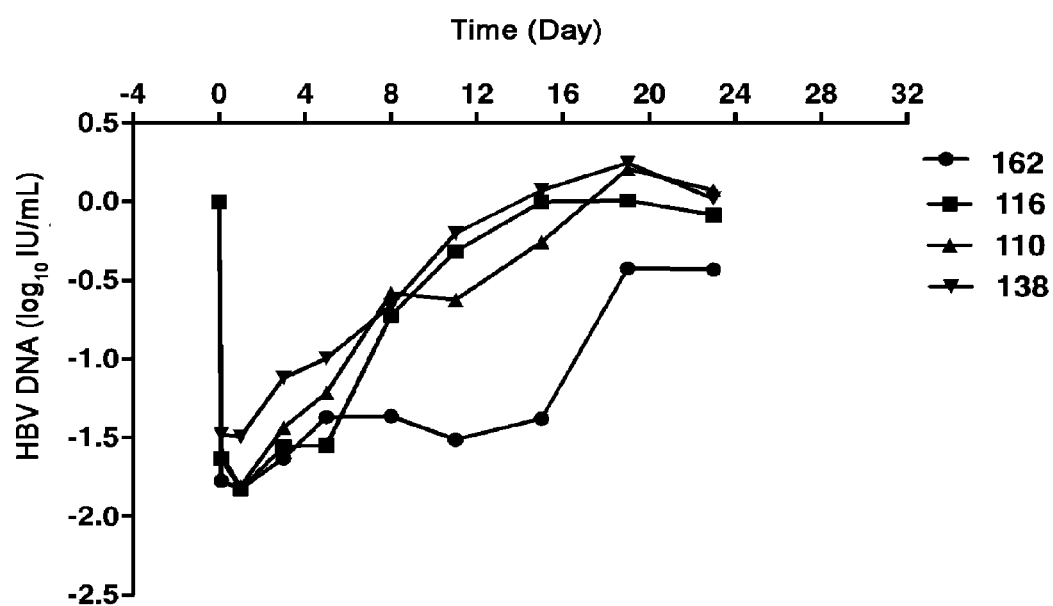

FIGS. 9A-9B showed that the humanized antibodies 24-40, 7-34-239, 162, 11-3, 162/41K, 116, 110 and 138 had good virus-clearing ability, and were superior to chimeric antibody 6D11-cAb in terms of the ability of clearing HBsAg in animal. There results showed that the humanized antibodies according to the invention not only had a very high humanization degree (up to 97%), could reduce the possibility of immunological rejection, but also exhibit a higher virus-clearing ability than chimeric antibody 6D11-cAb. Such technical effects were significant and unexpected.

The humanized antibodies having good virus-clearing ability were also analyzed for their heavy chain and light chain CDR sequences. The analytic results are summarized in Tables 9A-9B.

TABLE 9A

The heavy chain CDR sequences of the humanized antibodies having good virus-clearing ability in mice

| SEQ ID NO: | VH-CDR1 | SEQ ID NO: | VH-CDR2 | SEQ ID NO: | VH-CDR3 |
|---|---|---|---|---|---|
| 126 | RWYHWN | 146 | YISYDGTVLYNPSLEN | 180 | GFDH |
| 121 | RGYHWN | 151 | YISYDGTNLYNPSLEN | | |
| 124 | YGYHWN | 149 | YISYDGSVLYNPSLEN | | |
| 120 | SGYHWN | 142 | YISYDGSDHYNPSLEN | | |
| | | 155 | YISYDGSVLYNPSLKS | | |

TABLE 9B

The light chain CDR sequences of the humanized antibodies having good virus-clearing ability in mice

| SEQ ID NO: | VK-CDR1 | SEQ ID NO: | VK-CDR2 | SEQ ID NO: | VK-CDR3 |
|---|---|---|---|---|---|
| 233 | RSSQSLVHSYGDTYLH | 240 | KVSNRFS | 244 | SQNTHVPYT |
| 235 | RSSQSLVHTYGNTYLH | | | | |
| 236 | RSSQSLVHPYGSTYLH | | | | |

Example 6: Evaluation on Druggability of Humanized Antibodies 162, 116, 110, 153 and 138

1. Determination of Isoelectric Points of Humanized Antibodies 162, 116, 110, 153 and 138

Figure 10:
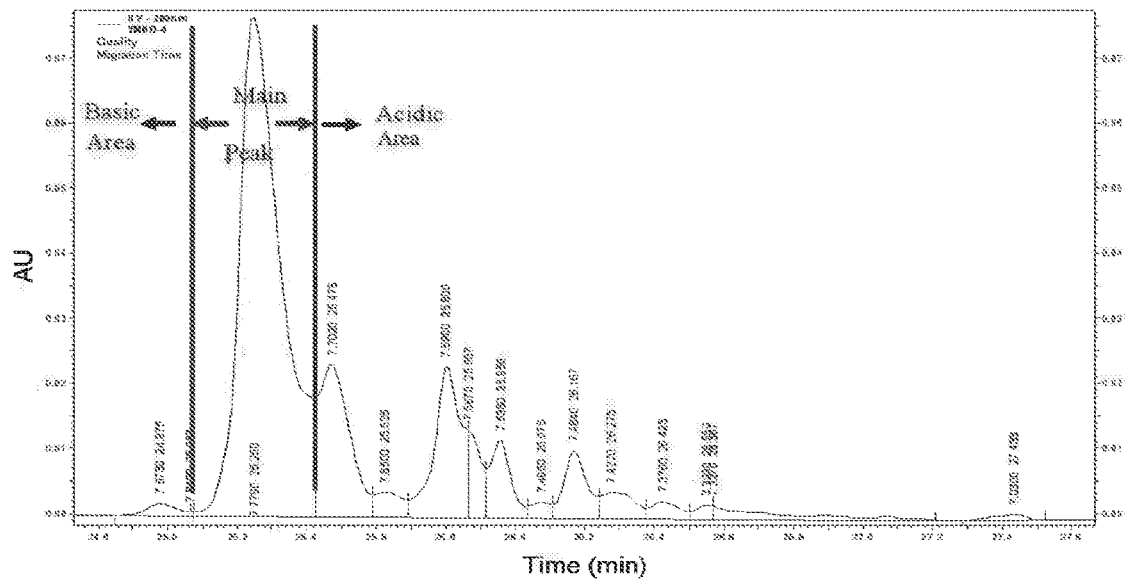
FIG. 10 shows the experimental result of capillary isoelectric focusing (cIEF) electrophoresis for determining the isoelectric point of humanized antibody 162. The result showed that humanized antibody 162 had pI value of 7.78 (in a range of: 7.03-7.87), wherein the basic peak accounts for 0.99%, the main peak accounts for 55.87%, and the acidic peak accounts for 43.14%.

The isoelectric point of humanized antibody 162 was determined by capillary isolecatric focusing electrophoresis (cIEF). The experimental result was shown in FIG. 10. The result showed that humanized antibody 162 had a pI value of 7.78 (range: 7.03-7.87), the basic peak accounted for 0.99%, the main peak accounted for 55.87%, and the acidic peak accounted for 43.14%.

Figure 11:
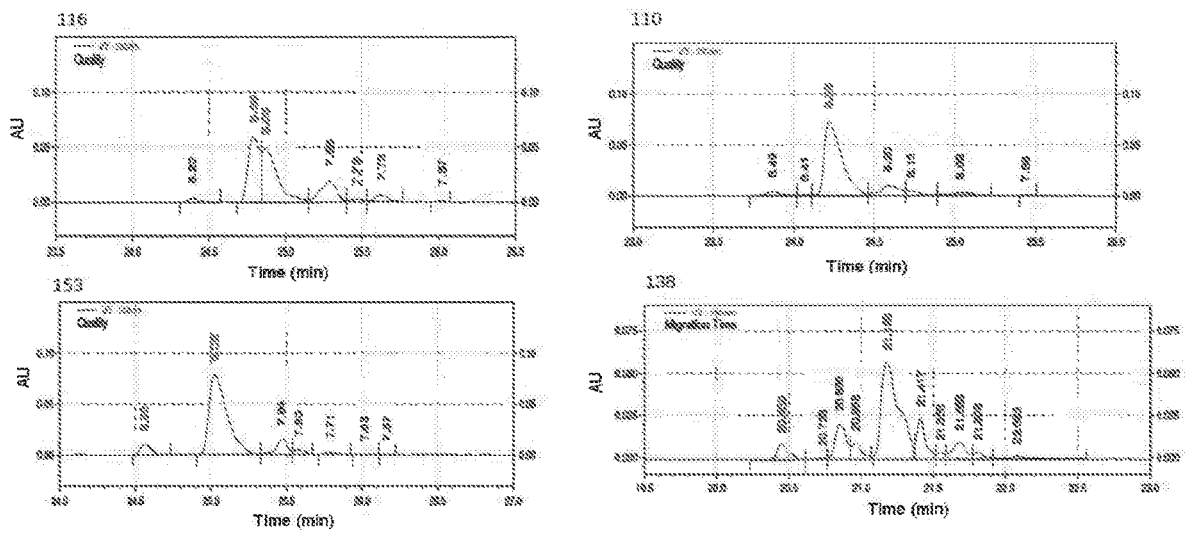
FIG. 11 shows the capillary electrophoresis result of humanized antibodies 116, 110, 153 and 138.

The isoelectric points of antibodies 162, 116, 110, 153 and 138 were determined, and the result was shown in FIG. 11, wherein the isoelectric points were in a range of 7.83-8.6. The isoelectric points of antibodies 162, 116, 110, 153 and 138 were summarized in Table 10.

TABLE 10

Isoelectric points of humanized antibodies

| | Isoelectric point | | Calibrated peak area | | |
|---|---|---|---|---|---|
| Sample | Main Peak | Range | Basic peak (%) | Main peak (%) | Acidic peak (%) |
| 116 | 8.06 | 7.57~8.22 | 2.78% | 75.26% | 21.96% |
| 110 | 8.35 | 7.86~8.49 | 4.49% | 76.04% | 19.47% |
| 153 | 8.02 | 7.57~8.20 | 6.70% | 78.99% | 14.31% |
| 138 | 8.60 | 8.27~8.88 | 22.70% | 64.33% | 12.97% |
| 162 | 7.77 | 7.02~7.87 | 1.31% | 55.78% | 42.91% |

2. Test on Stability of Humanized Antibodies

Figure 12:
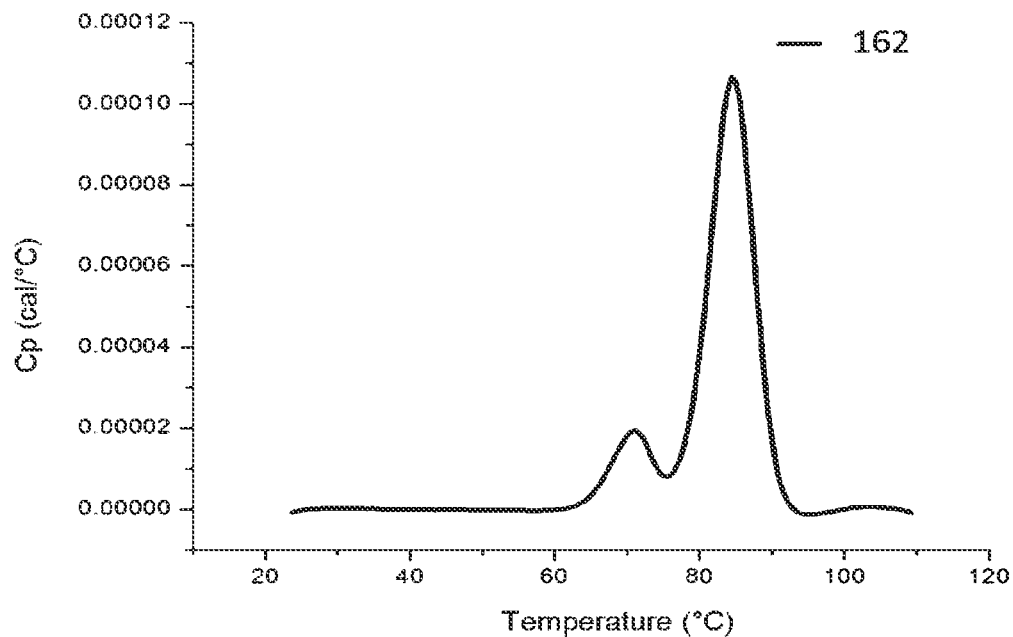
FIG. 12 shows the experimental result on stability of humanized antibody 162 by differential scanning calorimetry (DSC).
Figure 13:
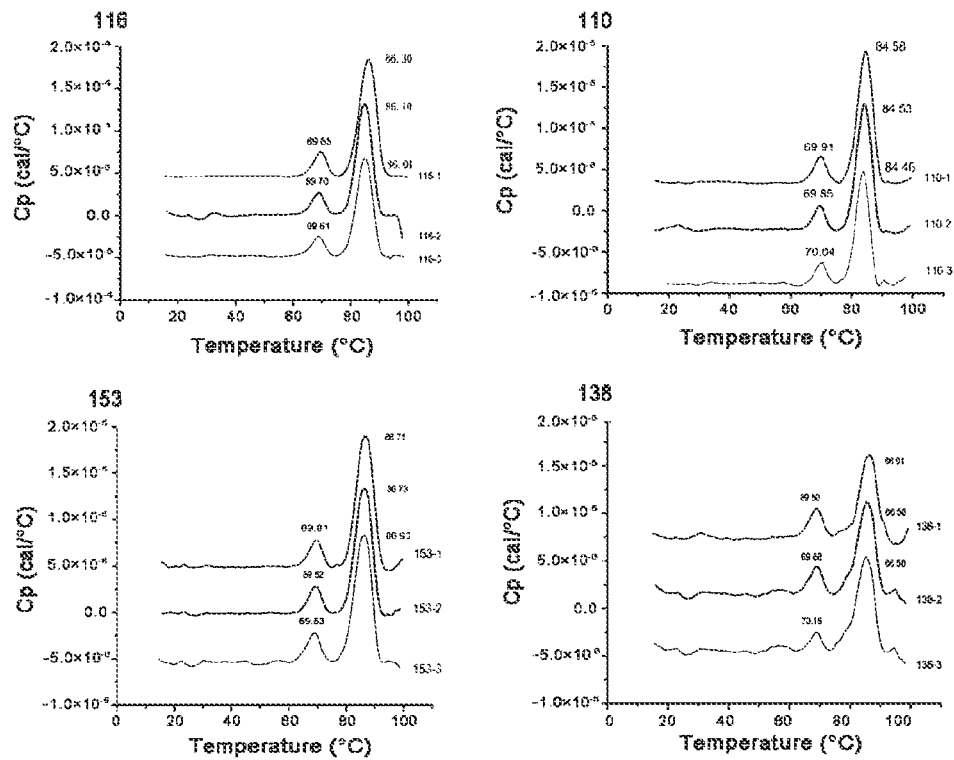
FIG. 13 shows the DSC experimental result of humanized antibodies 116, 110, 153 and 138.

Tm value is generally used to describe the stability of an antibody molecule. The higher a Tm value is, the better the thermal stability of an antibody molecule is. Humanized antibodies 162, 116, 110, 153 and 138 were diluted to 1 mg/ml, and were determined by differential scanning calorimetry (DSC). The scanning began at a temperature of 10° C., and ended at a temperature of 110° C., at a scan rate of 200° C./hr, wherein the cooling rate was set as Exp, the apparatus was finally held at a temperature of 25° C., the data acquisition frequency was 10 sec, and the capillary temperature was 30° C. before sample loading. The experimental results were shown in FIG. 12, FIG. 13, Table 11, and Table 12. The result showed that for humanized antibody 162, the Tm onset was 61.81° C., Tm 1 was 71.21° C., and Tm 2 was 84.48° C.; while Tm value was higher than 80° C. for antibodies 116, 110, 153 and 138, indicating that antibodies 162, 116, 110, 153 and 138 had good thermal stability.

TABLE 11

DSC result of humanized antibody 162

| Sample name | Tm onset | Tm 1 | Tm 2 |
|---|---|---|---|
| 162 | 61.81° C. | 71.21° C. | 84.48° C. |

TABLE 12

DSC results of humanized antibodies 116, 110, 153 and 138

| Sample name | Tm (° C.) | 1 | 2 | 3 | X ± S | Relative standard deviation (%) |
|---|---|---|---|---|---|---|
| 116 | Tm1 | 86.30 | 86.10 | 86.01 | 86.14 ± 0.15 | 0.17 |
| | Tm2 | 69.65 | 59.70 | 69.61 | 69.65 ± 0.05 | 0.06 |
| 110 | Tm1 | 84.58 | 84.53 | 84.46 | 84.52 ± 0.06 | 0.07 |
| | Tm2 | 69.91 | 69.86 | 70.04 | 69.94 ± 0.09 | 0.13 |
| 153 | Tm1 | 86.71 | 86.73 | 86.93 | 86.79 ± 012 | 0.14 |
| | Tm2 | 69.81 | 69.58 | 69.53 | 69.64 ± 0.15 | 0.21 |
| 138 | Tm1 | 86.91 | 86.58 | 86.58 | 86.69 ± 0.19 | 0.22 |
| | Tm2 | 69.50 | 69.68 | 70.18 | 69.79 ± 0.35 | 0.50 |

In addition, humanized antibody 162 was dissolved at a concentration of 60 mg/ml in three buffers containing 5% sucrose and 0.02% PS80 (i.e. Buffer 1 was a 25 mM citrate solution (pH 5.0); Buffer 2 was a 25 mM histidine solution (pH 6.0); Buffer 3 was a 25 mM phosphate solution (pH 7.0)), and then stored at 5° C., 25° C. and 40° C., respectively. The samples were monitored for their physiochemical properties (including appearance, pH value, protein concentration, particle size, etc.) at Week 0 (T0), Week 1 (T1W), Week 2 (T2W) and Week 4 (T4W).

Appearance Monitoring

The sample bottles were wiped clean, and the color and clarity of the samples were observed by Clarity Detector (black background and white background). The results were shown in Table 13. Table 13 showed changes in appearance of humanized antibody 162 under different storage conditions (different buffers, different temperatures, and different storage periods). The result showed that humanized antibody 162 dissolved in Buffer 1 turned opalescent after storage at 40° C. for 4 weeks, while the samples showed no significant change under other storage conditions.

TABLE 13

Changes in appearance of humanized antibody 162 under different storage conditions

| Buffer | pH | T0 | Clarity | | | | | | | | |
| --- | --- | --- | --- | --- | --- | --- | --- | --- | --- | --- | --- |
| | | | 5° C. | | | 25° C. | | | 40° C. | | |
| | | | T1W | T2W | T4W | T1W | T2W | T4W | T1W | T2W | T4W |
| 1 | 5.0 | SS | SS | SS | SS | SS | SS | SS | SS | SS | SO |
| 2 | 6.0 | SS | SS | SS | SS | SS | SS | SS | SS | SS | SS |
| 3 | 7.0 | SS | SS | SS | SS | SS | SS | SS | SS | SS | SS |

SS = slightly yellow, slightly opalescent;
SO = slightly yellow, opalescent.

Monitoring of pH Value and Protein Concentration

Figure 14:
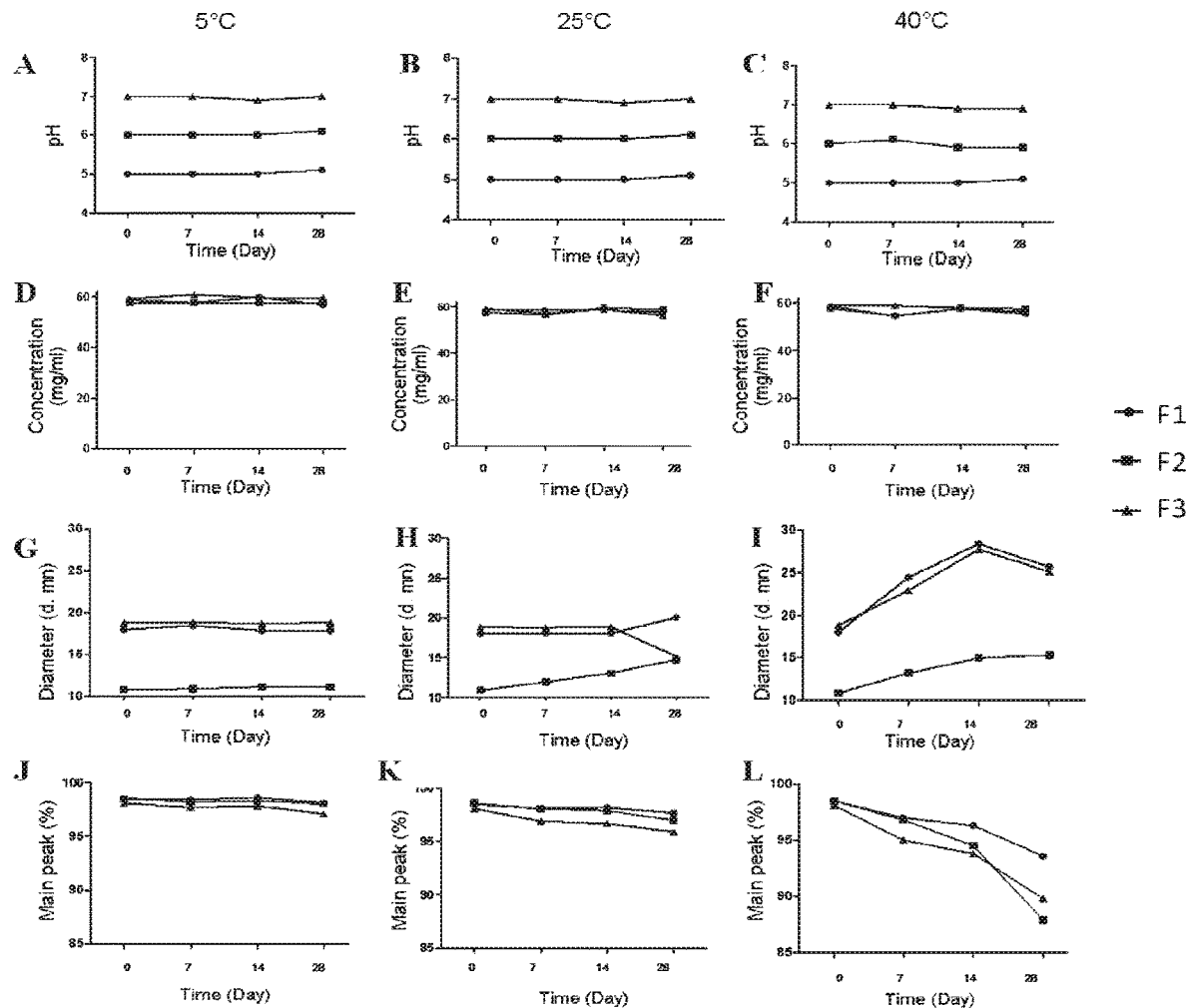
FIGS. 14A-14F show changes in pH value (FIGS. 14A-14C) and protein concentration (FIGS. 14D-14F) of humanized antibody 162 under different storage conditions. The result show that humanized antibody 162 had no significant change in pH value (FIGS. 14A-14C) and protein concentration (FIGS. 14D-14F) after storing in different buffers at different temperatures for 4 weeks.
FIGS. 14G-14I show changes in hydrodynamic diameter of humanized antibody 162 under different storage conditions. The result showed that humanized antibody 162 dissolved in different buffers was stable at 5° C.; and humanized antibody 162 dissolved in Buffer 2 (pH 6.0) was more stable than the one dissolved in Buffer 1 or 3.
FIGS. 14J-14L show SEC-HPLC results of samples of humanized antibody 162 stored under different conditions. The result showed that under different storage conditions (different buffers, different temperatures, and different storage periods), all the samples containing humanized antibody 162 had a main peak of above 85%. This indicates that humanized antibody 162 was stable.

The absorbance of the samples was determined at A280, and the protein concentration of the samples was calculated in accordance with Beer-Lambert law. In addition, the pH value of the samples was determined by pH meter, and was the mean of two determinations. The experimental results were shown in FIGS. 14A-14F. FIG. 14 showed changes in pH value (FIGS. 14A-14C) and protein concentration (FIGS. 14D-14F) of humanized antibody 162 under different storage conditions. The results showed that humanized antibody 162 showed no significant change in pH value (FIGS. 14A-14C) and protein concentration (FIGS. 14D-14F) after storage in different buffers at different temperatures for 4 weeks.

SDS-PAGE Analysis on Stability of Antibodies

Figure 15:
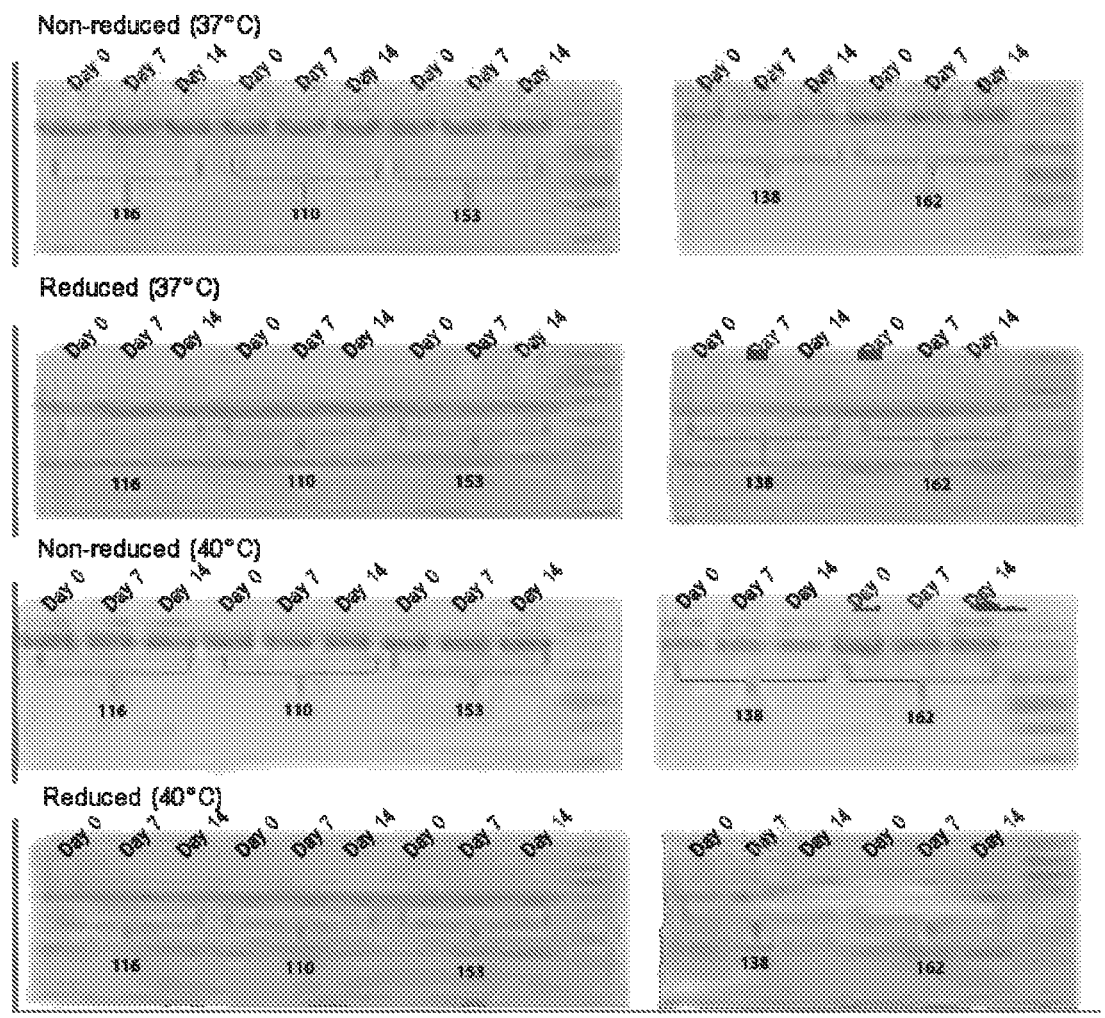
FIG. 15 shows electropherograms of reduced SDS-PAGE and non-reduced SDS-PAGE of antibodies 162, 116, 110, 153 and 138 after accelerated stability test. The result showed that antibodies 162, 116, 110, 153 and 138 remained stable after accelerated stability test.

Antibodies 162, 116, 110, 153 and 138, which were stored at 37° C. and 40° C. for different time, were subjected to non-reduced and reduced SDS-PAGE analysis, wherein in the non-reduced SDS-PAGE gel, the concentration of polyacrylamide was 10%, and in the reduced SDS-PAGE gel, the concentration of polyacrylamide was 12%. The experimental result was shown in FIG. 15. As seen from the electropherogram, the bands were substantively stable, and no significant degradation and aggregation occurred within two weeks since storage.

Particle-Size Analysis and SEC-HPLC Assay

In the samples of humanized antibody 162 stored under different conditions, the particle size of the molecular polymers were analyzed by DLS. In brief, in a biosafety cabinet, 40 μl sample was added into a sample cell of Nano ZS particle size analyzer by using micropipettor, and then tested in Nano ZS particle size analyzer. The experimental data was analyzed and processed by Zetasizer Nano software. The experimental results were shown in FIGS. 12G-12I. The results showed that humanized antibody 162, which was stored at different temperatures (5° C., 25° C. and 40° C.), and dissolved in Buffer 2 (pH 6.0), had the smallest hydrodynamic diameter; and at 5° C., humanized antibody 162 dissolved in different buffers had no significant change in hydrodynamic diameter, while at 25° C. and 40° C., humanized antibody 162 had hydrodynamic diameter increased with time. In addition, at 40° C., the particle size of humanized antibody 162 dissolved in Buffer 2 (pH 6.0) was substantively saturated at Week 4, which was about 16 nM. These results showed that humanized antibody 162 dissolved in different buffers were stable at 5° C.; and, compared to Buffer 1 and 3, humanized antibody 162 dissolved in Buffer 2 (pH 6.0) was more stable.

By SEC-HPLC using Agilent 1260 infinity, TSK G3000SWXL gel column (5 μm, 7.8 mm×300 mm), the samples of humanized antibody 162 stored under different conditions were analyzed, wherein, the mobile phase consisted of 50 mM PB and 300 mM NaCl, pH7.0±0.2; the flow rate was 1.0 mL/min; the detection wavelength was 280 nm; the sample concentration was 10 mg/ml, and the injection volume was 100. The experimental results were shown in FIGS. 12J-12L. The results showed that under different storage conditions (different buffers, different temperatures, and different storage periods), the samples containing humanized antibody 162 had a main peak of above 85%. This indicated that humanized antibody 162 was stable.

3. Analysis of Solubility of Humanized Antibodies 162, 116, 110, 153 and 138

Humanized antibody 162 was dissolved at a concentration of 60 mg/ml in a 25 mM histidine solution containing 5% sucrose and 0.02% PS80 (pH 6.0, Buffer 2), and was concentrated by centrifugal ultrafiltration (at a centrifugation temperature of 5° C., and a rotation rate of 4850 rpm), until the liquid level of the sample solution was not significantly decreased with the increase of centrifugation time. The sample was recovered carefully with a micropipettor, and the sample was observed. The result showed that the solution sample was yellow.

Then, 1000 μL solution sample was transferred to a 1.5 ml EP tube, and centrifuged at 10000 rpm for 20 min. The centrifugation result showed that no sample stratification occurred, the liquid was clear, and no precipitate appeared. The upper and lower part of the sample were carefully drawn with a micropipettor, and the protein concentration was determined by UV280. The result showed the upper solution of the sample of antibody 162 had a protein concentration of 171.81 mg/ml, and the lower solution had a protein concentration of 188.61 mg/ml. The protein concentration of the upper solution was used as the solubility of humanized antibody 162 in the buffer system (i.e. the solubility was 171.81 mg/ml). The solubility of antibody 116 was 185.99 mg/ml; the solubility of antibody 110 was 144.27 mg/ml; the solubility of antibody 153 was 159.87 mg/ml.

Figure 16:
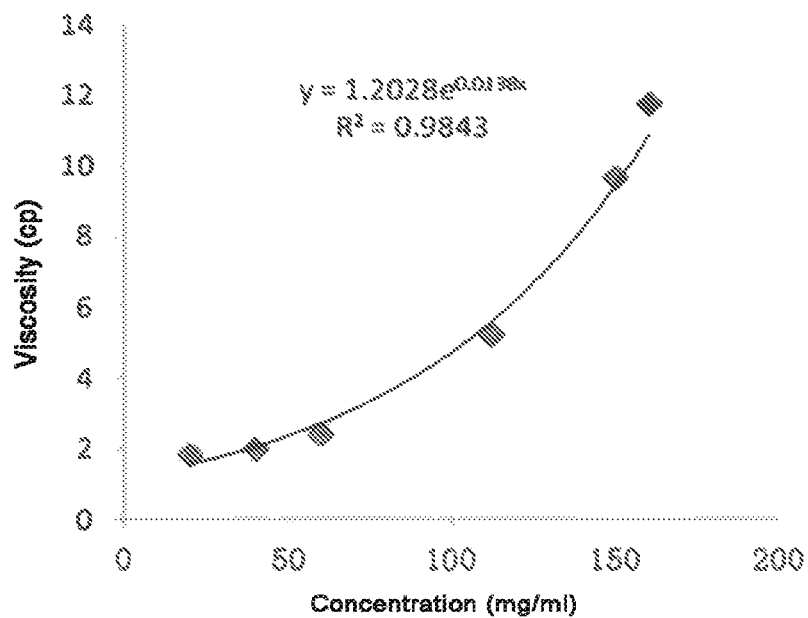
FIG. 16 shows the measurement result on viscosity of humanized antibody 162 dissolved in 25 mM histidine solution (pH 6.0, Buffer 2) containing 5% sucrose and 0.02% PS80. The result showed that in the buffer system, humanized antibody 162 had a viscosity of 9.66 cp (1 cP=1 mPa·s) at a concentration of 150 mg/ml, and a viscosity of 11.73 cp at a concentration of 160 mg/ml.
Figure 17:
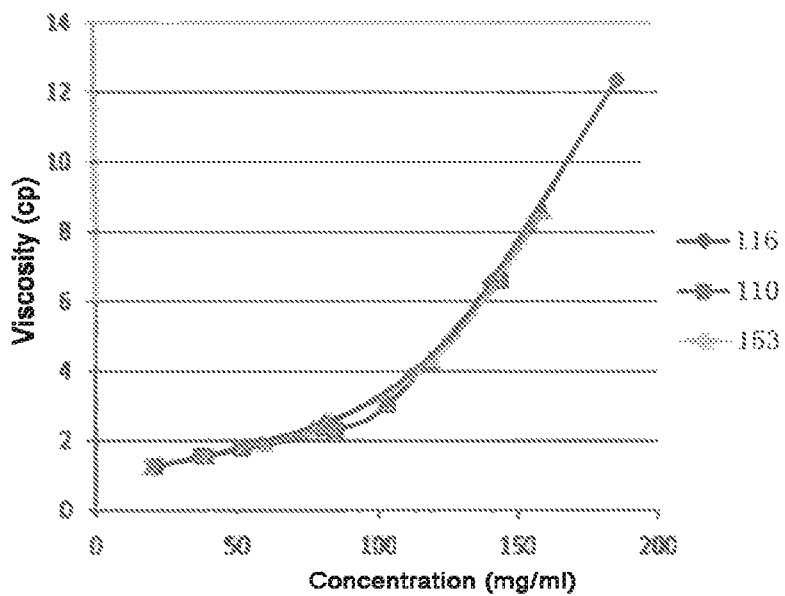
FIG. 17 shows the measured result on viscosity of humanized antibodies 116, 110, and 153 dissolved in 25 mM histidine solution (pH 6.0 Buffer 2) containing 5% sucrose and 0.02% PS80.

Furthermore, the viscosity of humanized antibody dissolved in a 25 mM histidine solution containing 5% sucrose and 0.02% PS80 (pH 6.0, Buffer 2), was measured. The measurement results were shown in FIG. 16 and FIG. 17. The results showed that in the buffer system, humanized antibody 162 had a viscosity of 9.66 cp (1 cP=1 mPa·s) at a concentration of 150 mg/ml, and had a viscosity of 11.73 cp at a concentration of 160 mg/ml. Antibody 116 had a viscosity of 12.37 cp at its highest solubility; antibody 110 had a viscosity of 6.6 cp at its highest solubility; and antibody 153 had a viscosity of 8.54 cp at its highest solubility.

Example 7: Evaluation on Pharmacokinetics and Toxicity after Single Intravenous Injection of CHO-HBsAg and Humanized Antibodies 162, 116, 110 and 153 to Cynomolgus Monkeys 9 male cynomolgus monkeys, which had not experienced any experiment including the administration of macromolecular (>2000 Dalton), were divided into 3 groups, 3 monkeys/group. A solution of HBsAg expressed by CHO cell (CHO-HBsAg) was administered to cynomolgus monkeys of Group 1 at a dose of 3 mg/kg by intravenous injection. A solution of humanized antibody 162 was administered to cynomolgus monkeys of Group 2 at a dose of 20 mg/kg by intravenous injection. By intravenous injection, a solution of CHO-HBsAg was administered to cynomolgus monkeys of Group 3 at a dose of 3 mg/kg, and 10 min later, a solution of humanized antibody 162 was administered at a dose of 20 mg/kg. Evaluation of pharmacokinetic characteristics and preliminary study on toxicity were performed after single intravenous injection of CHO-HBsAg and humanized antibody 162 to cynomolgus monkeys. The particular experimental design was as followed (Table 14):

TABLE 14

Experimental design for evaluating pharmacokinetic characteristics and toxicity of antibody 162

| Group | Substance to be administered | Animal amount | Administration route | Solvent | Dose | Volume | Concentration | Animal No. |
|---|---|---|---|---|---|---|---|---|
| 1 | CHO-HBsAg | 3 | Intravenous injection | PBS buffer | 3 mg/kg | 3 mL/kg | 1 mg/mL | P1001; P1002, P1003 |
| 2 | Antibody 162 | 3 | | | 20 mg/kg | 2 mL/kg | 10 mg/mL | P2001, P2002, P2003 |
| 3 | CHO-HBsAg + Antibody 162 | 3 | | | 3 mg/kg + 20 mL/kg | 3 mL/kg + 2 mL/kg | 1 mg/mL + 10 mg/mL | P3001, P3002, P3003 |

27 male cynomolgus monkeys, which had not experienced any experiment including the administration of macromolecular (>2000 Dalton), were divided into 9 groups, 3 monkeys/group. A solution of HBsAg expressed by CHO cell (CHO-HBsAg) was administered to cynomolgus monkeys of Group 9 at a dose of 3 mg/kg by intravenous injection. Solutions of humanized antibodies 116, 110, 153 and 138 were administered to cynomolgus monkeys of Groups 1, 3, 5 and 7 at a dose of 20 mg/kg by intravenous injection, respectively. By intravenous injection, to cynomolgus monkeys of Groups 2, 4, 6 and 8, solutions of CHO-HBsAg were administered at a dose of 3 mg/kg, and 10 min later, solutions of humanized antibodies 116, 110 and 153 were administered at a dose of 20 mg/kg, respectively. Evaluation of pharmacokinetic characteristics and preliminary study on toxicity were performed after single intravenous injection of CHO-HBsAg and humanized antibodies to cynomolgus monkeys. The particular experimental design was as followed (Table 15):

TABLE 15

Experimental design for evaluating pharmacokinetic characteristics and toxicity of humanized antibodies

| Group | Sample | Animal No. | Injection mode | Dose | Injection volume | Concentration |
|---|---|---|---|---|---|---|
| 1 | 116 | C1001 C1002 C1003 | intravenous injection | 20 mg/kg | 2 mL/kg | 10 mg/ml |
| 2 | CHO-HBsAg + 116 | C2001 C2002 C2003 | intravenous injection | 3 mg/kg + 20 mg/kg | 3 mL/kg + 2 mL/kg | 1 mg/ml + 10 mg/ml |
| 3 | 110 | C3001 C3002 C3003 | intravenous injection | 20 mg/kg | 2 mL/kg | 10 mg/ml |
| 4 | CHO-HBsAg + 110 | C4001 C4002 C4003 | intravenous injection | 3 mg/kg + 20mg/kg | 3 mL/kg + 2 mL/kg | 1 mg/ml + 10 mg/ml |
| 5 | 153 | C5001 C5002 C5003 | intravenous injection | 20 mg/kg | 2 mL/kg | 10 mg/ml |
| 6 | CHO-HBsAg + 153 | C6001 C6002 C6003 | intravenous injection | 3 mg/kg + 20 mg/kg | 3 mL/kg + 2 mL/kg | 1 mg/ml + 10 mg/ml |

TABLE 15-continued

Experimental design for evaluating pharmacokinetic characteristics and toxicity of humanized antibodies

| Group | Sample | Animal No. | Injection mode | Dose | Injection volume | Concentration |
|---|---|---|---|---|---|---|
| 7 | CHO-HBsAg | C7001 C7002 C7003 | intravenous injection | 3 mg/kg | 3 mL/kg | 1 mg/ml |

Before administration (0 h), the health and appearance state of experimental animals were observed twice (at 9:30 am and 4:00 pm). Before experiment, the experimental animals were subjected to physical examination to confirm the health status of animal. At the day of administration, the status of experimental animal was observed before and after each blood collection point, including the general status, behavior, activity amount, excretion, breathing and other abnormal symptoms of experimental animals. The result showed that no animal showed any abnormal reactions during administration and after administration (Note: due to a relatively fast administration rate (the period of injection was about 1 min) and a relatively low temperature of the drug solution (not heated to 37° C.), the experimental animal P1001 of Group 1 was discomforted for a short time after administration; while, the other experimental animals, which received the injection of the drug solution (heated to 37° C. before injection) for a period of about 3 min, did not show any paradoxical reaction.).

In addition, after administration, the body weight and body temperature of experimental animals were monitored. The results were shown in Tables 16-18.

TABLE 16

Body weight of the experimental animals after administration of antibody 162

| | | Weight (kg) | | |
|---|---|---|---|---|
| Group | Animal No. | Day 0 | Day 7 | Day 28 |
| 1 | P1001 | 5.47 | 5.53 | 5.71 |
|   | P1002 | 6.14 | 6.18 | 6.20 |
|   | P1003 | 5.59 | 5.70 | 5.86 |
| 2 | P2001 | 4.57 | 4.69 | 4.66 |
|   | P2002 | 5.66 | 5.76 | 5.96 |
|   | P2003 | 4.89 | 4.89 | 4.99 |
| 3 | P3001 | 3.78 | 3.80 | 3.91 |
|   | P3002 | 5.30 | 5.22 | 5.19 |
|   | P3003 | 6.30 | 6.31 | 6.45 |

TABLE 17

Body weight of the experimental animals after administration of antibodies 116, 110, 153 and 138

| | Body weight (kg) | | | | |
|---|---|---|---|---|---|
| Animal No. | Day 0 | Day 7 | Day 14 | Day 21 | Day 28 |
| C1001 | 3.10 | 2.98 | 3.06 | 3.24 | 3.11 |
| C1002 | 2.77 | 2.73 | 2.83 | 2.79 | 2.77 |
| C1003 | 2.54 | 2.55 | 2.65 | 2.68 | 2.59 |
| C2001 | 2.77 | 2.74 | 2.81 | 2.97 | 2.87 |
| C2002 | 2.54 | 2.65 | 2.68 | 2.76 | 2.7 |
| C2003 | 2.61 | 2.49 | 2.74 | 2.84 | 2.83 |
| C3001 | 2.81 | 2.84 | 2.87 | 2.87 | 2.86 |
| C3002 | 2.52 | 2.55 | 2.74 | 2.97 | 2.9 |
| C3003 | 2.51 | 2.46 | 2.61 | 2.68 | 2.6 |
| C4001 | 2.73 | 2.61 | 2.80 | 2.87 | 2.83 |
| C4002 | 2.63 | 2.64 | 2.77 | 2.73 | 2.77 |
| C4003 | 2.45 | 2.45 | 2.66 | 2.7 | 2.7 |
| C5001 | 2.79 | 2.75 | 2.87 | 2.96 | 2.95 |
| C5002 | 2.74 | 2.64 | 2.83 | 2.96 | 2.85 |
| C5003 | 2.34 | 2.26 | 2.44 | 2.56 | 2.49 |
| C6001 | 2.73 | 2.74 | 2.86 | 3 | 2.86 |
| C6002 | 2.58 | 2.49 | 2.63 | 2.67 | 2.68 |
| C6003 | 2.46 | 2.40 | 2.56 | 2.6 | 2.54 |
| C7001 | 2.71 | 2.59 | 2.76 | 2.84 | 2.78 |
| C7002 | 2.45 | 2.40 | 2.50 | 2.6 | 2.5 |
| C7003 | 2.34 | 2.24 | 2.40 | 2.47 | 2.37 |
| C8001 | 2.75 | 2.60 | 2.73 | 2.83 | 2.75 |
| C8002 | 2.55 | 2.44 | 2.53 | 2.7 | 2.53 |
| C8003 | 2.38 | 2.29 | 2.49 | 2.44 | 2.42 |
| C9001 | 2.80 | 2.70 | 2.93 | 2.97 | 2.85 |
| C9002 | 2.52 | 2.47 | 2.63 | 2.57 | 2.52 |
| C9003 | 2.29 | 2.19 | 2.29 | 2.42 | 2.28 |

TABLE 18

Body temperature of the experimental animals after administration of antibody 162

| Time (h) | Body temperature (° C.) | | | | | | | | |
|---|---|---|---|---|---|---|---|---|---|
|  | P1001 | P1002 | P1003 | P2001 | P2002 | P2003 | P3001 | P3002 | P3003 |
| 1 | 36.8 | 37.5 | 38.0 | 38.4 | 39.0 | 38.8 | 39.0 | 38.4 | 37.5 |
| 4 | 38.4 | 38.4 | 38.3 | 38.8 | 38.5 | 38.2 | 38.8 | 38.6 | 38.5 |
| 6 | 38.5 | 38.5 | 38.2 | 38.0 | 38.3 | 38.1 | 38.3 | 38.9 | 38.0 |
| 10 | 38.7 | 37.2 | 37.0 | 36.6 | 36.7 | 36.5 | 37.5 | 38.7 | 37.2 |
| 24 | 38.5 | 38.1 | 37.5 | 38.2 | 38.1 | 38.2 | 38.8 | 38.0 | 38.2 |

The experimental results showed that after administration of humanized antibodies 162, 116, 110, 153 and 138 to experimental animals, no adverse side effects occurred in the experimental animals, thereby preliminarily demonstrating the good safety of humanized antibodies 162, 116, 110, 153 and 138.

In addition, about 1.0 mL whole blood was collected from cephalic vein of experimental animals before administration (0 h), and at 0.25 h (15 min), 0.5 h (30 min), 1 h, 2 h, 4 h, 10 h, 24 h (Day 1), 48 h (Day 2), 72 h (Day 3), 96 h (Day 4), 144 h (Day 6), 192 h (Day 8), 240 h (Day 10), 336 h (Day 14, for experimental animals other than P1001), 360 h (Day 15, for experimental animal P1001), 408 h (Day 17), 504 h (Day 21) and 672 h (Day 28) after administration. The collected sera and whole blood were subjected to the following assays.

By using chemiluminescent immunoassay (CLIA), the concentration of CHO-HBsAg and humanized antibody 162 in sera of cynomolgus monkeys were determined. The lower limit of quantitation (LLOQ) of CHO-HBsAg in serum was 0.037 ng/mL, and the upper limit of quantitation (ULOQ) was 20 ng/mL. The lower limit of quantitation (LLOQ) of humanized antibody 162 in serum was 0.063 ng/mL, and the upper limit of quantitation (ULOQ) was 4.0 ng/mL. The detection results were shown in FIGS. 18-22.

Figure 18:
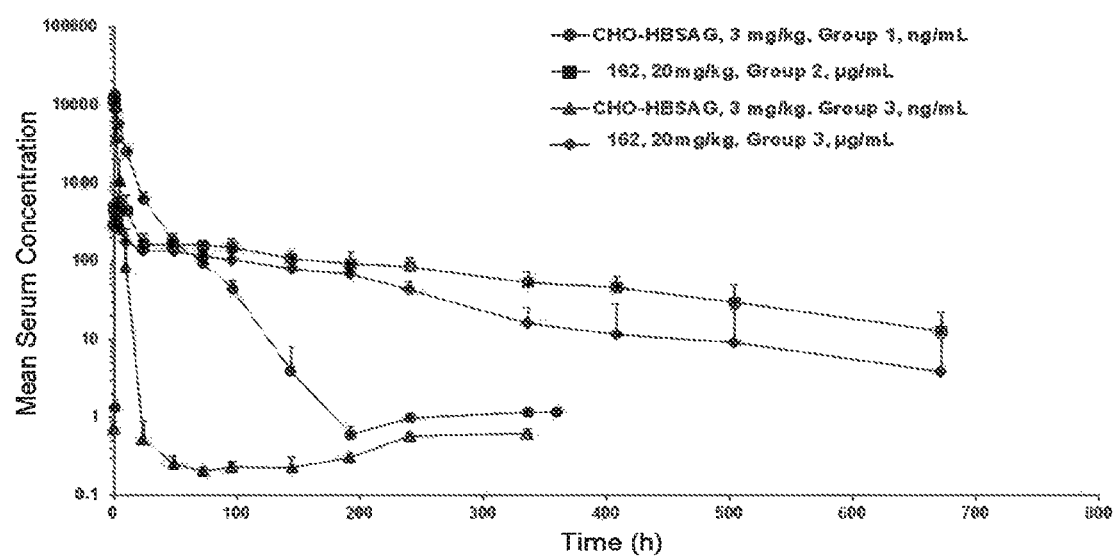
FIG. 18 shows the curve of mean blood concentration of CHO-HBsAg and humanized antibody 162 in sera of male cynomolgus monkeys of different groups vs. time, after single intravenous injection of CHO-HBsAg and/or humanized antibody 162.

FIG. 18 showed the curve of mean blood concentration of CHO-HBsAg and humanized antibody 162 in sera of male cynomolgus monkeys from different groups vs. time, after single intravenous injection of CHO-HBsAg and/or humanized antibody 162.

Figure 19:
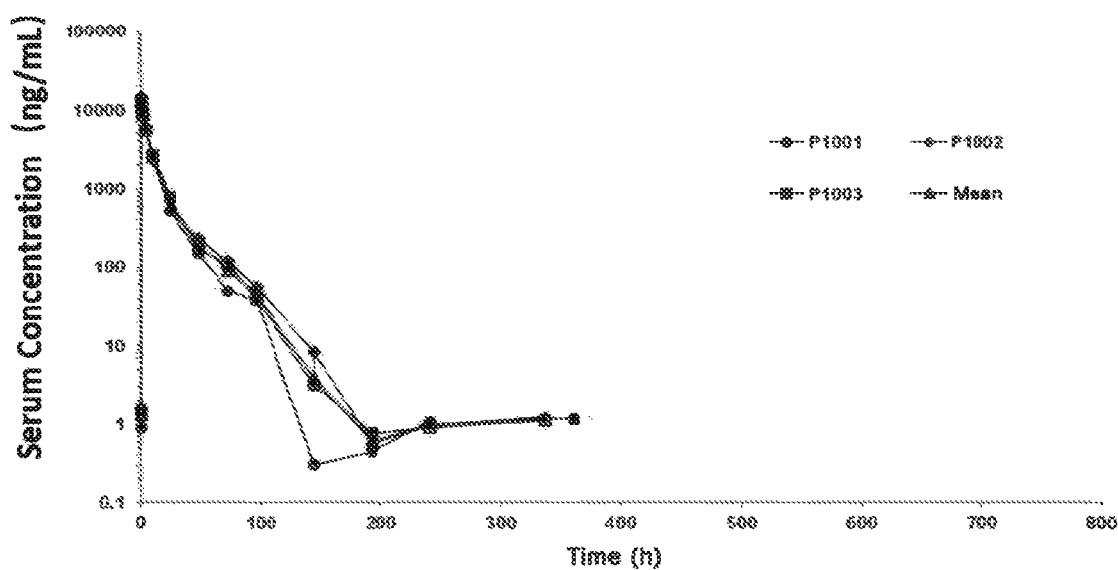
FIG. 19 shows the curve of blood concentration of CHO-HBsAg in serum of each cynomolgus monkey (Group 1) vs. time, after single intravenous injection of CHO-HBsAg at a dose of 3 mg/kg.

FIG. 19 showed the curve of blood concentration of CHO-HBsAg in serum of each cynomolgus monkey (Group 1) vs. time, after single intravenous injection of CHO-HBsAg at a dose of 3 mg/kg.

Figure 20:
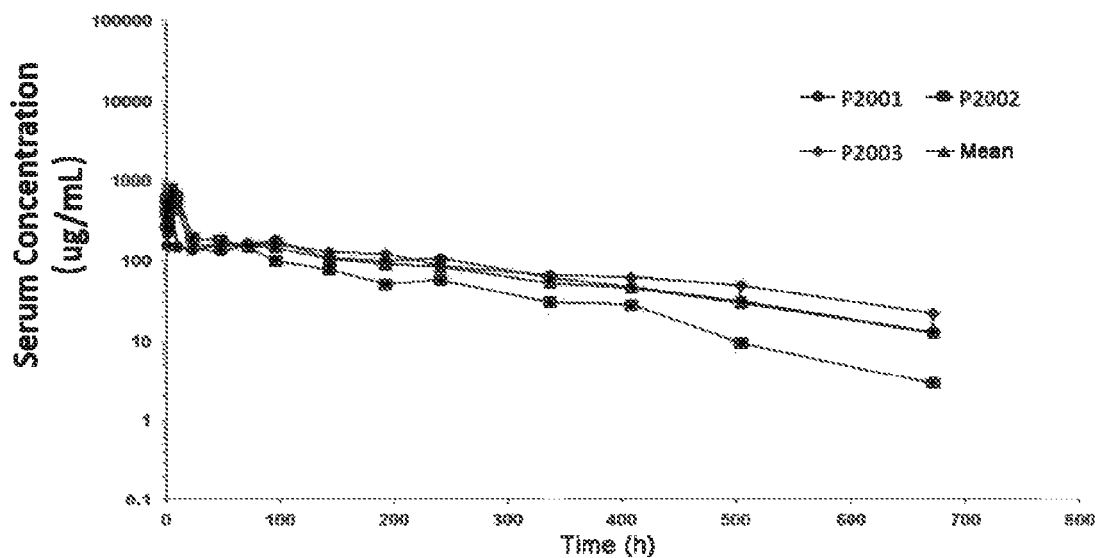
FIG. 20 shows the curve of blood concentration of humanized antibody 162 in serum of each cynomolgus monkey (Group 2) vs. time, after single intravenous injection of humanized antibody 162 at a dose of 20 mg/kg.

FIG. 20 showed the curve of blood concentration of humanized antibody 162 in serum of each cynomolgus monkey (Group 2) vs. time, after single intravenous injection of humanized antibody 162 at a dose of 20 mg/kg.

Figure 21:
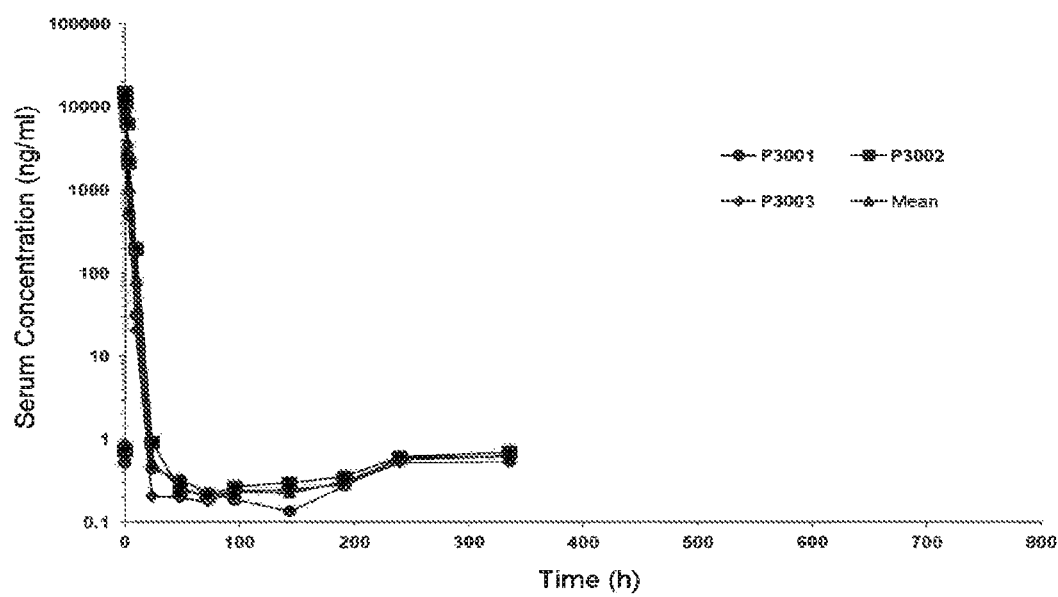
FIG. 21 shows the curve of blood concentration of CHO-HBsAg in serum of each cynomolgus monkey (Group 3) vs. time, after administration of CHO-HBsAg at a dose of 3 mg/kg and humanized antibody 162 at a dose of 20 mg/kg.

FIG. 21 showed the curve of blood concentration of CHO-HBsAg in serum of each cynomolgus monkey (Group 3) vs. time, after administration of CHO-HBsAg at a dose of 3 mg/kg and humanized antibody 162 at a dose of 20 mg/kg.

Figure 22:
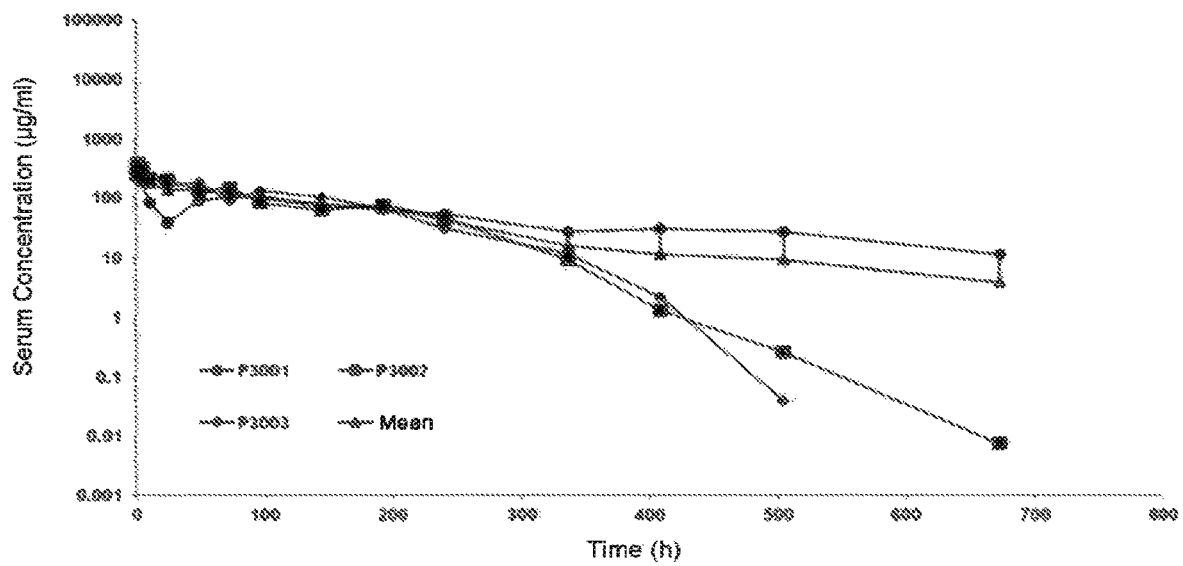
FIG. 22 shows the curve of blood concentration of humanized antibody 162 in serum of each cynomolgus monkey (Group 3) vs. time, after administration of CHO-HBsAg at a dose of 3 mg/kg and humanized antibody 162 at a dose of 20 mg/kg.

FIG. 22 showed the curve of blood concentration of humanized antibody 162 in serum of each cynomolgus monkey (Group 3) vs. time, after administration of CHO-HBsAg at a dose of 3 mg/kg and humanized antibody 162 at a dose of 20 mg/kg.

By using pharmacokinetic software WinNonlin™ Version 6.2.1 (Pharsight, Mountain View, Calif.), the experimental data of CHO-HBsAg and humanized antibody 162 were processed in a non-compartmental model of intravenous injection (IV bolus input).

Figure 23:
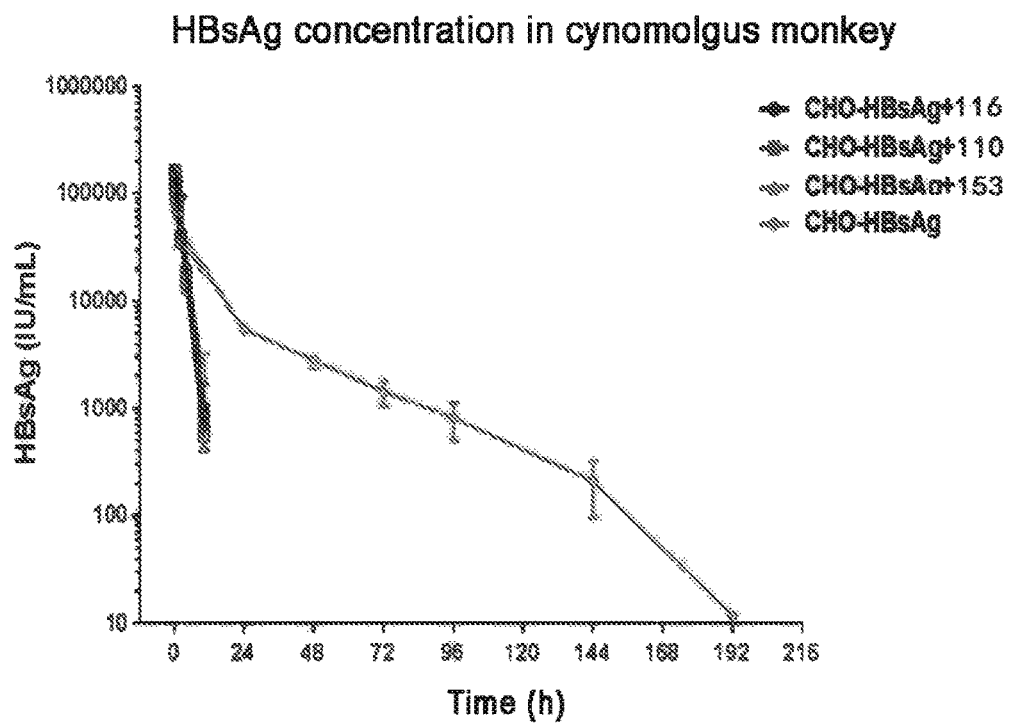
FIG. 23 shows the curves of blood concentration of CHO-HBsAg in sera of cynomolgus monkeys of each group (Group 3) vs. time, after administration of CHO-HBsAg at a dose of 3 mg/kg and humanized antibodies 116, 110 or 153 at a dose of 20 mg/kg.

FIG. 23 showed the curves of mean blood concentration of CHO-HBsAg in serum of each cynomolgus monkey (Group 3) vs. time, after administration of CHO-HBsAg at a dose of 3 mg/kg and humanized antibodies 116, 110 or 153 at a dose of 20 mg/kg.

Figure 24:
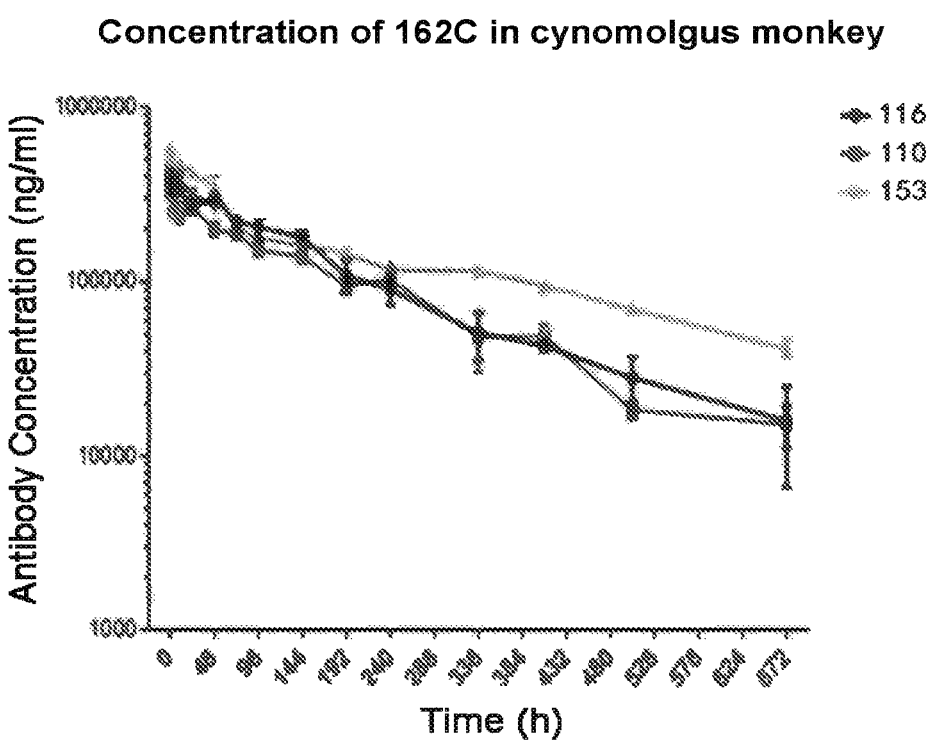
FIG. 24 shows the curves of blood concentration of humanized antibodies 116, 110 and 153 in sera of cynomolgus monkeys of each group vs. time, after administration of humanized antibodies 116, 110 or 153 at a dose of 20 mg/kg.

FIG. 24 showed the curves of blood concentration of humanized antibodies 116, 110 and 153 in sera of cynomolgus monkeys of each group vs. time, after administration of humanized antibodies 116, 110 or 153 at a dose of 20 mg/kg.

Figure 25:
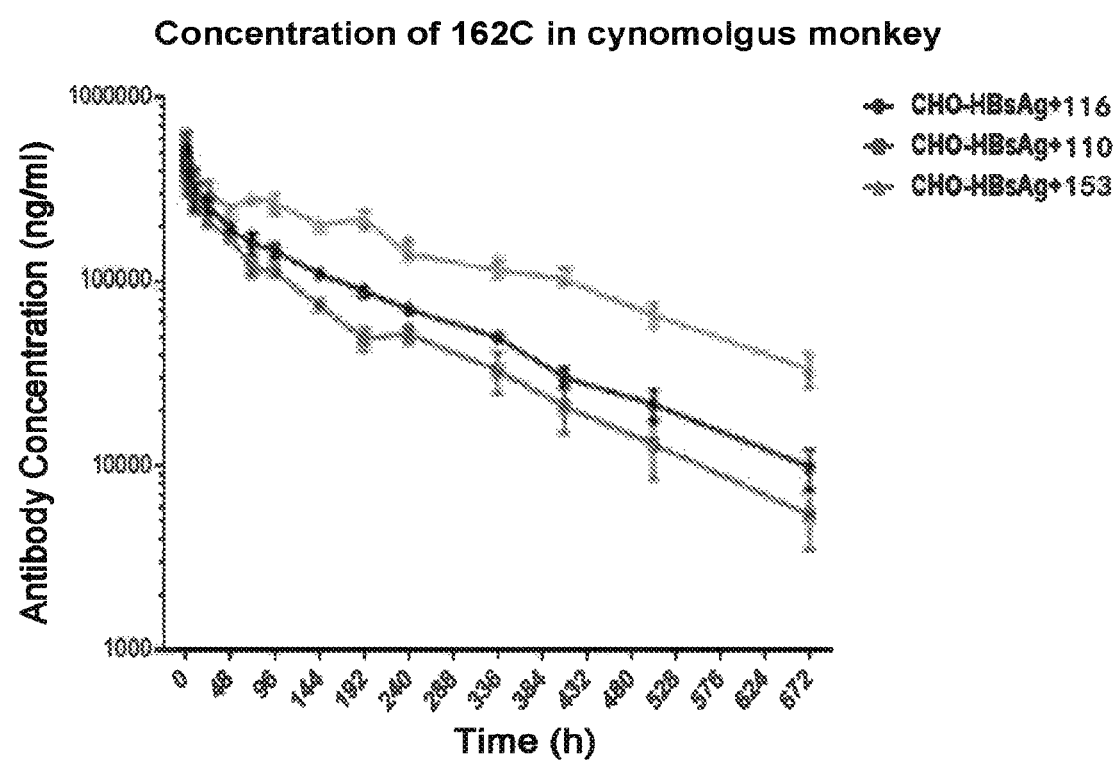
FIG. 25 shows the curves of blood concentration of humanized antibodies 116, 110 and 153 in sera of cynomolgus monkeys of each group vs. time, after administration of CHO-HBsAg at a dose of 3 mg/kg and humanized antibodies 116, 110 or 153 at a dose of 20 mg/kg.

FIG. 25 showed the curves of blood concentration of the humanized antibodies in sera of cynomolgus monkeys of each group vs. time, after administration of CHO-HBsAg at a dose of 3 mg/kg and humanized antibodies 116, 110 or 153 at a dose of 20 mg/kg.

The following parameters were calculated by using log-linear trapezoidal method: initial serum drug concentration (C0), last detectable time point ($T_{last}$), elimination half-life ($T_{1/2}$), apparent volume of distribution (Vdss), total clearance (CL), mean residence time from time point 0 to the last time point when concentration is detectable ($MRT_{0-last}$), mean residence time from time point 0 to infinity ($MRT_{0-inf}$), area under the serum concentration-time curve from time point 0 to the last time point when concentration is detectable ($AUC_{0-last}$), and area under the serum concentration-time curve from time point 0 to infinity ($AUC_{0-inf}$).

The results showed: after single intravenous injection of CHO-HBsAg at a dose of 3 mg/kg, male cynomolgus monkeys (Group 1) had a CL of 0.535±0.0188 mL/min/kg for CHO-HBsAg (which accounted for about 1.23% of hepatic blood flow). Cynomolgus monkeys had a mean elimination half-life ($t_{1/2}$) of 21.6±0.723 h for CHO-HBsAg. In sera of cynomolgus monkeys, Vdss and $AUC_{0-inf}$ of CHO-HBsAg were 0.430±0.0344 L/kg and 93533±323 5 ng·h/mL, respectively.

By comparison; after administration of CHO-HBsAg at a dose of 3 mg/kg and humanized antibody 162 at a dose of 20 mg/kg in combination, male cynomolgus monkeys (Group 3) had a total clearance (CL) for CHO-HBsAg increased to 2.09±0.603 mL/min/kg (which accounted for about 4.79% of hepatic blood flow), a mean elimination half-life ($t_1l_2$) of 24.7±1.04 h, an apparent volume of distribution of 0.357±0.0778 L/kg, and an $AUC_{0-inf}$ of 25567±8741 ng·h/mL. Therefore, in male cynomolgus monkeys of Group 3, the C0, $AUC_{0-inf}$ and CL value of CHO-HBsAg were 1.09, 0.273 and 3.91 folds of that in Group 1, respectively.

The results also showed that: after single intravenous injection of humanized antibody 162 at a dose of 20 mg/kg, male cynomolgus monkeys had a CL of 6.30±1.50 mL/min/kg for humanized antibody 162 (which accounted for about 14.4% of hepatic blood flow). The humanized antibody 162 had a mean elimination half-life ($t_{1/2}$) of 158±52.7 h. In sera of cynomolgus monkeys, humanized antibody 162 had Vdss and $AUC_{0-inf}$ value of 80.4±12.6 L/kg and 54967±13077 µg·h/mL, respectively.

By comparison, after administration of CHO-HBsAg at a dose of 3 mg/kg and humanized antibody 162 at a dose of 20 mg/kg in combination, male cynomolgus monkeys (Group 3) had a total clearance (CL) increased to 11.1±1.09 mL/min/kg for humanized antibody 162 (which accounted for about 25.5% of hepatic blood flow), a mean elimination half-life ($t_{1/2}$) of 87.6±102 h, an apparent volume of distribution of 109±60.4 L/kg, and an $AUC_{0-inf}$ of 30200±3100 µg·h/mL. Therefore, in male cynomolgus monkeys of Group 3, the C0, $AUC_{0-inf}$ and CL value of humanized antibody 162 were 0.867, 0.549 and 1.76 folds of that in Group 2, respectively.

The experimental results discussed above were also summarized in Table 19, Table 20 and Table 21.

TABLE 19

Main pharmacokinetic parameters of CHO-HBsAg and humanized antibody 162 in sera of male cynomolgus monkeys of Groups 1-3

| Test subject | CHO-HBsAg | | Humanized antibody 162 | |
|---|---|---|---|---|
| Group | 1 | 3 | 2 | 3 |
| C0 | 15067 ng/mL | 16467 ng/mL | 483 µg/mL | 419 µg/mL |
| $T_{last}$ (1) | 344 | 336 | 672 | 616 |
| $T_{1/2}$ (h) | 21.6 | 1.34 | 158 | 87.6 |
| $AUC_{0-last}$ | 93533 ng·h/mL | 25533 ng·h/mL | 51633 µg·h/mL | 29067 µg·h/mL |
| $AUC_{0-inf}$ | 93533 ng·h/mL | 25567 ng·h/mL | 54967 µg·h/mL | 30200 µg·h/mL |
| Vdss (L/kg) | 0.430 | 0.357 | 80.4 | 109 |
| Cl (mL/min/kg) | 0.535 | 2.09 | 6.30 | 11.1 |
| $MRT_{0-last}$ (h) | 13.3 | 2.58 | 186 | 146 |

TABLE 19-continued

Main pharmacokinetic parameters of CHO-HBsAg and humanized antibody 162 in sera of male cynomolgus monkeys of Groups 1-3

| Test subject | CHO-HBsAg | | Humanized antibody 162 | |
|---|---|---|---|---|
| Group | 1 | 3 | 2 | 3 |
| $MRT_{0-inf}$ (h) | 13.4 | 2.90 | 225 | 171 |
| AUCextra (%) | 0.0390 | 0.0869 | 5.40 | 3.37 |

TABLE 20

Half-life (h) of CHO-HBsAg in sera of cynomolgus monkeys

|  | CHO-HBsAg | CHO-HbsAg + 162C |
|---|---|---|
| CHO-HbsAg | 20.42 |  |
| CHO-HbsAg + 116 |  | 1.4 |
| CHO-HbsAg + 110 |  | 1.29 |
| CHO-HbsAg + 153 |  | 1.54 |

TABLE 21

Half-life (h) of antibody 116, 110 and 153 in sera of cynomolgus monkeys

|  | Ab | CHO-HBsAg +Ab |
|---|---|---|
| 116 | 125.87 | 151.51 |
| 110 | 154.33 | 128.35 |
| 153 | 233.23 | 184.12 |

In addition, the sera of the cynomolgus monkeys were subjected to blood routine test and chemical analysis. No obvious abnormality was observed in the indexes in the sera of cynomolgus monkeys (including levels of bilirubin, alanine aminotransferase, aspartate aminotransferase, total protein, albumin, alkaline phosphatase, γ-glutamyltransferase, glucose, urea, creatinine, calcium ion, phosphor, total cholesterol, triglyceride, sodium ion, potassium ion, chloride ion, globulin, etc.). These experimental results showed that single intravenous injection of CHO-HBsAg and humanized antibodies 162, 116, 110 and 153 was safe at a specified dose. Therefore, the humanized antibodies 162, 116, 110 and 153 according to the invention can be administered to a subject (such as human), to prevent and/or treat HBV infection or a disease associated with HBV infection (such as Hepatitis B).

Although the embodiments of the invention have been described in detail, a person skilled in the art would understand that according to all the disclosed teachings, details can be amended and modified, and these alterations all fall into the protection scope of the invention. The whole scope of the invention is defined by the attached claims and any equivalent thereof.

TABLE 16A

Result of blood routine test before and after administration of CHO-HBsAg and/or humanized antibody 162 to male cynomolgus monkey

| Time point | Animal No. | WBC (×10³) cells/μL | RBC (×10⁶) cells/μL | HGB (g/dL) | HCT (%) | MCV (fL) | MCH (pg) | MCHC (g/dL) | CHCM (g/dL) | CH (pg) | RDW (%) | HDW (g/dL) | PLT (×10³) cells/μL |
|---|---|---|---|---|---|---|---|---|---|---|---|---|---|
| Before administration | P1001 | 10.92 | 6.91 | 15.0 | 50.9 | 73.7 | 21.7 | 29.5 | 29.3 | 21.5 | 13.6 | 2.14 | 315 |
|  | P1002 | 7.92 | 5.67 | 13.7 | 45.9 | 81.0 | 24.1 | 29.8 | 30.2 | 24.4 | 14.0 | 1.99 | 285 |
|  | P1003 | 7.31 | 7.06 | 15.0 | 48.9 | 69.2 | 21.2 | 30.6 | 31.1 | 21.5 | 13.4 | 2.35 | 474 |
|  | P2001 | 9.54 | 5.83 | 13.7 | 46.7 | 80.0 | 23.5 | 29.4 | 30.1 | 24.0 | 13.5 | 1.99 | 328 |
|  | P2002 | 12.10 | 5.58 | 12.9 | 43.2 | 77.4 | 23.1 | 29.8 | 30.5 | 23.5 | 13.5 | 2.11 | 427 |
|  | P2003 | 15.49 | 6.62 | 14.7 | 48.4 | 73.2 | 22.2 | 30.3 | 31.9 | 23.3 | 14.2 | 2.17 | 276 |
|  | P3001 | 5.47 | 6.17 | 13.6 | 44.4 | 72.0 | 22.0 | 30.6 | 31.6 | 22.7 | 14.6 | 2.43 | 426 |
|  | P3002 | 8.19 | 6.57 | 15.0 | 49.7 | 75.6 | 22.8 | 30.2 | 31.1 | 23.5 | 14.0 | 2.20 | 453 |
|  | P3003 | 9.30 | 5.91 | 14.9 | 48.0 | 81.3 | 25.2 | 31.0 | 31.8 | 25.7 | 14.0 | 2.03 | 402 |
| 24 h after administration | P1001 | 16.40 | 6.12 | 13.2 | 45.7 | 74.7 | 21.6 | 28.9 | 28.7 | 21.4 | 13.6 | 2.11 | 239 |
|  | P1002 | 15.26 | 5.32 | 12.8 | 41.7 | 78.5 | 24.1 | 30.7 | 31.4 | 24.5 | 14.2 | 2.06 | 249 |
|  | P1003 | 9.25 | 6.86 | 14.3 | 46.9 | 68.4 | 20.8 | 30.5 | 31.5 | 21.5 | 13.4 | 2.40 | 405 |
|  | P2001 | 8.67 | 5.49 | 13.2 | 44.0 | 80.2 | 24.0 | 30.0 | 30.1 | 24.0 | 13.6 | 1.99 | 358 |
|  | P2002 | 8.29 | 5.35 | 12.4 | 40.8 | 76.2 | 23.2 | 30.4 | 31.1 | 23.6 | 13.5 | 2.16 | 461 |
|  | P2003 | 10.69 | 6.50 | 13.8 | 44.2 | 73.0 | 22.8 | 31.2 | 31.9 | 23.2 | 14.1 | 2.18 | 270 |
|  | P3001 | 10.87 | 5.72 | 12.5 | 40.7 | 71.2 | 21.8 | 30.7 | 32.0 | 22.7 | 14.6 | 2.48 | 375 |
|  | P3002 | 11.34 | 5.68 | 13.3 | 41.7 | 73.4 | 23.3 | 31.8 | 32.3 | 23.6 | 14.2 | 2.31 | 371 |
|  | P3003 | 11.13 | 5.54 | 14.0 | 43.8 | 79.0 | 25.2 | 31.9 | 33.0 | 25.9 | 14.2 | 2.12 | 356 |
| 48 h after administration | P1001 | 9.21 | 6.12 | 13.1 | 45.3 | 74.1 | 21.4 | 28.9 | 29.0 | 21.4 | 13.6 | 2.15 | 212 |
|  | P1002 | 11.05 | 5.55 | 13.4 | 43.5 | 78.3 | 24.2 | 30.9 | 31.0 | 24.2 | 13.7 | 2.03 | 244 |
|  | P1003 | 8.95 | 6.80 | 14.5 | 46.3 | 68.1 | 21.2 | 31.2 | 31.3 | 21.3 | 13.1 | 2.40 | 446 |
|  | P2001 | 11.73 | 5.61 | 13.4 | 44.1 | 78.7 | 24.0 | 30.4 | 30.6 | 24.0 | 13.7 | 2.05 | 374 |
|  | P2002 | 10.12 | 5.24 | 12.4 | 39.7 | 75.7 | 23.6 | 31.2 | 31.0 | 23.4 | 13.4 | 2.18 | 461 |
|  | P2003 | 12.21 | 5.96 | 13.7 | 42.5 | 71.4 | 22.9 | 32.1 | 32.5 | 23.1 | 14.0 | 2.22 | 298 |
|  | P3001 | 6.93 | 5.69 | 12.5 | 40.4 | 71.0 | 21.9 | 30.9 | 31.7 | 22.4 | 14.1 | 2.47 | 342 |
|  | P3002 | 9.10 | 5.69 | 13.1 | 41.7 | 73.3 | 23.1 | 31.5 | 31.9 | 23.3 | 13.8 | 2.34 | 374 |
|  | P3003 | 11.29 | 5.36 | 13.4 | 42.2 | 78.8 | 25.0 | 31.7 | 32.5 | 25.5 | 13.8 | 2.11 | 331 |
| 168 h after administration (Day 7) | P1001 | 6.94 | 6.00 | 12.9 | 42.3 | 70.6 | 21.4 | 30.4 | 30.7 | 21.6 | 14.1 | 2.42 | 288 |
|  | P1002 | 11.04 | 5.37 | 12.9 | 42.2 | 78.5 | 24.1 | 30.7 | 30.9 | 24.2 | 13.8 | 2.05 | 358 |
|  | P1003 | 7.51 | 6.62 | 13.9 | 45.0 | 68.0 | 21.0 | 30.9 | 31.3 | 21.3 | 13.5 | 2.42 | 457 |
|  | P2001 | 11.29 | 5.46 | 12.9 | 43.3 | 79.3 | 23.7 | 29.9 | 30.4 | 24.0 | 13.9 | 2.09 | 438 |

TABLE 16A-continued

Result of blood routine test before and after administration of CHO-HBsAg and/or humanized antibody 162 to male cynomolgus monkey

| Time point | Animal No. | WBC (×10³ cells/μL) | RBC (×10⁶ cells/μL) | HGB (g/dL) | HCT (%) | MCV (fL) | MCH (pg) | MCHC (g/dL) | CHCM (g/dL) | CH (pg) | RDW (%) | HDW (g/dL) | PLT (×10³ cells/μL) |
|---|---|---|---|---|---|---|---|---|---|---|---|---|---|
| | P2002 | 12.10 | 5.31 | 12.2 | 40.2 | 75.7 | 23.0 | 30.4 | 30.9 | 23.4 | 13.4 | 2.25 | 498 |
| | P2003 | 8.13 | 6.04 | 13.7 | 43.3 | 71.8 | 22.7 | 31.6 | 32.5 | 23.2 | 14.5 | 2.32 | 320 |
| | P3001 | 7.16 | 5.64 | 12,4 | 40.4 | 71,7 | 22.0 | 30.7 | 31.2 | 22.3 | 14.4 | 2.54 | 635 |
| | P3002 | 6.48 | 5.79 | 13.2 | 42.5 | 73.4 | 22.9 | 31.2 | 31.7 | 23.2 | 14.2 | 2.41 | 546 |
| | P3003 | 10.72 | 5.57 | 13.7 | 43.8 | 78.7 | 24.6 | 31.3 | 32.6 | 25.5 | 14.0 | 2.20 | 515 |
| 672 h after | P1001 | 11.47 | 6.49 | 14.0 | 50.3 | 77.4 | 21.5 | 27.8 | 27.2 | 21.0 | 13.4 | 2.06 | 306 |
| administration | P1002 | 10.83 | 6.03 | 14.3 | 47.4 | 78.5 | 23.7 | 30.2 | 30.6 | 24.0 | 13.7 | 1.97 | 332 |
| (Day 28) | P1003 | 6.75 | 7.08 | 15.0 | 48.6 | 68.6 | 21.1 | 30.8 | 31.0 | 21.2 | 13.5 | 2.32 | 434 |
| | P2001 | 8.80 | 5.92 | 14.2 | 47.7 | 80.6 | 24.1 | 29.9 | 30.1 | 24.2 | 13.6 | 1.95 | 417 |
| | P2002 | 15.62 | 5.89 | 13.7 | 45.3 | 76.9 | 23.2 | 30.2 | 30.4 | 23.3 | 13.4 | 2.12 | 457 |
| | P2003 | 9.02 | 6.03 | 14.0 | 44.7 | 74.1 | 23.2 | 31.3 | 31.6 | 23.3 | 14.4 | 2.15 | 283 |
| | P3001 | 6.86 | 6.35 | 14.0 | 45.6 | 71.8 | 22.0 | 30.7 | 31.5 | 22.5 | 14.2 | 2.45 | 416 |
| | P3002 | 5.85 | 6.23 | 14.3 | 46.2 | 74.2 | 22.9 | 30.9 | 31.6 | 23.4 | 14.0 | 2.24 | 431 |
| | P3003 | 13.72 | 5.57 | 14.2 | 44.7 | 80.4 | 25.4 | 31.7 | 32.3 | 25.9 | 14.4 | 2.09 | 411 |

TABLE 16B

Result of serum biochemical analysis before and after administration of CHO-HBsAg and/or humanized antibody 162 to male cynomolgus monkey

| Time point | Animal No. | TBIL (uM) | ALT (U/L) | AST (U/L) | TP (g/L) | ALB (g/L) | ALP (U/L) | GGT (U/L) | GLU (mM) | UREA (mM) | CRE (uM) | Ca (mM) | P (mM) | TCHO (mM) | TG (mM) | Na (mM) | K (mM) | CL (mM) | GLB (g/L) | A/G |
|---|---|---|---|---|---|---|---|---|---|---|---|---|---|---|---|---|---|---|---|---|
| Before administration | P1001 | 2.55 | 58 | 39 | 74.8 | 44.0 | 597 | 80 | 6.30 | 6.86 | 84 | 2.46 | 1.72 | 2.97 | 0.40 | 147 | 4.3 | 102 | 30.8 | 1.43 |
| | P1002 | 4.92 | 68 | 46 | 75.4 | 42.2 | 225 | 48 | 2.60 | 5.77 | 90 | 2.37 | 1.57 | 2.65 | 0.50 | 144 | 4.5 | 105 | 33.2 | 1.27 |
| | P1003 | 4.05 | 57 | 31 | 83.5 | 44.0 | 450 | 119 | 2.63 | 4.60 | 61 | 2.48 | 1.86 | 6.08 | 0.39 | 141 | 6.1 | 103 | 39.5 | 1.11 |
| | P2001 | 2.70 | 30 | 26 | 76.2 | 46.9 | 363 | 67 | 3.67 | 3.64 | 66 | 2.49 | 1.87 | 3.33 | 0.47 | 147 | 4.8 | 107 | 29.3 | 1.60 |
| | P2002 | 2.02 | 42 | 31 | 80.7 | 42.3 | 333 | 74 | 3.21 | 5.56 | 78 | 2.50 | 1.52 | 2.95 | 0.35 | 145 | 4.7 | 105 | 38.4 | 1.10 |
| | P2003 | 3.74 | 59 | 48 | 83.2 | 50.2 | 383 | 57 | 2.53 | 4.88 | 73 | 2.60 | 1.61 | 4.18 | 0.35 | 146 | 4.8 | 104 | 33.0 | 1.52 |
| | P3001 | 5.62 | 68 | 77 | 77.7 | 47.6 | 773 | 100 | 2.71 | 7.46 | 67 | 2.36 | 1.93 | 5.14 | 0.55 | 143 | 4.6 | 105 | 30.1 | 1.58 |
| | P3002 | 5.98 | 36 | 34 | 80.8 | 43.1 | 323 | 81 | 4.39 | 4.96 | 76 | 2.42 | 1.77 | 3.05 | 0.45 | 143 | 5.0 | 104 | 37.7 | 1.14 |
| | P3003 | 3.10 | 47 | 30 | 77.3 | 48.7 | 547 | 56 | 3.23 | 3.88 | 63 | 2.57 | 1.94 | 2.91 | 0.37 | 144 | 5.8 | 107 | 28.6 | 1.70 |
| 24 h after administration | P1001 | 3.86 | 103 | 99 | 73.3 | 42.1 | 577 | 74 | 4.76 | 6.06 | 83 | 2.34 | 1.94 | 2.91 | 0.37 | 147 | 5.7 | 105 | 31.2 | 1.35 |
| | P1002 | 3.09 | 103 | 108 | 75.9 | 41.4 | 259 | 49.0 | 3.90 | 5.64 | 89 | 2.36 | 1.07 | 2.55 | 0.34 | 148 | 4.8 | 108 | 34.50 | 1.20 |
| | P1003 | 3.42 | 63 | 36 | 81.3 | 42.3 | 400 | 121.0 | 3.64 | 3.69 | 62 | 2.45 | 1.37 | 2.23 | 0.26 | 146 | 4.7 | 107 | 39.00 | 1.08 |
| | P2001 | 2.62 | 45 | 68 | 79.7 | 47.9 | 346 | 69.0 | 5.24 | 3.13 | 74 | 2.43 | 1.87 | 5.51 | 0.21 | 151 | 5.4 | 108 | 31.80 | 1.51 |
| | P2002 | 2.87 | 53 | 41 | 81.2 | 42.5 | 352 | 77.0 | 3.60 | 4.63 | 78 | 2.47 | 1.18 | 3.37 | 0.30 | 145 | 4.3 | 106 | 38.70 | 1.10 |
| | P2003 | 4.20 | 59 | 59 | 84.6 | 50.6 | 365 | 56.0 | 2.91 | 4.53 | 76 | 2.56 | 1.39 | 2.75 | 0.28 | 148 | 4.2 | 104 | 34.00 | 1.49 |
| | P3001 | 3.95 | 98 | 130 | 75.9 | 45.5 | 652 | 97.0 | 3.72 | 4.99 | 71 | 2.33 | 1.31 | 4.19 | 0.25 | 148 | 4.8 | 110 | 30.40 | 1.50 |
| | P3002 | 15.47 | 108 | 352 | 74.1 | 38.6 | 422 | 75.0 | 2.62 | 6.56 | 83 | 2.27 | 1.29 | 4.48 | 0.27 | 147 | 4.5 | 107 | 35.50 | 1.09 |
| | P3003 | 4.62 | 115 | 227 | 72.3 | 45.4 | 507 | 54.0 | 3.00 | 4.19 | 68 | 2.43 | 1.40 | 2.07 | 0.77 | 149 | 4.9 | 110 | 26.90 | 1.69 |
| 48 h after administration | P1001 | 3.01 | 112 | 58 | 78.7 | 44.9 | 627 | 72.0 | 2.82 | 6.31 | 81 | 2.38 | 1.70 | 2.57 | 0.28 | 151 | 5.4 | 108 | 33.80 | 1.33 |
| | P1002 | 2.59 | 92 | 51.0 | 76.1 | 41.0 | 258 | 46.0 | 3.43 | 5.23 | 87 | 2.37 | 1.18 | 2.91 | 0.40 | 152 | 4.6 | 109 | 35.10 | 1.17 |
| | P1003 | 2.38 | 56 | 26.0 | 81.6 | 41.3 | 386 | 112.0 | 3.14 | 6.32 | 63 | 2.55 | 1.49 | 2.16 | 0.63 | 147 | 4.7 | 106 | 40.30 | 1.02 |
| | P2001 | 1.76 | 40 | 37.0 | 75.5 | 46.9 | 311 | 66.0 | 4.49 | 4.15 | 67 | 2.48 | 1.54 | 1.49 | 0.54 | 151 | 6.3 | 108 | 28.60 | 1.64 |
| | P2002 | 2.28 | 49 | 31.0 | 79.9 | 41.9 | 369 | 77.0 | 3.18 | 5.41 | 72 | 2.46 | 1.66 | 2.90 | 0.41 | 147 | 5.1 | 106 | 38.00 | 1.10 |
| | P2003 | 1.91 | 51 | 41.0 | 74.9 | 44.5 | 296 | 49.0 | 3.68 | 4.24 | 71 | 2.52 | 1.35 | 2.70 | 0.27 | 149 | 4.0 | 107 | 30.40 | 1.46 |
| | P3001 | 2.28 | 47 | 43 | 79.5 | 46.9 | 729 | 81.0 | 4.58 | 5.71 | 65 | 2.38 | 2.11 | 3.67 | 0.23 | 144 | 4.7 | 102 | 32.60 | 1.44 |
| | P3002 | 3.13 | 49 | 55 | 78.4 | 41.6 | 296 | 71.0 | 3.33 | 5.26 | 75 | 2.47 | 1.71 | 5.28 | 0.59 | 144 | 4.5 | 105 | 36.80 | 1.13 |
| | P3003 | 1.93 | 52 | 34 | 76.6 | 47.6 | 591 | 53.0 | 3.29 | 3.72 | 60 | 2.62 | 1.92 | 2.58 | 0.35 | 146 | 5.5 | 107 | 29.00 | 1.64 |
| 672 h after administration (Day 28) | P1001 | 2.18 | 41 | 24 | 74.8 | 45.5 | 625 | 66.0 | 6.61 | 6.75 | 94 | 2.51 | 2.35 | 2.57 | 0.37 | 151 | 4.3 | 102 | 29.30 | 1.55 |
| | P1002 | 4.69 | 41 | 31 | 80.4 | 45.4 | 205 | 52.0 | 2.93 | 4.28 | 94 | 2.56 | 1.19 | 3.10 | 0.27 | 146 | 4.6 | 105 | 35.00 | 1.30 |
| | P1003 | 3.77 | 56 | 24 | 82.5 | 42.9 | 417 | 125.0 | 2.42 | 5.32 | 62 | 2.56 | 1.76 | 2.34 | 0.25 | 143 | 4.6 | 104 | 39.60 | 1.08 |
| | P2001 | 2.60 | 26 | 28 | 79.5 | 49.3 | 316 | 73.0 | 4.06 | 4.13 | 60 | 2.48 | 2.24 | 6.07 | 0.37 | 148 | 5.8 | 108 | 30.20 | 1.63 |
| | P2002 | 2.79 | 50 | 30 | 79.7 | 42.2 | 350 | 78.0 | 3.56 | 5.53 | 72 | 2.48 | 1.96 | 3.20 | 0.32 | 144 | 4.6 | 105 | 37.50 | 1.13 |
| | P2003 | 2.47 | 47 | 41 | 75.6 | 45.6 | 325 | 41.0 | 2.95 | 5.60 | 65 | 2.42 | 1.97 | 2.85 | 0.35 | 147 | 4.3 | 110 | 30.00 | 1.52 |
| | P3001 | 2.92 | 54 | 44 | 85.0 | 50.1 | 715 | 110.0 | 2.87 | 6.80 | 60 | 2.50 | 1.99 | 3.70 | 0.52 | 145 | 4.7 | 105 | 34.90 | 1.44 |
| | P3002 | 6.48 | 33 | 38 | 82.2 | 44.5 | 273 | 75.0 | 3.36 | 5.23 | 82 | 2.46 | 1.64 | 5.57 | 0.38 | 145 | 4.4 | 106 | 37.70 | 1.18 |
| | P3003 | 3.39 | 30 | 25 | 75.6 | 49.3 | 625 | 74.0 | 3.03 | 3.13 | 75 | 2.56 | 2.01 | 2.65 | 0.23 | 146 | 4.7 | 108 | 26.30 | 1.87 |

Note:
mM: mmol/L; uM: μmol/L

The invention claimed is:

1. An antibody or an antigen binding fragment thereof, which can specifically bind to HBsAg, comprising:
   (a) three complementarity determining regions (CDRs) of heavy chain variable region (VH) selected from the group consisting of:
      (i) VH CDR1, consisting of the following sequence: SEQ ID NO: 3, or a sequence that differs from SEQ ID NO:3 by 1 or 2 substitutions selected from the group consisting of:
         (01) R or Y at H31; and
         (02) W at H32;
      (ii) VH CDR2, consisting of the following sequence: SEQ ID NO: 4, or a sequence that differs from SEQ ID NO:4 by 1, 2 or 3 substitutions selected from the group consisting of:
         (12) T at H56;
         (13) V or N at H57; and
         (14) L at H58;
      (iii) VH CDR3, consisting of the following sequence: SEQ ID NO: 5
   and
   (b) three CDRs of light chain variable region (VL) selected from the group consisting of:
      (iv) VL CDR1, consisting of the following sequence: SEQ ID NO: 6, or a sequence that differs from SEQ ID NO:6 by 1 or 2 substitutions selected from the group consisting of:
         (29) P or T at L27; and
         (32) S or N at L30;
      (v) VL CDR2, consisting of the following sequence: SEQ ID NO: 7, and
      (vi) VL CDR3, consisting of the following sequence: SEQ ID NO: 8;
   wherein, the amino acid positions mentioned above are numbered according to Kabat numbering system;
   and, the antibody or an antigen binding fragment thereof is humanized, and has a humanization degree of at least 85%.

2. The antibody or an antigen binding fragment thereof according to claim 1, wherein the antibody or an antigen binding fragment thereof is characterized by any one or more of (i), (ii) and (iii):

(i) the VH CDR1 has a sequence selected from the group consisting of:

SGYHWN; (SEQ ID NO: 3)

RGYHWN; (SEQ ID NO: 121)

RWYHWN; (SEQ ID NO: 126)

YGYHWN; (SEQ ID NO: 124)

(ii) the VH CDR2 has a sequence selected from the group consisting of:

YISYDGSDHYNPSLEN; (SEQ ID NO: 4)

YISYDGSVLYNPSLEN; (SEQ ID NO: 149)

YISYDGTNLYNPSLEN; (SEQ ID NO: 151)

YISYDGSVLYNPSLKS. (SEQ ID NO: 155)

3. The antibody or an antigen binding fragment thereof according to claim 1, wherein

RSSQSLVHSYGDTYLH; (SEQ ID NO: 6)

RSSQSLVHTYGNTYLH; (SEQ ID NO: 235)

RSSQSLVHPYGSTYLH. (SEQ ID NO: 236)

4. The antibody or an antigen binding fragment thereof according to claim 1, wherein the antibody comprises a VL comprising:
(a) VL CDR1 as set forth in RSSQSLVHSYGDTYLH (SEQ ID NO: 6); VL CDR2 as set forth in KVSNRFS (SEQ ID NO: 7); and VL CDR3 as set forth in SQNTHVPYT (SEQ ID NO: 8);
(k) VL CDR1 as set forth in RSSQSLVHTYGNTYLH (SEQ ID NO: 235); VL CDR2 as set forth in KVSN-RFS (SEQ ID NO: 7); and VL CDR3 as set forth in SQNTHVPYT (SEQ ID NO: 8); or
(l) VL CDR1 as set forth in RSSQSLVHPYGSTYLH (SEQ ID NO: 236); VL CDR2 as set forth in KVSN-RFS (SEQ ID NO: 7); and VL CDR3 as set forth in SQNTHVPYT (SEQ ID NO: 8).

5. The antibody or an antigen binding fragment thereof according to claim 4, wherein the antibody comprises a VH comprising:
(a) VH CDR1 as set forth in SGYHWN (SEQ ID NO: 3); VH CDR2 as set forth in YISYDGSDHYNPSLEN (SEQ ID NO: 4); and VH CDR3 as set forth in GFDH (SEQ ID NO: 5);
(j) VH CDR1 as set forth in RWYHWN (SEQ ID NO: 126); VH CDR2 as set forth in YISYDGTV-LYNPSLEN (SEQ ID NO: 146); and VH CDR3 as set forth in GFDH (SEQ ID NO: 5);
(z) VH CDR1 as set forth in YGYHWN (SEQ ID NO: 124); VH CDR2 as set forth in YISYDGSV-LYNPSLEN (SEQ ID NO: 149); and VH CDR3 as set forth in GFDH (SEQ ID NO: 5);
(ad) VH CDR1 as set forth in RGYHWN (SEQ ID NO: 121); VH CDR2 as set forth in YISYDGTN-LYNPSLEN (SEQ ID NO: 151); and VH CDR3 as set forth in GFDH (SEQ ID NO: 5);
QSYNPSLKG (SEQ ID NO: 157); and VH CDR3 as set forth in GFDH (SEQ ID NO: 5);
(ap) VH CDR1 as set forth in RGYHWN (SEQ ID NO: 121); VH CDR2 as set forth in YISYDGSV-LYNPSLKS (SEQ ID NO: 155); and VH CDR3 as set forth in GFDH (SEQ ID NO: 5); or,
(aq) VH CDR1 as set forth in SGYHWN (SEQ ID NO: 3); VH CDR2 as set forth in YISYDGSVLYNPSLKS (SEQ ID NO: 155); and VH CDR3 as set forth in GFDH (SEQ ID NO: 5).

6. The antibody or an antigen binding fragment thereof according to claim 1, wherein the antibody comprises 6 CDRs from heavy chain and light chain variable regions of an antibody selected from the group consisting of:

| Antibody name | Heavy chain variable region (SEQ ID NO:) | Light chain variable region (SEQ ID NO:) |
| --- | --- | --- |
| 110 | 72 | 201 |
| 11-3 | 69 | 189 |
| 116 | 73 | 202 |
| 138 | 91 | 205 |
| 162 | 36 | 187 |
| 162/41k | 36 | 189 |
| 24-40 | 20 | 187 |
| 7-34-239 | 41 | 187 |
| 138HA/162BK | 263 | 192. |

7. The antibody or an antigen binding fragment thereof according to claim 1, wherein the antibody has:
(i) a heavy chain variable region, which has an amino acid sequence identity of at least 80% with a heavy chain variable region selected from the group consisting of: heavy chain variable regions set forth in SEQ ID NOs: 20, 36, 41, 69, 72, 73, 91;
and
(ii) a light chain variable region, which has an amino acid sequence identity of at least 80%, with a light chain variable region selected from the group consisting of: light chain variable regions set forth in SEQ ID NOs: 187, 189, 201, 202, 205.

8. The antibody or an antigen binding fragment thereof according to claim 7, wherein, the antibody comprises:
(8) VH as set forth in SEQ ID NO: 69 and VL as set forth in SEQ ID NO: 189;
(10) VH as set forth in SEQ ID NO: 73 and VL as set forth in SEQ ID NO: 202;
(16) VH as set forth in SEQ ID NO: 91 and VL as set forth in SEQ ID NO: 205;
(18) VH as set forth in SEQ ID NO: 36 and VL as set forth in SEQ ID NO: 187;
(19) VH as set forth in SEQ ID NO: 36 and VL as set forth in SEQ ID NO: 189;
(27) VH as set forth in SEQ ID NO: 20 and VL as set forth in SEQ ID NO: 187;
or,
(49) VH as set forth in SEQ ID NO: 41 and VL as set forth in SEQ ID NO: 187.

9. The antibody or an antigen binding fragment thereof according to claim 1, wherein the antibody or an antigen binding fragment thereof is characterized by any one or more of (i), (ii) and (iii):

(i) the antibody or an antigen binding fragment thereof is selected from the group consisting of scFv, Fab, Fab', (Fab')$_2$, Fv fragment, diabody, bispecific antibody, and polyspecific antibody;
(ii) the antibody or an antigen binding fragment thereof is an antibody of IgG isotype or an antigen binding fragment thereof;
(iii) the antibody or an antigen binding fragment thereof is labeled.

10. The antibody or an antigen binding fragment thereof according to claim 1, wherein the antibody or an antigen binding fragment thereof is characterized by any one or more of (i) and (ii):
(i) the antibody or an antigen binding fragment thereof has a humanization degree of at least 85%;
(ii) the antibody or an antigen binding fragment thereof comprises no more than 20 murine amino acid residues in framework region.

11. An isolated nucleic acid molecule, encoding the antibody or an antigen binding fragment thereof according to claim 1.

12. A vector, comprising the nucleic acid molecule according to claim 11.

13. A host cell comprising the nucleic acid molecule according to claim 11 or a vector comprising the nucleic acid molecule.

14. A method for preparing the antibody or an antigen binding fragment thereof according to claim 1, comprising culturing a host cell under a condition allowing expression of the antibody or an antigen binding fragment thereof, and recovering the antibody or an antigen binding fragment thereof from a culture of the cultured host cell; wherein the host cell comprises a nucleic acid molecule encoding the antibody or an antigen binding fragment thereof or a vector comprising the nucleic acid molecule.

15. A pharmaceutical composition, comprising the antibody or an antigen binding fragment thereof according to claim 1, and a pharmaceutically acceptable carrier and/or excipient.

16. A method for preventing or treating HBV infection or a disease associated with HBV infection in a subject, for neutralizing HBV virulence in a subject, and/or for reducing the serum level of HBV DNA and/or HBsAg in a subject, comprising administering to a subject in need thereof an effective amount of the antibody or an antigen binding fragment thereof according to claim 1 or a pharmaceutical composition comprising the antibody or an antigen binding fragment thereof.

17. The method according to claim 16, wherein the method is characterized by any one or more of (i) and (ii):
(i) the disease associated with HBV infection is Hepatitis B;
(ii) the subject is human.

* * * * *

SEQUENCE LISTING

<160> NUMBER OF SEQ ID NOS: 320

<210> SEQ ID NO 1
<211> LENGTH: 113
<212> TYPE: PRT
<213> ORGANISM: Artificial Sequence
<220> FEATURE:
<223> OTHER INFORMATION: Synthetic peptide

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Pro Ile Thr Ser Gly
            20                  25                  30

Tyr His Trp Asn Trp Ile Arg Gln Phe Pro Gly Asn Lys Leu Val Trp
        35                  40                  45

Met Gly Tyr Ile Ser Tyr Asp Gly Ser Asp His Tyr Asn Pro Ser Leu
    50                  55                  60

Glu Asn Arg Ile Ser Ile Thr Arg Asp Ile Ser Lys Asn Gln Phe Phe
65                  70                  75                  80

Leu Ile Leu Arg Ser Val Thr Thr Glu Asp Thr Gly Lys Tyr Phe Cys
                85                  90                  95

Ala Ser Gly Phe Asp His Trp Gly Gln Gly Thr Thr Leu Thr Val Ser
            100                 105                 110

Ser

<210> SEQ ID NO 2
<211> LENGTH: 113
<212> TYPE: PRT
<213> ORGANISM: Artificial Sequence
<220> FEATURE:
<223> OTHER INFORMATION: Synthetic peptide

<400> SEQUENCE: 2

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Ser Gly Tyr His Trp Asn

```
<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Tyr Ile Ser Tyr Asp Gly Ser Asp His Tyr Asn Pro Ser Leu Glu Asn
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Gly Phe Asp His
1

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Ser Ser Gln Ser Leu Val His Ser Tyr Gly Asp Thr Tyr Leu His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Ser Gln Asn Thr His Val Pro Tyr Thr
1               5

<210> SEQ ID NO 9
<211> LENGTH: 98
<212> TYPE: PRT
<213> ORGANISM: Artificial Sequence
<220> FEATURE:
<223> OTHER INFORMATION: Synthetic peptide

<400> SEQUENCE: 9

Gln Val Gln Leu Gln Glu Ser Gly Pro Gly Leu Val Lys Pro Ser Gln
1               5                   10                  15
```

```
Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Ile Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 10
<211> LENGTH: 93
<212> TYPE: PRT
<213> ORGANISM: Artificial Sequence
<220> FEATURE:
<223> OTHER INFORMATION: Synthetic peptide

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 11
<211> LENGTH: 113
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Asp His Tyr Asn Pro Ser Leu
    50                  55                  60

Glu Asn Arg Ile Thr Ile Thr Arg Asp Thr Ser Lys Asn Gln Phe Ser
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser
```

```
<210> SEQ ID NO 12
<211> LENGTH: 113
<212> TYPE: PRT
<213> ORGANISM: Artificial Sequence
<220> FEATURE:
<223> OTHER INFORMATION: Synthetic peptide

<400> SEQUENCE: 12
```

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Val Phe Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

```
<210> SEQ ID NO 13
<211> LENGTH: 113
<212> TYPE: PRT
<213> ORGANISM: Artificial Sequence
<220> FEATURE:
<223> OTHER INFORMATION: Synthetic peptide

<400> SEQUENCE: 13
```

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

```
<210> SEQ ID NO 14
<211> LENGTH: 113
<212> TYPE: PRT
<213> ORGANISM: Artificial Sequence
<220> FEATURE:
<223> OTHER INFORMATION: Synthetic peptide

<400> SEQUENCE: 14
```

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Asn Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 15
<211> LENGTH: 113
<212> TYPE: PRT
<213> ORGANISM: Artificial Sequence
<220> FEATURE:
<223> OTHER INFORMATION: Synthetic peptide

<400> SEQUENCE: 15

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 16
<211> LENGTH: 113
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr His Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys

```
                    85                  90                  95

Ala Ser Gly Phe Asp Tyr Trp Gly Gln Gly Thr Thr Leu Thr Val Ser
                100                 105                 110

Ser

<210> SEQ ID NO 17
<211> LENGTH: 113
<212> TYPE: PRT
<213> ORGANISM: Artificial Sequence
<220> FEATURE:
<223> OTHER INFORMATION: Synthetic peptide

<400> SEQUENCE: 17

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
                20                  25                  30

Tyr His Trp Asn Trp Ile Arg Gln Phe Pro Gly Asn Lys Leu Glu Trp
                35                  40                  45

Ile Gly Tyr Ile Ser Tyr Asp Gly Ser Ile Leu Tyr Asn Pro Ser Leu
50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
                100                 105                 110

Ser

<210> SEQ ID NO 18
<211> LENGTH: 113
<212> TYPE: PRT
<213> ORGANISM: Artificial Sequence
<220> FEATURE:
<223> OTHER INFORMATION: Synthetic peptide

<400> SEQUENCE: 18

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Asp
                20                  25                  30

Tyr His Trp Asn Trp Ile Arg Gln Phe Pro Gly Asn Lys Leu Glu Trp
                35                  40                  45

Ile Gly Tyr Ile Ser Tyr Asp Gly Thr Val Leu Tyr Asn Pro Ser Leu
50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
                100                 105                 110

Ser

<210> SEQ ID NO 19
<211> LENGTH: 113
<212> TYPE: PRT
<213> ORGANISM: Artificial Sequence
<220> FEATURE:
```

<223> OTHER INFORMATION: Synthetic peptide

<400> SEQUENCE: 19

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Asn Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Leu Thr Val Ser
            100                 105                 110

Ser

<210> SEQ ID NO 20
<211> LENGTH: 113
<212> TYPE: PRT
<213> ORGANISM: Artificial Sequence
<220> FEATURE:
<223> OTHER INFORMATION: Synthetic peptide

<400> SEQUENCE: 20

Glu Val Gln Leu Gln Glu Ser Gly Pro Gly Leu Val Lys Pro Ser Gln
1               5                   10                  15

Thr Leu Ser Leu Thr Cys Ala Val Ser Gly Asn Ser Ile Ser Arg Trp
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Leu Thr Val Ser
            100                 105                 110

Ser

<210> SEQ ID NO 21
<211> LENGTH: 113
<212> TYPE: PRT
<213> ORGANISM: Artificial Sequence
<220> FEATURE:
<223> OTHER INFORMATION: Synthetic peptide

<400> SEQUENCE: 21

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Asn Lys Leu Glu Trp
        35                  40                  45

```
Ile Gly Tyr Ile Ser Tyr Asp Gly Thr Val Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Lys Tyr Tyr Cys
                 85                  90                  95

Ala Ser Gly Phe Asp His Trp Gly Gln Gly Thr Thr Leu Thr Val Ser
             100                 105                 110

Ser

<210> SEQ ID NO 22
<211> LENGTH: 113
<212> TYPE: PRT
<213> ORGANISM: Artificial Sequence
<220> FEATURE:
<223> OTHER INFORMATION: Synthetic peptide

<400> SEQUENCE: 22

Glu Val Gln Leu Gln Glu Ser Gly Pro Gly Leu Val Lys Pro Ser Gln
 1               5                  10                  15

Thr Leu Ser Leu Thr Cys Ala Val Ser Gly Ala Ser Ile Thr Arg Asp
                 20                  25                  30

Tyr His Trp Asn Trp Ile Arg Gln Phe Pro Gly Asn Lys Leu Glu Trp
             35                  40                  45

Ile Gly Tyr Ile Ser Tyr Asp Gly Thr Ile Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Lys Tyr Tyr Cys
                 85                  90                  95

Ala Ser Gly Phe Asp His Trp Gly Gln Gly Thr Thr Leu Thr Val Ser
             100                 105                 110

Ser

<210> SEQ ID NO 23
<211> LENGTH: 113
<212> TYPE: PRT
<213> ORGANISM: Artificial Sequence
<220> FEATURE:
<223> OTHER INFORMATION: Synthetic peptide

<400> SEQUENCE: 23

Glu Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Ser His Gly
                 20                  25                  30

Tyr His Trp Asn Trp Ile Arg Gln Phe Pro Gly Asn Lys Leu Glu Trp
             35                  40                  45

Ile Gly Tyr Ile Ser Tyr Asp Gly Thr Ile Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Lys Tyr Tyr Cys
                 85                  90                  95

Ala Ser Gly Phe Asp His Trp Gly Gln Gly Thr Thr Leu Thr Val Ser
             100                 105                 110

Ser
```

<210> SEQ ID NO 24
<211> LENGTH: 113
<212> TYPE: PRT
<213> ORGANISM: Artificial Sequence
<220> FEATURE:
<223> OTHER INFORMATION: Synthetic peptide

<400> SEQUENCE: 24

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 25
<211> LENGTH: 113
<212> TYPE: PRT
<213> ORGANISM: Artificial Sequence
<220> FEATURE:
<223> OTHER INFORMATION: Synthetic peptide

<400> SEQUENCE: 25

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr His Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ser Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 26
<211> LENGTH: 113
<212> TYPE: PRT
<213> ORGANISM: Artificial Sequence
<220> FEATURE:
<223> OTHER INFORMATION: Synthetic peptide

<400> SEQUENCE: 26

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 27
<211> LENGTH: 113
<212> TYPE: PRT
<213> ORGANISM: Artificial Sequence
<220> FEATURE:
<223> OTHER INFORMATION: Synthetic peptide

<400> SEQUENCE: 27

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 28
<211> LENGTH: 113
<212> TYPE: PRT
<213> ORGANISM: Artificial Sequence
<220> FEATURE:
<223> OTHER INFORMATION: Synthetic peptide

<400> SEQUENCE: 28

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
            85                  90                  95

Ala Ser Gly Phe Asp Tyr Trp Gly Gln Gly Thr Thr Leu Thr Val Ser
            100                 105                 110

Ser

<210> SEQ ID NO 29
<211> LENGTH: 113
<212> TYPE: PRT
<213> ORGANISM: Artificial Sequence
<220> FEATURE:
<223> OTHER INFORMATION: Synthetic peptide

<400> SEQUENCE: 29

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
            85                  90                  95

Ala Ser Gly Phe Asp Thr Trp Gly Gln Gly Thr Thr Leu Thr Val Ser
            100                 105                 110

Ser

<210> SEQ ID NO 30
<211> LENGTH: 113
<212> TYPE: PRT
<213> ORGANISM: Artificial Sequence
<220> FEATURE:
<223> OTHER INFORMATION: Synthetic peptide

<400> SEQUENCE: 30

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Asn Phe
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Val Leu Tyr Asn Pro Ser Leu
50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
            85                  90                  95

Ala Ser Gly Phe Asp His Trp Gly Gln Gly Thr Thr Leu Thr Val Ser
            100                 105                 110

Ser

<210> SEQ ID NO 31
<211> LENGTH: 113
<212> TYPE: PRT
<213> ORGANISM: Artificial Sequence

```
<220> FEATURE:
<223> OTHER INFORMATION: Synthetic peptide

<400> SEQUENCE: 31

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 32
<211> LENGTH: 113
<212> TYPE: PRT
<213> ORGANISM: Artificial Sequence
<220> FEATURE:
<223> OTHER INFORMATION: Synthetic peptide

<400> SEQUENCE: 32

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 33
<211> LENGTH: 113
<212> TYPE: PRT
<213> ORGANISM: Artificial Sequence
<220> FEATURE:
<223> OTHER INFORMATION: Synthetic peptide

<400> SEQUENCE: 33

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr His Gly
            20                  25                  30

Tyr His Trp Asn Trp Ile Arg Gln Phe Pro Gly Asn Lys Leu Glu Trp
        35                  40                  45
```

```
Ile Gly Tyr Ile Ser Tyr Asp Gly Thr Ile Leu Tyr Asn Pro Ser Leu
        50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Leu Thr Val Ser
                100                 105                 110

Ser

<210> SEQ ID NO 34
<211> LENGTH: 113
<212> TYPE: PRT
<213> ORGANISM: Artificial Sequence
<220> FEATURE:
<223> OTHER INFORMATION: Synthetic peptide

<400> SEQUENCE: 34

Glu Val Gln Leu Gln Glu Ser Gly Pro Gly Leu Val Lys Pro Ser Gln
  1               5                  10                  15

Thr Leu Ser Leu Thr Cys Ala Val Ser Gly Ser Ile Thr Ser Gly
                20                  25                  30

Tyr His Trp Asn Trp Ile Arg Gln Phe Pro Gly Asn Lys Leu Glu Trp
                35                  40                  45

Ile Gly Tyr Ile Ser Tyr Asp Gly Thr Val Leu Tyr Asn Pro Ser Leu
        50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Leu Thr Val Ser
                100                 105                 110

Ser

<210> SEQ ID NO 35
<211> LENGTH: 113
<212> TYPE: PRT
<213> ORGANISM: Artificial Sequence
<220> FEATURE:
<223> OTHER INFORMATION: Synthetic peptide

<400> SEQUENCE: 35

Glu Val Gln Leu Gln Glu Ser Gly Pro Gly Leu Val Lys Pro Ser Gln
  1               5                  10                  15

Thr Leu Ser Leu Thr Cys Ala Val Ser Gly Tyr Ser Ile Ser Ser Gly
                20                  25                  30

Tyr His Trp Asn Trp Ile Arg Gln Phe Pro Gly Asn Lys Leu Glu Trp
                35                  40                  45

Ile Gly Tyr Ile Ser Tyr Asp Gly Thr Ile Leu Tyr Asn Pro Ser Leu
        50                  55                  60

Glu Asn Arg Val Thr Ile Thr Arg Asp Thr Ser Lys Asn Gln Phe Phe
 65                  70                  75                  80

Leu Lys Leu Ser Ser Val Thr Ala Glu Asp Thr Ala Arg Tyr Tyr Cys
                85                  90                  95

Ala Ser Gly Phe Asp His Trp Gly Gln Gly Thr Leu Thr Val Ser
                100                 105                 110
```

Ser

<210> SEQ ID NO 36
<211> LENGTH: 113
<212> TYPE: PRT
<213> ORGANISM: Artificial Sequence
<220> FEATURE:
<223> OTHER INFORMATION: Synthetic peptide

<400> SEQUENCE: 36

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 37
<211> LENGTH: 113
<212> TYPE: PRT
<213> ORGANISM: Artificial Sequence
<220> FEATURE:
<223> OTHER INFORMATION: Synthetic peptide

<400> SEQUENCE: 37

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Asn Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 38
<211> LENGTH: 113
<212> TYPE: PRT
<213> ORGANISM: Artificial Sequence
<220> FEATURE:
<223> OTHER INFORMATION: Synthetic peptide

<400> SEQUENCE: 38

Glu Val Gln Leu Gln Glu Ser Gly Pro Gly Leu Val Lys Pro Ser Gln

```
1               5                   10                  15
Thr Leu Ser Leu Thr Cys Ala Val Ser Gly Tyr Ser Ile Ser Ser Gly
            20                  25                  30

Tyr His Trp Asn Trp Val Arg Gln Phe Pro Gly Asn Lys Leu Glu Trp
            35                  40                  45

Ile Gly Tyr Ile Ser Tyr Asp Gly Thr Asn Leu Tyr Asn Pro Ser Leu
            50                  55                  60

Glu Asn Arg Val Thr Ile Thr Arg Asp Thr Ser Lys Asn Gln Phe Phe
65                      70                  75                  80

Leu Lys Leu Ser Ser Val Thr Ala Glu Asp Thr Ala Lys Tyr Tyr Cys
                    85                  90                  95

Ala Ser Gly Phe Asp His Trp Gly Gln Gly Thr Thr Leu Thr Val Ser
                100                 105                 110

Ser
```

<210> SEQ ID NO 39
<211> LENGTH: 113
<212> TYPE: PRT
<213> ORGANISM: Artificial Sequence
<220> FEATURE:
<223> OTHER INFORMATION: Synthetic peptide

<400> SEQUENCE: 39

```
Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr His Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Val Leu Tyr Asn Pro Ser Leu
            50                  55                  60

Glu Asn Arg Val Thr Ile Thr Arg Asp Thr Ser Lys Asn Gln Phe Phe
65                      70                  75                  80

Leu Lys Leu Ser Ser Val Thr Ala Glu Asp Thr Ala Lys Tyr Tyr Cys
                    85                  90                  95

Ala Ser Gly Phe Asp His Trp Gly Gln Gly Thr Thr Leu Thr Val Ser
                100                 105                 110

Ser
```

<210> SEQ ID NO 40
<211> LENGTH: 113
<212> TYPE: PRT
<213> ORGANISM: Artificial Sequence
<220> FEATURE:
<223> OTHER INFORMATION: Synthetic peptide

<400> SEQUENCE: 40

```
Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr His Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Asn Leu Tyr Asn Pro Ser Leu
            50                  55                  60

Glu Asn Arg Val Thr Ile Thr Arg Asp Thr Ser Lys Asn Gln Phe Phe
65                      70                  75                  80
```

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 41
<211> LENGTH: 113
<212> TYPE: PRT
<213> ORGANISM: Artificial Sequence
<220> FEATURE:
<223> OTHER INFORMATION: Synthetic peptide

<400> SEQUENCE: 41

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Asn Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 42
<211> LENGTH: 113
<212> TYPE: PRT
<213> ORGANISM: Artificial Sequence
<220> FEATURE:
<223> OTHER INFORMATION: Synthetic peptide

<400> SEQUENCE: 42

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr His Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 43
<211> LENGTH: 113
<212> TYPE: PRT

<213> ORGANISM: Artificial Sequence
<220> FEATURE:
<223> OTHER INFORMATION: Synthetic peptide

<400> SEQUENCE: 43

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 44
<211> LENGTH: 113
<212> TYPE: PRT
<213> ORGANISM: Artificial Sequence
<220> FEATURE:
<223> OTHER INFORMATION: Synthetic peptide

<400> SEQUENCE: 44

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Ser Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val His Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 45
<211> LENGTH: 113
<212> TYPE: PRT
<213> ORGANISM: Artificial Sequence
<220> FEATURE:
<223> OTHER INFORMATION: Synthetic peptide

<400> SEQUENCE: 45

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Asn Phe
            20                  25                  30

Tyr His Trp Asn Trp Ile Arg Gln Phe Pro Gly Asn Lys Leu Glu Trp

```
                    35                  40                  45
Ile Gly Tyr Ile Ser Tyr Asp Gly Asn Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
                100                 105                 110

Ser

<210> SEQ ID NO 46
<211> LENGTH: 113
<212> TYPE: PRT
<213> ORGANISM: Artificial Sequence
<220> FEATURE:
<223> OTHER INFORMATION: Synthetic peptide

<400> SEQUENCE: 46

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Arg Asp
                20                  25                  30

Tyr His Trp Asn Trp Ile Gln Gln Phe Pro Gly Asn Lys Leu Glu Trp
            35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
                100                 105                 110

Ser

<210> SEQ ID NO 47
<211> LENGTH: 113
<212> TYPE: PRT
<213> ORGANISM: Artificial Sequence
<220> FEATURE:
<223> OTHER INFORMATION: Synthetic peptide

<400> SEQUENCE: 47

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Tyr
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Ile Arg Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
                100                 105                 110
```

-continued

Ser

<210> SEQ ID NO 48
<211> LENGTH: 113
<212> TYPE: PRT
<213> ORGANISM: Artificial Sequence
<220> FEATURE:
<223> OTHER INFORMATION: Synthetic peptide

<400> SEQUENCE: 48

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val His Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp Tyr Trp Gly Gln Gly Thr Thr Leu Thr Val Ser
            100                 105                 110

Ser

<210> SEQ ID NO 49
<211> LENGTH: 113
<212> TYPE: PRT
<213> ORGANISM: Artificial Sequence
<220> FEATURE:
<223> OTHER INFORMATION: Synthetic peptide

<400> SEQUENCE: 49

Glu Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Thr Arg Asp
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 50
<211> LENGTH: 113
<212> TYPE: PRT
<213> ORGANISM: Artificial Sequence
<220> FEATURE:
<223> OTHER INFORMATION: Synthetic peptide

<400> SEQUENCE: 50

Glu Val Gln Leu Gln Glu Ser Gly Pro Gly Leu Val Lys Ala Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Leu Pro Gly Asn Lys Leu Glu Trp
            35                  40                  45

Ile Gly Tyr Ile Ser Tyr Asp Gly Ser Asp His Tyr Asn Pro Ser Leu
    50                  55                  60

Glu Asn Arg Ile Thr Ile Ser Arg Asp Thr Ser Lys Asn Gln Phe Phe
65                  70                  75                  80

Leu Lys Leu Arg Ser Val Thr Ala Glu Asp Thr Ala Lys Tyr Phe Cys
                85                  90                  95

Ala Ser Gly Phe Asp His Trp Gly Gln Gly Thr Leu Thr Val Ser
            100                 105                 110

Ser

<210> SEQ ID NO 51
<211> LENGTH: 113
<212> TYPE: PRT
<213> ORGANISM: Artificial Sequence
<220> FEATURE:
<223> OTHER INFORMATION: Synthetic peptide

<400> SEQUENCE: 51

Asp Val Gln Leu Gln Glu Ser Gly Pro Gly Leu Val Lys Pro Ser Gln
1               5                   10                  15

Thr Leu Ser Leu Thr Cys Ala Val Ser Gly Tyr Pro Ile Thr Ser Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Asp His Tyr Asn Pro Ser Leu
    50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Leu Thr Val Ser
            100                 105                 110

Ser

<210> SEQ ID NO 52
<211> LENGTH: 113
<212> TYPE: PRT
<213> ORGANISM: Artificial Sequence
<220> FEATURE:
<223> OTHER INFORMATION: Synthetic peptide

<400> SEQUENCE: 52

His Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Asp His Tyr Asn Pro Ser Leu
    50                  55                  60

Glu Asn Arg Val Thr Ile Thr Arg Asp Thr Ser Lys Asn Gln Phe Phe

```
              65                  70                  75                  80
Leu Lys Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
                100                 105                 110

Ser

<210> SEQ ID NO 53
<211> LENGTH: 113
<212> TYPE: PRT
<213> ORGANISM: Artificial Sequence
<220> FEATURE:
<223> OTHER INFORMATION: Synthetic peptide

<400> SEQUENCE: 53

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Asp His Tyr Asn Pro Ser Leu
        50                  55                  60

Glu Asn Arg Val Ser Ile Thr Arg Asp Thr Ser Lys Asn Gln Phe Phe
65                  70                  75                  80

Leu Lys Leu Ser Ser Val Thr Ala Glu Asp Thr Ala Lys Tyr Phe Cys
                85                  90                  95

Ala Ser Gly Phe Asp His Trp Gly Gln Gly Thr Thr Leu Thr Val Ser
                100                 105                 110

Ser

<210> SEQ ID NO 54
<211> LENGTH: 113
<212> TYPE: PRT
<213> ORGANISM: Artificial Sequence
<220> FEATURE:
<223> OTHER INFORMATION: Synthetic peptide

<400> SEQUENCE: 54

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Pro Ile Ser Ser Gly
                20                  25                  30

Tyr His Trp Asn Trp Ile Arg Gln Phe Pro Gly Lys Lys Leu Glu Trp
            35                  40                  45

Ile Gly Tyr Ile Ser Tyr Asp Gly Ser Asp His Tyr Asn Pro Ser Leu
        50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Ile Tyr Phe Cys
                85                  90                  95

Ala Ser Gly Phe Asp His Trp Gly Gln Gly Thr Thr Leu Thr Val Ser
                100                 105                 110

Ser

<210> SEQ ID NO 55
<211> LENGTH: 113
```

```
<212> TYPE: PRT
<213> ORGANISM: Artificial Sequence
<220> FEATURE:
<223> OTHER INFORMATION: Synthetic peptide

<400> SEQUENCE: 55

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Tyr Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 56
<211> LENGTH: 113
<212> TYPE: PRT
<213> ORGANISM: Artificial Sequence
<220> FEATURE:
<223> OTHER INFORMATION: Synthetic peptide

<400> SEQUENCE: 56

His Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 57
<211> LENGTH: 113
<212> TYPE: PRT
<213> ORGANISM: Artificial Sequence
<220> FEATURE:
<223> OTHER INFORMATION: Synthetic peptide

<400> SEQUENCE: 57

His Val Gln Leu Gln Glu Ser Gly Pro Gly Leu Val Lys Pro Ser Gln
1               5                   10                  15

Thr Leu Ser Leu Thr Cys Ala Val Ser Gly Asn Ser Ile Ser Arg Trp
            20                  25                  30
```

Tyr His Trp Asn Trp Ile Arg Gln Phe Pro Gly Asn Lys Leu Glu Trp
            35                  40                  45

Ile Gly Tyr Ile Ser Tyr Asp Gly Thr Val Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Arg Ser Val Thr Ala Glu Asp Thr Ala Ile Tyr Tyr Cys
                 85                  90                  95

Ala Ser Gly Phe Asp His Trp Gly Gln Gly Thr Thr Leu Thr Val Ser
            100                 105                 110

Ser

<210> SEQ ID NO 58
<211> LENGTH: 113
<212> TYPE: PRT
<213> ORGANISM: Artificial Sequence
<220> FEATURE:
<223> OTHER INFORMATION: Synthetic peptide

<400> SEQUENCE: 58

His Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Ser His Gly
                 20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Val Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Arg Ser Val Thr Ala Glu Asp Thr Ala Ile Tyr Tyr Cys
                 85                  90                  95

Ala Ser Gly Phe Asp His Trp Gly Gln Gly Thr Thr Leu Thr Val Ser
            100                 105                 110

Ser

<210> SEQ ID NO 59
<211> LENGTH: 113
<212> TYPE: PRT
<213> ORGANISM: Artificial Sequence
<220> FEATURE:
<223> OTHER INFORMATION: Synthetic peptide

<400> SEQUENCE: 59

His Val Gln Leu Gln Glu Ser Gly Pro Gly Leu Val Lys Pro Ser Gln
 1               5                  10                  15

Thr Leu Ser Leu Thr Cys Ala Val Ser Gly Ala Ser Ile Thr Arg Asp
                 20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Ile Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Arg Ser Val Thr Ala Glu Asp Thr Ala Ile Tyr Tyr Cys
                 85                  90                  95

Ala Ser Gly Phe Asp His Trp Gly Gln Gly Thr Thr Leu Thr Val Ser

```
<210> SEQ ID NO 60
<211> LENGTH: 113
<212> TYPE: PRT
<213> ORGANISM: Artificial Sequence
<220> FEATURE:
<223> OTHER INFORMATION: Synthetic peptide

<400> SEQUENCE: 60
```

His Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Tyr Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

```
<210> SEQ ID NO 61
<211> LENGTH: 113
<212> TYPE: PRT
<213> ORGANISM: Artificial Sequence
<220> FEATURE:
<223> OTHER INFORMATION: Synthetic peptide

<400> SEQUENCE: 61
```

His Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr Arg Trp
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Val Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Ile Tyr Tyr Cys
                85                  90                  95

Ala Ser Gly Phe Asp Tyr Trp Gly Gln Gly Thr Thr Leu Thr Val Ser
            100                 105                 110

Ser

```
<210> SEQ ID NO 62
<211> LENGTH: 113
<212> TYPE: PRT
<213> ORGANISM: Artificial Sequence
<220> FEATURE:
<223> OTHER INFORMATION: Synthetic peptide

<400> SEQUENCE: 62
```

Asp Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Asn Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Ile Leu Tyr Asn Pro Ser Leu
        50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 63
<211> LENGTH: 113
<212> TYPE: PRT
<213> ORGANISM: Artificial Sequence
<220> FEATURE:
<223> OTHER INFORMATION: Synthetic peptide

<400> SEQUENCE: 63

Asp Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Ile Leu Tyr Asn Pro Ser Leu
        50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 64
<211> LENGTH: 113
<212> TYPE: PRT
<213> ORGANISM: Artificial Sequence
<220> FEATURE:
<223> OTHER INFORMATION: Synthetic peptide

<400> SEQUENCE: 64

Asp Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr Arg Gly
            20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Ile Leu Tyr Asn Pro Ser Leu
        50                  55                  60

-continued

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 65
<211> LENGTH: 113
<212> TYPE: PRT
<213> ORGANISM: Artificial Sequence
<220> FEATURE:
<223> OTHER INFORMATION: Synthetic peptide

<400> SEQUENCE: 65

Asp Val Gln Leu Gln Glu Ser Gly Pro Gly Leu Val Lys Pro Ser Gln
1               5                   10                  15

Thr Leu Ser Leu Thr Cys Ala Val Ser Gly Asn Ser Ile Ser Arg Trp
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Thr Val Leu Tyr Asn Pro Ser Leu
50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 66
<211> LENGTH: 113
<212> TYPE: PRT
<213> ORGANISM: Artificial Sequence
<220> FEATURE:
<223> OTHER INFORMATION: Synthetic peptide

<400> SEQUENCE: 66

Asp Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Tyr Gly
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Val Leu Tyr Asn Pro Ser Leu
50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 67

```
<211> LENGTH: 113
<212> TYPE: PRT
<213> ORGANISM: Artificial Sequence
<220> FEATURE:
<223> OTHER INFORMATION: Synthetic peptide

<400> SEQUENCE: 67

Asp Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Thr Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Asn Leu Tyr Asn Pro Ser Leu
    50                  55                  60

Glu Asn Arg Val Ser Ile Thr Arg Asp Thr Ser Lys Asn Gln Phe Phe
65                  70                  75                  80

Leu Ile Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 68
<211> LENGTH: 113
<212> TYPE: PRT
<213> ORGANISM: Artificial Sequence
<220> FEATURE:
<223> OTHER INFORMATION: Synthetic peptide

<400> SEQUENCE: 68

His Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Ile Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 69
<211> LENGTH: 113
<212> TYPE: PRT
<213> ORGANISM: Artificial Sequence
<220> FEATURE:
<223> OTHER INFORMATION: Synthetic peptide

<400> SEQUENCE: 69

Asp Val Gln Leu Gln Glu Ser Gly Pro Gly Leu Val Lys Pro Ser Gln
 1               5                  10                  15

Thr Leu Ser Leu Thr Cys Thr Val Ser Gly Tyr Pro Ile Thr Ser Gly
            20                  25                  30
```

Tyr His Trp Asn Trp Ile Arg Gln Phe Pro Gly Asn Lys Leu Val Trp
            35                  40                  45

Met Gly Tyr Ile Ser Tyr Asp Gly Ser Asp His Tyr Asn Pro Ser Leu
 50                  55                  60

Glu Asn Arg Val Ser Ile Ser Arg Asp Ile Ser Lys Asn Gln Phe Phe
65                  70                  75                  80

Leu Lys Leu Ser Ser Val Thr Ala Ala Asp Thr Ala Val Tyr Phe Cys
                85                  90                  95

Ala Ser Gly Phe Asp His Trp Gly Gln Gly Thr Met Leu Thr Val Ser
            100                 105                 110

Ser

<210> SEQ ID NO 70
<211> LENGTH: 113
<212> TYPE: PRT
<213> ORGANISM: Artificial Sequence
<220> FEATURE:
<223> OTHER INFORMATION: Synthetic peptide

<400> SEQUENCE: 70

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Tyr Gly
            20                  25                  30

Tyr His Trp Asn Trp Ile Arg Gln Phe Pro Gly Lys Gly Leu Glu Trp
            35                  40                  45

Ile Gly Tyr Ile Ser Tyr Asp Gly Ser Val Leu Tyr Asn Pro Ser Leu
 50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 71
<211> LENGTH: 113
<212> TYPE: PRT
<213> ORGANISM: Artificial Sequence
<220> FEATURE:
<223> OTHER INFORMATION: Synthetic peptide

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Asn Gly
            20                  25                  30

Tyr His Trp Asn Trp Ile Arg Gln Phe Pro Gly Lys Ser Leu Glu Trp
            35                  40                  45

Ile Gly Tyr Ile Ala Tyr Asp Gly Val Gln Ser Tyr Asn Pro Ser Leu
 50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

```
Ala Ser Gly Phe Asp His Trp Gly Gln Gly Thr Leu Val Thr Val Ser
                100                 105                 110
Ser
```

<210> SEQ ID NO 72
<211> LENGTH: 113
<212> TYPE: PRT
<213> ORGANISM: Artificial Sequence
<220> FEATURE:
<223> OTHER INFORMATION: Synthetic peptide

<400> SEQUENCE: 72

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
                100                 105                 110
Ser
```

<210> SEQ ID NO 73
<211> LENGTH: 113
<212> TYPE: PRT
<213> ORGANISM: Artificial Sequence
<220> FEATURE:
<223> OTHER INFORMATION: Synthetic peptide

<400> SEQUENCE: 73

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
                100                 105                 110
Ser
```

<210> SEQ ID NO 74
<211> LENGTH: 113
<212> TYPE: PRT
<213> ORGANISM: Artificial Sequence
<220> FEATURE:
<223> OTHER INFORMATION: Synthetic peptide

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Asn Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 75
<211> LENGTH: 113
<212> TYPE: PRT
<213> ORGANISM: Artificial Sequence
<220> FEATURE:
<223> OTHER INFORMATION: Synthetic peptide

<400> SEQUENCE: 75

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Gly Tyr Asp Gly Ala Val Gln Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 76
<211> LENGTH: 113
<212> TYPE: PRT
<213> ORGANISM: Artificial Sequence
<220> FEATURE:
<223> OTHER INFORMATION: Synthetic peptide

<400> SEQUENCE: 76

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Lys Ser Leu Glu Trp
        35                  40                  45

Ile Gly Tyr Ile Ser Tyr Asn Gly Ser Val Leu Tyr Asn Pro Ser Leu
    50                  55                  60

```
Lys Ser Arg Val Thr Ile Ser Val Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Ser Gly Phe Asp His Trp Gly Gln Gly Thr Leu Val Thr Val Ser
            100                 105                 110

Ser
```

<210> SEQ ID NO 77
<211> LENGTH: 113
<212> TYPE: PRT
<213> ORGANISM: Artificial Sequence
<220> FEATURE:
<223> OTHER INFORMATION: Synthetic peptide

<400> SEQUENCE: 77

```
Gln Val Gln Leu Gln Glu Ser Gly Pro Gly Leu Val Lys Pro Ser Gln
  1               5                  10                  15

Thr Leu Ser Leu Thr Cys Ala Val Ser Gly Tyr Ser Ile Ser Arg Gly
                 20                  25                  30

Tyr His Trp Asn Trp Ile Arg Gln Phe Pro Gly Lys Gly Leu Glu Trp
             35                  40                  45

Ile Gly Tyr Ile Ser Tyr Asp Gly Ser Arg Leu Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Ser Gly Phe Asp His Trp Gly Gln Gly Thr Leu Val Thr Val Ser
            100                 105                 110

Ser
```

<210> SEQ ID NO 78
<211> LENGTH: 113
<212> TYPE: PRT
<213> ORGANISM: Artificial Sequence
<220> FEATURE:
<223> OTHER INFORMATION: Synthetic peptide

<400> SEQUENCE: 78

```
Gln Val Gln Leu Gln Glu Ser Gly Pro Gly Leu Val Lys Pro Ser Gln
  1               5                  10                  15

Thr Leu Ser Leu Thr Cys Ala Val Ser Gly Tyr Ser Ile Ser Asn Gly
                 20                  25                  30

Tyr His Trp Asn Trp Ile Arg Gln Phe Pro Gly Lys Gly Leu Glu Trp
             35                  40                  45

Ile Gly Tyr Ile Ser Tyr Asn Gly Ser Val Leu Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95

Ala Ser Gly Phe Asp His Trp Gly Gln Gly Thr Leu Val Thr Val Ser
            100                 105                 110

Ser
```

```
<210> SEQ ID NO 79
<211> LENGTH: 113
<212> TYPE: PRT
<213> ORGANISM: Artificial Sequence
<220> FEATURE:
<223> OTHER INFORMATION: Synthetic peptide

<400> SEQUENCE: 79
```

| Glu | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Ser | Gly | Tyr | Ser | Ile | Thr | Ser | Gly |
|---|---|---|---|---|---|---|---|---|---|---|---|---|---|---|---|
| | | | 20 | | | | | 25 | | | | | 30 | | |

| Tyr | His | Trp | Asn | Trp | Ile | Arg | Gln | Phe | Pro | Gly | Lys | Arg | Leu | Glu | Trp |
|---|---|---|---|---|---|---|---|---|---|---|---|---|---|---|---|
| | | 35 | | | | | 40 | | | | | 45 | | | |

| Met | Gly | Tyr | Ile | Ser | Tyr | Asp | Gly | Ser | Asp | His | Tyr | Asn | Pro | Ser | Leu |
|---|---|---|---|---|---|---|---|---|---|---|---|---|---|---|---|
| | 50 | | | | | 55 | | | | | 60 | | | | |

| Glu | Asn | Arg | Ile | Thr | Ile | Thr | Arg | Asp | Thr | Ser | Lys | Asn | Gln | Phe | Phe |
|---|---|---|---|---|---|---|---|---|---|---|---|---|---|---|---|
| 65 | | | | | 70 | | | | | 75 | | | | | 80 |

| Leu | Lys | Leu | Arg | Ser | Val | Thr | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ser | Gly | Phe | Asp | His | Trp | Gly | Gln | Gly | Thr | Thr | Leu | Thr | Val | Ser |
|---|---|---|---|---|---|---|---|---|---|---|---|---|---|---|---|
| | | | 100 | | | | | 105 | | | | | 110 | | |

Ser

```
<210> SEQ ID NO 80
<211> LENGTH: 113
<212> TYPE: PRT
<213> ORGANISM: Artificial Sequence
<220> FEATURE:
<223> OTHER INFORMATION: Synthetic peptide

<400> SEQUENCE: 80
```

| Glu | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Ser | Gly | Tyr | Pro | Ile | Thr | Ser | Gly |
|---|---|---|---|---|---|---|---|---|---|---|---|---|---|---|---|
| | | | 20 | | | | | 25 | | | | | 30 | | |

| Tyr | His | Trp | Asn | Trp | Ile | Arg | Gln | Phe | Pro | Gly | Asn | Lys | Leu | Glu | Trp |
|---|---|---|---|---|---|---|---|---|---|---|---|---|---|---|---|
| | | 35 | | | | | 40 | | | | | 45 | | | |

| Ile | Gly | Tyr | Ile | Ser | Tyr | Asp | Gly | Ser | Asp | His | Tyr | Asn | Pro | Ser | Leu |
|---|---|---|---|---|---|---|---|---|---|---|---|---|---|---|---|
| | 50 | | | | | 55 | | | | | 60 | | | | |

| Glu | Asn | Arg | Val | Ser | Ile | Thr | Arg | Asp | Thr | Ser | Lys | Asn | Gln | Phe | Phe |
|---|---|---|---|---|---|---|---|---|---|---|---|---|---|---|---|
| 65 | | | | | 70 | | | | | 75 | | | | | 80 |

| Leu | Lys | Leu | Arg | Ser | Val | Thr | Ala | Glu | Asp | Thr | Ala | Ile | Tyr | Phe | Cys |
|---|---|---|---|---|---|---|---|---|---|---|---|---|---|---|---|
| | | | | 85 | | | | | 90 | | | | | 95 | |

| Ala | Ser | Gly | Phe | Asp | His | Trp | Gly | Gln | Gly | Thr | Thr | Leu | Thr | Val | Ser |
|---|---|---|---|---|---|---|---|---|---|---|---|---|---|---|---|
| | | | 100 | | | | | 105 | | | | | 110 | | |

Ser

```
<210> SEQ ID NO 81
<211> LENGTH: 113
<212> TYPE: PRT
<213> ORGANISM: Artificial Sequence
<220> FEATURE:
<223> OTHER INFORMATION: Synthetic peptide

<400> SEQUENCE: 81
```

| Glu | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Ser | Gly | Tyr | Ser | Ile | Thr | Ser | Gly |
|---|---|---|---|---|---|---|---|---|---|---|---|---|---|---|---|

```
                20                  25                  30
Tyr His Trp Asn Trp Ile Arg Gln Phe Pro Gly Asn Glu Leu Glu Trp
        35                  40                  45

Ile Gly Tyr Ile Ser Tyr Asp Gly Ser Asp His Tyr Asn Pro Ser Leu
 50                  55                  60

Glu Asn Arg Ile Thr Ile Thr Arg Asp Thr Ser Lys Asn Gln Phe Phe
 65                  70                  75                  80

Leu Lys Leu Arg Ser Val Thr Ala Glu Asp Thr Ala Lys Tyr Tyr Cys
            85                  90                  95

Ala Ser Gly Phe Asp His Trp Gly Gln Gly Thr Thr Leu Thr Val Ser
                100                 105                 110

Ser

<210> SEQ ID NO 82
<211> LENGTH: 113
<212> TYPE: PRT
<213> ORGANISM: Artificial Sequence
<220> FEATURE:
<223> OTHER INFORMATION: Synthetic peptide

<400> SEQUENCE: 82

His Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Thr Asn Gly
                20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Thr Ile Leu Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Lys Leu Arg Ser Val Thr Ala Glu Asp Thr Ala Ile Tyr Tyr Cys
            85                  90                  95

Ala Ser Gly Phe Asp His Trp Gly Gln Gly Thr Thr Leu Thr Val Ser
                100                 105                 110

Ser

<210> SEQ ID NO 83
<211> LENGTH: 113
<212> TYPE: PRT
<213> ORGANISM: Artificial Sequence
<220> FEATURE:
<223> OTHER INFORMATION: Synthetic peptide

<400> SEQUENCE: 83

Glu Val Gln Leu Gln Glu Ser Gly Pro Gly Leu Val Lys Pro Ser Gln
 1               5                  10                  15

Thr Leu Ser Leu Thr Cys Ala Val Ser Gly Tyr Ser Ile Ser Ser Gly
                20                  25                  30

Tyr His Trp Asn Trp Ile Arg Gln Phe Pro Gly Asn Arg Leu Glu Trp
        35                  40                  45

Ile Gly Tyr Ile Ser Tyr Asp Gly Ser Asp His Tyr Asn Pro Ser Leu
 50                  55                  60

Glu Asn Arg Val Thr Ile Thr Arg Asp Thr Ser Lys Asn Gln Phe Phe
 65                  70                  75                  80

Leu Ile Leu Arg Ser Val Thr Ala Glu Asp Thr Ala Lys Tyr Tyr Cys
            85                  90                  95
```

Ala Ser Gly Phe Asp His Trp Gly Gln Gly Thr Thr Leu Thr Val Ser
            100                 105                 110
Ser

<210> SEQ ID NO 84
<211> LENGTH: 113
<212> TYPE: PRT
<213> ORGANISM: Artificial Sequence
<220> FEATURE:
<223> OTHER INFORMATION: Synthetic peptide

<400> SEQUENCE: 84

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Asp His Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Arg Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110
Ser

<210> SEQ ID NO 85
<211> LENGTH: 113
<212> TYPE: PRT
<213> ORGANISM: Artificial Sequence
<220> FEATURE:
<223> OTHER INFORMATION: Synthetic peptide

<400> SEQUENCE: 85

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Asn Arg Leu Glu Trp
        35                  40                  45

Met Gly Tyr Ile Ser Tyr Asp Gly Ser Asp His Tyr Asn Pro Ser Leu
    50                  55                  60

Glu Asn Arg Ile Ser Ile Thr Arg Asp Thr Ser Lys Asn Gln Phe Phe
65                  70                  75                  80

Leu Lys Leu Ser Ser Val Thr Ala Glu Asp Thr Ala Lys Tyr Phe Cys
                85                  90                  95

Ala Ser Gly Phe Asp His Trp Gly Gln Gly Thr Thr Leu Thr Val Ser
            100                 105                 110
Ser

<210> SEQ ID NO 86
<211> LENGTH: 113
<212> TYPE: PRT
<213> ORGANISM: Artificial Sequence
<220> FEATURE:
<223> OTHER INFORMATION: Synthetic peptide

<400> SEQUENCE: 86

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Asp His Tyr Asn Pro Ser Leu
    50                  55                  60

Glu Asn Arg Ile Thr Ile Thr Arg Asp Thr Ser Lys Asn Gln Phe Ser
65                  70                  75                  80

Leu Lys Leu Arg Ser Val Thr Ala Glu Asp Thr Ala Val Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 87
<211> LENGTH: 113
<212> TYPE: PRT
<213> ORGANISM: Artificial Sequence
<220> FEATURE:
<223> OTHER INFORMATION: Synthetic peptide

<400> SEQUENCE: 87

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Asp His Tyr Asn Pro Ser Leu
    50                  55                  60

Glu Asn Arg Val Thr Ile Thr Arg Asp Thr Ser Lys Asn Gln Phe Phe
65                  70                  75                  80

Leu Lys Leu Ser Ser Val Thr Ala Glu Asp Thr Ala Lys Tyr Tyr Cys
                85                  90                  95

Ala Ser Gly Phe Asp His Trp Gly Gln Gly Thr Thr Leu Thr Val Ser
            100                 105                 110

Ser

<210> SEQ ID NO 88
<211> LENGTH: 113
<212> TYPE: PRT
<213> ORGANISM: Artificial Sequence
<220> FEATURE:
<223> OTHER INFORMATION: Synthetic peptide

<400> SEQUENCE: 88

Gln Val Gln Gln Gln Glu Ser Gly Pro Gly Gln Val Lys Pro Ser Gln
1               5                   10                  15

Thr Leu Ser Leu Thr Cys Ala Val Ser Gly Tyr Pro Ile Ser Ser Gly
            20                  25                  30

Tyr His Trp Asn Trp Ile Arg Gln Phe Pro Gly Asn Lys Leu Glu Trp
        35                  40                  45

Met Gly Tyr Ile Ser Tyr Asp Gly Ser Asp His Tyr Asn Pro Ser Leu

```
                50                  55                  60
Glu Asn Arg Ile Thr Ile Thr Arg Asp Thr Ser Lys Asn Gln Phe Phe
 65                  70                  75                  80

Leu Lys Leu Arg Ser Val Thr Ala Glu Asp Thr Ala Lys Tyr Tyr Cys
                 85                  90                  95

Ala Ser Gly Phe Asp His Trp Gly Gln Gly Thr Thr Leu Thr Val Ser
                100                 105                 110

Ser
```

<210> SEQ ID NO 89
<211> LENGTH: 113
<212> TYPE: PRT
<213> ORGANISM: Artificial Sequence
<220> FEATURE:
<223> OTHER INFORMATION: Synthetic peptide

<400> SEQUENCE: 89

```
Gln Val Gln Leu Gln Glu Ser Gly Pro Gly Leu Val Lys Pro Ser Gln
  1               5                  10                  15

Thr Leu Ser Leu Thr Cys Ala Val Ser Gly Tyr Ser Ile Thr Ser Gly
                 20                  25                  30

Tyr His Trp Asn Trp Ile Arg Gln Phe Pro Gly Asn Lys Leu Glu Trp
             35                  40                  45

Met Gly Tyr Ile Ser Tyr Asp Gly Ser Asp His Tyr Asn Pro Ser Leu
         50                  55                  60

Glu Asn Arg Ile Thr Ile Thr Arg Asp Thr Ser Lys Asn Gln Phe Phe
 65                  70                  75                  80

Leu Ile Leu Arg Ser Val Thr Ala Glu Asp Thr Ala Ile Tyr Tyr Cys
                 85                  90                  95

Ala Ser Gly Phe Asp His Trp Gly Gln Gly Thr Thr Leu Thr Val Ser
                100                 105                 110

Ser
```

<210> SEQ ID NO 90
<211> LENGTH: 113
<212> TYPE: PRT
<213> ORGANISM: Artificial Sequence
<220> FEATURE:
<223> OTHER INFORMATION: Synthetic peptide

<400> SEQUENCE: 90

```
His Val Gln Leu Gln Glu Ser Gly Pro Gly Leu Val Lys Pro Ser Gln
  1               5                  10                  15

Thr Leu Ser Leu Thr Cys Ala Val Ser Gly Tyr Ser Ile Ser Ser Gly
                 20                  25                  30

Tyr His Trp Asn Trp Ile Arg Gln Phe Pro Gly Asn Glu Leu Glu Trp
             35                  40                  45

Ile Gly Tyr Ile Ser Tyr Asp Gly Ser Asp His Tyr Asn Pro Ser Leu
         50                  55                  60

Glu Asn Arg Ile Thr Ile Thr Arg Asp Thr Ser Lys Asn Gln Phe Phe
 65                  70                  75                  80

Leu Lys Leu Arg Ser Val Thr Ala Glu Asp Thr Ala Lys Tyr Tyr Cys
                 85                  90                  95

Ala Ser Gly Phe Asp His Trp Gly Gln Gly Thr Thr Leu Thr Val Ser
                100                 105                 110

Ser
```

<210> SEQ ID NO 91
<211> LENGTH: 113
<212> TYPE: PRT
<213> ORGANISM: Artificial Sequence
<220> FEATURE:
<223> OTHER INFORMATION: Synthetic peptide

<400> SEQUENCE: 91

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Thr Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser
```

<210> SEQ ID NO 92
<211> LENGTH: 113
<212> TYPE: PRT
<213> ORGANISM: Artificial Sequence
<220> FEATURE:
<223> OTHER INFORMATION: Synthetic peptide

<400> SEQUENCE: 92

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser His Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser
```

<210> SEQ ID NO 93
<211> LENGTH: 30
<212> TYPE: PRT
<213> ORGANISM: Artificial Sequence
<220> FEATURE:
<223> OTHER INFORMATION: Synthetic peptide

<400> SEQUENCE: 93

```
Glu Val Gln Leu Gln Glu Ser Gly Pro Gly Leu Val Lys Pro Ser Gln
1               5                   10                  15
```

Thr Leu Ser Leu Thr Cys Ala Val Ser Gly Tyr Ser Ile Ser
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: Synthetic peptide

<400> SEQUENCE: 94

Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: Synthetic peptide

<400> SEQUENCE: 95

Glu Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: Synthetic peptide

<400> SEQUENCE: 96

Glu Val Gln Leu Gln Glu Ser Gly Pro Gly Leu Val Lys Pro Ser Gln
1               5                   10                  15

Thr Leu Ser Leu Thr Cys Ala Val Ser Gly Asn Ser Ile Ser
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Synthetic peptide

<400> SEQUENCE: 97

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Thr
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Synthetic peptide

<400> SEQUENCE: 98

Glu Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: Synthetic peptide

<400> SEQUENCE: 99

Glu Val Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Ser
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Synthetic peptide

<400> SEQUENCE: 100

Glu Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Thr
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Synthetic peptide

<400> SEQUENCE: 101

Glu Val Gln Leu Gln Glu Ser Gly Pro Gly Leu Val Lys Ala Ser Gln
1               5                   10                  15

Thr Leu Ser Leu Thr Cys Ala Val Ser Gly Tyr Ser Ile Ser
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: Synthetic peptide

<400> SEQUENCE: 102

Asp Val Gln Leu Gln Glu Ser Gly Pro Gly Leu Val Lys Pro Ser Gln
1               5                   10                  15

Thr Leu Ser Leu Thr Cys Ala Val Ser Gly Tyr Pro Ile Thr
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Synthetic peptide

<400> SEQUENCE: 103

His Val Gln Leu Gln Glu Ser Gly Pro Gly Leu Val Lys Pro Ser Gln

```
            1               5                   10                  15
Thr Leu Ser Leu Thr Cys Ala Val Ser Gly Tyr Ser Ile Thr
                    20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetic peptide

<400> SEQUENCE: 104

Glu Val Gln Leu Gln Glu Ser Gly Pro Gly Leu Val Lys Pro Ser Gln
1               5                   10                  15
Thr Leu Ser Leu Thr Cys Ala Val Ser Gly Tyr Pro Ile Ser
                    20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Synthetic peptide

<400> SEQUENCE: 105

Gln Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Ser
                    20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Synthetic peptide

<400> SEQUENCE: 106

His Val Gln Leu Gln Glu Ser Gly Pro Gly Leu Val Lys Pro Ser Gln
1               5                   10                  15
Thr Leu Ser Leu Thr Cys Ala Val Ser Gly Thr Ser Ile Thr
                    20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Synthetic peptide

<400> SEQUENCE: 107

His Val Gln Leu Gln Glu Ser Gly Pro Gly Leu Val Lys Pro Ser Gln
1               5                   10                  15
Thr Leu Ser Leu Thr Cys Ala Val Ser Gly Asn Ser Ile Ser
                    20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetic peptide

<400> SEQUENCE: 108
```

His Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Ser
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Synthetic peptide

<400> SEQUENCE: 109

His Val Gln Leu Gln Glu Ser Gly Pro Gly Leu Val Lys Pro Ser Gln
1               5                   10                  15
Thr Leu Ser Leu Thr Cys Ala Val Ser Gly Ala Ser Ile Thr
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Synthetic peptide

<400> SEQUENCE: 110

His Val Gln Leu Gln Glu Ser Gly Pro Gly Leu Val Lys Pro Ser Gln
1               5                   10                  15
Thr Leu Ser Leu Thr Cys Ala Val Ser Gly Ser Ser Ile Thr
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetic peptide

<400> SEQUENCE: 111

Asp Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Thr
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Synthetic peptide

<400> SEQUENCE: 112

Asp Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Ser
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Synthetic peptide

<400> SEQUENCE: 113

```
Asp Val Gln Leu Gln Glu Ser Gly Pro Gly Leu Val Lys Pro Ser Gln
1               5                   10                  15

Thr Leu Ser Leu Thr Cys Ala Val Ser Gly Thr Ser Ile Thr
            20                  25                  30
```

<210> SEQ ID NO 114
<211> LENGTH: 30
<212> TYPE: PRT
<213> ORGANISM: Artificial Sequence
<220> FEATURE:
<223> OTHER INFORMATION: Synthetic peptide

<400> SEQUENCE: 114

```
Asp Val Gln Leu Gln Glu Ser Gly Pro Gly Leu Val Lys Pro Ser Gln
1               5                   10                  15

Thr Leu Ser Leu Thr Cys Ala Val Ser Gly Asn Ser Ile Ser
            20                  25                  30
```

<210> SEQ ID NO 115
<211> LENGTH: 30
<212> TYPE: PRT
<213> ORGANISM: Artificial Sequence
<220> FEATURE:
<223> OTHER INFORMATION: Synthetic peptide

<400> SEQUENCE: 115

```
Asp Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr
            20                  25                  30
```

<210> SEQ ID NO 116
<211> LENGTH: 30
<212> TYPE: PRT
<213> ORGANISM: Artificial Sequence
<220> FEATURE:
<223> OTHER INFORMATION: Synthetic peptide

<400> SEQUENCE: 116

```
Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Pro Ile Thr
            20                  25                  30
```

<210> SEQ ID NO 117
<211> LENGTH: 30
<212> TYPE: PRT
<213> ORGANISM: Artificial Sequence
<220> FEATURE:
<223> OTHER INFORMATION: Synthetic peptide

<400> SEQUENCE: 117

```
Glu Val Gln Leu Gln Glu Ser Gly Pro Gly Leu Val Lys Pro Ser Gln
1               5                   10                  15

Thr Leu Ser Leu Thr Cys Ala Val Ser Gly Tyr Pro Ile Thr
            20                  25                  30
```

<210> SEQ ID NO 118
<211> LENGTH: 30
<212> TYPE: PRT
<213> ORGANISM: Artificial Sequence
<220> FEATURE:
<223> OTHER INFORMATION: Synthetic peptide -continued

<400> SEQUENCE: 118

Gln Val Gln Gln Gln Glu Ser Gly Pro Gly Gln Val Lys Pro Ser Gln
1               5                   10                  15

Thr Leu Ser Leu Thr Cys Ala Val Ser Gly Tyr Pro Ile Ser
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Synthetic peptide

<400> SEQUENCE: 119

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr
            20                  25                  30

<210> SEQ ID NO 120
<211> LENGTH: 6
<212> TYPE: PRT
<213> ORGANISM: Artificial Sequence
<220> FEATURE:
<223> OTHER INFORMATION: Synthetic peptide

<400> SEQUENCE: 120

Ser Gly Tyr His Trp Asn
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic peptide

<400> SEQUENCE: 121

Arg Gly Tyr His Trp Asn
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic peptide

<400> SEQUENCE: 122

His Gly Tyr His Trp Asn
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic peptide

<400> SEQUENCE: 123

Asn Gly Tyr His Trp Asn
1               5

<210> SEQ ID NO 124
<211> LENGTH: 6

```
<212> TYPE: PRT
<213> ORGANISM: Artificial Sequence
<220> FEATURE:
<223> OTHER INFORMATION: Synthetic peptide

<400> SEQUENCE: 124

Tyr Gly Tyr His Trp Asn
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic peptide

<400> SEQUENCE: 125

Arg Asp Tyr His Trp Asn
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic peptide

<400> SEQUENCE: 126

Arg Trp Tyr His Trp Asn
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic peptide

<400> SEQUENCE: 127

Asn Phe Tyr His Trp Asn
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic peptide

<400> SEQUENCE: 128

Arg Tyr Tyr His Trp Asn
1               5

<210> SEQ ID NO 129
<211> LENGTH: 14
<212> TYPE: PRT
<213> ORGANISM: Artificial Sequence
<220> FEATURE:
<223> OTHER INFORMATION: Synthetic peptide

<400> SEQUENCE: 129

Trp Ile Arg Gln Phe Pro Gly Asn Lys Leu Glu Trp Ile Gly
1               5                   10

<210> SEQ ID NO 130
<211> LENGTH: 14
<212> TYPE: PRT
```

<213> ORGANISM: Artificial Sequence
<220> FEATURE:
<223> OTHER INFORMATION: Synthetic peptide

<400> SEQUENCE: 130

Trp Val Arg Gln Phe Pro Gly Asn Lys Leu Glu Trp Ile Gly
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Synthetic peptide

<400> SEQUENCE: 131

Trp Ile Gln Gln Phe Pro Gly Asn Lys Leu Glu Trp Ile Gly
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Synthetic peptide

<400> SEQUENCE: 132

Trp Ile Arg Gln Leu Pro Gly Asn Lys Leu Glu Trp Ile Gly
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic peptide

<400> SEQUENCE: 133

Trp Ile Arg Gln Phe Pro Gly Lys Lys Leu Glu Trp Ile Gly
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Synthetic peptide

<400> SEQUENCE: 134

Trp Ile Arg Gln Phe Pro Gly Lys Gly Leu Glu Trp Ile Gly
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic peptide

<400> SEQUENCE: 135

Trp Ile Arg Gln Phe Pro Gly Asn Lys Leu Val Trp Met Gly
1               5                   10

<210> SEQ ID NO 136
<211> LENGTH: 14
<212> TYPE: PRT
<213> ORGANISM: Artificial Sequence

```
<220> FEATURE:
<223> OTHER INFORMATION: Synthetic peptide

<400> SEQUENCE: 136

Trp Ile Arg Gln Phe Pro Gly Lys Ser Leu Glu Trp Ile Gly
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthetic peptide

<400> SEQUENCE: 137

Trp Ile Arg Gln Phe Pro Gly Lys Arg Leu Glu Trp Met Gly
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic peptide

<400> SEQUENCE: 138

Trp Ile Arg Gln Phe Pro Gly Asn Glu Leu Glu Trp Ile Gly
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthetic peptide

<400> SEQUENCE: 139

Trp Ile Arg Gln Phe Pro Gly Asn Arg Leu Glu Trp Ile Gly
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Synthetic peptide

<400> SEQUENCE: 140

Trp Ile Arg Gln Phe Pro Gly Asn Arg Leu Glu Trp Met Gly
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic peptide

<400> SEQUENCE: 141

Trp Ile Arg Gln Phe Pro Gly Asn Lys Leu Glu Trp Met Gly
1               5                   10

<210> SEQ ID NO 142
<211> LENGTH: 16
<212> TYPE: PRT
<213> ORGANISM: Artificial Sequence
<220> FEATURE:
```

<223> OTHER INFORMATION: Synthetic peptide

<400> SEQUENCE: 142

Tyr Ile Ser Tyr Asp Gly Ser Asp His Tyr Asn Pro Ser Leu Glu Asn
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic peptide

<400> SEQUENCE: 143

Tyr Ile Ser Tyr Asp Gly Ser Val Phe Tyr Asn Pro Ser Leu Glu Asn
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic peptide

<400> SEQUENCE: 144

Tyr Ile Ser Tyr Asp Gly Ser Ile Leu Tyr Asn Pro Ser Leu Glu Asn
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Synthetic peptide

<400> SEQUENCE: 145

Tyr Ile Ser Tyr Asp Gly Thr Ile Leu Tyr Asn Pro Ser Leu Glu Asn
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic peptide

<400> SEQUENCE: 146

Tyr Ile Ser Tyr Asp Gly Thr Val Leu Tyr Asn Pro Ser Leu Glu Asn
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic peptide

<400> SEQUENCE: 147

Tyr Ile Ser Tyr Asp Gly Asn Val Leu Tyr Asn Pro Ser Leu Glu Asn
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic peptide

```
<400> SEQUENCE: 148

Tyr Ile Ser Tyr Asp Gly Thr Ser Leu Tyr Asn Pro Ser Leu Glu Asn
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic peptide

<400> SEQUENCE: 149

Tyr Ile Ser Tyr Asp Gly Ser Val Leu Tyr Asn Pro Ser Leu Glu Asn
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic peptide

<400> SEQUENCE: 150

Tyr Ile Ser Tyr Asp Gly Asn Ile Leu Tyr Asn Pro Ser Leu Glu Asn
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic peptide

<400> SEQUENCE: 151

Tyr Ile Ser Tyr Asp Gly Thr Asn Leu Tyr Asn Pro Ser Leu Glu Asn
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic peptide

<400> SEQUENCE: 152

Tyr Ile Ser Tyr Asp Gly Ser Asn Leu Tyr Asn Pro Ser Leu Glu Asn
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic peptide

<400> SEQUENCE: 153

Tyr Ile Ser Tyr Asp Gly Thr Val His Tyr Asn Pro Ser Leu Glu Asn
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 154

Tyr Ile Ser Tyr Asp Gly Thr Ile Arg Tyr Asn Pro Ser Leu Glu Asn
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic peptide

<400> SEQUENCE: 155

Tyr Ile Ser Tyr Asp Gly Ser Val Leu Tyr Asn Pro Ser Leu Lys Ser
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Synthetic peptide

<400> SEQUENCE: 156

Tyr Ile Ser Tyr Asp Gly Ser Val Leu Tyr Asn Pro Ser Leu Lys Gly
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Synthetic peptide

<400> SEQUENCE: 157

Tyr Ile Ala Tyr Asp Gly Val Gln Ser Tyr Asn Pro Ser Leu Lys Gly
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic peptide

<400> SEQUENCE: 158

Tyr Ile Gly Tyr Asp Gly Ala Val Gln Tyr Asn Pro Ser Leu Lys Ser
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Synthetic peptide

<400> SEQUENCE: 159

Tyr Ile Ser Tyr Asn Gly Ser Val Leu Tyr Asn Pro Ser Leu Lys Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Synthetic peptide

<400> SEQUENCE: 160
```

```
Tyr Ile Ser Tyr Asp Gly Ser Arg Leu Tyr Asn Pro Ser Leu Lys Ser
1               5                   10                  15
```

<210> SEQ ID NO 161
<211> LENGTH: 32
<212> TYPE: PRT
<213> ORGANISM: Artificial Sequence
<220> FEATURE:
<223> OTHER INFORMATION: Synthetic peptide

<400> SEQUENCE: 161

```
Arg Ile Thr Ile Thr Arg Asp Thr Ser Lys Asn Gln Phe Ser Leu Ile
1               5                   10                  15

Leu Arg Ser Val Thr Ala Glu Asp Thr Ala Ile Tyr Tyr Cys Ala Ser
            20                  25                  30
```

<210> SEQ ID NO 162
<211> LENGTH: 32
<212> TYPE: PRT
<213> ORGANISM: Artificial Sequence
<220> FEATURE:
<223> OTHER INFORMATION: Synthetic peptide

<400> SEQUENCE: 162

```
Arg Val Thr Ile Thr Arg Asp Thr Ser Lys Asn Gln Phe Phe Leu Lys
1               5                   10                  15

Leu Ser Ser Val Thr Ala Glu Asp Thr Ala Lys Tyr Tyr Cys Ala Ser
            20                  25                  30
```

<210> SEQ ID NO 163
<211> LENGTH: 32
<212> TYPE: PRT
<213> ORGANISM: Artificial Sequence
<220> FEATURE:
<223> OTHER INFORMATION: Synthetic peptide

<400> SEQUENCE: 163

```
Arg Val Thr Ile Thr Arg Asp Thr Ser Lys Asn Gln Phe Phe Leu Lys
1               5                   10                  15

Leu Ser Ser Val Thr Ala Glu Asp Thr Ala Arg Tyr Tyr Cys Ala Ser
            20                  25                  30
```

<210> SEQ ID NO 164
<211> LENGTH: 32
<212> TYPE: PRT
<213> ORGANISM: Artificial Sequence
<220> FEATURE:
<223> OTHER INFORMATION: Synthetic peptide

<400> SEQUENCE: 164

```
Arg Ile Thr Ile Ser Arg Asp Thr Ser Lys Asn Gln Phe Phe Leu Lys
1               5                   10                  15

Leu Arg Ser Val Thr Ala Glu Asp Thr Ala Lys Tyr Phe Cys Ala Ser
            20                  25                  30
```

<210> SEQ ID NO 165
<211> LENGTH: 32
<212> TYPE: PRT
<213> ORGANISM: Artificial Sequence
<220> FEATURE:
<223> OTHER INFORMATION: Synthetic peptide

<400> SEQUENCE: 165

```
Arg Val Ser Ile Thr Arg Asp Thr Ser Lys Asn Gln Phe Phe Leu Ile
```

```
                1               5                  10                  15
Leu Arg Ser Val Thr Ala Glu Asp Thr Ala Ile Tyr Tyr Cys Ala Ser
                20                  25                  30
```

<210> SEQ ID NO 166
<211> LENGTH: 32
<212> TYPE: PRT
<213> ORGANISM: Artificial Sequence
<220> FEATURE:
<223> OTHER INFORMATION: Synthetic peptide

<400> SEQUENCE: 166

```
Arg Val Thr Ile Thr Arg Asp Thr Ser Lys Asn Gln Phe Phe Leu Lys
1               5                   10                  15
Leu Arg Ser Val Thr Ala Glu Asp Thr Ala Ile Tyr Tyr Cys Ala Ser
                20                  25                  30
```

<210> SEQ ID NO 167
<211> LENGTH: 32
<212> TYPE: PRT
<213> ORGANISM: Artificial Sequence
<220> FEATURE:
<223> OTHER INFORMATION: Synthetic peptide

<400> SEQUENCE: 167

```
Arg Val Ser Ile Thr Arg Asp Thr Ser Lys Asn Gln Phe Phe Leu Lys
1               5                   10                  15
Leu Ser Ser Val Thr Ala Glu Asp Thr Ala Lys Tyr Phe Cys Ala Ser
                20                  25                  30
```

<210> SEQ ID NO 168
<211> LENGTH: 32
<212> TYPE: PRT
<213> ORGANISM: Artificial Sequence
<220> FEATURE:
<223> OTHER INFORMATION: Synthetic peptide

<400> SEQUENCE: 168

```
Arg Val Thr Ile Thr Arg Asp Thr Ser Lys Asn Gln Phe Phe Leu Lys
1               5                   10                  15
Leu Arg Ser Val Thr Ala Glu Asp Thr Ala Ile Tyr Phe Cys Ala Ser
                20                  25                  30
```

<210> SEQ ID NO 169
<211> LENGTH: 32
<212> TYPE: PRT
<213> ORGANISM: Artificial Sequence
<220> FEATURE:
<223> OTHER INFORMATION: Synthetic peptide

<400> SEQUENCE: 169

```
Arg Val Thr Ile Ser Val Asp Thr Ser Lys Asn Gln Phe Ser Leu Lys
1               5                   10                  15
Leu Ser Ser Val Thr Ala Glu Asp Thr Ala Val Tyr Tyr Cys Ala Ser
                20                  25                  30
```

<210> SEQ ID NO 170
<211> LENGTH: 32
<212> TYPE: PRT
<213> ORGANISM: Artificial Sequence
<220> FEATURE:
<223> OTHER INFORMATION: Synthetic peptide

<400> SEQUENCE: 170

-continued

Arg Val Ser Ile Ser Arg Asp Ile Ser Lys Asn Gln Phe Phe Leu Lys
1               5                   10                  15

Leu Ser Ser Val Thr Ala Ala Asp Thr Ala Val Tyr Phe Cys Ala Ser
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic peptide

<400> SEQUENCE: 171

Arg Ile Thr Ile Thr Arg Asp Thr Ser Lys Asn Gln Phe Phe Leu Lys
1               5                   10                  15

Leu Arg Ser Val Thr Ala Glu Asp Thr Ala Val Tyr Tyr Cys Ala Ser
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic peptide

<400> SEQUENCE: 172

Arg Val Ser Ile Thr Arg Asp Thr Ser Lys Asn Gln Phe Phe Leu Lys
1               5                   10                  15

Leu Arg Ser Val Thr Ala Glu Asp Thr Ala Ile Tyr Phe Cys Ala Ser
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Synthetic peptide

<400> SEQUENCE: 173

Arg Ile Thr Ile Thr Arg Asp Thr Ser Lys Asn Gln Phe Phe Leu Lys
1               5                   10                  15

Leu Arg Ser Val Thr Ala Glu Asp Thr Ala Lys Tyr Tyr Cys Ala Ser
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Synthetic peptide

<400> SEQUENCE: 174

Arg Val Thr Ile Thr Arg Asp Thr Ser Lys Asn Gln Phe Phe Leu Ile
1               5                   10                  15

Leu Arg Ser Val Thr Ala Glu Asp Thr Ala Lys Tyr Tyr Cys Ala Ser
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Synthetic peptide

<400> SEQUENCE: 175

```
Arg Val Thr Ile Thr Arg Asp Thr Ser Lys Asn Gln Phe Phe Leu Lys
1               5                   10                  15

Leu Arg Ser Val Thr Ala Glu Asp Thr Ala Lys Tyr Tyr Cys Ala Ser
            20                  25                  30
```

<210> SEQ ID NO 176
<211> LENGTH: 32
<212> TYPE: PRT
<213> ORGANISM: Artificial Sequence
<220> FEATURE:
<223> OTHER INFORMATION: Synthetic peptide

<400> SEQUENCE: 176

```
Arg Ile Ser Ile Thr Arg Asp Thr Ser Lys Asn Gln Phe Phe Leu Lys
1               5                   10                  15

Leu Ser Ser Val Thr Ala Glu Asp Thr Ala Lys Tyr Phe Cys Ala Ser
            20                  25                  30
```

<210> SEQ ID NO 177
<211> LENGTH: 32
<212> TYPE: PRT
<213> ORGANISM: Artificial Sequence
<220> FEATURE:
<223> OTHER INFORMATION: Synthetic peptide

<400> SEQUENCE: 177

```
Arg Ile Thr Ile Thr Arg Asp Thr Ser Lys Asn Gln Phe Ser Leu Lys
1               5                   10                  15

Leu Arg Ser Val Thr Ala Glu Asp Thr Ala Val Tyr Tyr Cys Ala Ser
            20                  25                  30
```

<210> SEQ ID NO 178
<211> LENGTH: 32
<212> TYPE: PRT
<213> ORGANISM: Artificial Sequence
<220> FEATURE:
<223> OTHER INFORMATION: Synthetic peptide

<400> SEQUENCE: 178

```
Arg Ile Thr Ile Thr Arg Asp Thr Ser Lys Asn Gln Phe Phe Leu Ile
1               5                   10                  15

Leu Arg Ser Val Thr Ala Glu Asp Thr Ala Ile Tyr Tyr Cys Ala Ser
            20                  25                  30
```

<210> SEQ ID NO 179
<211> LENGTH: 32
<212> TYPE: PRT
<213> ORGANISM: Artificial Sequence
<220> FEATURE:
<223> OTHER INFORMATION: Synthetic peptide

<400> SEQUENCE: 179

```
Arg Val Thr Ile Ser Val Asp Thr Ser Lys Asn Gln Phe Ser Leu Lys
1               5                   10                  15

Leu Ser Ser Val Thr Thr Glu Asp Thr Ala Val Tyr Tyr Cys Ala Ser
            20                  25                  30
```

<210> SEQ ID NO 180
<211> LENGTH: 4
<212> TYPE: PRT
<213> ORGANISM: Artificial Sequence
<220> FEATURE:
<223> OTHER INFORMATION: Synthetic peptide

<400> SEQUENCE: 180

Gly Phe Asp His
1

<210> SEQ ID NO 181
<211> LENGTH: 4
<212> TYPE: PRT
<213> ORGANISM: Artificial Sequence
<220> FEATURE:
<223> OTHER INFORMATION: Synthetic peptide

<400> SEQUENCE: 181

Gly Phe Asp Tyr
1

<210> SEQ ID NO 182
<211> LENGTH: 4
<212> TYPE: PRT
<213> ORGANISM: Artificial Sequence
<220> FEATURE:
<223> OTHER INFORMATION: Synthetic peptide

<400> SEQUENCE: 182

Gly Phe Asp Thr
1

<210> SEQ ID NO 183
<211> LENGTH: 11
<212> TYPE: PRT
<213> ORGANISM: Artificial Sequence
<220> FEATURE:
<223> OTHER INFORMATION: Synthetic peptide

<400> SEQUENCE: 183

Trp Gly Gln Gly Thr Thr Leu Thr Val Ser Ser
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic peptide

<400> SEQUENCE: 184

Trp Gly Gln Gly Thr Leu Val Thr Val Ser Ser
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Synthetic peptide

<400> SEQUENCE: 185

Trp Gly Gln Gly Thr Met Leu Thr Val Ser Ser
1               5                   10

<210> SEQ ID NO 186
<211> LENGTH: 113
<212> TYPE: PRT
<213> ORGANISM: Artificial Sequence
<220> FEATURE:
<223> OTHER INFORMATION: Synthetic peptide

<400> SEQUENCE: 186

```
Asp Val Val Met Thr Gln Ser Pro Leu Ser Leu Pro Val Thr Leu Gly
1               5                   10                  15

Glu Pro Ala Ser Ile Ser Cys Arg Ser Asn Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Thr Glu Asp Val Gly Val Tyr Tyr Cys Ser Gln Asn
                85                  90                  95

Thr His Val Pro Tyr Thr Phe Gly Gly Gly Thr Lys Leu Glu Ile Lys
                100                 105                 110

Arg
```

<210> SEQ ID NO 187
<211> LENGTH: 113
<212> TYPE: PRT
<213> ORGANISM: Artificial Sequence
<220> FEATURE:
<223> OTHER INFORMATION: Synthetic peptide

<400> SEQUENCE: 187

```
Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Thr Glu Asp Leu Gly Val Tyr Tyr Cys Ser Gln Asn
                85                  90                  95

Thr His Val Pro Tyr Thr Phe Gly Gly Gly Thr Lys Leu Glu Ile Lys
                100                 105                 110

Arg
```

<210> SEQ ID NO 188
<211> LENGTH: 113
<212> TYPE: PRT
<213> ORGANISM: Artificial Sequence
<220> FEATURE:
<223> OTHER INFORMATION: Synthetic peptide

<400> SEQUENCE: 188

```
Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

-continued

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 189
<211> LENGTH: 113
<212> TYPE: PRT
<213> ORGANISM: Artificial Sequence
<220> FEATURE:
<223> OTHER INFORMATION: Synthetic peptide

<400> SEQUENCE: 189

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
                20                  25                  30

Tyr Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 190
<211> LENGTH: 113
<212> TYPE: PRT
<213> ORGANISM: Artificial Sequence
<220> FEATURE:
<223> OTHER INFORMATION: Synthetic peptide

<400> SEQUENCE: 190

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
                20                  25                  30

Tyr Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 191

<211> LENGTH: 113
<212> TYPE: PRT
<213> ORGANISM: Artificial Sequence
<220> FEATURE:
<223> OTHER INFORMATION: Synthetic peptide

<400> SEQUENCE: 191

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Ser Gln Asn
                85                  90                  95

Thr His Leu Pro Tyr Thr Phe Gly Gly Gly Thr Lys Leu Glu Ile Lys
            100                 105                 110

Arg

<210> SEQ ID NO 192
<211> LENGTH: 113
<212> TYPE: PRT
<213> ORGANISM: Artificial Sequence
<220> FEATURE:
<223> OTHER INFORMATION: Synthetic peptide

<400> SEQUENCE: 192

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 193
<211> LENGTH: 113
<212> TYPE: PRT
<213> ORGANISM: Artificial Sequence
<220> FEATURE:
<223> OTHER INFORMATION: Synthetic peptide

<400> SEQUENCE: 193

Asp Val Val Met Thr Gln Thr Pro Leu Ser Leu Pro Val Asn Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Asn
                 85                  90                  95

Thr His Val Pro Tyr Thr Phe Gly Gly Gly Thr Lys Leu Glu Ile Lys
                100                 105                 110

Arg

<210> SEQ ID NO 194
<211> LENGTH: 113
<212> TYPE: PRT
<213> ORGANISM: Artificial Sequence
<220> FEATURE:
<223> OTHER INFORMATION: Synthetic peptide

<400> SEQUENCE: 194

Asp Val Val Met Thr Gln Ser Pro Leu Ser Leu Pro Val Thr Leu Gly
 1               5                  10                  15

Glu Pro Ala Ser Ile Ser Cys Arg Ser Ser Gln Ser Leu Val His Ser
                 20                  25                  30

Tyr Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Asn
                 85                  90                  95

Ala Lys Thr Pro Tyr Thr Phe Gly Gln Gly Thr Lys Leu Glu Ile Lys
                100                 105                 110

Arg

<210> SEQ ID NO 195
<211> LENGTH: 113
<212> TYPE: PRT
<213> ORGANISM: Artificial Sequence
<220> FEATURE:
<223> OTHER INFORMATION: Synthetic peptide

<400> SEQUENCE: 195

Asp Val Val Met Thr Gln Ser Pro Leu Ser Leu Pro Val Thr Leu Gly
 1               5                  10                  15

Glu Pro Ala Ser Ile Ser Cys Arg Ser Ser Gln Ser Leu Val His Ser
                 20                  25                  30

Tyr Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Asn
                 85                  90                  95

-continued

Ala Arg Val Pro Tyr Thr Phe Gly Gln Gly Thr Lys Leu Glu Ile Lys
            100                 105                 110

Arg

<210> SEQ ID NO 196
<211> LENGTH: 113
<212> TYPE: PRT
<213> ORGANISM: Artificial Sequence
<220> FEATURE:
<223> OTHER INFORMATION: Synthetic peptide

<400> SEQUENCE: 196

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Ser Tyr Val Pro Tyr Thr Phe Gly Gln Gly Thr Lys Leu Glu Ile Lys
            100                 105                 110

Arg

<210> SEQ ID NO 197
<211> LENGTH: 113
<212> TYPE: PRT
<213> ORGANISM: Artificial Sequence
<220> FEATURE:
<223> OTHER INFORMATION: Synthetic peptide

<400> SEQUENCE: 197

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr Ile Pro Pro Tyr Thr Phe Gly Gln Gly Thr Lys Leu Glu Ile Lys
            100                 105                 110

Arg

<210> SEQ ID NO 198
<211> LENGTH: 113
<212> TYPE: PRT
<213> ORGANISM: Artificial Sequence
<220> FEATURE:
<223> OTHER INFORMATION: Synthetic peptide -continued

<400> SEQUENCE: 198

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Ser Met Ala Pro Tyr Thr Phe Gly Gln Gly Thr Lys Leu Glu Ile Lys
            100                 105                 110

Arg

<210> SEQ ID NO 199
<211> LENGTH: 113
<212> TYPE: PRT
<213> ORGANISM: Artificial Sequence
<220> FEATURE:
<223> OTHER INFORMATION: Synthetic peptide

<400> SEQUENCE: 199

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Pro Thr Tyr Leu His Trp Tyr Leu Gln Lys Pro Gly Gln Ser
        35                  40                  45

Pro Gln Leu Leu Ile Tyr Lys Val Ser Lys Arg Asn Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 200
<211> LENGTH: 113
<212> TYPE: PRT
<213> ORGANISM: Artificial Sequence
<220> FEATURE:
<223> OTHER INFORMATION: Synthetic peptide

<400> SEQUENCE: 200

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Pro Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Tyr Thr Phe Gly Gln Gly Thr Lys Leu Glu Ile Lys
                100                 105                 110

Arg

<210> SEQ ID NO 201
<211> LENGTH: 113
<212> TYPE: PRT
<213> ORGANISM: Artificial Sequence
<220> FEATURE:
<223> OTHER INFORMATION: Synthetic peptide

<400> SEQUENCE: 201

Asp Val Val Met Thr Gln Ser Pro Leu Ser Leu Pro Val Thr Leu Gly
 1               5                  10                  15

Glu Pro Ala Ser Ile Ser Cys Arg Ser Ser Gln Ser Leu Val His Thr
                 20                  25                  30

Tyr Gly Asn Thr Tyr Leu His Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Tyr Thr Phe Gly Gln Gly Thr Lys Leu Glu Ile Lys
                100                 105                 110

Arg

<210> SEQ ID NO 202
<211> LENGTH: 113
<212> TYPE: PRT
<213> ORGANISM: Artificial Sequence
<220> FEATURE:
<223> OTHER INFORMATION: Synthetic peptide

<400> SEQUENCE: 202

Asp Val Val Met Thr Gln Ser Pro Leu Ser Leu Pro Val Thr Leu Gly
 1               5                  10                  15

Glu Pro Ala Ser Ile Ser Cys Arg Ser Ser Gln Ser Leu Val His Pro
                 20                  25                  30

Tyr Gly Ser Thr Tyr Leu His Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Tyr Thr Phe Gly Gln Gly Thr Lys Leu Glu Ile Lys
                100                 105                 110

Arg
```

<210> SEQ ID NO 203
<211> LENGTH: 113
<212> TYPE: PRT
<213> ORGANISM: Artificial Sequence
<220> FEATURE:
<223> OTHER INFORMATION: Synthetic peptide

<400> SEQUENCE: 203

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Arg
            20                  25                  30

Tyr Gly Thr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 204
<211> LENGTH: 113
<212> TYPE: PRT
<213> ORGANISM: Artificial Sequence
<220> FEATURE:
<223> OTHER INFORMATION: Synthetic peptide

<400> SEQUENCE: 204

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Ala Thr Tyr Leu His Trp Tyr Leu Gln Lys Pro Gly Gln Ser
        35                  40                  45

Pro Gln Leu Leu Ile Tyr Lys Ala Ser Gln Arg Asn Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 205
<211> LENGTH: 113
<212> TYPE: PRT
<213> ORGANISM: Artificial Sequence
<220> FEATURE:
<223> OTHER INFORMATION: Synthetic peptide

<400> SEQUENCE: 205

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser

```
            20                  25                  30
Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 206
<211> LENGTH: 113
<212> TYPE: PRT
<213> ORGANISM: Artificial Sequence
<220> FEATURE:
<223> OTHER INFORMATION: Synthetic peptide

<400> SEQUENCE: 206

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Pro Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Ala His Leu Pro Tyr Thr Phe Gly Gln Gly Thr Lys Leu Glu Ile Lys
            100                 105                 110

Arg

<210> SEQ ID NO 207
<211> LENGTH: 113
<212> TYPE: PRT
<213> ORGANISM: Artificial Sequence
<220> FEATURE:
<223> OTHER INFORMATION: Synthetic peptide

<400> SEQUENCE: 207

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Phe Cys Ser Gln Asn
                85                  90                  95
```

```
Thr His Val Pro Tyr Thr Phe Gly Gly Gly Thr Lys Leu Glu Ile Lys
            100                 105                 110
Arg

<210> SEQ ID NO 208
<211> LENGTH: 113
<212> TYPE: PRT
<213> ORGANISM: Artificial Sequence
<220> FEATURE:
<223> OTHER INFORMATION: Synthetic peptide

<400> SEQUENCE: 208

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110
Arg

<210> SEQ ID NO 209
<211> LENGTH: 113
<212> TYPE: PRT
<213> ORGANISM: Artificial Sequence
<220> FEATURE:
<223> OTHER INFORMATION: Synthetic peptide

<400> SEQUENCE: 209

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Arg Thr Tyr Leu His Trp Tyr Leu Gln Lys Pro Gly Gln Ser
        35                  40                  45

Pro Gln Leu Leu Ile Tyr Arg Ser Ser His Arg Asn Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110
Arg

<210> SEQ ID NO 210
<211> LENGTH: 113
<212> TYPE: PRT
<213> ORGANISM: Artificial Sequence
<220> FEATURE:
<223> OTHER INFORMATION: Synthetic peptide
```

<400> SEQUENCE: 210

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 211
<211> LENGTH: 113
<212> TYPE: PRT
<213> ORGANISM: Artificial Sequence
<220> FEATURE:
<223> OTHER INFORMATION: Synthetic peptide

<400> SEQUENCE: 211

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Asp Thr Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

Arg

<210> SEQ ID NO 212
<211> LENGTH: 113
<212> TYPE: PRT
<213> ORGANISM: Artificial Sequence
<220> FEATURE:
<223> OTHER INFORMATION: Synthetic peptide

<400> SEQUENCE: 212

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Thr Glu Asp Leu Gly Val Tyr Tyr Cys Ser Gln Asn
                    85                  90                  95

Thr His Val Pro Tyr Thr Phe Gly Gly Gly Thr Lys Leu Glu Ile Lys
                100                 105                 110

Arg
```

<210> SEQ ID NO 213
<211> LENGTH: 113
<212> TYPE: PRT
<213> ORGANISM: Artificial Sequence
<220> FEATURE:
<223> OTHER INFORMATION: Synthetic peptide

<400> SEQUENCE: 213

```
Asp Val Val Met Thr Gln Ser Pro Leu Ser Leu Pro Val Thr Leu Gly
 1                   5                  10                  15

Glu Gln Ala Ser Ile Ser Cys Arg Ser Ser Gln Ser Leu Val His Ser
                    20                  25                  30

Tyr Gly Asp Thr Tyr Leu His Trp Tyr Leu Gln Lys Pro Gly Gln Ser
                35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Leu Gly Val Tyr Tyr Cys Ser Gln Asn
                    85                  90                  95

Thr His Val Pro Tyr Thr Phe Gly Gly Gly Thr Lys Leu Glu Ile Lys
                100                 105                 110

Arg
```

<210> SEQ ID NO 214
<211> LENGTH: 113
<212> TYPE: PRT
<213> ORGANISM: Artificial Sequence
<220> FEATURE:
<223> OTHER INFORMATION: Synthetic peptide

<400> SEQUENCE: 214

```
Asp Ile Val Met Thr Gln Ser Pro Leu Ser Leu Pro Val Thr Pro Gly
 1                   5                  10                  15

Glu Pro Ala Ser Ile Ser Cys Arg Ser Ser Gln Ser Leu Val His Ser
                    20                  25                  30

Tyr Gly Asp Thr Tyr Leu His Trp Tyr Leu Gln Lys Pro Gly Gln Ser
                35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Val Gly Val Tyr Phe Cys Ser Gln Asn
                    85                  90                  95

Thr His Val Pro Tyr Thr Phe Gly Gly Gly Thr Lys Leu Glu Ile Lys
                100                 105                 110

Arg
```

<210> SEQ ID NO 215
<211> LENGTH: 23
<212> TYPE: PRT
<213> ORGANISM: Artificial Sequence
<220> FEATURE:
<223> OTHER INFORMATION: Synthetic peptide

<400> SEQUENCE: 215

Asp Val Val Met Thr Gln Ser Pro Leu Ser Leu Pro Val Thr Leu Gly
1               5                   10                  15

Glu Pro Ala Ser Ile Ser Cys
            20

<210> SEQ ID NO 216
<211> LENGTH: 23
<212> TYPE: PRT
<213> ORGANISM: Artificial Sequence
<220> FEATURE:
<223> OTHER INFORMATION: Synthetic peptide

<400> SEQUENCE: 216

Asp Ile Val Met Thr Gln Ser Pro Leu Ser Leu Pro Val Thr Leu Gly
1               5                   10                  15

Glu Pro Ala Ser Ile Ser Cys
            20

<210> SEQ ID NO 217
<211> LENGTH: 23
<212> TYPE: PRT
<213> ORGANISM: Artificial Sequence
<220> FEATURE:
<223> OTHER INFORMATION: Synthetic peptide

<400> SEQUENCE: 217

Asp Val Val Met Thr Gln Thr Pro Leu Ser Leu Pro Val Asn Leu Gly
1               5                   10                  15

Glu Pro Ala Ser Ile Ser Cys
            20

<210> SEQ ID NO 218
<211> LENGTH: 23
<212> TYPE: PRT
<213> ORGANISM: Artificial Sequence
<220> FEATURE:
<223> OTHER INFORMATION: Synthetic peptide

<400> SEQUENCE: 218

Asp Ile Val Met Thr Gln Ser Pro Leu Ser Leu Pro Val Thr Leu Gly
1               5                   10                  15

Glu Gln Ala Ser Ile Ser Cys
            20

<210> SEQ ID NO 219
<211> LENGTH: 23
<212> TYPE: PRT
<213> ORGANISM: Artificial Sequence
<220> FEATURE:
<223> OTHER INFORMATION: Synthetic peptide

<400> SEQUENCE: 219

Asp Val Val Met Thr Gln Ser Pro Leu Ser Leu Pro Val Thr Leu Gly
1               5                   10                  15

Glu Gln Ala Ser Ile Ser Cys
            20

```
<210> SEQ ID NO 220
<211> LENGTH: 23
<212> TYPE: PRT
<213> ORGANISM: Artificial Sequence
<220> FEATURE:
<223> OTHER INFORMATION: Synthetic peptide

<400> SEQUENCE: 220

Asp Ile Val Met Thr Gln Ser Pro Leu Ser Leu Pro Val Thr Pro Gly
 1               5                  10                  15

Glu Pro Ala Ser Ile Ser Cys
            20

<210> SEQ ID NO 221
<211> LENGTH: 15
<212> TYPE: PRT
<213> ORGANISM: Artificial Sequence
<220> FEATURE:
<223> OTHER INFORMATION: Synthetic peptide

<400> SEQUENCE: 221

Trp Tyr Leu Gln Lys Pro Gly Gln Ser Pro Lys Leu Leu Ile Tyr
 1               5                  10                  15

<210> SEQ ID NO 222
<211> LENGTH: 15
<212> TYPE: PRT
<213> ORGANISM: Artificial Sequence
<220> FEATURE:
<223> OTHER INFORMATION: Synthetic peptide

<400> SEQUENCE: 222

Trp Tyr Leu Gln Lys Pro Gly Gln Ser Pro Gln Leu Leu Ile Tyr
 1               5                  10                  15

<210> SEQ ID NO 223
<211> LENGTH: 32
<212> TYPE: PRT
<213> ORGANISM: Artificial Sequence
<220> FEATURE:
<223> OTHER INFORMATION: Synthetic peptide

<400> SEQUENCE: 223

Gly Val Pro Asp Arg Phe Ser Gly Ser Gly Ser Gly Thr Asp Phe Thr
 1               5                  10                  15

Leu Lys Ile Ser Arg Val Glu Thr Glu Asp Val Gly Val Tyr Tyr Cys
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Synthetic peptide

<400> SEQUENCE: 224

Gly Val Pro Asp Arg Phe Ser Gly Ser Gly Ser Gly Thr Asp Phe Thr
 1               5                  10                  15

Leu Lys Ile Ser Arg Val Glu Thr Glu Asp Leu Gly Val Tyr Tyr Cys
            20                  25                  30

<210> SEQ ID NO 225
<211> LENGTH: 32
<212> TYPE: PRT
```

```
<213> ORGANISM: Artificial Sequence
<220> FEATURE:
<223> OTHER INFORMATION: Synthetic peptide

<400> SEQUENCE: 225

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Synthetic peptide

<400> SEQUENCE: 226

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Synthetic peptide

<400> SEQUENCE: 227

Gly Val Pro Asp Arg Phe Ser Gly Ser Gly Ser Gly Thr Asp Phe Thr
1               5                   10                  15

Leu Lys Ile Ser Arg Val Glu Thr Glu Asp Leu Gly Val Tyr Phe Cys
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Synthetic peptide

<400> SEQUENCE: 228

Gly Val Pro Asp Arg Phe Ser Gly Ser Gly Ser Gly Thr Asp Phe Thr
1               5                   10                  15

Leu Lys Ile Ser Arg Val Asp Thr Glu Asp Leu Gly Val Tyr Phe Cys
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Synthetic peptide

<400> SEQUENCE: 229

Gly Val Pro Asp Arg Phe Ser Gly Ser Gly Ser Gly Thr Asp Phe Thr
1               5                   10                  15

Leu Lys Ile Ser Arg Val Glu Thr Glu Asp Val Gly Val Tyr Phe Cys
            20                  25                  30

<210> SEQ ID NO 230
<211> LENGTH: 11
```

<212> TYPE: PRT
<213> ORGANISM: Artificial Sequence
<220> FEATURE:
<223> OTHER INFORMATION: Synthetic peptide

<400> SEQUENCE: 230

Phe Gly Gly Gly Thr Lys Leu Glu Ile Lys Arg
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Synthetic peptide

<400> SEQUENCE: 231

Phe Gly Gln Gly Thr Lys Leu Glu Ile Lys Arg
1               5                   10

<210> SEQ ID NO 232
<211> LENGTH: 16
<212> TYPE: PRT
<213> ORGANISM: Artificial Sequence
<220> FEATURE:
<223> OTHER INFORMATION: Synthetic peptide

<400> SEQUENCE: 232

Arg Ser Asn Gln Ser Leu Val His Ser Tyr Gly Asp Thr Tyr Leu His
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Synthetic peptide

<400> SEQUENCE: 233

Arg Ser Ser Gln Ser Leu Val His Ser Tyr Gly Asp Thr Tyr Leu His
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Synthetic peptide

<400> SEQUENCE: 234

Arg Ser Ser Gln Ser Leu Val His Pro Tyr Gly Pro Thr Tyr Leu His
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Synthetic peptide

<400> SEQUENCE: 235

Arg Ser Ser Gln Ser Leu Val His Thr Tyr Gly Asn Thr Tyr Leu His
1               5                   10                  15

<210> SEQ ID NO 236
<211> LENGTH: 16
<212> TYPE: PRT

<213> ORGANISM: Artificial Sequence
<220> FEATURE:
<223> OTHER INFORMATION: Synthetic peptide

<400> SEQUENCE: 236

Arg Ser Ser Gln Ser Leu Val His Pro Tyr Gly Ser Thr Tyr Leu His
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic peptide

<400> SEQUENCE: 237

Arg Ser Ser Gln Ser Leu Val His Arg Tyr Gly Thr Thr Tyr Leu His
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Synthetic peptide

<400> SEQUENCE: 238

Arg Ser Ser Gln Ser Leu Val His Pro Tyr Gly Ala Thr Tyr Leu His
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Synthetic peptide

<400> SEQUENCE: 239

Arg Ser Ser Gln Ser Leu Val His Pro Tyr Gly Arg Thr Tyr Leu His
1               5                   10                  15

<210> SEQ ID NO 240
<211> LENGTH: 7
<212> TYPE: PRT
<213> ORGANISM: Artificial Sequence
<220> FEATURE:
<223> OTHER INFORMATION: Synthetic peptide

<400> SEQUENCE: 240

Lys Val Ser Asn Arg Phe Ser
1               5

<210> SEQ ID NO 241
<211> LENGTH: 7
<212> TYPE: PRT
<213> ORGANISM: Artificial Sequence
<220> FEATURE:
<223> OTHER INFORMATION: Synthetic peptide

<400> SEQUENCE: 241

Lys Val Ser Lys Arg Asn Ser
1               5

<210> SEQ ID NO 242
<211> LENGTH: 7
<212> TYPE: PRT
<213> ORGANISM: Artificial Sequence

```
<220> FEATURE:
<223> OTHER INFORMATION: Synthetic peptide

<400> SEQUENCE: 242

Lys Ala Ser Gln Arg Asn Ser
1               5

<210> SEQ ID NO 243
<211> LENGTH: 7
<212> TYPE: PRT
<213> ORGANISM: Artificial Sequence
<220> FEATURE:
<223> OTHER INFORMATION: Synthetic peptide

<400> SEQUENCE: 243

Arg Ser Ser His Arg Asn Ser
1               5

<210> SEQ ID NO 244
<211> LENGTH: 9
<212> TYPE: PRT
<213> ORGANISM: Artificial Sequence
<220> FEATURE:
<223> OTHER INFORMATION: Synthetic peptide

<400> SEQUENCE: 244

Ser Gln Asn Thr His Val Pro Tyr Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Synthetic peptide

<400> SEQUENCE: 245

Ser Gln Asn Thr His Leu Pro Tyr Thr
1               5

<210> SEQ ID NO 246
<211> LENGTH: 9
<212> TYPE: PRT
<213> ORGANISM: Artificial Sequence
<220> FEATURE:
<223> OTHER INFORMATION: Synthetic peptide

<400> SEQUENCE: 246

Gly Gln Asn Ala Lys Thr Pro Tyr Thr
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic peptide

<400> SEQUENCE: 247

Gly Gln Asn Ala Arg Val Pro Tyr Thr
1               5

<210> SEQ ID NO 248
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 248

Ser Gln Asn Ser Tyr Val Pro Tyr Thr
1               5

<210> SEQ ID NO 249
<211> LENGTH: 9
<212> TYPE: PRT
<213> ORGANISM: Artificial Sequence
<220> FEATURE:
<223> OTHER INFORMATION: Synthetic peptide

<400> SEQUENCE: 249

Ser Gln Asn Thr Ile Pro Pro Tyr Thr
1               5

<210> SEQ ID NO 250
<211> LENGTH: 9
<212> TYPE: PRT
<213> ORGANISM: Artificial Sequence
<220> FEATURE:
<223> OTHER INFORMATION: Synthetic peptide

<400> SEQUENCE: 250

Gly Gln Asn Ser Met Ala Pro Tyr Thr
1               5

<210> SEQ ID NO 251
<211> LENGTH: 9
<212> TYPE: PRT
<213> ORGANISM: Artificial Sequence
<220> FEATURE:
<223> OTHER INFORMATION: Synthetic peptide

<400> SEQUENCE: 251

Gly Gln Asn Ala His Leu Pro Tyr Thr
1               5

<210> SEQ ID NO 252
<211> LENGTH: 59
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (38)..(39)
<223> OTHER INFORMATION: n is a, c, g, or t

<400> SEQUENCE: 252
gactgtgaga gttgtgcctt ggccccagtg gtcaaavnna ctcgcacagt aatatatgg       59

<210> SEQ ID NO 253
<211> LENGTH: 43
<212> TYPE: DNA
<213> ORGANISM: Artificial Sequence
<220> FEATURE:
<223> OTHER INFORMATION: Synthetic nucleotide

<400> SEQUENCE: 253
gcacaactct cacagtctcc tcaggaggtg gcggatctgg agg                        43

<210> SEQ ID NO 254
<211> LENGTH: 51
<212> TYPE: DNA
<213> ORGANISM: Artificial Sequence
```

```
<220> FEATURE:
<223> OTHER INFORMATION: Synthetic nucleotide

<400> SEQUENCE: 254
gttattactc gtggcccagc cggccatggc agaggtgcag ctgcaggagt c       51

<210> SEQ ID NO 255
<211> LENGTH: 51
<212> TYPE: DNA
<213> ORGANISM: Artificial Sequence
<220> FEATURE:
<223> OTHER INFORMATION: Synthetic nucleotide

<400> SEQUENCE: 255
gtcgaccagg cccccgaggc ccgttttat ttccagcttg gtcccccctc c        51

<210> SEQ ID NO 256
<211> LENGTH: 59
<212> TYPE: DNA
<213> ORGANISM: Artificial Sequence
<220> FEATURE:
<223> OTHER INFORMATION: Synthetic nucleotide

<400> SEQUENCE: 256
acggatctct agcgaattca tgggaaggct tacttcttca ttcctgctac tgattgtcc    59

<210> SEQ ID NO 257
<211> LENGTH: 38
<212> TYPE: DNA
<213> ORGANISM: Artificial Sequence
<220> FEATURE:
<223> OTHER INFORMATION: Synthetic nucleotide

<400> SEQUENCE: 257
tgggcccttg aagcttgctg aggagactgt gagagttg                      38

<210> SEQ ID NO 258
<211> LENGTH: 43
<212> TYPE: DNA
<213> ORGANISM: Artificial Sequence
<220> FEATURE:
<223> OTHER INFORMATION: Synthetic nucleotide

<400> SEQUENCE: 258
ttttcctttt gcggccgctt atttacccgg agacagggag agg                43

<210> SEQ ID NO 259
<211> LENGTH: 59
<212> TYPE: DNA
<213> ORGANISM: Artificial Sequence
<220> FEATURE:
<223> OTHER INFORMATION: Synthetic nucleotide

<400> SEQUENCE: 259
cggatctcta gcgaattcat gtctgtgcca actcaggtcc tggggttgct gctgctgtg    59

<210> SEQ ID NO 260
<211> LENGTH: 40
<212> TYPE: DNA
<213> ORGANISM: Artificial Sequence
<220> FEATURE:
<223> OTHER INFORMATION: Synthetic nucleotide

<400> SEQUENCE: 260
acagatggtg cagccacagt ccgtttttatt tccagcttgg                   40
```

<210> SEQ ID NO 261
<211> LENGTH: 33
<212> TYPE: DNA
<213> ORGANISM: Artificial Sequence
<220> FEATURE:
<223> OTHER INFORMATION: Synthetic nucleotide

<400> SEQUENCE: 261
actgtggctg caccatctgt cttcatcttc ccg                                    33

<210> SEQ ID NO 262
<211> LENGTH: 52
<212> TYPE: DNA
<213> ORGANISM: Artificial Sequence
<220> FEATURE:
<223> OTHER INFORMATION: Synthetic nucleotide

<400> SEQUENCE: 262
aaacgggccc tctagattaa cactctcccc tgttgaagct ctttgtgacg gg               52

<210> SEQ ID NO 263
<211> LENGTH: 113
<212> TYPE: PRT
<213> ORGANISM: Artificial Sequence
<220> FEATURE:
<223> OTHER INFORMATION: Synthetic peptide

<400> SEQUENCE: 263

Gln Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Thr Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 264
<211> LENGTH: 113
<212> TYPE: PRT
<213> ORGANISM: Artificial Sequence
<220> FEATURE:
<223> OTHER INFORMATION: Synthetic peptide

<400> SEQUENCE: 264

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Asn Lys Leu Glu Trp
        35                  40                  45

Ile Gly Tyr Ile Ser Tyr Asp Gly Ser Val Leu Tyr Asn Pro Ser Leu
    50                  55                  60

Glu Asn Arg Val Thr Ile Thr Arg Asp Thr Ser Lys Asn Gln Phe Ser
65                  70                  75                  80

Leu Lys Leu Ser Ser Val Thr Thr Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 265
<211> LENGTH: 113
<212> TYPE: PRT
<213> ORGANISM: Artificial Sequence
<220> FEATURE:
<223> OTHER INFORMATION: Synthetic peptide

<400> SEQUENCE: 265

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Tyr Gly
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Val Leu Tyr Asn Pro Ser Leu
50                  55                  60

Glu Asn Arg Val Thr Ile Thr Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 266
<211> LENGTH: 113
<212> TYPE: PRT
<213> ORGANISM: Artificial Sequence
<220> FEATURE:
<223> OTHER INFORMATION: Synthetic peptide

<400> SEQUENCE: 266

Gln Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr Tyr Gly
                20                  25                  30

Tyr His Trp Asn Trp Ile Arg Gln Phe Pro Gly Asn Lys Leu Glu Trp
            35                  40                  45

Ile Gly Tyr Ile Ser Tyr Asp Gly Ser Val Leu Tyr Asn Pro Ser Leu
50                  55                  60

Glu Asn Arg Val Thr Ile Thr Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 267

```
<211> LENGTH: 113
<212> TYPE: PRT
<213> ORGANISM: Artificial Sequence
<220> FEATURE:
<223> OTHER INFORMATION: Synthetic peptide

<400> SEQUENCE: 267

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Arg Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 268
<211> LENGTH: 113
<212> TYPE: PRT
<213> ORGANISM: Artificial Sequence
<220> FEATURE:
<223> OTHER INFORMATION: Synthetic peptide

<400> SEQUENCE: 268

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Val Ser Val Asp Thr Ser Lys Asn Gln Phe Ser
65                  70                  75                  80

Leu Lys Leu Ser Ser Val Thr Thr Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser

<210> SEQ ID NO 269
<211> LENGTH: 113
<212> TYPE: PRT
<213> ORGANISM: Artificial Sequence
<220> FEATURE:
<223> OTHER INFORMATION: Synthetic peptide

<400> SEQUENCE: 269

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30
```

```
Tyr His Trp Asn Trp Ile Arg Gln Phe Pro Gly Lys Gly Leu Glu Trp
            35                  40                  45

Ile Gly Tyr Ile Ser Tyr Asp Gly Ser Val Leu Tyr Asn Pro Ser Leu
 50                      55                  60

Lys Ser Arg Val Thr Ile Ser Val Asp Thr Ser Lys Asn Gln Phe Ser
 65                  70                  75                  80

Leu Lys Leu Ser Ser Val Thr Thr Glu Asp Ser Ala Val Tyr Tyr Cys
                 85                  90                  95

Ser Ser Gly Phe Asp His Trp Gly Gln Gly Thr Leu Val Thr Val Ser
            100                 105                 110

Ser
```

<210> SEQ ID NO 270
<211> LENGTH: 113
<212> TYPE: PRT
<213> ORGANISM: Artificial Sequence
<220> FEATURE:
<223> OTHER INFORMATION: Synthetic peptide

<400> SEQUENCE: 270

```
Gln Val Gln Leu Gln Glu Ser Gly Pro Gly Leu Val Lys Pro Ser Gln
 1               5                   10                  15

Thr Leu Ser Leu Thr Cys Ala Val Ser Gly Tyr Ser Ile Ser Arg Gly
             20                  25                  30

Tyr His Trp Asn Trp Ile Arg Gln Phe Pro Gly Lys Gly Leu Glu Trp
            35                  40                  45

Ile Gly Tyr Ile Ser Tyr Asp Gly Ser Val Leu Tyr Asn Pro Ser Leu
 50                      55                  60

Lys Ser Arg Val Thr Ile Ser Val Asp Thr Ser Lys Asn Gln Phe Ser
 65                  70                  75                  80

Leu Lys Leu Ser Ser Val Thr Thr Glu Asp Thr Ala Val Tyr Tyr Cys
                 85                  90                  95

Ala Ser Gly Phe Asp His Trp Gly His Gly Thr Leu Val Thr Val Ser
            100                 105                 110

Ser
```

<210> SEQ ID NO 271
<211> LENGTH: 113
<212> TYPE: PRT
<213> ORGANISM: Artificial Sequence
<220> FEATURE:
<223> OTHER INFORMATION: Synthetic peptide

<400> SEQUENCE: 271

```
Gln Val Gln Leu Gln Glu Ser Gly Pro Gly Leu Val Lys Pro Ser Gln
 1               5                   10                  15

Thr Leu Ser Leu Thr Cys Ala Val Ser Gly Tyr Ser Ile Ser Arg Gly
             20                  25                  30

Tyr His Trp Asn Trp Ile Arg Gln Tyr Pro Gly Lys Gly Leu Glu Trp
            35                  40                  45

Ile Gly Tyr Ile Ser Tyr Asp Gly Ser Val Leu Tyr Asn Pro Ser Leu
 50                      55                  60

Lys Ser Arg Val Ala Ile Ser Val Asp Thr Ser Lys Asn Gln Phe Ser
 65                  70                  75                  80

Leu Lys Leu Ser Ser Val Thr Ala Glu Asp Thr Ala Val Tyr Tyr Cys
                 85                  90                  95
```

Ala Ser Gly Phe Asp His Trp Gly Gln Gly Thr Leu Val Thr Val Ser
                100                 105                 110

Ser

<210> SEQ ID NO 272
<211> LENGTH: 113
<212> TYPE: PRT
<213> ORGANISM: Artificial Sequence
<220> FEATURE:
<223> OTHER INFORMATION: Synthetic peptide

<400> SEQUENCE: 272

Gln Val Gln Leu Gln Glu Ser Gly Pro Gly Leu Val Lys Pro Ser Gln
1               5                   10                  15

Thr Leu Ser Leu Ser Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
                100                 105                 110

Ser

<210> SEQ ID NO 273
<211> LENGTH: 113
<212> TYPE: PRT
<213> ORGANISM: Artificial Sequence
<220> FEATURE:
<223> OTHER INFORMATION: Synthetic peptide

<400> SEQUENCE: 273

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Leu Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
                100                 105                 110

Ser

<210> SEQ ID NO 274
<211> LENGTH: 113
<212> TYPE: PRT
<213> ORGANISM: Artificial Sequence
<220> FEATURE:
<223> OTHER INFORMATION: Synthetic peptide

<400> SEQUENCE: 274

Gln Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Ser Arg Gly
            20                  25                  30
Tyr His Trp Asn Trp Ile Arg Gln Phe Pro Gly Lys Gly Leu Glu Trp
        35                  40                  45
Ile Gly Tyr Ile Ser Tyr Asp Gly Ser Val Leu Tyr Asn Pro Ser Leu
    50                  55                  60
Lys Ser Arg Val Thr Ile Ser Glu Asp Thr Ser Lys Asn Gln Phe Ser
65                  70                  75                  80
Leu Lys Leu Ser Ser Val Thr Ala Glu Asp Thr Ala Val Tyr Tyr Cys
                85                  90                  95
Ala Ser Gly Phe Asp His Trp Gly Gln Gly Thr Leu Val Thr Val Ser
            100                 105                 110
Ser

<210> SEQ ID NO 275
<211> LENGTH: 113
<212> TYPE: PRT
<213> ORGANISM: Artificial Sequence
<220> FEATURE:
<223> OTHER INFORMATION: Synthetic peptide

<400> SEQUENCE: 275

Gln Val Gln Leu Gln Glu Ser Gly Pro Gly Leu Val Lys Pro Ser Gln
1               5                   10                  15
Thr Leu Ser Leu Thr Cys Ala Val Ser Gly Tyr Ser Ile Ser Ser Gly
            20                  25                  30
Tyr His Trp Asn Trp Ile Arg Gln Phe Pro Gly Lys Gly Leu Glu Trp
        35                  40                  45
Ile Gly Tyr Ile Ser Tyr Asp Gly Ser Val Leu Tyr Asn Pro Ser Leu
    50                  55                  60
Lys Ser Arg Val Thr Ile Ser Met Asp Thr Ser Lys Asn His Phe Ser
65                  70                  75                  80
Leu Lys Leu Ser Ser Val Thr Ala Glu Asp Thr Ala Val Tyr Tyr Cys
                85                  90                  95
Ala Ser Gly Phe Asp His Trp Gly Gln Gly Thr Leu Val Thr Val Ser
            100                 105                 110
Ser

<210> SEQ ID NO 276
<211> LENGTH: 113
<212> TYPE: PRT
<213> ORGANISM: Artificial Sequence
<220> FEATURE:
<223> OTHER INFORMATION: Synthetic peptide

<400> SEQUENCE: 276

Gln Val Gln Leu Gln Glu Ser Gly Pro Gly Arg Val Lys Pro Ser Gln
1               5                   10                  15
Thr Leu Ser Leu Thr Cys Ala Val Ser Gly Tyr Ser Ile Ser Arg Gly
            20                  25                  30
Tyr His Trp Asn Trp Ile Arg Gln Phe Pro Gly Lys Gly Leu Glu Trp
        35                  40                  45
Ile Gly Tyr Ile Ser Tyr Asp Gly Ser Val Leu Tyr Asn Pro Ser Leu
    50                  55                  60

```
Lys Ser Arg Val Thr Ile Ser Val Asp Thr Ser Lys Asn Gln Phe Ser
65                  70                  75                  80

Leu Lys Leu Ser Ser Val Thr Thr Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser
```

<210> SEQ ID NO 277
<211> LENGTH: 113
<212> TYPE: PRT
<213> ORGANISM: Artificial Sequence
<220> FEATURE:
<223> OTHER INFORMATION: Synthetic peptide

<400> SEQUENCE: 277

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
                20                  25                  30

Tyr His Trp Asn Trp Ile Arg Gln Phe Pro Gly Lys Gly Leu Glu Trp
            35                  40                  45

Ile Gly Tyr Ile Ser Tyr Asp Gly Ser Val Leu Phe Asn Pro Ser Leu
        50                  55                  60

Lys Ser Arg Val Thr Ile Ser Val Asp Arg Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Pro Gly Thr Gln Val Thr Val Ser
            100                 105                 110

Ser
```

<210> SEQ ID NO 278
<211> LENGTH: 113
<212> TYPE: PRT
<213> ORGANISM: Artificial Sequence
<220> FEATURE:
<223> OTHER INFORMATION: Synthetic peptide

<400> SEQUENCE: 278

```
Gln Val Gln Leu Gln Glu Ser Gly Pro Gly Leu Val Lys Pro Ser Gln
1               5                   10                  15

Thr Leu Ser Leu Ser Cys Ala Val Ser Gly Tyr Ser Ile Ser Ser Gly
                20                  25                  30

Tyr His Trp Asn Trp Ile Arg Gln Phe Pro Gly Lys Gly Leu Glu Trp
            35                  40                  45

Ile Gly Tyr Ile Ser Tyr Asp Gly Ser Val Leu Tyr Asn Pro Ser Leu
        50                  55                  60

Lys Ser Arg Val Thr Ile Gly Val Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Ser Gly Phe Asp His Trp Gly Gln Gly Thr Leu Val Thr Val Ser
            100                 105                 110

Ser
```

```
<210> SEQ ID NO 279
<211> LENGTH: 113
<212> TYPE: PRT
<213> ORGANISM: Artificial Sequence
<220> FEATURE:
<223> OTHER INFORMATION: Synthetic peptide

<400> SEQUENCE: 279
```

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Arg Gly
            20                  25                  30

Tyr His Trp Asn Trp Ile Arg Gln Phe Pro Gly Lys Gly Leu Glu Trp
        35                  40                  45

Ile Gly Tyr Ile Ser Tyr Asp Gly Ser Val Leu Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Arg Ser Val Thr Asp Glu Asp Ser Ala Val Tyr Tyr Cys
                85                  90                  95

Ala Ser Gly Phe Asp His Trp Gly Gln Gly Thr Leu Val Thr Val Ser
            100                 105                 110

Ser

```
<210> SEQ ID NO 280
<211> LENGTH: 30
<212> TYPE: PRT
<213> ORGANISM: Artificial Sequence
<220> FEATURE:
<223> OTHER INFORMATION: Synthetic peptide

<400> SEQUENCE: 280
```

Gln Val Gln Leu Gln Glu Ser Gly Pro Gly Leu Val Lys Pro Ser Gln
1               5                   10                  15

Thr Leu Ser Leu Thr Cys Ala Val Ser Gly Ser Ser Ile Thr
            20                  25                  30

```
<210> SEQ ID NO 281
<211> LENGTH: 30
<212> TYPE: PRT
<213> ORGANISM: Artificial Sequence
<220> FEATURE:
<223> OTHER INFORMATION: Synthetic peptide

<400> SEQUENCE: 281
```

Gln Val Gln Leu Gln Glu Ser Gly Pro Gly Leu Val Lys Pro Ser Gln
1               5                   10                  15

Thr Leu Ser Leu Ser Cys Ala Val Ser Gly Tyr Ser Ile Ser
            20                  25                  30

```
<210> SEQ ID NO 282
<211> LENGTH: 30
<212> TYPE: PRT
<213> ORGANISM: Artificial Sequence
<220> FEATURE:
<223> OTHER INFORMATION: Synthetic peptide

<400> SEQUENCE: 282
```

Gln Val Gln Leu Gln Glu Ser Gly Pro Gly Arg Val Lys Pro Ser Gln
1               5                   10                  15

Thr Leu Ser Leu Thr Cys Ala Val Ser Gly Tyr Ser Ile Ser
            20                  25                  30

<210> SEQ ID NO 283
<211> LENGTH: 14
<212> TYPE: PRT
<213> ORGANISM: Artificial Sequence
<220> FEATURE:
<223> OTHER INFORMATION: Synthetic peptide

<400> SEQUENCE: 283

Trp Ile Arg Gln Tyr Pro Gly Lys Gly Leu Glu Trp Ile Gly
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Synthetic peptide

<400> SEQUENCE: 284

Trp Ile Arg Gln Phe Pro Gly Lys Gly Leu Glu Trp Leu Gly
1               5                   10

<210> SEQ ID NO 285
<211> LENGTH: 16
<212> TYPE: PRT
<213> ORGANISM: Artificial Sequence
<220> FEATURE:
<223> OTHER INFORMATION: Synthetic peptide

<400> SEQUENCE: 285

Tyr Ile Ser Tyr Asp Gly Ser Val Leu Phe Asn Pro Ser Leu Lys Ser
1               5                   10                  15

<210> SEQ ID NO 286
<211> LENGTH: 32
<212> TYPE: PRT
<213> ORGANISM: Artificial Sequence
<220> FEATURE:
<223> OTHER INFORMATION: Synthetic peptide

<400> SEQUENCE: 286

Arg Val Thr Ile Thr Arg Asp Thr Ser Lys Asn Gln Phe Ser Leu Lys
1               5                   10                  15

Leu Ser Ser Val Thr Thr Glu Asp Thr Ala Val Tyr Tyr Cys Ala Ser
            20                  25                  30

<210> SEQ ID NO 287
<211> LENGTH: 32
<212> TYPE: PRT
<213> ORGANISM: Artificial Sequence
<220> FEATURE:
<223> OTHER INFORMATION: Synthetic peptide

<400> SEQUENCE: 287

Arg Val Thr Ile Thr Arg Asp Thr Ser Lys Asn Gln Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 288
<211> LENGTH: 32
<212> TYPE: PRT
<213> ORGANISM: Artificial Sequence
<220> FEATURE:
<223> OTHER INFORMATION: Synthetic peptide

<400> SEQUENCE: 288

Arg Val Thr Ile Ser Val Asp Arg Ser Lys Asn Gln Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 289
<211> LENGTH: 32
<212> TYPE: PRT
<213> ORGANISM: Artificial Sequence
<220> FEATURE:
<223> OTHER INFORMATION: Synthetic peptide

<400> SEQUENCE: 289

Arg Val Thr Val Ser Val Asp Thr Ser Lys Asn Gln Phe Ser Leu Lys
1               5                   10                  15

Leu Ser Ser Val Thr Thr Glu Asp Thr Ala Val Tyr Tyr Cys Ala Ser
            20                  25                  30

<210> SEQ ID NO 290
<211> LENGTH: 32
<212> TYPE: PRT
<213> ORGANISM: Artificial Sequence
<220> FEATURE:
<223> OTHER INFORMATION: Synthetic peptide

<400> SEQUENCE: 290

Arg Val Thr Ile Ser Val Asp Thr Ser Lys Asn Gln Phe Ser Leu Lys
1               5                   10                  15

Leu Ser Ser Val Thr Thr Glu Asp Ser Ala Val Tyr Tyr Cys Ser Ser
            20                  25                  30

<210> SEQ ID NO 291
<211> LENGTH: 32
<212> TYPE: PRT
<213> ORGANISM: Artificial Sequence
<220> FEATURE:
<223> OTHER INFORMATION: Synthetic peptide

<400> SEQUENCE: 291

Arg Val Ala Ile Ser Val Asp Thr Ser Lys Asn Gln Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Synthetic peptide

<400> SEQUENCE: 292

Arg Val Thr Ile Ser Glu Asp Thr Ser Lys Asn Gln Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 293
<211> LENGTH: 32
<212> TYPE: PRT
<213> ORGANISM: Artificial Sequence
<220> FEATURE:

<223> OTHER INFORMATION: Synthetic peptide

<400> SEQUENCE: 293

Arg Val Thr Ile Ser Met Asp Thr Ser Lys Asn His Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Synthetic peptide

<400> SEQUENCE: 294

Arg Val Thr Ile Gly Val Asp Thr Ser Lys Asn Gln Phe Ser Leu Lys
1               5                   10                  15

Leu Ser Ser Val Thr Ala Glu Asp Thr Ala Val Tyr Tyr Cys Ala Ser
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Synthetic peptide

<400> SEQUENCE: 295

Arg Val Thr Ile Ser Val Asp Thr Ser Lys Asn Gln Phe Ser Leu Lys
1               5                   10                  15

Leu Arg Ser Val Thr Asp Glu Asp Ser Ala Val Tyr Tyr Cys Ala Ser
            20                  25                  30

<210> SEQ ID NO 296
<211> LENGTH: 11
<212> TYPE: PRT
<213> ORGANISM: Artificial Sequence
<220> FEATURE:
<223> OTHER INFORMATION: Synthetic peptide

<400> SEQUENCE: 296

Trp Gly His Gly Thr Leu Val Thr Val Ser Ser
1               5                   10

<210> SEQ ID NO 297
<211> LENGTH: 11
<212> TYPE: PRT
<213> ORGANISM: Artificial Sequence
<220> FEATURE:
<223> OTHER INFORMATION: Synthetic peptide

<400> SEQUENCE: 297

Trp Gly Pro Gly Thr Gln Val Thr Val Ser Ser
1               5                   10

<210> SEQ ID NO 298
<211> LENGTH: 113
<212> TYPE: PRT
<213> ORGANISM: Artificial Sequence
<220> FEATURE:
<223> OTHER INFORMATION: Synthetic peptide

<400> SEQUENCE: 298

Asp Val Val Met Thr Gln Ser Pro Ile Ser Leu Pro Val Thr Leu Gly

```
                1               5                  10                  15
            Glu Pro Ala Ser Ile Ser Cys Arg Ser Ser Gln Ser Leu Val His Pro
                            20                  25                  30

Tyr Gly Ser Thr Tyr Leu His Trp Tyr Leu Gln Lys Pro Gly Gln Ser
                        35                  40                  45

Pro Gln Leu Leu Ile Tyr Lys Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Ser Gln Asn
                            85                  90                  95

Thr His Val Pro Tyr Thr Phe Gly Gln Gly Thr Lys Leu Glu Ile Lys
                            100                 105                 110

Arg

<210> SEQ ID NO 299
<211> LENGTH: 113
<212> TYPE: PRT
<213> ORGANISM: Artificial Sequence
<220> FEATURE:
<223> OTHER INFORMATION: Synthetic peptide

<400> SEQUENCE: 299

Asp Val Val Met Thr Gln Ser Pro Leu Ser Leu Pro Val Thr Leu Gly
            1               5                   10                  15

Glu Pro Ala Ser Ile Ser Cys Arg Ser Ser Gln Ser Leu Val His Pro
                            20                  25                  30

Tyr Gly Ser Thr Tyr Leu His Trp Tyr Leu Gln Lys Pro Gly Gln Pro
                        35                  40                  45

Pro Gln Leu Leu Ile Tyr Lys Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Ser Gln Asn
                            85                  90                  95

Thr His Val Pro Tyr Thr Phe Gly Gln Gly Thr Lys Leu Glu Ile Lys
                            100                 105                 110

Arg

<210> SEQ ID NO 300
<211> LENGTH: 113
<212> TYPE: PRT
<213> ORGANISM: Artificial Sequence
<220> FEATURE:
<223> OTHER INFORMATION: Synthetic peptide

<400> SEQUENCE: 300

Asp Val Val Met Thr Gln Ser Pro Leu Ser Leu Ser Val Thr Leu Gly
            1               5                   10                  15

Glu Pro Ala Ser Ile Ser Cys Arg Ser Ser Gln Ser Leu Val His Pro
                            20                  25                  30

Tyr Gly Pro Thr Tyr Leu His Trp Tyr Leu Gln Lys Pro Gly Gln Ser
                        35                  40                  45

Pro Gln Leu Leu Ile Tyr Lys Val Ser Asn Arg Phe Ser Gly Val Pro
                    50                  55                  60

Asp Arg Phe Ser Gly Ser Gly Ser Gly Thr Asp Tyr Thr Leu Lys Ile
            65                  70                  75                  80
```

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Leu Glu Ile Lys
            100                 105                 110

Arg

<210> SEQ ID NO 301
<211> LENGTH: 113
<212> TYPE: PRT
<213> ORGANISM: Artificial Sequence
<220> FEATURE:
<223> OTHER INFORMATION: Synthetic peptide

<400> SEQUENCE: 301

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Tyr Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Tyr Thr Phe Gly Gln Gly Thr Lys Leu Glu Ile Lys
            100                 105                 110

Arg

<210> SEQ ID NO 302
<211> LENGTH: 113
<212> TYPE: PRT
<213> ORGANISM: Artificial Sequence
<220> FEATURE:
<223> OTHER INFORMATION: Synthetic peptide

<400> SEQUENCE: 302

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Tyr Gly Pro Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Ala Tyr Tyr Cys Ser Gln Asn
            85                  90                  95

Thr His Val Pro Tyr Thr Phe Gly Gln Gly Thr Lys Leu Glu Ile Lys
            100                 105                 110

Arg

<210> SEQ ID NO 303
<211> LENGTH: 113
<212> TYPE: PRT

<213> ORGANISM: Artificial Sequence
<220> FEATURE:
<223> OTHER INFORMATION: Synthetic peptide

<400> SEQUENCE: 303

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Pro
            20                  25                  30

Phe Gly Pro Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 304
<211> LENGTH: 113
<212> TYPE: PRT
<213> ORGANISM: Artificial Sequence
<220> FEATURE:
<223> OTHER INFORMATION: Synthetic peptide

<400> SEQUENCE: 304

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Ala His Pro
            20                  25                  30

Tyr Gly Ser Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Tyr Thr Phe Gly Gln Gly Thr Lys Leu Glu Ile Lys
            100                 105                 110

Arg

<210> SEQ ID NO 305
<211> LENGTH: 113
<212> TYPE: PRT
<213> ORGANISM: Artificial Sequence
<220> FEATURE:
<223> OTHER INFORMATION: Synthetic peptide

<400> SEQUENCE: 305

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
            20                  25                  30

Tyr Gly Asp Thr Tyr Leu His Trp Tyr Leu Gln Lys Pro Gly Gln Ser

```
                35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Tyr Thr Phe Gly Gln Gly Thr Arg Leu Glu Ile Lys
                100                 105                 110
Arg

<210> SEQ ID NO 306
<211> LENGTH: 113
<212> TYPE: PRT
<213> ORGANISM: Artificial Sequence
<220> FEATURE:
<223> OTHER INFORMATION: Synthetic peptide

<400> SEQUENCE: 306

Asp Val Val Met Thr Gln Ser Pro Leu Ser Leu Pro Val Thr Leu Gly
1               5                   10                  15
Glu Pro Ala Ser Ile Ser Cys Arg Ser Ser Gln Ser Leu Val His Pro
                20                  25                  30
Tyr Gly Pro Thr Tyr Leu His Trp Tyr Leu Gln Lys Pro Gly Gln Ser
                35                  40                  45
Pro Gln Leu Leu Ile Tyr Lys Val Ser Asn Arg Phe Ser Gly Val Pro
    50                  55                  60
Asp Arg Phe Ser Gly Gly Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Tyr Thr Phe Gly Gln Gly Thr Lys Leu Glu Ile Lys
                100                 105                 110
Arg

<210> SEQ ID NO 307
<211> LENGTH: 113
<212> TYPE: PRT
<213> ORGANISM: Artificial Sequence
<220> FEATURE:
<223> OTHER INFORMATION: Synthetic peptide

<400> SEQUENCE: 307

Asp Val Val Met Thr Gln Ser Pro Leu Ser Leu Pro Val Thr Leu Gly
1               5                   10                  15
Glu Pro Ala Ser Ile Ser Cys Arg Ser Ser Gln Ser Leu Val His Pro
                20                  25                  30
Tyr Gly Pro Thr Tyr Leu His Trp Tyr Leu Gln Lys Pro Gly Gln Ser
                35                  40                  45
Pro Gln Leu Leu Val Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Tyr Thr Phe Gly Gln Gly Thr Lys Leu Glu Ile Lys
                100                 105                 110
```

Arg

<210> SEQ ID NO 308
<211> LENGTH: 113
<212> TYPE: PRT
<213> ORGANISM: Artificial Sequence
<220> FEATURE:
<223> OTHER INFORMATION: Synthetic peptide

<400> SEQUENCE: 308

Asp Val Val Met Thr Gln Ser Pro Leu Ser Leu Pro Val Thr Leu Gly
1               5                   10                  15
Glu Pro Ala Ser Ile Ser Cys Arg Ser Ser Gln Ser Leu Val His Pro
            20                  25                  30
Tyr Gly Ser Thr Tyr Phe His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Gly Gly Val Tyr Tyr Cys Ser Gln Asn
                85                  90                  95
Thr His Val Pro Tyr Thr Phe Gly Gln Gly Thr Lys Leu Glu Ile Lys
            100                 105                 110
Arg

<210> SEQ ID NO 309
<211> LENGTH: 23
<212> TYPE: PRT
<213> ORGANISM: Artificial Sequence
<220> FEATURE:
<223> OTHER INFORMATION: Synthetic peptide

<400> SEQUENCE: 309

Asp Val Val Met Thr Gln Ser Pro Ile Ser Leu Pro Val Thr Leu Gly
1               5                   10                  15
Glu Pro Ala Ser Ile Ser Cys
            20

<210> SEQ ID NO 310
<211> LENGTH: 23
<212> TYPE: PRT
<213> ORGANISM: Artificial Sequence
<220> FEATURE:
<223> OTHER INFORMATION: Synthetic peptide

<400> SEQUENCE: 310

Asp Val Val Met Thr Gln Ser Pro Leu Ser Leu Ser Val Thr Leu Gly
1               5                   10                  15
Glu Pro Ala Ser Ile Ser Cys
            20

<210> SEQ ID NO 311
<211> LENGTH: 15
<212> TYPE: PRT
<213> ORGANISM: Artificial Sequence
<220> FEATURE:
<223> OTHER INFORMATION: Synthetic peptide

<400> SEQUENCE: 311

Trp Tyr Leu Gln Lys Pro Gly Gln Pro Pro Gln Leu Leu Ile Tyr

<210> SEQ ID NO 312
<211> LENGTH: 15
<212> TYPE: PRT
<213> ORGANISM: Artificial Sequence
<220> FEATURE:
<223> OTHER INFORMATION: Synthetic peptide

<400> SEQUENCE: 312

Trp Tyr Leu Gln Lys Pro Gly Gln Ser Pro Gln Leu Leu Val Tyr
1               5                   10                  15

<210> SEQ ID NO 313
<211> LENGTH: 32
<212> TYPE: PRT
<213> ORGANISM: Artificial Sequence
<220> FEATURE:
<223> OTHER INFORMATION: Synthetic peptide

<400> SEQUENCE: 313

Gly Val Pro Asp Arg Phe Ser Gly Ser Gly Ser Gly Thr Asp Tyr Thr
1               5                   10                  15

Leu Lys Ile Ser Arg Val Glu Ala Glu Asp Val Gly Val Tyr Tyr Cys
            20                  25                  30

<210> SEQ ID NO 314
<211> LENGTH: 32
<212> TYPE: PRT
<213> ORGANISM: Artificial Sequence
<220> FEATURE:
<223> OTHER INFORMATION: Synthetic peptide

<400> SEQUENCE: 314

Gly Val Pro Asp Arg Phe Ser Gly Ser Gly Ser Gly Thr Glu Phe Thr
1               5                   10                  15

Leu Lys Ile Ser Arg Val Glu Ala Glu Asp Val Gly Ala Tyr Tyr Cys
            20                  25                  30

<210> SEQ ID NO 315
<211> LENGTH: 32
<212> TYPE: PRT
<213> ORGANISM: Artificial Sequence
<220> FEATURE:
<223> OTHER INFORMATION: Synthetic peptide

<400> SEQUENCE: 315

Gly Val Pro Asp Arg Phe Ser Gly Gly Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Synthetic peptide

<400> SEQUENCE: 316

Gly Val Pro Asp Arg Phe Ser Gly Ser Gly Ser Gly Thr Asp Phe Thr
1               5                   10                  15

Leu Lys Ile Ser Arg Val Glu Ala Glu Asp Gly Gly Val Tyr Tyr Cys
            20                  25                  30

```
<210> SEQ ID NO 317
<211> LENGTH: 11
<212> TYPE: PRT
<213> ORGANISM: Artificial Sequence
<220> FEATURE:
<223> OTHER INFORMATION: Synthetic peptide

<400> SEQUENCE: 317

Phe Gly Gln Gly Thr Arg Leu Glu Ile Lys Arg
1               5                   10

<210> SEQ ID NO 318
<211> LENGTH: 16
<212> TYPE: PRT
<213> ORGANISM: Artificial Sequence
<220> FEATURE:
<223> OTHER INFORMATION: Synthetic peptide

<400> SEQUENCE: 318

Arg Ser Ser Gln Ser Leu Val His Pro Phe Gly Pro Thr Tyr Leu His
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Synthetic peptide

<400> SEQUENCE: 319

Arg Ser Ser Gln Ser Leu Ala His Pro Tyr Gly Ser Thr Tyr Leu His
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Synthetic peptide

<400> SEQUENCE: 320

Arg Ser Ser Gln Ser Leu Val His Pro Tyr Gly Ser Thr Tyr Phe His
1               5                   10                  15
```